United States Patent
Hodgson et al.

(10) Patent No.: US 8,507,543 B2
(45) Date of Patent: *Aug. 13, 2013

(54) COMPOUNDS

(71) Applicants: Simon Teanby Hodgson, Stevenage (GB); Yannick Maurice Lacroix, Stevenage (GB); Panayiotis Alexandrou Procopiou, Stevenage (GB)

(72) Inventors: Simon Teanby Hodgson, Stevenage (GB); Yannick Maurice Lacroix, Stevenage (GB); Panayiotis Alexandrou Procopiou, Stevenage (GB)

(73) Assignee: Glaxo Group Limited, Brentford, Middlesex (GB)

( * ) Notice: Subject to any disclaimer, the term of this patent is extended or adjusted under 35 U.S.C. 154(b) by 0 days.

This patent is subject to a terminal disclaimer.

(21) Appl. No.: 13/633,382

(22) Filed: Oct. 2, 2012

(65) Prior Publication Data

US 2013/0030031 A1    Jan. 31, 2013

Related U.S. Application Data

(62) Division of application No. 12/711,283, filed on Feb. 24, 2010, now Pat. No. 8,304,446.

(51) Int. Cl.
*A61K 31/415* (2006.01)

(52) U.S. Cl.
USPC .......................................... 514/407

(58) Field of Classification Search
None
See application file for complete search history.

(56) References Cited

FOREIGN PATENT DOCUMENTS

| WO | 2004/062662 | 7/2004 |
| WO | 2004/108717 | 12/2004 |
| WO | 2008/089307 | 7/2008 |

*Primary Examiner* — Brandon Fetterolf
*Assistant Examiner* — Jean Cornet
(74) *Attorney, Agent, or Firm* — Robert J. Smith

(57) ABSTRACT

Indazole compounds, processes for their preparation, intermediates usable in these processes, pharmaceutical compositions containing such compounds and their use in therapy.

4 Claims, No Drawings

COMPOUNDS

RELATED APPLICATION DATA

This application is a divisional application of Ser. No. 12/711,283, allowed, filed on Feb. 24, 2010, which claims priority from U.S. Provisional Application No. 61/155,702 filed Feb. 26, 2009.

FIELD OF THE INVENTION

The present invention relates to indazole compounds, processes for their preparation, intermediates usable in these processes, pharmaceutical compositions containing such compounds and to their use in therapy.

BACKGROUND OF THE INVENTION

Chemokines are believed to play an important role in immune and inflammatory responses in a number of diseases or conditions The CC-chemokine receptor 4 (hereafter CCR4) was originally cloned from a basophilic cell line (Power et al, J. Biol. Chem.; 270: 19495: 1995). Small molecule CCR4 receptor antagonists are known in the art, with examples of such being described in Andrews et al (Mol. Pharmacol 73: 855, 2008).

SUMMARY OF THE INVENTION

In a first aspect of the present invention, there is provided a compound of formula (I) or a salt thereof, more particularly a compound of formula (I) or a pharmaceutically acceptable salt thereof

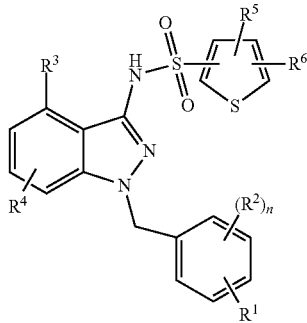

(I)

In a second aspect of the present invention, there is provided a pharmaceutical composition comprising a compound of formula (I) or a pharmaceutically acceptable salt thereof and one or more pharmaceutically acceptable carriers, diluents and excipients.

In a third aspect of the present invention, there is provided a compound of formula (I), or a pharmaceutically acceptable salt thereof for use in therapy, in particular in the treatment of a disease or condition for which a CCR4 receptor antagonist is indicated.

In a fourth aspect of the present invention, there is provided a method of treating a disease or condition for which a CCR4 receptor antagonist is indicated in a subject in need thereof which comprises administering a therapeutically effective amount of compound of formula (I) or a pharmaceutically acceptable salt thereof.

In a fifth aspect of the present invention, there is provided the use of a compound of formula (I), or a pharmaceutically acceptable salt thereof in the manufacture of a medicament for the treatment of a disease or condition for which a CCR4 receptor antagonist is indicated.

DETAILED DESCRIPTION OF THE INVENTION

The present invention relates to a compound of formula (I) or a salt thereof

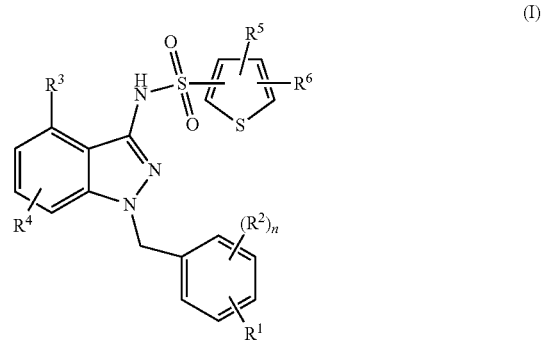

(I)

wherein
$R^1$ is selected from the group consisting of (1), (2), (3) (4) and (5)
(1) a group of formula (a)

(a)

in which A is selected from the group consisting of (i), (ii), (iii), (iv), (v), (vi), (vii) and (viii)
(i) hydrogen;
(ii) $C_{1-6}$alkyl optionally substituted by one or more $-NR^aR^b$, $-OR^c$, $-C(O)NR^aR^b$, $-C(O)OR^c$, heterocyclyl, phenyl or heteroaryl groups;
(iii) $C_{3-7}$cycloalkyl optionally substituted by a $-C(O)OR^c$ or $-NR^aR^b$ group;
(iv) heterocyclyl optionally substituted by one or more $C_{1-6}$alkyl;
(v) heteroaryl optionally substituted by one or more halogen or $C_{1-6}$alkyl
(vi) $-NR^aR^b$;
(vii) phenyl substituted by a $-(CH_2)_pC(O)OH$ group in which p is 0, 1, 2 or 3; or
(viii) $-(CH_2)_7C(O)OH$
(2) a group of formula (b)

(b)

in which B is $C_{1-6}$alkyl;
(3) $-C(O)NR^aR^b$ or $-CH_2C(O)NR^aR^b$;
(4) $-S(O)_2NR^aR^b$;

(5) $C_{1-6}$alkoxy optionally substituted by $NR^aR^b$;

$R^a$, $R^b$ and W are independently hydrogen or $C_{1-6}$alkyl;

$R^2$ is halogen, $C_{1-6}$alkyl, $CF_3$, hydroxy or $C_{1-6}$alkoxy;

$R^3$ is halogen, $CF_3$, hydroxy, $C_{1-6}$alkoxy, $CR^dR^eOH$ or $CHF_2$; in which $R^d$ and $R^e$ are independently hydrogen or methyl;

$R^4$ is hydrogen, halogen, $C_{1-6}$alkyl or $CF_3$;

$R^5$ and $R^6$ are independently hydrogen, halogen or $C_{1-6}$alkyl; and n is 0 or 1.

In one embodiment the invention relates to a compound of formula (I) or a salt thereof.

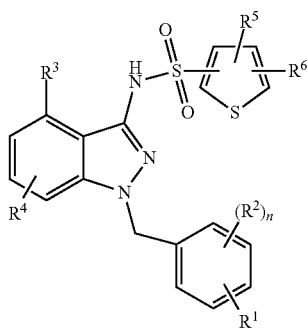

(I)

wherein $R^1$ is selected from the group consisting of (1), (2), (3) (4) and (5)

(1) a group of formula (a)

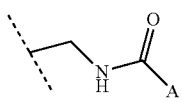

(a)

in which A is selected from the group consisting of (i), (ii), (iii), (iv), (v) and (vi):

(i) hydrogen;

(ii) $C_{1-6}$alkyl optionally substituted by one or more $-NR^aR^b$, $-OR^a$, $-C(O)NR^aR^b$, $-C(O)OR^c$, heterocyclyl, phenyl or heteroaryl groups;

(iii) $C_{3-7}$cycloalkyl optionally substituted by a $-NR^aR^b$ group;

(iv) heterocyclyl optionally substituted by one or more $C_{1-6}$alkyl;

(v) heteroaryl optionally substituted by one or more halogen or $C_{1-6}$alkyl (vi) $-NR^aR^b$;

(2) a group of formula (b)

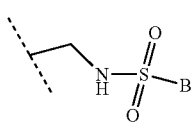

(b)

in which B is $C_{1-6}$alkyl;

(3) $-C(O)NR^aR^b$;

(4) $-S(O)_2NR^aR^b$;

(5) $C_{1-6}$alkoxy optionally substituted by $NR^aR^b$;

$R^a$, $R^b$ and W are independently hydrogen or $C_{1-6}$alkyl;

$R^2$ is halogen, $C_{1-6}$alkyl, $CF_3$, hydroxy or $C_{1-6}$alkoxy;

$R^3$ is halogen, $CF_3$, hydroxy, $C_{1-6}$alkoxy, $CH_2OH$ or $CHF_2$ $R^4$ is hydrogen, halogen, $C_{1-6}$alkyl or $CF_3$;

$R^5$ and $R^6$ are independently hydrogen, halogen or $C_{1-6}$alkyl; and n is 0 or 1.

In one embodiment the $R^1$ group is substituted at the meta position (3 position).

In one embodiment $R^1$ is a group of formula (a) in which A is $C_{1-6}$alkyl such as methyl, ethyl, isopropyl or t-butyl.

In a further embodiment $R^1$ is a group of formula (a) in which A is $C_{1-6}$alkyl substituted by one or more $-NR^aR^b$ (such as $NH_2$, NHMe or $NMe_2$), $-OR^c$ (such as OH or OMe), $-C(O)NR^aR^b$ (such as $C(O)NH_2$), $-C(O)OR^c$ (such as C(O)OH or C(O)OMe), pyrrolidinyl, phenyl or imidazolyl.

In a yet further embodiment $R^1$ is a group of formula (a) in which A is a heterocyclyl selected from the group consisting of pyrrolidinyl, piperidinyl and morpholinyl.

In a yet further embodiment $R^1$ is a group of formula (a) in which A is a heteroaryl selected from the group consisting of furyl, imidazolyl, pyrazolyl and oxazolyl.

In one embodiment, when n is 1 $R^2$ is selected from the group consisting of halogen (such as fluorine or chlorine), $C_{1-6}$alkyl (such as methyl) or $C_{1-6}$alkoxy (such as methoxy).

In one embodiment $R^3$ is halogen (such as fluorine), hydroxy or $C_{1-4}$alkoxy (such as methoxy). In a further embodiment $R^3$ is methoxy.

In one embodiment $R^4$ is hydrogen or fluorine.

In one embodiment $R^5$ and $R^6$ are independently hydrogen, halogen (such as chlorine) or $C_{1-6}$alkyl (such as methyl). In a further embodiment $R^5$ is chlorine and $R^6$ is hydrogen.

In one embodiment $R^a$, $R^b$ and are independently hydrogen or methyl.

In a particular embodiment the present invention provides for compounds of formula (Ia) or a salt thereof

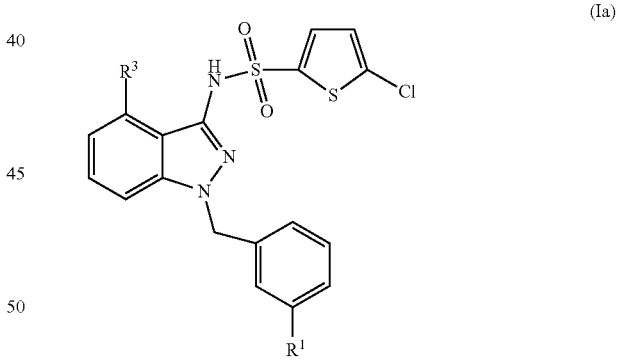

(Ia)

in which $R^1$ and $R^3$ are as defined above.

While the embodiments for each variable have generally been listed above separately for each variable this invention includes those compounds in which several or each embodiment in formula (I) is selected from each of the embodiments listed above. Therefore, this invention is intended to include all combinations of embodiments for each variable described hereinabove including salts thereof.

Specific compounds according to the invention include Examples 1-166 as described herein or a salt thereof.

Particular compounds according to the invention are

N-[(3-{[3-{[(5-Chloro-2-thienyl)sulfonyl]amino}-4-(methyloxy)-1H-indazol-1-yl]methyl}phenyl)methyl]acetamide, N-[(3-{[3-{[(5-chloro-2-thienyl)sulfonyl]amino}-4-(methyloxy)-1H-indazol-1-yl]methyl}phenyl)methyl]-3-morpholinecarboxamide, N-[(3-{[3-{[(5-Chloro-2-thienyl)sulfonyl]amino}-4-(methyloxy)-1H-indazol-1-yl]methyl}phenyl)methyl]-2-hydroxy-2-methylpropanamide N-[(3-{[3-{[(5-Chloro-2-thienyl)sulfonyl]amino}-4-(methyloxy)-1H-indazol-1-yl]methyl}phenyl)methyl]-2-hydroxypropanamide, (2S)—N-[(3-{[3-{[(5-Chloro-2-thienyl)sulfonyl]amino}-4-(methyloxy)-1H-indazol-1-yl]methyl}phenyl)methyl]-2-hydroxypropanamide or a salt thereof.

Throughout the present specification, unless otherwise stated:
- the term "halogen" is used to describe a group selected from fluorine, chlorine or bromine;
- the term "$C_{1-6}$alkyl" is used to describe a group or a part of the group comprising a linear or branched alkyl group containing from 1 to 6 carbon atoms respectively. Suitable examples of such groups include methyl, ethyl, propyl, isopropyl, n-butyl, isobutyl, t-butyl, pentyl and hexyl;
- the term "$C_{1-6}$alkoxy" is used to describe a group or a part of the group comprising a linear or branched alkyl group containing from 1 to 6 carbon atoms. Suitable examples include methoxy, ethoxy, propoxy, isopropoxy, n-butoxy, isobutoxy, t-butoxy, pentoxy or hexoxy;
- the term "heterocyclyl" or "heterocyclyl ring" is used to describe a saturated 4-7 membered monocyclic ring containing one or two heteroatoms selected from nitrogen, oxygen or sulphur. Suitable examples include azetidinyl, pyrrolidinyl, piperidinyl, piperazinyl, morpholinyl, tetrahydrofuranyl and tetrahydropyranyl;
- the term "heteroaryl" is used to describe an aromatic or a benzofused aromatic ring containing 1 to 3 heteroatoms selected from oxygen, nitrogen and sulphur. Suitable examples of such aromatic rings include thienyl, furyl, pyrrolyl, triazolyl, imidazolyl, oxazolyl, thiazolyl, oxadiazolyl, isothiazolyl, isoxazolyl, thiadiazolyl, pyrazolyl, pyrimidyl, pyridazinyl, pyrazinyl and pyridyl. Suitable examples of such benzofused aromatic rings include quinolinyl, isoquinolinyl, indolyl, benzofuryl, benzothienyl, benzimidazolyl, benzoxazolyl;
- the term "$C_{3-7}$cycloalkyl" is used to describe a non aromatic carbocyclic ring containing at least three and at most seven carbon atoms. Examples of $C_{3-7}$cycloalkyl include cyclopropyl, cyclobutyl, cyclopentyl, cyclohexyl or cycloheptyl.

It will be appreciated that the present invention covers compounds of formula (I) as the free base and as salts thereof, for example as a pharmaceutically acceptable salt thereof. In one embodiment the invention relates to compounds of formula (I) or a pharmaceutically acceptable salt thereof.

Because of their potential use in medicine, salts of the compounds of formula (I) are desirably pharmaceutically acceptable. Suitable pharmaceutically acceptable salts can include acid or base addition salts. For a review on suitable salts see Berge et al., J. Pharm. Sci., 66:1-19, (1977). Typically, a pharmaceutically acceptable salt may be readily prepared by using a desired acid or base as appropriate. The resultant salt may precipitate from solution and be collected by filtration or may be recovered by evaporation of the solvent.

A pharmaceutically acceptable base addition salt can be formed by reaction of a compound of formula (I) with a suitable inorganic or organic base, (e.g. triethylamine, ethanolamine, triethanolamine, choline, arginine, lysine or histidine), optionally in a suitable solvent, to give the base addition salt which is usually isolated, for example, by crystallisation and filtration. Pharmaceutically acceptable base salts include ammonium salts, alkali metal salts such as those of sodium and potassium, alkaline earth metal salts such as those of calcium and magnesium and salts with organic bases, including salts of primary, secondary and tertiary amines, such as isopropylamine, diethylamine, ethanolamine, trimethylamine, dicyclohexyl amine and N-methyl-D-glucamine.

A pharmaceutically acceptable acid addition salt can be formed by reaction of a compound of formula (I) with a suitable inorganic or organic acid (such as hydrobromic, hydrochloric, sulphuric, nitric, phosphoric, succinc, maleic, acetic, propionic, fumaric, citric, tartaric, lactic, benzoic, salicylic, glutamaic, aspartic, p-toluenesulfonic, benzenesulfonic, methanesulfonic, ethanesulfonic, naphthalenesulfonic such as 2-naphthalenesulfonic, or hexanoic acid), optionally in a suitable solvent such as an organic solvent, to give the salt which is usually isolated for example by crystallisation and filtration. A pharmaceutically acceptable acid addition salt of a compound of formula (I) can comprise or be for example a hydrobromide, hydrochloride, sulfate, nitrate, phosphate, succinate, maleate, acetate, propionate, fumarate, citrate, tartrate, lactate, benzoate, salicylate, glutamate, aspartate, p-toluenesulfonate, benzenesulfonate, methanesulfonate, ethanesulfonate, naphthalenesulfonate (e.g. 2-naphthalenesulfonate) or hexanoate salt.

Other non-pharmaceutically acceptable salts, e.g. formates, oxalates or trifluoroacetates, may be used, for example in the isolation of the compounds of formula (I), and are included within the scope of this invention.

The invention includes within its scope all possible stoichiometric and non-stoichiometric forms of the salts of the compounds of formula (I).

It will be appreciated that many organic compounds can form complexes with solvents in which they are reacted or from which they are precipitated or crystallized. These complexes are known as "solvates". For example, a complex with water is known as a "hydrate". Solvents with high boiling points and/or capable of forming hydrogen bonds such as water, xylene, N-methylpyrrolidinone, methanol and ethanol may be used to form solvates. Methods for identification of solvates include, but are not limited to, NMR and microanalysis. Solvates of the compounds of formula (I) are within the scope of the invention.

The invention includes within its scope all possible stoichiometric and non-stoichiometric forms of the solvates of the compounds of formula (I).

The compounds of formula (I) may be in crystalline or amorphous form. Furthermore, some of the crystalline forms of the compounds of formula (I) may exist as polymorphs, which are included within the scope of the present invention. Polymorphic forms of compounds of formula (I) may be characterized and differentiated using a number of conventional analytical techniques, including, but not limited to, X-ray powder diffraction (XRPD) patterns, infrared (IR) spectra, Raman spectra, differential scanning calorimetry (DSC), thermogravimetric analysis (TGA) and solid state nuclear magnetic resonance (SSNMR).

Certain of the compounds described herein may contain one or more chiral atoms so that optical isomers, e.g. —enantiomers or diastereoisomers may be formed. Accordingly, the present invention encompasses all isomers of the compounds of formula (I) whether as individual isomers isolated such as to be substantially free of the other isomer (i.e. pure) or as mixtures (i.e. racemates and racemic mixtures). An individual isomer isolated such as to be substantially free of the other isomer (i.e. pure) may be isolated such that less than 10%, particularly less than about 1%, for example less than about 0.1% of the other isomer is present.

Separation of isomers may be achieved by conventional techniques known to those skilled in the art, e.g. by fractional crystallisation, chromatography or HPLC.

Certain compounds of formula (I) may exist in one of several tautomeric forms. It will be understood that the present invention encompasses all tautomers of the compounds of formula (I) whether as individual tautomers or as mixtures thereof.

It will be appreciated from the foregoing that included within the scope of the invention are solvates, hydrates, complexes, isomers and polymorphic forms of the compounds of formula (I) and salts thereof.

The compounds of the invention may be made by a variety of methods, including standard chemistry. Any previously defined variable will continue to have the previously defined meaning unless otherwise indicated. Illustrative general synthetic methods are set out below and then specific compounds of the invention are prepared in the working Examples.

The present invention further provides for a process for the preparation of a compound of formula (I) or a salt thereof which comprises a process selected from (a), (b), (c) or (d) in which:

(a) involves reacting a compound of formula (II) or a salt thereof

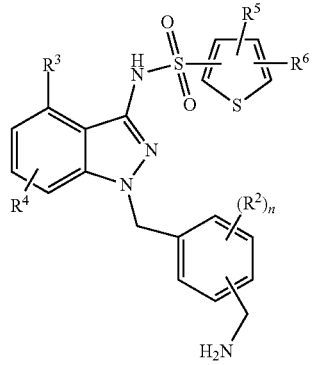

(II)

in which $R^2$-$R^6$ and n are as hereinbefore defined with a compound of formula (IIIa), (IIIb), (IIIc) or (IIId) or a protected derivative thereof.

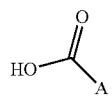

(IIIa)

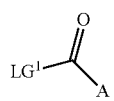

(IIIb)

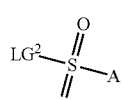

(IIIc)

(IIId)

in which A is as hereinbefore defined;
and optionally thereafter de-protecting the resulting product;

(b) involves reacting a compound of formula (IV) or a protected derivative thereof

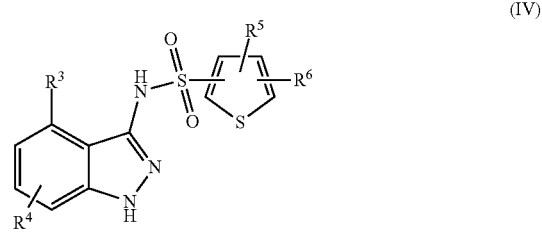

(IV)

in which $R^3$-$R^6$ are as hereinbefore defined with a compound of formula (Va) or (Vb)

(Va)

(Vb)

in which $R^1$, $R^2$ and n are as hereinbefore defined and Hal is halogen;
and optionally thereafter de-protecting the resulting product;

(c) involves reacting a compound of formula (VI)

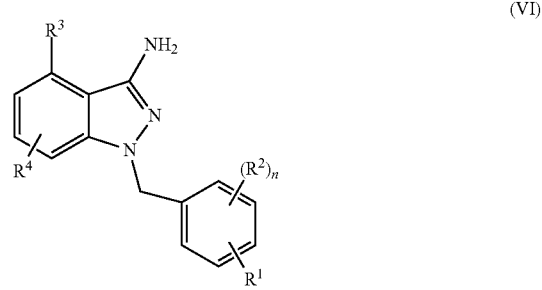

(VI)

in which $R^1$-$R^4$ and n are as hereinbefore defined with a compound of formula (VII)

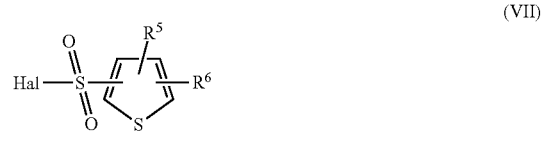

(VII)

in which $R^5$ and $R^6$ are as hereinbefore defined and Hal is halogen;

(d) involves converting a compound of formula (I) or a salt thereof into a further compound of formula (I) or a salt thereof.

Process (a)

The compounds of formula (II) and carboxylic acid of formula (IIIa) are reacted under amide forming conditions that are familiar to those skilled in the art. Such reactions may be carried out in a suitable organic solvent (e.g. DMF or acetonitrile) with a base (e.g. DIPEA or triethylamine) in the presence of a suitable activating group (e.g. HATU or TBTU).

The compounds of formula (II) and carboxylic acid of formula (IIIa) may also be reacted in the presence of an activating reagent such as 1-chloro N,N,2-trimethyl-1-propen-1-amine in a suitable organic solvent (e.g. THF or dichloromethane) with a suitable base (e.g. DIPEA or triethylamine). Such methodology is described in Schmidt et al (Synthesis, 1988, 475).

Suitable examples of the compounds of formula (IIIb) are acid chlorides or acid anhydrides (i.e. in which leaving group LG$^1$ is Cl or OC(O)R). The reaction between compounds of formula (II) and formula (IIIb) is typically carried out in an inert organic solvent (such as tetrahydrofuran, DMF, chloroform or dichloromethane) at ambient or lower temperature, optionally in the presence of a suitable base e.g. an organic base (such as triethylamine or diisopropylethylamine), an alkali metal carbonate (such as potassium carbonate) or an alkali metal hydrogen carbonate (such as sodium hydrogen carbonate).

Suitable examples of the compounds of formula (IIIc) are those in which leaving group LG$^2$ is chloro. The compounds of formula (II) and formula (IIIc) are typically reacted in a suitable solvent (such as tetrahydrofuran or dichloromethane) in the presence of a suitable base (such as triethylamine or pyridine).

The compounds of formula (II) and formula (IIId) are typically reacted in a suitable organic solvent (e.g. dichloromethane) in the presence of a suitable amine (e.g. triethylamine).

It will be appreciated that in the reaction of a compound of formula (II) and a compound of formula (III) it may be advantageous to protect one or more functional groups of the compounds of formula (III). Examples of protecting groups and the means for their removal can be found in T. W. Greene 'Protective Groups in Organic Synthesis' (3rd edition, J. Wiley and Sons, 1999). Suitable amine protecting groups include acyl (e.g. acetyl, carbamate (e.g. 2',2',2'-trichloroethoxycarbonyl, benzyloxycarbonyl or t-butoxycarbonyl) and arylalkyl (e.g. benzyl), which may be removed by hydrolysis (e.g. using an acid such as hydrochloric acid in dioxane or trifluoroacetic acid in dichloromethane) or reductively (e.g. hydrogenolysis of a benzyl or benzyloxycarbonyl group or reductive removal of a 2',2',2'-trichloroethoxycarbonyl group using zinc in acetic acid) as appropriate. Other suitable amine protecting groups include trifluoroacetyl (—COCF$_3$) which may be removed by base catalysed hydrolysis.

Compounds of formula (II) may be prepared by methods described herein. By way of illustration, a representative compound of formula (II) (i.e. in which n is O, R$^4$ and R$^6$ are hydrogen, R$^5$ is chloro and R$^3$ is methoxy) can be prepared by methods described in Scheme 1.

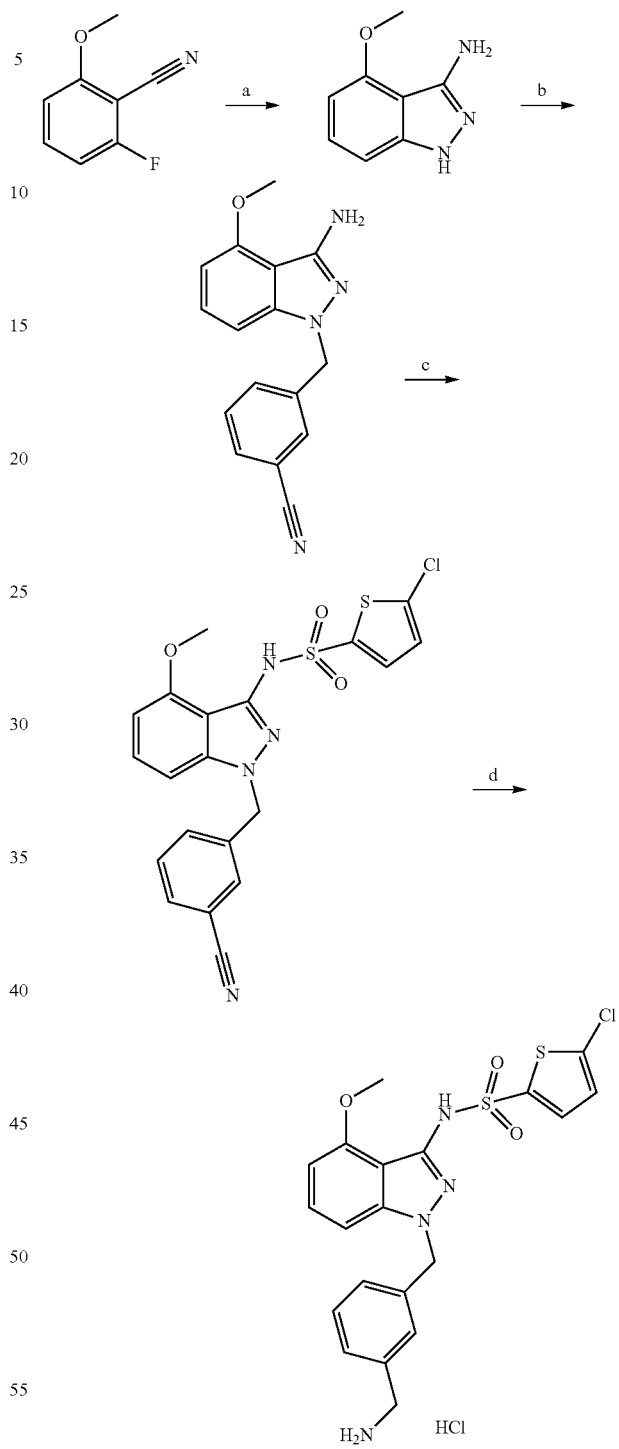

Scheme 1

Reagents and conditions: a) NH$_2$NH$_2$·H$_2$O, 1-butanol, reflux, 92%; b) KOH, DMSO, 3-cyanobenzyl chloride, 60%; c) 5-chloro-2-thiophenesulfonyl chloride, pyridine, 85%; d) 1M LiAlH$_4$ solution in ether, THF, 2M HCl, MeOH, 77%

The compounds of formula (III)(a)-(d) can be obtained from commercial sources.

Process (b)

For compounds of formula (Va) a suitable Hal group is chlorine, bromine, iodine particularly chlorine. Typically the compounds of formula (IV) is in the form of a protected derivative thereof (e.g. using a silyl ether such as β-(trimethylsilyl)ethoxy)methyl (SEM) as a protecting group). The alkylation reaction between the protected derivatives of the compounds of formula (IV) and the compounds of formula (Va) may be carried out under microwave irradiation in an inert organic solvent (such as DMF) at ambient or elevated temperature, optionally in the presence of a suitable base such as potassium or caesium carbonate. The silyl ether protecting group can be removed from the product thus formed by standard procedures such as by reaction with tetra-n-butylammonium fluoride (TBAF) in a suitable solvent such as THF.

The reaction between the compounds of formula (IV) and (Vb) may be carried out using conditions of the Mitsunobu reaction which are familiar to those skilled in the art. The compounds of formula (IV) are typically in the form of a protected derivative thereof (e.g. using a sulphonamide protecting group). Typically the reaction is carried out using triphenylphosphine with an azodicarboxylate compound (such as TBAD, DIAD or DEAD) in a suitable organic solvent (such as THF or DMF). The sulphonamide protecting group may be removed from the product thus formed by treatment with sodium hydroxide in methanol.

Compounds of formula (IV) or a protected derivative thereof may be prepared by methods described herein. Compounds of formula (Va) or (Vb) are either commercially available or can be prepared by methods described herein.

Process (c)

The reaction between a compound of formula (VI) and (VII) is typically carried out in a suitable organic solvent (such as pyridine).

Compounds of formula (VI) may be prepared by methods described herein. By way of illustration, a representative compound of formula (VI) (i.e. in which n is 0, $R^4$ is hydrogen, $R^3$ is methoxy and $R^1$ is C(O)NH$_2$) can be prepared by methods described in the Scheme 2.

Scheme 2

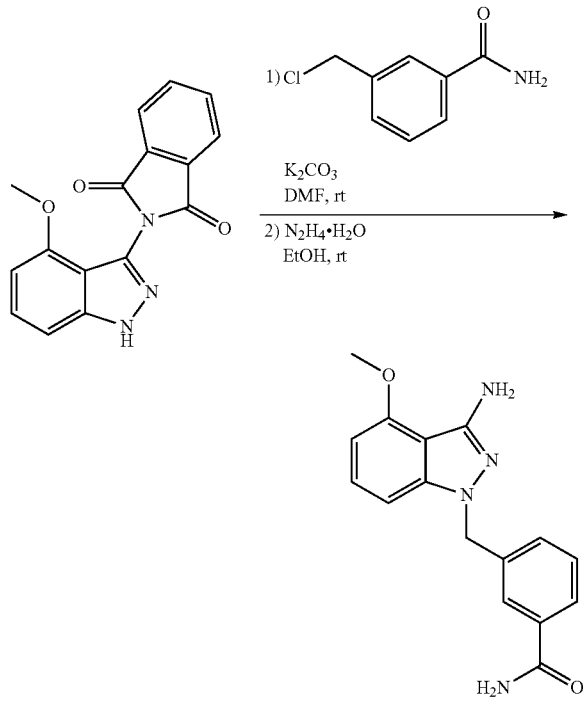

Suitable compounds of formula (VII) e.g. 5-chloro-2-thiophenesulfonyl chloride, 5-methyl-2-thiophenesulfonyl chloride and 5-bromo-2-thiophenesulfonyl chloride are commercially available.

Process (d)

It will be appreciated that certain compounds of formula (I) may be reacted to form further compounds of formula (I). For example, compounds in which $R^3$ is $C_{1-6}$alkoxy (such as methoxy) can be converted into the corresponding compounds in which $R^3$ is hydroxy by reaction with a demethylating agent (such as boron tribromide) in a suitable organic solvent (such as DCM).

It will be appreciated that in any of the routes (a) to (d) described above, the precise order of the synthetic steps by which the various groups and moieties are introduced into the molecule may be varied. It will be within the skill of the practitioner in the art to ensure that groups or moieties introduced at one stage of the process will not be affected by subsequent transformations and reactions, and to select the order of synthetic steps accordingly.

In a further aspect of the present invention there is provided a compound of formula (II) or a salt thereof.

Certain compounds of formulae (IV) and (VI) are also believed to be novel and therefore form a yet further aspect of the invention.

The compounds of formula (I) and salts thereof are believed to be inhibitors of CC chemokine receptor activity, particularly CCR4 receptor activity, and thus have potential utility in the treatment of diseases or conditions for which a CCR4 compound is indicated.

The present invention thus provides a compound of formula (I) or a pharmaceutically acceptable salt thereof for use in therapy. The compound of formula (I) or pharmaceutically salt thereof can be for use in the treatment of a disease or condition for which a CCR4 receptor antagonist is indicated.

The present invention thus provides a compound of formula (I) or a pharmaceutically acceptable salt thereof for use in the treatment of a disease or condition for which a CCR4 receptor antagonist is indicated.

Also provided is the use of a compound of formula (I) or a pharmaceutically acceptable salt thereof in the manufacture of a medicament for the treatment of a disease or condition for which a CCR4 receptor antagonist is indicated.

Also provided is a method of treating a disease or conditions for which a CCR4 receptor antagonist is indicated in a subject in need thereof which comprises administering a therapeutically effective amount of compound of formula (I) or a pharmaceutically acceptable salt thereof.

Suitably the subject in need thereof is a mammal, particularly a human.

As used herein, the term "effective amount" means that amount of a drug or pharmaceutical agent that will elicit the biological or medical response of a tissue, system, animal or human that is being sought, for instance, by a researcher or clinician. Furthermore, the term "therapeutically effective amount" means any amount which, as compared to a corresponding subject who has not received such amount, results in improved treatment, healing, prevention, or amelioration of a disease, disorder, or side effect, or a decrease in the rate of advancement of a disease or disorder. The term also includes within its scope amounts effective to enhance normal physiological function.

CCR4 antagonists are believed to be useful in the treatment of a variety of diseases or conditions such as immunoregulatory, inflammatory and/or allergic diseases. Examples include: asthma, chronic obstructive pulmonary disease (COPD) including chronic bronchitis and emphysema, idiopathic pulmonary fibrosis, atopic or contact dermatitis, urticaria, allergic rhinitis (seasonal or perennial), vasomotor rhinitis, nasal polyps, allergic conjunctivitis, vernal conjunctivitis, occupational conjunctivitis, infective conjunctivitis, eosinophilic syndromes, eosinophilic granuloma, psoriasis, rheumatoid arthritis, ulcerative colitis, Crohn's disease, thrombosis, reperfusion injury of the myocardium and brain, chronic glomerulonephritis, sepsis, adult respiratory distress syndrome, multiple sclerosis, memory impairment (including Alzheimer's disease), pain and cancer.

CCR4 antagonists are also believed to useful in the treatment of diseases or conditions such as allergic bronchopulmonary aspergillosis, allergic fungal sinusitis, severe asthma with fungal sensitization and diseases involving a pathogenic role for fungi including invasion or colonisation (such as invasive aspergillosis, aspergilloma or candidiasis)

The term "disease or condition for which a CCR4 inhibitor is indicated", is intended to include any or all of the above disease states.

In one embodiment the disease or condition for which a CCR4 inhibitor is indicated is selected from asthma, COPD, rhinitis, idiopathic pulmonary fibrosis, psoriasis and contact dermatitis. In a particular embodiment the disease or condition for which a CCR4 inhibitor is indicated is asthma.

While it is possible that for use in therapy, a compound of formula (I) as well as pharmaceutically acceptable salts thereof may be administered as the raw chemical, it is common to present the active ingredient as a pharmaceutical composition.

The present invention therefore provides in a further aspect a pharmaceutical composition comprising a compound of formula (I) or a pharmaceutically acceptable salt and one or more or pharmaceutically acceptable carriers, diluents and/or excipients. The compounds of the formula (I) and pharmaceutically acceptable salts, are as described above. The carrier(s), diluent(s) or excipient(s) must be acceptable in the sense of being compatible with the other ingredients of the composition and not deleterious to the recipient thereof. In accordance with another aspect of the invention there is also provided a process for the preparation of a pharmaceutical composition including admixing a compound of the formula (I), or a pharmaceutically acceptable salt thereof, with one or more pharmaceutically acceptable carriers, diluents or excipients. The pharmaceutical composition can be for use in the treatment of any of the conditions described herein. Further provided is a pharmaceutical composition for the treatment of diseases or conditions for which a CCR4 inhibitor is indicated comprising a compound of formula (I) or a pharmaceutically acceptable salt thereof.

Further provided is a pharmaceutical composition comprising 0.05 to 1000 mg of a compound of formula (I) or a pharmaceutical salt thereof and 0.1 to 2 g of one or more pharmaceutically acceptable carriers, diluents or excipients.

Since the compounds of formula (I) are intended for use in pharmaceutical compositions it will be readily understood that they are each preferably provided in substantially pure form, for example, at least 60% pure, more suitably at least 75% pure and preferably at least 85% pure, especially at least 98% pure (% in a weight for weight basis).

Pharmaceutical compositions may be presented in unit dose forms containing a predetermined amount of active ingredient per unit dose. Preferred unit dosage compositions are those containing a daily dose or sub-dose, or an appropriate fraction thereof, of an active ingredient. Such unit doses may therefore be administered more than once a day. Preferred unit dosage compositions are those containing a daily dose or sub-dose (for administration more than once a day), as herein above recited, or an appropriate fraction thereof, of an active ingredient.

Pharmaceutical compositions may be adapted for administration by any appropriate route, for example by the oral (including buccal or sublingual), rectal, inhaled, intranasal, topical (including buccal, sublingual or transdermal), vaginal or parenteral (including subcutaneous, intramuscular, intravenous or intradermal) route. Such compositions may be prepared by any method known in the art of pharmacy, for example by bringing into association the active ingredient with the carrier(s) or excipient(s).

In one embodiment the pharmaceutical composition is adapted for oral administration.

Pharmaceutical compositions adapted for oral administration may be presented as discrete units such as capsules or tablets; powders or granules; solutions or suspensions in aqueous or non-aqueous liquids; edible foams or whips; or oil-in-water liquid emulsions or water-in-oil liquid emulsions.

For instance, for oral administration in the form of a tablet or capsule, the active drug component can be combined with an oral, non-toxic pharmaceutically acceptable inert carrier such as ethanol, glycerol, water and the like. Powders suitable for incorporating into tablets or capsules may be prepared by reducing the compound to a suitable fine size (e.g. by micronisation) and mixing with a similarly prepared pharmaceutical carrier such as an edible carbohydrate, as, for example, starch or mannitol. Flavoring, preservative, dispersing and coloring agent can also be present.

Capsules may be made by preparing a powder mixture, as described above, and filling formed gelatin sheaths. Glidants and lubricants such as colloidal silica, talc, magnesium stearate, calcium stearate or solid polyethylene glycol can be added to the powder mixture before the filling operation. A disintegrating or solubilizing agent such as agar-agar, calcium carbonate or sodium carbonate can also be added to improve the availability of the medicament when the capsule is ingested.

Moreover, when desired or necessary, suitable binders, glidants, lubricants, sweetening agents, flavours, disintegrating agents and coloring agents can also be incorporated into the mixture. Suitable binders include starch, gelatin, natural sugars such as glucose or beta-lactose, corn sweeteners, natural and synthetic gums such as acacia, tragacanth or sodium alginate, carboxymethylcellulose, polyethylene glycol, waxes and the like. Lubricants used in these dosage forms include sodium oleate, sodium stearate, magnesium stearate, sodium benzoate, sodium acetate, sodium chloride and the like. Disintegrators include, without limitation, starch, methyl cellulose, agar, bentonite, xanthan gum and the like. Tablets are formulated, for example, by preparing a powder mixture, granulating or slugging, adding a lubricant and disintegrant and pressing into tablets. A powder mixture is prepared by mixing the compound, suitably comminuted, with a diluent or base as described above, and optionally, with a binder such as carboxymethylcellulose, an aliginate, gelatin, or polyvinyl pyrrolidone, a solution retardant such as paraffin, a resorption accelerator such as a quaternary salt and/or an absorption agent such as bentonite, kaolin or dicalcium phosphate. The powder mixture can be granulated by wetting with a binder such as syrup, starch paste, acadia mucilage or solutions of cellulosic or polymeric materials and forcing through a screen. As an alternative to granulating, the powder mixture can be run through the tablet machine and the result is imperfectly formed slugs broken into granules. The granules can be lubricated to prevent sticking to the tablet forming dies by means of the addition of stearic acid, a stearate salt, talc or mineral oil. The lubricated mixture is then compressed into tablets. The compounds of the present invention can also be combined with a free flowing inert carrier and compressed into tablets directly without going through the granulating or slugging steps. A clear or opaque protective coating consisting of a sealing coat of shellac, a coating of sugar or polymeric material and a polish coating of wax can be provided. Dyestuffs can be added to these coatings to distinguish different unit dosages.

Oral fluids such as solution, syrups and elixirs can be prepared in dosage unit form so that a given quantity contains a predetermined amount of the compound. Syrups can be prepared by dissolving the compound in a suitably flavored aqueous solution, while elixirs are prepared through the use of a non-toxic alcoholic vehicle. Suspensions can be formulated by dispersing the compound in a non-toxic vehicle. Solubilizers and emulsifiers such as ethoxylated isostearyl alcohols and polyoxy ethylene sorbitol ethers, preservatives, flavor additive such as peppermint oil or natural sweeteners or saccharin or other artificial sweeteners, and the like can also be added.

Where appropriate, dosage unit compositions for oral administration can be microencapsulated. The formulation can also be prepared to prolong or sustain the release as for example by coating or embedding particulate material in polymers, wax or the like.

The compounds of the invention can also be administered in the form of liposome delivery systems, such as small unilamellar vesicles, large unilamellar vesicles and multilamellar vesicles. Liposomes can be formed from a variety of phospholipids, such as cholesterol, stearylamine or phosphatidylcholines.

Pharmaceutical compositions adapted for transdermal administration may be presented as discrete patches intended to remain in intimate contact with the epidermis of the recipient for a prolonged period of time.

Pharmaceutical compositions adapted for topical administration may be formulated as ointments, creams, suspensions, lotions, powders, solutions, pastes, gels, sprays, aerosols or oils.

For treatments of the eye or other external tissues, for example mouth and skin, the compositions are preferably applied as a topical ointment or cream. When formulated in an ointment, the active ingredient may be employed with either a paraffinic or a water-miscible ointment base. Alternatively, the active ingredient may be formulated in a cream with an oil-in-water cream base or a water-in-oil base.

Pharmaceutical compositions adapted for topical administrations to the eye include eye drops wherein the active ingredient is dissolved or suspended in a suitable carrier, especially an aqueous solvent.

Pharmaceutical compositions adapted for topical administration in the mouth include lozenges, pastilles and mouth washes.

Pharmaceutical compositions adapted for rectal administration may be presented as suppositories or as enemas.

Dosage forms for nasal or inhaled administration may conveniently be formulated as aerosols, solutions, suspensions, gels or dry powders.

For compositions suitable and/or adapted for inhaled administration, it is preferred that the compound of the invention is in a particle-size-reduced form, and more preferably the size-reduced form is obtained or obtainable by micronisation. The preferable particle size of the size-reduced (e.g. micronised) compound or salt is defined by a D50 value of about 0.5 to about 10 microns (for example as measured using laser diffraction).

Aerosol formulations, e.g. for inhaled administration, can comprise a solution or fine suspension of the active substance in a pharmaceutically acceptable aqueous or non-aqueous solvent. Aerosol formulations can be presented in single or multidose quantities in sterile form in a sealed container, which can take the form of a cartridge or refill for use with an atomising device or inhaler. Alternatively the sealed container may be a unitary dispensing device such as a single dose nasal inhaler or an aerosol dispenser fitted with a metering valve (metered dose inhaler) which is intended for disposal once the contents of the container have been exhausted.

Where the dosage form comprises an aerosol dispenser, it preferably contains a suitable propellant under pressure such as compressed air, carbon dioxide or an organic propellant such as a hydrofluorocarbon (HFC). Suitable HFC propellants include 1,1,1,2,3,3,3-heptafluoropropane and 1,1,1,2-tetrafluoroethane. The aerosol dosage forms can also take the form of a pump-atomiser. The pressurised aerosol may contain a solution or a suspension of the active compound. This may require the incorporation of additional excipients e.g. co-solvents and/or surfactants to improve the dispersion characteristics and homogeneity of suspension formulations. Solution formulations may also require the addition of co-solvents such as ethanol. Other excipient modifiers may also be incorporated to improve, for example, the stability and/or taste and/or fine particle mass characteristics (amount and/or profile) of the formulation.

For pharmaceutical compositions suitable and/or adapted for inhaled administration, the pharmaceutical composition may be a dry powder inhalable composition. Such a composition can comprise a powder base such as lactose, glucose, trehalose, mannitol or starch, the compound of formula (I) or salt thereof (preferably in particle-size-reduced form, e.g. in micronised form), and optionally a performance modifier such as L-leucine or another amino acid and/or metals salts of stearic acid such as magnesium or calcium stearate. Preferably, the dry powder inhalable composition comprises a dry powder blend of lactose and the compound of formula (I) or salt thereof. The lactose is preferably lactose hydrate e.g. lactose monohydrate and/or is preferably inhalation-grade and/or fine-grade lactose. Preferably, the particle size of the lactose is defined by 90% or more (by weight or by volume) of the lactose particles being less than 1000 microns (micrometres) (e.g. 10-1000 microns e.g. 30-1000 microns) in diameter, and/or 50% or more of the lactose particles being less than 500 microns (e.g. 10-500 microns) in diameter. More preferably, the particle size of the lactose is defined by 90% or more of the lactose particles being less than 300 microns (e.g. 10-300 microns e.g. 50-300 microns) in diameter, and/or 50% or more of the lactose particles being less than 100 microns in diameter. Optionally, the particle size of the lactose is defined by 90% or more of the lactose particles being less than 100-200 microns in diameter, and/or 50% or more of the lactose particles being less than 40-70 microns in diameter. Most importantly, it is preferable that about 3 to about 30% (e.g. about 10%) (by weight or by volume) of the particles are less than 50 microns or less than 20 microns in diameter. For example, without limitation, a suitable inhalation-grade lactose is E9334 lactose (10% fines) (Borculo Domo Ingredients, Hanzeplein 25, 8017 J D Zwolle, Netherlands).

Optionally, in particular for dry powder inhalable compositions, a pharmaceutical composition for inhaled administration can be incorporated into a plurality of sealed dose containers (e.g. containing the dry powder composition) mounted longitudinally in a strip or ribbon inside a suitable inhalation device. The container is rupturable or peel-openable on demand and the dose of e.g. the dry powder composition can be administered by inhalation via the device such as the DISKUS™ device, marketed by GlaxoSmithKline. The DISKUS™ inhalation device is for example described in GB 2242134 A, and in such a device at least one container for the pharmaceutical composition in powder form (the container or containers preferably being a plurality of sealed dose containers mounted longitudinally in a strip or ribbon) is defined between two members peelably secured to one another; the device comprises: a means of defining an opening station for the said container or containers; a means for peeling the members apart at the opening station to open the container; and an outlet, communicating with the opened container, through which a user can inhale the pharmaceutical composition in powder form from the opened container.

The compounds of the invention thereof may be formulated as a fluid formulation for delivery from a fluid dispenser, for example a fluid dispenser having a dispensing nozzle or dispensing orifice through which a metered dose of the fluid formulation is dispensed upon the application of a user-applied force to a pump mechanism of the fluid dispenser. Such fluid dispensers are generally provided with a reservoir of multiple metered doses of the fluid formulation, the doses being dispensable upon sequential pump actuations. The dispensing nozzle or orifice may be configured for insertion into the nostrils of the user for spray dispensing of the fluid formulation into the nasal cavity. A fluid dispenser of the aforementioned type is described and illustrated in WO-A-2005/044354, the entire content of which is hereby incorporated herein by reference. The dispenser has a housing which houses a fluid discharge device having a compression pump mounted on a container for containing a fluid formulation. The housing has at least one finger-operable side lever which is movable inwardly with respect to the housing to cam the container upwardly in the housing to cause the pump to compress and pump a metered dose of the formulation out of a pump stem through a nasal nozzle of the housing. A particularly preferred fluid dispenser is of the general type illustrated in FIGS. 30-40 of WO-A-2005/044354.

Pharmaceutical compositions adapted for vaginal administration may be presented as pessaries, tampons, creams, gels, pastes, foams or spray formulations.

Pharmaceutical compositions adapted for parenteral administration include aqueous and non-aqueous sterile injection solutions which may contain anti-oxidants, buffers, bacteriostats and solutes which render the composition isotonic with the blood of the intended recipient; and aqueous and non-aqueous sterile suspensions which may include suspending agents and thickening agents. The compositions may be presented in unit-dose or multi-dose containers, for example sealed ampoules and vials, and may be stored in a freeze-dried (lyophilized) condition requiring only the addition of the sterile liquid carrier, for example water for injections, immediately prior to use. Extemporaneous injection solutions and suspensions may be prepared from sterile powders, granules and tablets.

A therapeutically effective amount of a compound of the present invention will depend upon a number of factors including, for example, the age and weight of the subject, the precise condition requiring treatment and its severity, the nature of the formulation, and the route of administration, and will ultimately be at the discretion of the attendant physician or veterinarian. In the pharmaceutical composition, each dosage unit for oral or parenteral administration preferably contains from 0.01 to 3000 mg, more preferably 0.5 to 1000 mg, of a compound of the invention calculated as the free base. Each dosage unit for nasal or inhaled administration preferably contains from 0.001 to 50 mg, more preferably 0.01 to 5 mg, of a compound of the formula (I) or a pharmaceutically acceptable salt thereof, calculated as the free base.

The pharmaceutically acceptable compounds the invention can be administered in a daily dose (for an adult patient) of, for example, an oral or parenteral dose of 0.01 mg to 3000 mg per day or 0.5 to 1000 mg per day, or a nasal or inhaled dose of 0.001 to 50 mg per day or 0.01 to 5 mg per day, of the compound of the formula (I) or a pharmaceutically acceptable salt thereof, calculated as the free base. This amount may be given in a single dose per day or more usually in a number (such as two, three, four, five or six) of sub-doses per day such that the total daily dose is the same. An effective amount of a salt thereof, may be determined as a proportion of the effective amount of the compound of formula (I) per se.

The compounds of the invention and may be employed alone or in combination with other therapeutic agents. Combination therapies according to the present invention thus comprise the administration of at least one compound of formula (I) or a pharmaceutically acceptable salt thereof, and the use of at least one other pharmaceutically active agent. Preferably, combination therapies according to the present invention comprise the administration of at least one compound of formula (I) or a pharmaceutically acceptable salt thereof, and at least one other pharmaceutically active agent. The compound(s) of the invention and the other pharmaceutically active agent(s) may be administered together in a single pharmaceutical composition or separately and, when administered separately this may occur simultaneously or sequentially in any order. The amounts of the compound(s) of the invention and the other pharmaceutically active agent(s) and the relative timings of administration will be selected in order to achieve the desired combined therapeutic effect. Thus in a further aspect, there is provided a combination comprising a compound of the invention and at least one other pharmaceutically active agent.

Thus in one aspect, the compound and pharmaceutical compositions according to the invention may be used in combination with or include one or more other therapeutic agents, for example selected from anti-inflammatory agents (including a steroid), anticholinergic agents (particularly an $M_1/M_2/M_3$ receptor antagonist), $β_2$-adrenoreceptor agonists, anti-allergy agents, antiinfective agents (such as antibiotics or antivirals), or antihistamines. The invention thus provides, in a further aspect, a combination pharmaceutical product comprising a compound of formula (I) or a pharmaceutically acceptable salt thereof together with one or more other therapeutically active agents, for example selected from an anti-inflammatory agent such as a corticosteroid or an NSAID, an anticholinergic agent, a $β_2$-adrenoreceptor agonist, an anti-allergy agent, an antiinfective agent (such as an antibiotic or an antiviral), or an antihistamine.

It will be appreciated that when the compound of the present invention is administered in combination with other therapeutic agents normally administered by the inhaled, intravenous, oral or intranasal route, that the resultant pharmaceutical composition may be administered by the same routes. Alternatively the individual components of the composition may be administered by different routes.

One embodiment of the invention encompasses combinations comprising one or two other therapeutic agents.

Suitable anti-inflammatory agents include corticosteroids. Anti-inflammatory corticosteroids are well known in the art. Representative examples include fluticasone propionate, beclomethasone 17-propionate ester, beclomethasone 17,21-dipropionate ester, dexamethasone or an ester thereof, mometasone or an ester thereof (e.g. mometasone furoate), ciclesonide, budesonide, flunisolide, methyl prednisolone, prednisolone, and dexamethasone. Further examples of anti-inflammatory corticosteroids are described in WO 02/12266 A1 (Glaxo Group Ltd), in particular, the compounds of Example 1 (6α,9α-difluoro-17α-[(2-furanylcarbonyl)oxy]-11β-hydroxy-16α-methyl-3-oxo-androsta-1,4-diene-17β-carbothioic acid S-fluoromethyl ester) and Example 41 (6α, 9α-difluoro-11β-hydroxy-16α-methyl-17α-[(4-methyl-1,3-thiazole-5-carbonyl)oxy]-3-oxo-androsta-1,4-diene-17β-carbothioic acid S-fluoromethyl ester), or a pharmaceutically acceptable salt thereof.

Examples of β$_2$-adrenoreceptor agonists include salmeterol (e.g. as racemate or a single enantiomer such as the R-enantiomer), salbutamol, formoterol, salmefamol, fenoterol or terbutaline and salts thereof, for example the xinafoate salt of salmeterol, the sulphate salt or free base of salbutamol or the fumatrate salt of formoterol. In one embodiment, the B$_2$-adrenoreceptor agonists are long-acting B$_2$-adrenoreceptor agonists, for example, those having a therapeutic effect over a 24 hour period, such as salmeterol or formoterol. A further example of a β$_2$-adrenoreceptor agonist is the compound 4-{(1R)-2-[(6-{2-[(2,6-dichlorophenyl)methyoxy]ethoxy}hexyl)amino]-1-hydroxyethyl}-2-(hydroxyethyl)phenol triphenylacetete (Vilanterol Trifenatate).

Examples of anticholinergic compounds which may be used in combination with a compound of formula (I) or a pharmaceutically acceptable salt thereof are described in WO 03/011274 A2 and WO 02/069945 A2/US 2002/0193393 A1 and US 2002/052312 A1. For example, anticholinergic agents include muscarinic receptor antagonists, in particular, compounds which are antagonists of the M$_1$ or M$_3$ receptors, dual antagonists of M$_1$/M$_3$ or M$_2$/M$_3$ receptors or pan antagonists of M$_1$/M$_2$/M$_3$ receptors such as ipratropium bromide, oxitropium bromide or tiotropium bromide.

An anti-histamine usable in a combination of a compound of the invention can for example be methapyrilene or H1 antagonists. Examples of H1 antagonists include, without limitation, amelexanox, astemizole, azatadine, azelastine, acrivastine, brompheniramine, cetirizine, levocetirizine, efletirizine, chlorpheniramine, clemastine, cyclizine, carebastine, cyproheptadine, carbinoxamine, descarboethoxyloratadine, doxylamine, dimethindene, ebastine, epinastine, efletirizine, fexofenadine, hydroxyzine, ketotifen, loratadine, levocabastine, mizolastine, mequitazine, mianserin, noberastine, meclizine, norastemizole, olopatadine, picumast, pyrilamine, promethazine, terfenadine, tripelennamine, temelastine, trimeprazine and triprolidine, particularly cetirizine, levocetirizine, efletirizine and fexofenadine. In a further embodiment the invention provides a combination comprising a compound of the invention together with an H3 antagonist (and/or inverse agonist). Examples of H3 antagonists include, for example, those compounds disclosed in WO2004/035556 and in WO2006/045416.

Other suitable combinations include, for example combinations comprising a compound of the invention together with other anti-inflammatory agents such as an anti-flammatory corticosteroid; or a non-steroidal anti-inflammatory drug (NSAID) such as leukotriene antagonist (e.g. montelukast), an iNOS inhibitor, a tryptase inhibitor, IKK2 inhibitors, a p38 inhibitor, Syk inhibitors, an elastase inhibitor, a beta-2 integrin antagonist, an adenosine a2a agonist, a chemokine antagonist such as a CCR3 antagonist, a mediator release inhibitor such as sodium chromoglycate, a 5-lipoxygenase inhibitor, a DP1 antagonist, a DP2 antagonist, a CTTh2 inhibitor, a pI3K delta inhibitor, an ITK inhibitor, a LP (lysophosphatidic) inhibitor and a FLAP (five lipoxygenase activating protein) inhibitor.

Other suitable combinations include a compound of the invention together with an anti-nfective agent (e.g. an antibiotic or an antiviral), an anti-hypertensive agent, an anti-thrombotic agent, a statin or a cholinesterase inhibitor.

The combinations referred to above may conveniently be presented for use in the form of a pharmaceutical composition and thus pharmaceutical compositions comprising a combination as defined above together with a pharmaceutically acceptable diluent or carrier represent a further aspect of the invention.

In one aspect, the present invention also provides for so-called "triple combination" therapy, comprising a compound of the invention together with β$_2$-adrenoreceptor agonist and an anti-inflammatory corticosteroid. Preferably this combination is for treatment and/or prophylaxis of asthma, COPD or allergic rhinitis. The β$_2$-adrenoreceptor agonist and/or the anti-inflammatory corticosteroid can be as described above and/or as described in WO 03/030939 A1. A representative example of such a "triple" combination comprises a compound of the invention, salmeterol or a pharmaceutically acceptable salt (e.g. salmeterol xinafoate) and fluticasone propionate. A further representative example of a "triple" combination comprises a compound of the invention, 4-{(1R)-2-[(6-{2-[(2,6-dichlorophenyl)methyoxy]ethoxy}hexyl)amino]-1-hydroxyethyl}-2-(hydroxyethyl)phenol triphenylacetete (Vilanterol Trifenatate) and 6α,9α-difluoro-17α-[(2-furanylcarbonyl)oxy]-11β-hydroxy-16α-methyl-3-oxo-androsta-1,4-diene-17β-carbothioic acid S-fluoromethyl ester (fluticasone furoate).

Rheumatoid arthritis (RA) is a further inflammatory disease where combination therapy may be contemplated. Thus in a further aspect, the present invention provides a compound of the invention in combination with a further therapeutic agent useful in the treatment of rheumatoid arthritis, said combination being useful for the treatment of rheumatoid arthritis.

The compound and pharmaceutical compositions according to the invention may be used in combination with or include one or more other therapeutic agents, for example selected from NSAIDS, corticosteroids, COX-2 inhibitors, cytokine inhibitors, anti-TNF agents, inhibitors of oncostatin M, anti-malarials, immunosuppressive and cytostatics.

Anti-TNF agents include infliximab (Remicade), etanercept (Enbrel) and adalimum (Humira). Other "biological" treatments include anakinra (Kineret), Rituximab, Lymphostat-B, BAFF/APRIL inhibitors and CTLA-4-Ig or mimetics thereof. Other cytokine inhibitors include lefluonomide (Arava). Further second line drugs include gold preparations (Auranofin (Ridaura tablets) or Aurothiomalate (Myocrisin injection)), medicines used for malaria: (Hydroxychloroquine (Plaquenil)), medicines that suppress the immune system (Azathioprine (Imuran, Thioprine), methotrexate (Methoblastin, Ledertrexate, Emethexate), cyclosporine (Sandimmun, Neoral)), Cyclophosphamide (Cycloblastin), Cytoxan, Endoxan), D-Penicillamine (D-Penamine), Sulphasalazine (Salazopyrin), nonsteroidal anti inflammatory drugs (including aspirin and ibrufen).

It will be clear to a person skilled in the art that, where appropriate, the other therapeutic ingredient(s) may be used in the form of salts, for example as alkali metal or amine salts or as acid addition salts, or prodrugs, or as esters, for example lower alkyl esters, or as solvates, for example hydrates, to optimise the activity and/or stability and/or physical characteristics, such as solubility, of the therapeutic ingredient. It will be clear also that, where appropriate, the therapeutic ingredients may be used in optically pure form.

The combinations referred to above may conveniently be presented for use in the form of a pharmaceutical composition and thus pharmaceutical compositions comprising a combination as defined above together with a pharmaceutically acceptable diluent or carrier represent a further aspect of the invention.

The individual compounds of such combinations may be administered either sequentially or simultaneously in separate or combined pharmaceutical compositions. Preferably, the individual compounds will be administered simultaneously in a combined pharmaceutical composition. Appropriate doses of known therapeutic agents will be readily appreciated by those skilled in the art.

General Experimental Details

Analytical LCMS

Analytical LCMS was conducted on one of the following systems A to F. The UV detection to all systems was an averaged signal from wavelength of 220 nm to 350 nm and mass spectra were recorded on a mass spectrometer using alternate-scan positive and negative mode electrospray ionization.

Experimental details of LCMS systems A-F as referred to herein are as follows:

System A
  Column: 50 mm×2.1 mm ID, 1.7 µm Acquity ultra performance liquid chromatography (HPLC) BEH $C_{18}$
  Flow Rate: 1 mL/min.
  Temp.: 40° C.
  Solvents: A: 0.1% v/v formic acid in water
  B: 0.1% v/v formic acid in acetonitrile
  Gradient:

| Time (min) | A % | B % |
|---|---|---|
| 0 | 97 | 3 |
| 1.5 | 0 | 100 |
| 1.9 | 0 | 100 |
| 2.0 | 97 | 3 |

System B
  Column: 30 mm×4.6 mm ID, 3.5 µm Sunfire $C_{18}$ column
  Flow Rate: 3 mL/min.
  Temp.: 30° C.
  Solvents: A: 0.1% v/v solution of formic acid in water
  B: 0.1% v/v solution of formic acid in acetonitrile
Gradient:

| Time (min) | A % | B % |
|---|---|---|
| 0 | 97 | 3 |
| 0.1 | 97 | 3 |
| 4.2 | 0 | 100 |
| 4.8 | 0 | 100 |
| 4.9 | 97 | 3 |
| 5.0 | 97 | 3 |

System C
  Column: 50 mm×4.6 mm ID, 3.5 µm XBridge $C_{18}$ column
  Flow Rate: 3 mL/min.
  Temp.: 30° C.
  Solvents: A: 10 mM ammonium bicarbonate in water adjusted to pH10 with ammonia solution
  B: Acetonitrile
  Gradient:

| Time (min) | A % | B % |
|---|---|---|
| 0 | 99 | 1 |
| 0.1 | 99 | 1 |
| 4.0 | 3 | 97 |
| 5.0 | 3 | 97 |

System D
  Column: 50 mm×2.1 mm ID, 1.7 µm Acquity HPLC BEH $C_{18}$
  Flow Rate: 1 mL/min.
  Temp.: 40° C.
  Solvents: A: 0.1% v/v solution of trifluoroacetic acid in water
  B: 0.1% v/v solution of trifluoroacetic acid in acetonitrile
  Gradient:

| Time (min) | A % | B % |
|---|---|---|
| 0 | 97 | 3 |
| 1.5 | 0 | 100 |
| 1.9 | 0 | 100 |
| 2.0 | 97 | 3 |

System E
  Column: 30 mm×4.6 mm ID, 3.5 µm Sunfire $C_{18}$ column
  Flow Rate: 3 mL/min.
  Temp.: 30° C.
  Solvents: A: 0.1% v/v solution of trifluoroacetic acid in water
  B: 0.1% v/v solution of trifluoroacetic acid in acetonitrile
  Gradient:

| Time (min) | A % | B % |
|---|---|---|
| 0 | 97 | 3 |
| 0.1 | 97 | 3 |
| 4.2 | 0 | 100 |
| 4.8 | 0 | 100 |
| 4.9 | 97 | 3 |
| 5.0 | 97 | 3 |

System F
  Column: 50 mm×2.1 mm ID, 1.7 µm Acquity HPLC BEH $C_{18}$ column
  Flow Rate: 1 mL/min.
  Temp.: 40° C.
  Solvents: A: 10 mM ammonium bicarbonate in water adjusted to pH10 with ammonia solution
  B: Acetonitrile
  Gradient:

| Time (min) | A % | B % |
|---|---|---|
| 0 | 99 | 1 |
| 1.5 | 3 | 97 |
| 1.9 | 3 | 97 |
| 2.0 | 0 | 100 |

Mass Directed Auto-Preparative HPLC

Crude products were purified by MDAP HPLC by one of the following methods A-D. The run time was 15 min unless otherwise stated. The UV detection for all methods was an averaged signal from wavelength of 220 nm to 350 nm and mass spectra were recorded on a mass spectrometer using alternate-scan positive and negative mode electrospray ionization.

Method A:

Method A was conducted on a Sunfire $C_{18}$ column (typically 150 mm×30 mm i.d. 5 µm packing diameter) at ambient temperature. The solvents employed were:
A=0.1% v/v solution of Formic acid in water
B=0.1% v/v solution of Formic acid in acetonitrile.
The gradient employed was:

| Time (min) | Flow Rate (mL/min) | % A | % B |
| --- | --- | --- | --- |
| 0 | 40 | 95 | 5 |
| 1 | 40 | 95 | 5 |
| 10 | 40 | 70 | 30 |
| 10.5 | 40 | 1 | 99 |
| 15 | 40 | 1 | 99 |

Method B:

Method B was conducted on a Sunfire $C_{18}$ column (typically 150 mm×30 mm i.d. 5 µm packing diameter) at ambient temperature. The solvents employed were:
A=0.1% v/v solution of trifluoroacetic acid in water
B=0.1% v/v solution of trifluoroacetic acid in acetonitrile.
The gradient employed was:

| Time (min) | Flow Rate (mL/min) | % A | % B |
| --- | --- | --- | --- |
| 0 | 40 | 50 | 50 |
| 1 | 40 | 50 | 50 |
| 10 | 40 | 1 | 99 |
| 10.5 | 40 | 1 | 99 |
| 15 | 40 | 1 | 99 |

Method C:

Method C was conducted on an XBridge $C_{18}$ column (typically 150 mm×19 mm i.d. 5 µm packing diameter) at ambient temperature. The solvents employed were:
A=10 mM aqueous ammonium bicarbonate adjusted to pH 10 with ammonia solution.
B=acetonitrile.
The gradient employed was:

| Time (min) | Flow Rate (mL/min) | % A | % B |
| --- | --- | --- | --- |
| 0 | 40 | 99 | 1 |
| 1 | 40 | 99 | 1 |
| 10 | 40 | 70 | 30 |
| 11 | 40 | 1 | 99 |
| 15 | 40 | 1 | 99 |

Method D:

Method D was conducted on an ATLANTIS dC18 column (typically 100 mm×19 mm i.d. 5 µm packing diameter). The solvents employed were:
A=0.1% v/v solution of Formic Acid in Water.
B=0.05% v/v solution of Formic Acid in 95% Acetonitrile plus 5% Water.

The gradient employed was:

| Time (min) | Flow Rate (mL/min) | % A | % B |
| --- | --- | --- | --- |
| 0.0 | 20 | 95 | 5 |
| 1.0 | 20 | 95 | 5 |
| 8.5 | 20 | 35 | 65 |
| 8.6 | 20 | 5 | 95 |
| 9.5 | 20 | 5 | 95 |
| 9.6 | 20 | 95 | 5 |
| 11.0 | 20 | 95 | 5 |

Method E:

Method E was conducted on a Sunfire C18 column (typically 100 mm×19 mm i.d. 5 µm packing diameter). The solvents employed were:
A=0.1% v/v solution of Formic Acid in Water.
B=0.1% v/v solution of Formic Acid in Acetonitrile.
The gradient employed was:

| Time (min) | Flow Rate (mL/min) | % A | % B |
| --- | --- | --- | --- |
| 0.0 | 20 | 70 | 30 |
| 1.0 | 20 | 70 | 30 |
| 10 | 20 | 15 | 85 |
| 10.5 | 20 | 5 | 95 |
| 12.5 | 20 | 5 | 95 |
| 13 | 20 | 70 | 30 |
| 14 | 20 | 70 | 30 |

ABBREVIATIONS

The following list provides definitions of certain abbreviations as used herein. It will be appreciated that the list is not exhaustive, but the meaning of those abbreviations not herein below defined will be readily apparent to those skilled in the art.

Ac (acetyl)
Bu (butyl)
CV (column volume)
DCM (dichloromethane)
DEAD (diethyl azodicarboxylate)
DIAD (diisopropyl azodicarboxylate)
DIBAL-H (Diisobutylaluminium hydride)
DMF (N,N-dimethylformamide)
DMSO (dimethylsulfoxide)
Et (ethyl)
EtOAc (ethyl acetate)
h (hour/hours)
HATU [O-(7-Azabenzotriazol-1-yl)-N,N,N',N'-tetramethyluronium hexafluorophosphate
HCl (Hydrochloric acid)
L (liters)
M (molar)
MDAP (mass directed auto-preparative HPLC)
Me (methyl)
MeOH (methanol)
NOE (nuclear overhauser effect)
Ph (phenyl)
$^i$Pr (isopropyl)
Si (Silica)
SEM ({[2-(trimethylsily)ethyl]oxy}methyl)
SPE (solid phase extraction)
TBAD (tert-butyl azodicarboxylate)

TBD (1,3,4,6,7,8-hexahydro-2H-pyrimido[1,2-a]pyrimidine)
TBTU [O-(benzotriazol-1-yl)-N,N,WN-tetramethyluronium tetrafluoroborate]
TEA (triethylamine)
TFA (trifluoroacetic acid)
THF (tetrahydrofuran)
TLC (thin layer chromatography)
TMS (trimethylsilyl)

All references to ether are to diethyl ether and brine refers to a saturated aqueous solution of NaCl.

Intermediate 1

4-(Methyloxy)-1H-indazol-3-amine

A mixture of 2-fluoro-6-(methyloxy)benzonitrile (available from Apollo) (10 g, 66 mmol) and hydrazine hydrate (9.63 mL, 198 mmol) in n-butanol (100 mL) was heated at reflux under nitrogen for 18 hours. The reaction mixture was allowed to cool, water (300 mL) was added, and the organic phase was removed. The solid in the aqueous phase was collected by filtration and dried in vacuo at 40° C. to give a white solid (0.6 g). The butanol phase was evaporated in vacuo, and the residue and the aqueous mother liquors were combined and extracted using ethyl acetate (2×200 mL). The combined ethyl acetate extractions were dried over magnesium sulphate and evaporated in vacuo. The residue was dissolved in DCM and applied to a 100 g silica cartridge. This was eluted with cyclohexane (500 ml), cyclohexane-ethyl acetate (1:1v/v, 500 mL) and ethyl acetate (500 mL). The required fractions were combined and evaporated in vacuo to give the title compound (9.92 g, 92%) as an off-white solid. LCMS (System A) RT=0.5 min, ES+ve m/z 164 (M+H)+.

Intermediate 2

3-{[(3-Amino-4-(methyloxy)-1H-indazol-1-yl]methyl}benzonitrile

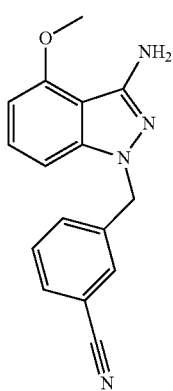 [SMILES: COc1cccc2c1c(N)nn2Cc1cccc(C#N)c1]

To a solution of ground potassium hydroxide (6.75 g, 120 mmol) in DMSO (300 mL) at room temperature under nitrogen was added 4-(methyloxy)-1H-indazol-3-amine (for a preparation see Intermediate 1) (7.85 g, 48.1 mmol), and this gave a deep red solution. After 5 minutes 3-(chloromethyl)benzonitrile (8.84 g, 58.3 mmol) was added in one portion. The reaction mixture was stirred for 20 minutes and then poured into water (500 mL), forming an emulsion. This was extracted using chloroform (3×500 mL). The combined organic solutions were washed with water (400 mL) and passed through a hydrophobic frit. The solvent was removed in vacuo, the residue was applied to a 340 g silica cartridge, and eluted with a gradient of 0-100% ethyl acetate in cyclohexane over 8CV. This gave an orange solid which was treated with ethyl acetate (10 mL) and cyclohexane (90 mL). The solid was collected by filtration and washed with cyclohexane (50 mL). The solid was dried in vacuo to give the title compound (7.89 g, 59%) as a pale orange solid. LCMS (System A) RT=0.93 min, ES+ve m/z 279 (M+H)+.

Intermediate 3

5-Chloro-N-[1-[(3-cyanophenyl)methyl]-4-(methyloxy)-1H-indazol-3-yl]-2-thiophenesulfonamide

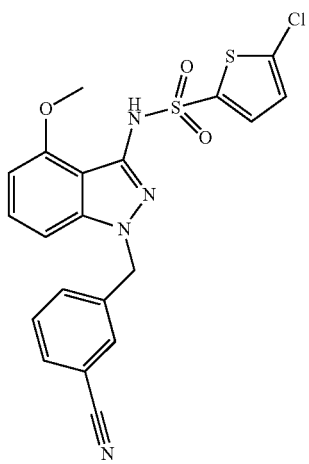 [SMILES: COc1cccc2c1c(NS(=O)(=O)c1ccc(Cl)s1)nn2Cc1cccc(C#N)c1]

To 3-{[3-amino-4-(methyloxy)-1H-indazol-1-yl]methyl}benzonitrile (for a preparation see Intermediate 2) (7.89 g, 28.3 mmol) was added a solution of 5-chloro-2-thiophenesulfonyl chloride (Aldrich) (6.15 g, 28.3 mmol) in pyridine (9.17 mL, 113 mmol) under nitrogen at room temperature. Reaction was exothermic and went deep red. After 40 minutes the reaction mixture was separated between ethyl acetate (500 mL) and 2N hydrochloric acid (500 mL). The aqueous phase was washed with ethyl acetate (400 mL). The combined organic solutions were dried over magnesium sulphate and evaporated in vacuo. The deep red residue was dissolved in DCM and applied to a 340 g silica cartridge. The cartridge was eluted with a gradient of 0-10% ethyl acetate in dichloromethane over 8CV. Evaporation of the appropriate fractions gave the title compound (11.1 g, 85%) as an off-white solid. LCMS (System A) RT=1.15 min, ES+ve m/z 459/461 (M+H)+.

Intermediate 4

N-[1-{[3-(Aminomethyl)phenyl]methyl}-4-(methyloxy)-1H-indazol-3-yl]-5-chloro-2-thiophenesulfonamide Hydrochloride

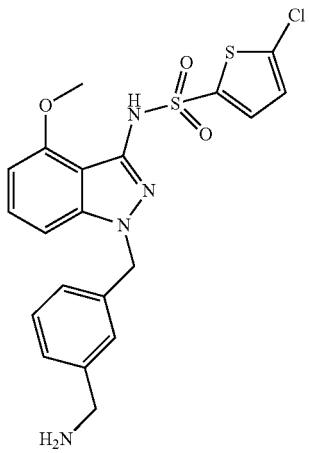 [SMILES: COc1cccc2c1c(NS(=O)(=O)c1ccc(Cl)s1)nn2Cc1cccc(CN)c1]

To a cooled, 0° C., solution of 5-chloro-N-[1-[(3-cyanophenyl)methyl]-4-(methyloxy)-1H-indazol-3-yl]-2-thiophenesulfonamide (for a preparation see Intermediate 3) (11.1 g, 24.2 mmol) in THF (150 mL) was added, dropwise maintaining temp below 10° C., 1.0M lithium aluminium hydride solution in ether (60.5 mL, 60.5 mmol), effervescence occurred, and the suspension was stirred at room temperature for one hour. The reaction was quenched by addition of water (7 mL), followed by a 2.0M solution of sodium hydroxide (42.5 mL). After stirring for 30 minutes the solid was removed by filtration and washed with THF. The combined filtrate and washings were treated with 140 g SCX silica. This was filtered and washed with methanol (1 L), and then 10% 2N hydrochloric acid in methanol (2 L). The required fractions were combined and concentrated. The resultant solid was collected by filtration and washed with water. The solid was dried in vacuo to give the title compound (N7916-76-1) (9.3 g, 77%) as a white solid. LCMS (System A) RT=0.85 min, ES+ve m/z 463/465 (M+H)$^+$.

Intermediate 5

1,1-Dimethylethyl 3-amino-4-(methyloxy)-1H-indazole-1-carboxylate

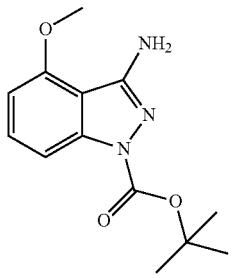 [SMILES: COc1cccc2c1c(N)nn2C(=O)OC(C)(C)C]

To a solution of 4-(methyloxy)-1H-indazol-3-amine (5.56 g, 34 mmol), DMAP (2.08 g, 17 mmol) and triethylamine (4.75 mL, 34 mmol) in DCM (30 mL) was added dropwise at 0° C. a solution of di-tert-butyl dicarbonate (7.44 g, 34 mmol) in DCM (20 mL). The reaction mixture was stirred at room temperature for 1 h, then 50 mL of brine were added. The organic layer was partitioned and the aqueous phase was further extracted with 50 mL of DCM. The organic solutions were combined, washed with brine (100 mL), dried over an hydrophobic frit and concentrated under reduced pressure. The crude solid was triturated with 50 mL of Et$_2$O, the filtrate was concentrated under reduced pressure, and triturated again with 20 mL of Et$_2$O. Solids were combined to give the title compound (8.97 g, 67%) which was used without further purification. LCMS (System B) RT=2.9 min, ES+ve m/z 264 (M+H)$^+$.

Intermediate 6

1,1-Dimethylethyl 3-{[(5-chloro-2-thienyl)sulfonyl]amino}-4-(methyloxy)-1H-indazole-1-carboxylate

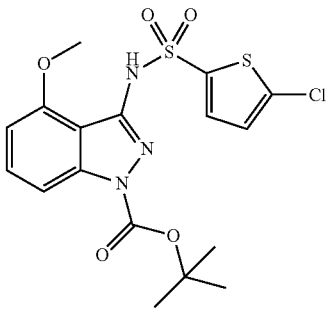 [SMILES: COc1cccc2c1c(NS(=O)(=O)c1ccc(Cl)s1)nn2C(=O)OC(C)(C)C]

To a solution of 1,1-dimethylethyl 3-amino-4-(methyloxy)-1H-indazole-1-carboxylate (for a preparation see Intermediate 5) (6.03 g, 22.9 mmol) and 5-chloro-2-thiophenesulfonyl chloride (3.07 mL, 22.9 mmol) in DCM (30 mL) was added dropwise at 0° C. a solution of pyridine (3.7 mL, 46 mmol) in DCM. The reaction mixture was stirred allowing to warm from 0° C. to room temperature over 2 h, then stirred at room temperature over the weekend. Pyridine (50 mL) were added and resulting mixture was stirred at 50° C. for another 24 h. The reaction mixture was then quenched with 50 mL of a saturated NaHCO$_3$ solution. The organic layer was partitioned and the aqueous layer was further extracted with 50 mL of DCM. The organic solutions were combined, washed with water (50 mL) then brine (50 mL), and dried with an hydrophobic frit. The crude product was purified by chromatography on two 100 g Si cartridges on Flashmaster, eluting with 0 to 25% gradient of EtOAc in DCM, over 60 min to give the desired product as a pale orange solid: (2.21 g, 22%). LCMS (System A) RT=1.35 min, ES+ve m/z 444 (M+H)$^+$.

Intermediate 7

1,1-Dimethylethyl 3-[[(5-chloro-2-thienyl)sulfonyl]({[2-(trimethylsily)-ethyl]oxy}methyl)amino]-4-(methyloxy)-1H-indazole-1-carboxylate

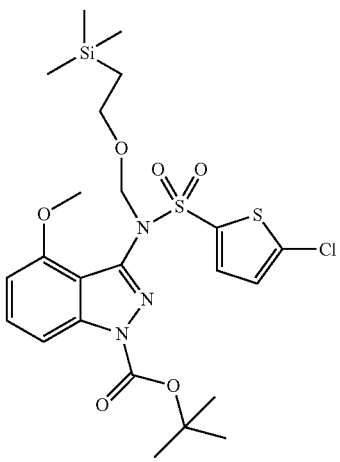 [SMILES: COc1cccc2c1c(N(COCC[Si](C)(C)C)S(=O)(=O)c1ccc(Cl)s1)nn2C(=O)OC(C)(C)C]

To a solution of 1,1-dimethylethyl 3-{[(5-chloro-2-thienyl)sulfonyl]amino}-4-(methyloxy)-1H-indazole-1-carboxylate (for a preparation see Intermediate 6) (2.21 g, 4.98 mmol) in DCM (20 mL) was added at 0° C. 2-(trimethylsilyl)ethoxymethyl chloride (1.23 mL, 6.97 mmol). Then was added at 0° C. in a dropwise fashion diisopropylamine (1.419 mL, 9.96 mmol) and the reaction mixture was stirred at room temperature. The reaction was quenched with water (50 mL), the organic layer was separated, and the aqueous layer was further extracted with 30 mL of DCM. The organic solutions were combined, dried with an hydrophobic frit and concentrated under reduced pressure to give a yellow oil that was used without further purification (3.12 g) LCMS (System A) RT=1.64 min, ES+ve m/z 574/576 (M+H)+.

Intermediate 8

5-Chloro-N-[4-(methyloxy)-1H-indazol-3-yl]-N-({[2-(trimethylsilyl)ethyl]oxy}methyl)-2-thiophenesulfonamide

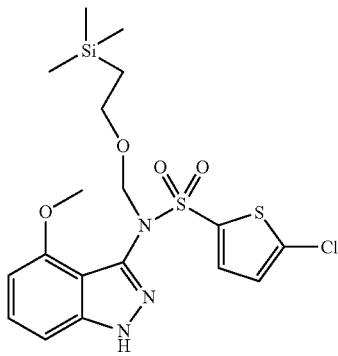 [SMILES: COc1cccc2[nH]nc(N(COCC[Si](C)(C)C)S(=O)(=O)c3ccc(Cl)s3)c12]

To a solution of 1,1-dimethylethyl 3-[[(5-chloro-2-thienyl)sulfonyl]({[2-(trimethylsilyl)ethyl]oxy}methyl)amino]-4-(methyloxy)-1H-indazole-1-carboxylate (for a preparation see Intermediate 7) (3.12 g, 5.43 mmol) in DMF (20 mL) was added a solution of sodium carbonate (0.864 g, 8.15 mmol) in water (20 mL) at room temperature. A white suspension was obtained and a warming of the medium was noticed. The resulting suspension was stirred overnight at 80° C., the reaction mixture was then cooled to room temperature, and more sodium carbonate (300 mg) was added. The resulting mixture was then stirred at 85° C. After 3 h of stirring, 50 mL of water and 50 mL of DCM were added to the reaction mixture. The organic layer was partitioned and the aqueous layer was further extracted with 30 mL of DCM. The organic solutions were combined, dried with an hydrophobic frit and concentrated under reduced pressure. The crude oil was purified by chromatography on two 100 g Si cartridges on Flashmaster, eluting with a 0 to 25% gradient of EtOAc in cyclohexane, over 25 min. The pure fractions were combined to give the title product as an orange gum (1.62 g, 63%) LCMS (System A) RT=1.41 min, ES+ve m/z 474/476 (M+H)+. Impure fractions were combined and repurified by chromatography on a 70 g silica cartridge on Flashmaster, eluting with a 0 to 25% gradient of EtOAc in cyclohexane over 40 min. Fractions containing pure product were combined to give more of the desired product (277 mg, 11%)

Intermediate 9

1,1-Dimethylethyl 3-{bis[(5-chloro-2-thienyl)sulfonyl]amino}-4-(methyloxy)-1H-indazole-1-carboxylate

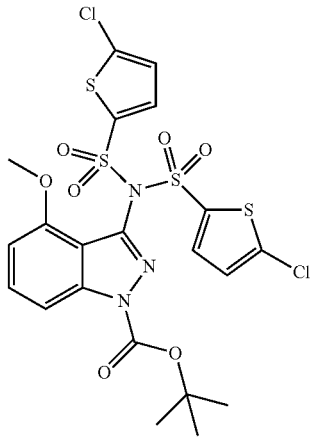 [SMILES: COc1cccc2c1c(N(S(=O)(=O)c1ccc(Cl)s1)S(=O)(=O)c1ccc(Cl)s1)nn2C(=O)OC(C)(C)C]

To a solution of 1,1-dimethylethyl 3-amino-4-(methyloxy)-1H-indazole-1-carboxylate (for a preparation see Intermediate 5) (3.24 g, 12.31 mmol) and 5-chloro-2-thiophenesulfonyl chloride (8.01 g, 36.9 mmol) in DCM (50 mL) was added pyridine (9.95 mL, 123 mmol). The reaction mixture was stirred at 45° C. under nitrogen for 3 days. The reaction mixture was quenched using saturated sodium bicarbonate solution (100 mL) and diluted with DCM (100 mL). The phases were separated and the aqueous phase was extracted using DCM (100 mL). The combined organic solutions were washed with brine and filtered through an hydrophobic frit. The solvent was removed in vacuo and the residue was dissolved in DCM (30 mL). This was applied to a 330 g silica cartridge and eluted with a gradient of 0-25% ethyl acetate in DCM over 10CV. The required fractions were evaporated in vacuo to give the title compound (4.17 g, 54%) as a white solid LCMS (System B) RT=4.12 min, ES+ve m/z 624/626/628, and 1,1-dimethylethyl 3-{[(5-chloro-2-thienyl)sulfonyl]amino}-4-(methyloxy)-1H-indazole-1-carboxylate (1.45 g, 26%) as a pale yellow solid LCMS (System B) RT=3.72 min, ES+ve m/z 444/446 (M+H)+.

Intermediate 10

5-Chloro-N-[(5-chloro-2-thienyl)sulfonyl]-N-[4-(methyloxy)-1H-indazol-3-yl]-2-thiophenesulfonamide

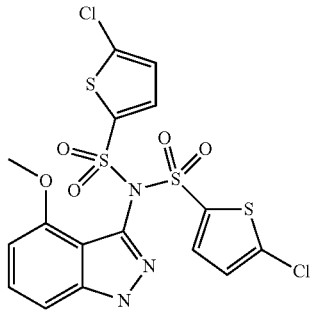 [SMILES: COc1cccc2[nH]nc(N(S(=O)(=O)c3ccc(Cl)s3)S(=O)(=O)c3ccc(Cl)s3)c12]

To a cooled, ice/water bath, solution of 1,1-dimethylethyl 3-{bis[(5-chloro-2-thienyl)sulfonyl]amino}-4-(methyloxy)-1H-indazole-1-carboxylate (for a preparation see Intermediate 9) (4.17 g, 6.68 mmol) in DCM (20 mL) was added TFA (10.29 mL, 134 mmol) and the solution was stirred at room temperature for 4 hours. The reaction mixture was diluted with DCM (100 mL) and water (50 mL). The organic phase was passed through an hydrophobic frit and the solvent was removed in vacuo to give the product (3.78 g) as a white solid. This was dried in vacuo at 45° C. for 2 days to give the title compound (3.55 g, 100%) as a white solid. LCMS (System A) RT=1.33 min, ES+ve m/z 524/526/528 (M+H)+.

Intermediate 11

2-[4-(Methyloxy)-1H-indazol-3-yl]-1H-isoindole-1,3 (2H)-dione

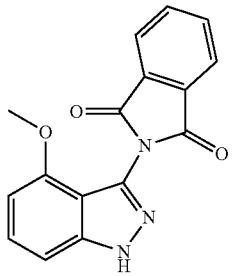 [SMILES: COc1cccc2[nH]nc(N3C(=O)c4ccccc4C3=O)c12]

4-(Methyloxy)-1H-indazol-3-amine (for a preparation see Intermediate 1) (500 mg, 3 mmol) and phthalic anhydride (680 mg, 4.6 mmol) (available from Aldrich) were dissolved in 1,4-dioxane (5 mL) at room temperature. The reaction mixture was stirred at 110° C. overnight, and then it was cooled and concentrated under reduced pressure. The residue was triturated and sonicated with 50 mL of ether. The solid was collected by filtration and dried in a vacuum oven to obtain a brown solid (711 mg, 81%). LCMS (System B) RT=2.82 min, ES+ve m/z 294 (M+H)+.

Intermediate 12

3-{[3-Amino-4-(methyloxy)-1H-indazol-1-yl]methyl}benzamide

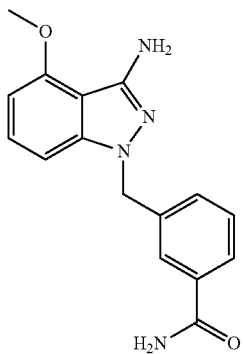 [SMILES: COc1cccc2c1c(N)nn2Cc1cccc(C(N)=O)c1]

To a solution of 2-[4-(methyloxy)-1H-indazol-3-yl]-1H-isoindole-1,3(2H)-dione (for a preparation see Intermediate 11) (1 g, 3.4 mmol) in DMF (3 mL) was added at ambient temperature potassium carbonate (0.707 g, 5.11 mmol) and 3-(chloromethyl)benzamide (Maybridge) (0.752 g, 4.43 mmol) and the resulting mixture was stirred at 80° C. overnight. The solvent was evaporated under a nitrogen stream in a blowdown unit. The residue was dissolved in 20 mL of DCM and 20 mL of water added. A precipitate formed which was collected by filtration, and used directly in the next step. LCMS (System A) RT=0.92 min, ES+ve m/z 459 (M+H)+.

The solid was dissolved in ethanol (3 mL) and added dropwise at ambient temperature to hydrazine hydrate (0.497 mL, 10.2 mmol). The resulting suspension was stirred at ambient temperature for 1 h, then acetone (3 mL) was added, and the resulting suspension was stirred overnight. The reaction mixture was diluted with DCM (30 mL) and water (30 mL). A precipitate formed, which was collected by filtration, LCMS however, showed that the reaction was incomplete. The solid was re-suspended in ethanol (3 mL) and treated with hydrazine hydrate (0.497 mL, 10.2 mmol) and stirred at ambient temperature overnight. The reaction mixture was treated with acetone (3 mL) and the resulting suspension was stirred overnight. The solid was collected by filtration, washed with DCM (10 mL) to give the title compound (785 mg, 78%) as a white solid. LCMS RT=0.81 min, ES+ve m/z 297 (M+H)+.

Intermediate 13

2-[7-Fluoro-4-(methyloxy)-1H-indazol-3-yl]-1H-isoindole-1,3(2H)-dione

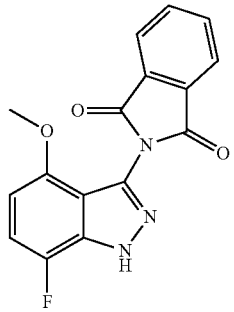 [SMILES: COc1ccc(F)c2[nH]nc(N3C(=O)c4ccccc4C3=O)c12]

2,3-Difluoro-6-methoxybenzonitrile (600 mg, 3.5 mmol) (available from JRD Fluorochemicals) was dissolved in dry N-methylpyrrolidinone (3 mL). and then treated with hydrazine hydrate (4 equiv., 0.65 mL) (available from Aldrich) and the resulting mixture was heated in a Biotage microwave vial at high absorption level for 15 minutes at 150° C. Acetone (3 mL) was added, and the solution stirred for 15 minutes and left to stand overnight. The solution was then loaded onto a 50 g SCX-2 cartridge. The column was eluted with methanol, and then 2M ammonia solution in ethanol. The basic fractions were combined and evaporated under reduced pressure. The crude oil obtained was treated with phthalic anhydride (789 mg, 5.3 mmol) (available from Aldrich) and dry 1,4-dioxane (10 mL). The reaction mixture was stirred for 48 hours at 110° C. The dioxane was removed under reduced pressure, and the residue was partitioned between dichloromethane (50 mL) and water (50 mL). The organic phase was separated and the aqueous was further extracted with 50 mL of dichloromethane. The combined organic solutions were dried through an hydrophobic frit, and concentrated under reduced pressure. The residue was purified by chromatography on silica (100 g cartridge) on Flashmaster eluting with a gradient of 0-100% ethyl acetate in cyclohexane over 80 minutes to give the title compound (510 mg, 47%). LCMS (System A) RT=0.98 min, ES+ve m/z 312 (M+H)+.

Intermediate 14

3-{[3-Amino-7-fluoro-4-(methyloxy)-1H-indazol-1-yl]methyl}benzamide

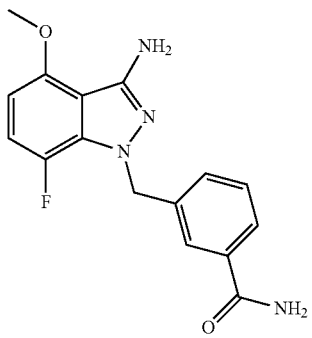 [SMILES: COc1ccc(F)c2c1c(N)nn2Cc1cccc(C(N)=O)c1]

A solution of 2-[7-fluoro-4-(methyloxy)-1H-indazol-3-yl]-1H-isoindole-1,3(2H)-dione (for a preparation see Intermediate 13) (62.0 mg, 0.2 mmol) in anhydrous DMF (2.5 mL) was treated with potassium carbonate (55.1 mg, 0.4 mmol), followed by 3-(chloromethyl)benzamide (40.5 mg, 0.24 mmol) and stirred at 80° C. for 17 hours. The cooled reaction mixture was partitioned between saturated aqueous sodium hydrogen carbonate solution and ethyl acetate. The organic layer was separated, washed with brine-water (1:1), passed through an hydrophobic frit and evaporated in-vacuo to yield a pale brown solid which was used in the next stage without further purification. LCMS (System B) RT=2.45 min, ES+ve m/z 445 (M+H)$^+$ The solid was suspended in anhydrous ethanol (3 mL) and treated at room temperature with hydrazine monohydrate (0.048 mL, 1 mmol). The resulting suspension was stirred at room temperature for 1 hour. The reaction mixture was treated with acetone (3 mL) and stirred at room temperature for 30 min. The mixture was evaporated in-vacuo to yield an orange solid, which was partitioned between saturated aqueous sodium hydrogen carbonate solution and ethyl acetate. The organic layer was separated, passed through an hydrophobic frit and evaporated in-vacuo to yield an orange solid. The residue was dissolved in MeOH-DMSO (1 mL) and purified by MDAP on Sunfire C18 column, eluting with solvents A/B (A: 0.1% v/v solution of formic acid in water, B: 0.1% v/v solution of formic acid in acetonitrile) over 25 min. Appropriate fraction was partitioned between saturated aqueous sodium hydrogen carbonate solution and dichloromethane. The organic layer was passed through an hydrophobic frit and evaporated in-vacuo to yield a white solid (22 mg, 35%) LCMS (System B) RT=1.96 min, ES+ve m/z 315 (M+H)$^+$.

Intermediate 15

N-(1-{[3-(Aminomethyl)phenyl]methyl}-4-hydroxy-1H-indazol-3-yl)-5-chloro-2-thiophenesulfonamide Formate Salt

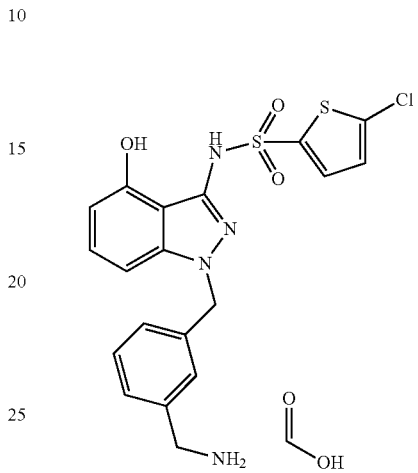

A suspension of N-[1-{[3-(aminomethyl)phenyl]methyl}-4-(methyloxy)-1H-indazol-3-yl]-5-chloro-2-thiophenesulfonamide hydrochloride (for a preparation see Intermediate 4) (266 mg, 0.533 mmol) in anhydrous DCM (7.5 mL) under nitrogen atmosphere was treated dropwise with boron tribromide solution in DCM (1M, 0.533 mL, 0.533 mmol) at room temperature, and the reaction mixture was stirred at room temperature for 1 hour (reaction not in solution—sticky orange gum had formed). A further portion of boron tribromide (1M, 0.533 mL) was added and the reaction mixture was stirred at room temperature for 1 hour (reaction still not in solution). Anhydrous methanol was added dropwise until the reaction was in solution. Reaction mixture was then stirred at room temperature for a further 30 min. Saturated aqueous sodium bicarbonate solution (10 mL) was added dropwise with care to quench the reaction, on addition of which both a white precipitate (suspended in the aqueous layer) and a dark green sticky gum (stuck to the side of the flask) formed. The aqueous and organic layers were applied to a hydrophobic frit and the organic layer collected and retained. The remaining green gum in the flask was dissolved in 1:1 methanol-dichloromethane, passed through a hydrophobic frit, combined with the retained organic and evaporated in-vacuo to yield a dark green sticky solid (265 mg). This was dissolved in DMSO (3×1 mL) and purified by MDAP Sunfire C18 column, eluting with solvents NB (A: 0.1% v/v solution of formic acid in water, B: 0.1% v/v solution of formic acid in acetonitrile) (25 min run). Appropriate fractions were combined and evaporated in-vacuo to yield the title compound as a colourless oil (86 mg, 33%). LCMS (System B) RT=1.63 min, ES+ve m/z 449/451 (M+H)$^+$.

Intermediate 16

Methyl 3-{[2-(dimethylamino)-2-oxoethyl]oxy}benzoate

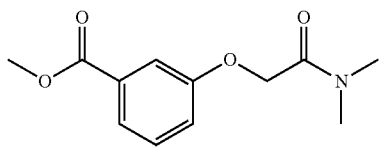

A mixture of methyl 3-hydroxybenzoate (Aldrich) (1.52 g, 10 mmol) and K$_2$CO$_3$ (1.38 g, 10 mmol) in DMF (10 mL) was stirred for 1 h. 2-Chloro-N,N-dimethylacetamide (Merck) (1.03 mL, 10 mmol) was added and the mixture was stirred for 1 h at RT and then stood at RT for 6 days. The mixture was then acidified with 2M HCl and extracted with EtOAc. The aqueous layer was extracted twice more with EtOAc and the combined organic solutions were washed with 2M HCl (×3), aq. sat NaHCO$_3$, brine, dried (MgSO$_4$) and evaporated under reduced pressure to give the title compound (2.22 g, 94%) as a white solid. LCMS (System A) RT=0.80 min, 91%, ES+ve m/z 238 (M+H)$^+$.

Intermediate 17

(3-{[2-(Dimethylamino)ethyl]oxy}phenyl)methanol

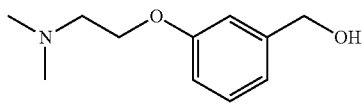

Methyl 3-{[2-(dimethylamino)-2-oxoethyl]oxy}benzoate (for a preparation see Intermediate 16) (2.22 g, 9.36 mmol) was dissolved in THF (15 mL) and cooled in ice. The solution was then treated dropwise with an ether solution of LiAlH$_4$ (1M, 10 mL) under nitrogen, and the mixture was stirred in an ice-bath for 1.5 h. LCMS indicated only completion. The mixture was cooled in ice and aqueous saturated sodium sulfate solution was added until a white precipitate formed. The mixture was stirred for 2 h and then allowed to stand O/W at RT. The mixture was then filtered, the solid was washed with ethyl acetate, and the filtrate and washings concentrated under reduced pressure. The resulting colourless oil was dissolved in methanol and applied to a pre-washed SCX-2 cartridge. The cartridge was washed with methanol and then eluted with 10% aqueous ammonia in methanol. The ammoniacal fractions were combined and evaporated under reduced pressure to give the title compound (1.236 g, 68%). LCMS (System A) RT=0.36 min, ES+ve m/z 196 (M+H)$^+$.

Intermediate 18

5-Chloro-N-[(5-chloro-2-thienyl)sulfonyl]-N-[1-[(3-{[2-(dimethylamino)ethyl]oxy}phenyl)methyl]-4-(methyloxy)-1H-indazol-3-yl]-2-thiophenesulfonamide

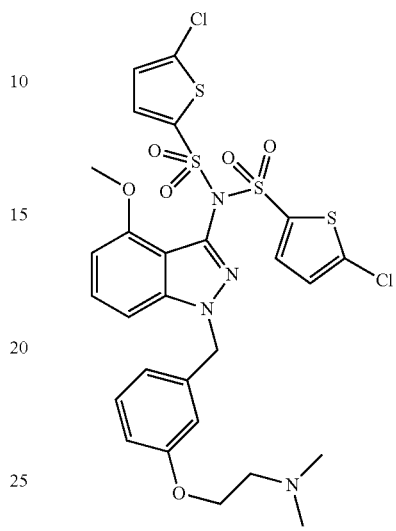

A mixture of 5-chloro-N-[(5-chloro-2-thienyl)sulfonyl]-N-[4-(methyloxy)-1H-indazol-3-yl]-2-thiophenesulfonamide (for a preparation see Intermediate 10) (150 mg, 0.28 mmol), (3-{[2-(dimethylamino)ethyl]oxy}phenyl)methanol (73 mg, 0.37 mmol), triphenylphosphine (113 mg, 0.43 mmol) and di-tert-butyl azodicarboxylate (132 mg, 0.57 mmol) in THF (15 mL) was heated to 65° C., O/N. The mixture was evaporated under reduced pressure, the residue was dissolved in MeOH, and then loaded on a SCX-2 ion-exchange cartridge (20 g) and eluted with sequential solvents methanol, 2M ammonia in methanol. The appropriate fractions were combined and evaporated in vacuo to give the crude product. This was dissolved in DCM and purified by chromatography on silica (20 g cartridge) on Flashmaster using a 0-15% methanol (containing 1% Et$_3$N)-dichloromethane over 20 min. The appropriate fraction was evaporated in vacuo to give the title product (140 mg, 70%) as a white foam. LCMS (System F) RT=1.27 min, ES+ve m/z 701/703 (M+H)$^+$.

Intermediate 19

Methyl 4-{[2-(dimethylamino)-2-oxoethyl]oxy}benzoate

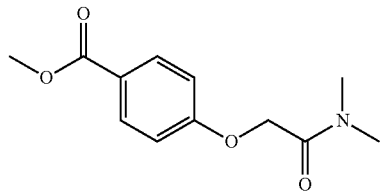

Methyl 4-hydroxybenzoate (Fluka) (1.52 g, 10 mmol) and potassium carbonate (1.38 g, 10 mmol) in DMF (10 mL) was treated with 2-chloro-N,N-dimethylacetamide (Merck) (1.03 ml, 10 mmol) and the mixture was stirred at RT overnight. The reaction mixture was worked up by partitioning between ethyl acetate and 2M hydrochloric acid, washing with HCl, brine, dried (MgSO$_4$) and evaporating to dryness. The residue was dissolved in DMF (5 mL) and treated with potassium carbonate (1.38 g, 10 mmol) and 2-chloro-N,N-dimethylacetamide (Merck) (1.03 ml, 10 mmol). The mixture was stirred at RT over the weekend, and then worked up. Partitioned between ethyl acetate and 2M HCl and the organic solution was washed with HCl (×2), brine (×3), dried (MgSO$_4$), and evaporated to give the title compound (1.62 g, 68%) as a white solid. LCMS (System A) RT=0.73 min, ES+ve m/z 238 (M+H)$^+$.

Intermediate 20

(4-{[2-(Dimethylamino)ethyl]oxy}phenyl)methanol

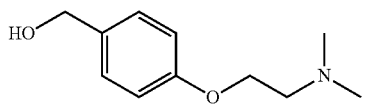

Methyl 4-{[2-(dimethylamino)-2-oxoethyl]oxy}benzoate (for a preparation see Intermediate 19) (1.61 g, 6.79 mmol) in THF (40 mL) was cooled in ice and then treated with a 1M solution of LiAlH$_4$ in diethyl ether (6.8 ml) and the mixture was stirred under nitrogen for 4 h. The reaction mixture was cautiously treated with saturated aq. sodium sulfate solution until the hydrogen evolution ceased. The mixture was then stirred under nitrogen for 1 h and filtered. The solid was washed with diethyl ether and the combined filtrate and washings evaporated under reduced pressure to give the title compound (1.32 g, 100%). LCMS (System B) RT=1.70 min, ES+ve m/z 196 (M+H)$^+$.

Intermediate 21

5-Chloro-N-[(5-chloro-2-thienyl)sulfonyl]-N-[1-[(4-{[2-(dimethylamino)ethyl]oxy}phenyl)methyl]-4-(methyloxy)-1H-indazol-3-yl]-2-thiophenesulfonamide

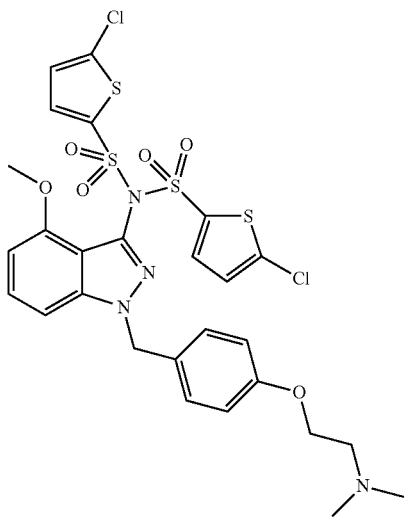 [SMILES: COc1cccc2c1c(N(S(=O)(=O)c1ccc(Cl)s1)S(=O)(=O)c1ccc(Cl)s1)nn2Cc1ccc(OCCN(C)C)cc1]

A mixture of 5-chloro-N-[(5-chloro-2-thienyl)sulfonyl]-N-[4-(methyloxy)-1H-indazol-3-yl]-2-thiophenesulfonamide (for a preparation see Intermediate 10) (0.262 g, 0.5 mmol) and (4-{[2-(dimethylamino)ethyl]oxy}phenyl)methanol (98 mg, 0.5 mmol), triphenylphosphine (197 mg, 0.75 mmol) and di tert-butyl azodicarboxylate (230 mg, 1 mmol) in THF (30 mL) was heated to 65° C. for h. LCMS indicated complete reaction. The mixture was concentrated and the residue was dissolved in methanol and applied to an SCX-2 ion-exchange cartridge (50 g) eluting with methanol, followed by 10% aq. ammonia in methanol. The ammoniacal fractions were combined and evaporated in vacuo to give the crude product (400 mg) as a yellow gum. The mixture was loaded in dichloromethane on a silica cartridge (20 g) and purified by chromatography on Flashmaster using a gradient of 0-15% methanol (containing 1% Et$_3$N)-dichloromethane over 40 min. The appropriate fractions were combined and evaporated in vacuo to give impure product (167 mg) as a colourless gum. The sample was dissolved in 1:1 MeOH-DMSO (2 mL) and purified by MDAP on Xbridge column using acetonitrile water with an ammonium carbonate modifier Appropriate fractions were combined and the solvent was evaporated in vacuo to give the title compound (91 mg, 26%) LCMS (System C) (5 min run) RT=3.76 min, ES+ve m/z 701/703 (M+H)$^+$.

Intermediate 22

Methyl 4-{[2-(dimethylamino)-2-oxoethyl]oxy}-3-(methyloxy)benzoate

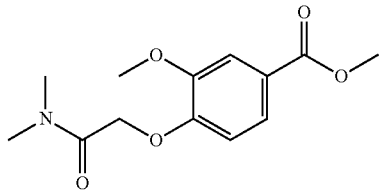

Methyl 4-hydroxy-3-(methyloxy)benzoate (methyl vanillate, Aldrich) (3.85 g, 21.1 mmol) and potassium carbonate (2.92 g, 21.1 mmol) in DMF (10 mL) was treated at RT with 2-chloro-N,N-dimethylacetamide (Merck) (2.18 mL, 21.1 mmol) and the mixture was stirred over the weekend. The mixture was partitioned between ethyl acetate and 2M HCl. The organic phase was washed with, 2M HCl, saturated sodium bicarbonate solution (turns lightly coloured), acid (loses colour), brine, dried (MgSO$_4$), and evaporated under reduced pressure, to give the product contaminated with starting material (5.0 g). The mixture was therefore re-dissolved in DMF (5 mL) and treated with potassium carbonate (1.38 g, 10 mmol) and 2-chloro-N,N-dimethylacetamide (1 mL, 10 mmol) for another day. The mixture was then partitioned between ethyl acetate and 2M HCl and treated as above. The filtrate was evaporated to give a solid (2.614 g) which was loaded in chloroform to a silica cartridge (70 g) and purified by chromatography on Flashmaster using a 0-100% ethyl acetate-cyclohexane gradient over 30 min. The appropriate fractions were combined and evaporated in vacuo to give the title compound (1.4 g, 25%) as a white solid. LCMS (System A) RT=0.69 min, ES+ve m/z 268 (M+H)$^+$.

Intermediate 23

[4-{[2-(Dimethylamino)ethyl]oxy}-3-(methyloxy)phenyl]methanol

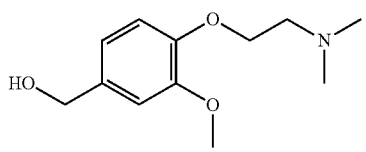 [SMILES: COc1cc(CO)ccc1OCCN(C)C]

Methyl 4-{[2-(dimethylamino)-2-oxoethyl]oxy}-3-(methyloxy)benzoate (for a preparation see Intermediate 22) (1.4 g, 5.2 mmol) was dissolved in THF (50 ml) and cooled in an ice-bath under nitrogen. The mixture was then treated cautiously with 1M ether solution of lithium aluminium hydride (5.5 mL) and the mixture was stirred at 5° C. allowing to warm to RT overnight. The reaction mixture was quenched by cautious addition of aq. saturated NaHCO$_3$ solution (1 mL), followed by MgSO$_4$ (2 g) and stirring for 30 min. The solids were removed by filtration, washed with ethyl acetate, and the filtrate was evaporated to give the title compound (1.18 g, 100%) as a yellow oil: LCMS (System A) RT=0.34 min, ES+ve m/z 226 (M+H)$^+$.

Intermediate 24

3-(Hydroxymethyl)benzenesulfonamide

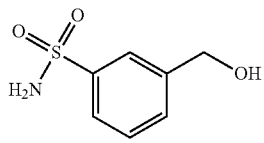 [SMILES: NS(=O)(=O)c1cccc(CO)c1]

To a solution of 3-(aminosulfonyl)benzoic acid (Fluorochem) (150 mg, 0746 mmol) in THF (1 mL) was added dropwise at 0° C. Borane-THF complex (3.73 mL, 3.73 mmol). The resulting solution was stirred 10 min at 0° C., and then at room temperature overnight. The reaction mixture was carefully quenched with 10 mL of water at 0° C. The reaction mixture was diluted with 30 mL of EtOAc and 20 ml of water. The aqueous layer was further extracted with 30 mL of EtOAc. The combined organic solutions were washed with brine (30 mL), dried over an hydrophobic frit and concentrated under reduced pressure. The residue was loaded in dichloromethane to a silica cartridge (20 g), and purified by chromatography on Flashmaster using a 0-100% ethyl acetate-dichloromethane over 40 min. The appropriate fractions were combined and evaporated in vacuo to give the title compound (86.4 mg, 62%) as a gum. LCMS (System A) RT=0.41 min, ES+ve m/z 188 (M+H)$^+$.

Intermediate 25

1-{[3,4-Bis(methyloxy)phenyl]methyl}-4-(methyloxy)-1H-indazol-3-amine

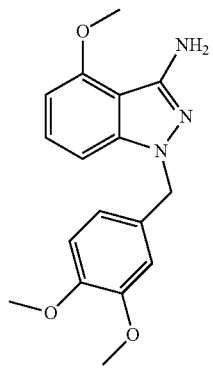 [SMILES: COc1ccc(Cn2nc(N)c3c(OC)cccc32)cc1OC]

Powdered KOH (0.494 g, 8.80 mmol) was dissolved in DMSO (20 mL) under nitrogen and 4-(methyloxy)-1H-indazol-3-amine (for a preparation see Intermediate 1) (0.653 g, 4 mmol) was added. The mixture was stirred for 15 min to give a deep red solution. 4-(Chloromethyl)-1,2-bis(methyloxy)benzene (0.896 g, 4.80 mmol) was added in one portion and the mixture was stirred for 2 h. The mixture was added to water (150 mL) and extracted with dichloromethane (3×50 mL). The dried (Na$_2$SO$_4$) extract was evaporated and the residue was triturated with diethyl ether (3×3 mL) to give the title compound (1.05 g, 84%) as an orange solid. LCMS (System B) RT=1.42 min, ES+ve m/z 314 (M+H)$^+$.

Intermediate 26

5-Chloro-N-[4-(methyloxy)-1H-indazol-3-yl]-2-thiophenesulfonamide

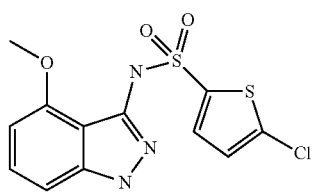 [SMILES: COc1cccc2[nH]nc(NS(=O)(=O)c3ccc(Cl)s3)c12]

A solution of 1,1-dimethylethyl 3-{[(5-chloro-2-thienyl)sulfonyl]amino}-4-(methyloxy)-1H-indazole-1-carboxylate (for a preparation see Intermediate 6) (155 mg, 0.35 mmol) was dissolved in DCM (0.2 mL) and TFA (0.4 mL) was added. The solution was stood at room temperature for 30 min, and then blown down to dryness under a stream of nitrogen in a Radley's blow down unit to give the title compound (200 mg). LCMS (System D) RT=1.02 min, ES+ve m/z 344 (M+H)$^+$.

Intermediate 27

2-{[(3-{[3-{[(5-Chloro-2-thienyl)sulfonyl]amino}-4-(methyloxy)-1H-indazol-1-yl]methyl}phenyl)methyl]amino}-1,1-dimethyl-2-oxoethyl Acetate

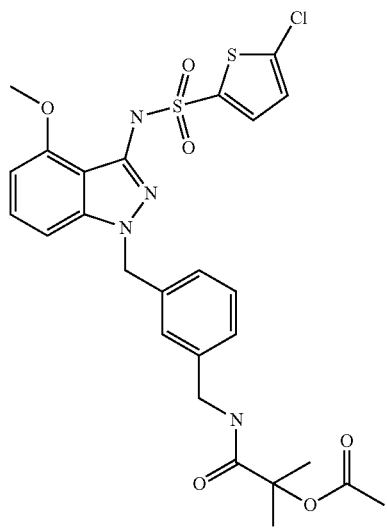 [SMILES: COc1cccc2c1c(NS(=O)(=O)c1ccc(Cl)s1)nn2Cc1cccc(CNC(=O)C(C)(C)OC(C)=O)c1]

A stirring suspension of N-[1-{[3-(aminomethyl)phenyl]methyl}-4-(methyloxy)-1H-indazol-3-yl]-5-chloro-2-thiophenesulfonamide (40.5 g, 87 mmol) in dichloromethane (1000 mL) and triethylamine (36.4 mL, 262 mmol) was cooled down and then 2-chloro-1,1-dimethyl-2-oxoethyl acetate (12.52 mL, 87 mmol) was added dropwise. The reaction mixture was stirred at room temperature under nitrogen for 1 h and 20 min. It was then washed with 2M HCl (300 ml), $NaHCO_3$ solution (300 ml), brine, dried over magnesium sulphate and filtered. The filtrate was evaporated in vacuo to give a white solid. The residue was dissolved in DCM and loaded onto a 1500 g silica column and eluted with 40-100% ethyl acetate in cyclohexane over 8 CV. The required fractions were combined and evaporated in vacuo to give the title compound in two batches (37.87 g, 73%) and (3.39 g) as white foams. HPLC showed that the latter batch was not pure, therefore it was purified again on a 120 g silica column using a gradient of 40-75% ethyl acetate in cyclohexane over 8 CV. The required fractions were combined and evaporated in vacuo to give the title compound (2.16 g, 4%) as a white foam.

LCMS (System A) RT=1.10 min, ES+ve m/z 591/593 $(M+H)^+$.

Intermediate 28

1,1-Dimethylethyl[(4-{[3-{bis[(5-chloro-2-thienyl)sulfonyl]amino}-4-(methyloxy)-1H-indazol-1-yl]methyl}phenyl)methyl]carbamate

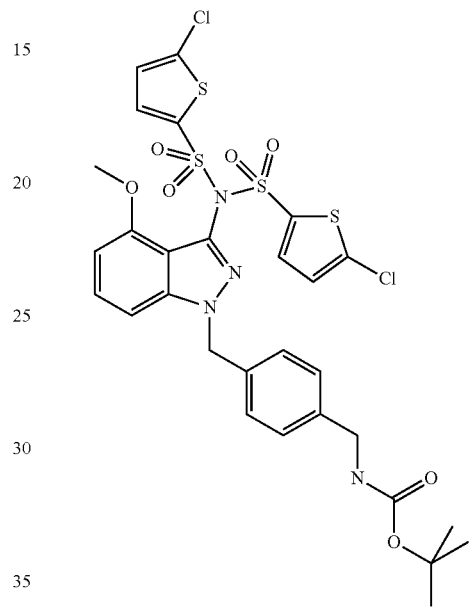

A solution of 5-chloro-N-[(5-chloro-2-thienyl)sulfonyl]-N-[4-(methyloxy)-1H-indazol-3-yl]-2-thiophenesulfonamide (for a preparation see Intermediate 10) (400 mg, 0.763 mmol), triphenylphosphine (400 mg, 1.52 mmol) and 1,1-dimethylethyl{[4-(hydroxymethyl)phenyl]methyl}carbamate (Maybridge) (362 mg, 1.52 mmol) in THF (3 mL) was added at room temperature DIAD (0.300 mL, 1.52 mmol). The resulting mixture was stirred at 65° C. for 3 hours. The reaction mixture was partitioned between DCM (3 mL) and water (3 mL). The organic phase was separated, and the aqueous layer was further extracted with DCM (3 mL). The combined organic solutions were dried over an hydrophobic frit and evaporated under a nitrogen stream in a blowdown unit. The residue was loaded in dichloromethane on a silica (50 g) cartridge and purified by chromatography on Flashmaster II using a gradient of 0-100% dichloromethane-cyclohexane over 40 min. The appropriate fractions were combined and evaporated in vacuo to give the title compound (498 mg, 88%) as a gum.

LCMS (System A) RT=1.48 min, ES+ve m/z 760/762 $(M+NH_4)^+$.

Intermediate 29

1,1-Dimethylethyl[(4-{[3-{[(5-chloro-2-thienyl)sulfonyl]amino}-4-(methyloxy)-1H-indazol-1-yl]methyl}phenyl)methyl]carbamate

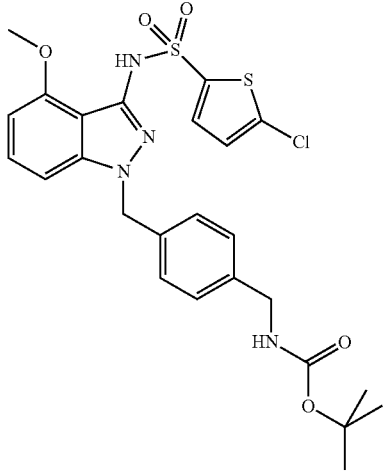 [SMILES: COc1cccc2c1c(NS(=O)(=O)c1ccc(Cl)s1)nn2Cc1ccc(CNC(=O)OC(C)(C)C)cc1]

To a solution of 1,1-dimethylethyl[(4-{[3-{bis[(5-chloro-2-thienyl)sulfonyl]amino}-4-(methyloxy)-1H-indazol-1-yl]methyl}phenyl)methyl]carbamate (for a preparation see intermediate 28) (497 mg, 0.67 mmol) in methanol (3 mL) was added sodium hydroxide (2M, 3.34 mL) and the mixture was stirred at 60° C. for 3 h. The solvents were evaporated off under a nitrogen stream in a blowdown unit. The residue was partitioned between DCM (5 mL) and water (5 mL) and a solution of dilute HCl solution was added until the pH of the aqueous layer was around 1. The organic phase was separated and the aqueous layer was further extracted with DCM (5 mL). The combined organic solutions were washed with brine (2 mL), dried over an hydrophobic frit, and concentrated under a stream of nitrogen in a blowdown unit. The residue was dissolved in 1:1 MeOH-DMSO (1 mL) and purified by Mass Directed AutoPrep (supelcosil ABZ+Plus column) eluting with solvents NB (A: Water+0.1% Formic acid, B: MeCN:Water 95:5+0.05% Formic acid). The solvent was removed under a stream of nitrogen in the Radleys blowdown apparatus to give the title compound (112 mg, 30%) as a white solid. LCMS (System A) RT=1.26 min, ES+ve m/z 563/565 (M+H)+.

Intermediate 30

N-[1-{[4-(Aminomethyl)phenyl]methyl}-4-(methyloxy)-1H-indazol-3-yl]-5-chloro-2-thiophenesulfonamide Formate Salt

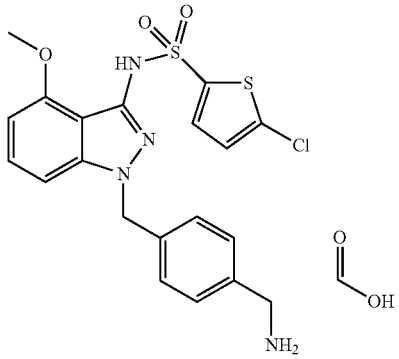 [SMILES: COc1cccc2c1c(NS(=O)(=O)c1ccc(Cl)s1)nn2Cc1ccc(CN)cc1 ; O=CO]

To a solution of 1,1-dimethylethyl[(4-{[3-{[(5-chloro-2-thienyl)sulfonyl]amino}-4-(methyloxy)-1H-indazol-1-yl]methyl}phenyl)methyl]carbamate (for a preparation see Intermediate 29) (92 mg, 0.16 mmol) in dichloromethane (3 mL) was added dropwise hydrogen chloride (0.041 mL, 0.163 mmol). The resulting mixture was stirred at room temperature for 4 h, and then additional portion of hydrogen chloride (0.041 mL, 0.163 mmol) was added dropwise and the mixture was stirred at room temperature overnight. The solvents were then evaporated in a nitrogen blowdown unit. The residue was dissolved in 1:1 MeOH-DMSO (1 mL) and purified by Mass Directed AutoPrep (supelcosil ABZ+Plus column) eluting with solvents NB (A: Water+0.1% Formic acid, B: MeCN:Water 95:5+0.05% Formic acid). The solvent was dried under a stream of nitrogen in the Radleys blowdown apparatus to give the title compound (69 mg, 83%). LCMS (System E) RT=2.10 min, ES+ve m/z 463/465 (M+H)+.

Intermediate 31

Methyl 3-{[3-[[(5-chloro-2-thienyl)sulfonyl]({[2-(trimethylsilyl)ethyl]oxy}methyl)amino]-4-(methyloxy)-1H-indazol-1-yl]methyl}benzoate

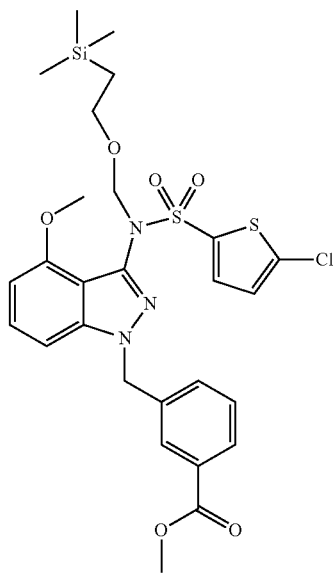 [SMILES: COC(=O)c1cccc(Cn2nc(N(COCC[Si](C)(C)C)S(=O)(=O)c3ccc(Cl)s3)c3c(OC)cccc32)c1]

A solution of 5-chloro-N-[4-(methyloxy)-1H-indazol-3-yl]-N-({[2-(trimethylsilyl)ethyl]oxy}methyl)-2-thiophenesulfonamide (for a preparation see Intermediate 8) (1 g, 2.11 mmol) in DMF (10 mL) was treated at ambient temperature with potassium carbonate (0.583 g, 4.22 mmol) and methyl 3-(bromomethyl)benzoate (Alfa Aesar) (0.580 g, 2.53 mmol). The resulting mixture was stirred at 50° C. for 2 h and the LCMS then showed product as the major peak. The mixture was diluted with DCM (20 mL) and of water (20 mL). The organic phase was separated and the aqueous layer was further extracted with DCM (20 mL). The combined organic solutions were washed with brine (30 mL), dried over an hydrophobic frit, and concentrated under reduced pressure.

The residue was loaded in dichloromethane to a silica 100 g cartridge and purified by chromatography on Flashmaster II using a 0-100% gradient B in A, A being neat DCM and B being a 5% EtOAC in DCM solution over 40 min. and then further purified on a second cartridge silica 70 g using a 0-100% gradient B in A, A being neat DCM and B being a 5% EtOAC in DCM solution over 40 min. The appropriate fractions were combined and evaporated in vacuo to give the title compound (571 mg, 44%) as a gum. LCMS (System A) RT=1.60 min, ES+ve m/z 639/641 (M+NH$_4$)$^+$.

Intermediate 32

4-{[3-Amino-4-(methyloxy)-1H-indazol-1-yl]methyl}benzamide

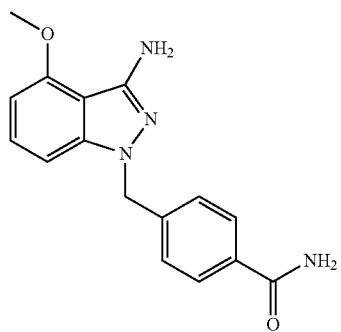 [SMILES: COc1cccc2c1c(N)nn2Cc1ccc(C(N)=O)cc1]

To a solution of 4-(methyloxy)-1H-indazol-3-amine (for a preparation see Intermediate 1) (0.816 g, 5 mmol) in DMSO (50 mL) at room temperature under nitrogen was added potassium hydroxide (0.561 g, 10.0 mmol). After stirring the resulting deep red solution for 25 min 4-(chloromethyl)benzamide (0.848 g, 5.00 mmol) was added in one portion. The reaction mixture was stirred for a further 30 min and then poured into water (250 mL), forming an emulsion. The reaction mixture was extracted using chloroform (3×250 mL). The combined organic solutions were washed with water (250 mL) and passed through hydrophobic frit. The solvent was removed in vacuo and the residue was loaded in dichloromethane to a silica (100 g) cartridge and purified by chromatography on Flashmaster eluting with 0-100% ethyl acetate-cyclohexane+0-20% methanol-ethyl acetate over 60 min. The appropriate fractions were combined and evaporated in vacuo to give the title compound (1.18 g, 80%). LCMS: (System A) RT=0.69 min, ES+ve m/z 297 (M+H)$^+$.

Intermediate 33

1-{[3,4-Bis(methyloxy)phenyl]methyl}-4-(methyloxy)-1H-indazol-3-amine(

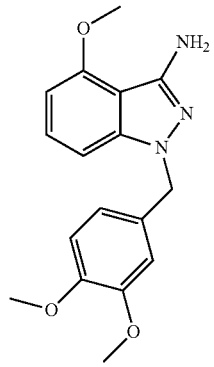 [SMILES: COc1ccc(Cn2nc(N)c3c(OC)cccc32)cc1OC]

Powdered KOH (0.494 g, 8.80 mmol) was dissolved in DMSO (20 mL) under nitrogen and 4-(methyloxy)-1H-indazol-3-amine (for a preparation see Intermediate 1) (0.653 g, 4 mmol) was added. The mixture was stirred for 15 min to give a deep red solution. 4-(Chloromethyl)-1,2-bis(methyloxy)benzene (0.896 g, 4.80 mmol) was added in one portion and the mixture was stirred for 2 h. The mixture was added to water (150 mL) and extracted with dichloromethane (3×50 mL). The dried (Na$_2$SO$_4$) extract was evaporated and the residue was triturated with diethyl ether (3×3 mL) to give the title compound (1.05 g, 84%) as an orange solid. LCMS (System B) RT=2.22 min, ES+ve m/z 314 (M+H)$^+$.

Intermediate 34

N-[(3-{[3-amino-4-(methyloxy)-1H-indazol-1-yl]methyl}phenyl)methyl]acetamide

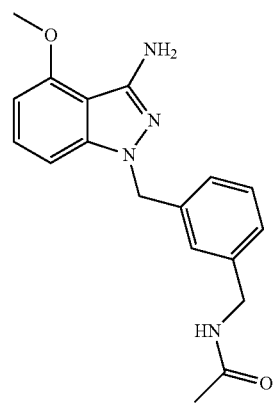 [SMILES: COc1cccc2c1c(N)nn2Cc1cccc(CNC(C)=O)c1]

The title compound was prepared in array format according to the procedure described for Intermediate 33.
LCMS (System A) RT=0.76 min, ES+ve m/z 325 (M+H)$^+$.

Intermediate 35

1,1-Dimethylethyl (3R)-3-({[(3-{[3-amino-4-(methyloxy)-1H-indazol-1-yl]methyl}phenyl)methyl]amino}carbonyl)-4-morpholinecarboxylate

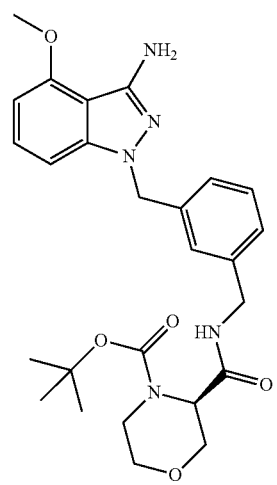 [SMILES: COc1cccc2c1c(N)nn2Cc1cccc(CNC(=O)[C@H]2COCCN2C(=O)OC(C)(C)C)c1]

The title compound was prepared in array format according to the procedure described in Intermediate 33. LCMS (System A) RT=0.98 min, ES+ve m/z 496 (M+H)$^+$.

Intermediate 36

4-Fluoro-1H-indazol-3-amine

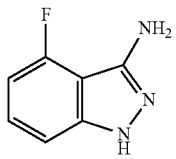

To a solution of 2,6-difluorobenzonitrile (3 g, 21.6 mmol) in anhydrous ethanol (50 mL) was added hydrazine hydrate (4.18 mL, 86 mmol). The reaction was heated at 90° C. under nitrogen for 4 hours. Reaction mixture was cooled to room temperature, treated with acetone (20 mL) and left to stand for 18 hours. The mixture was evaporated in-vacuo to yield an orange/brown solid which was partitioned between saturated aqueous sodium hydrogen carbonate solution and dichloromethane. The organic layer was passed through a hydrophobic frit and evaporated in-vacuo to yield a brown solid (4.58 g), which was absorbed onto Florisil (60-100 mesh), applied to a 100 g silica SPE cartridge and purified on a Flashmaster II using a 0-10% methanol in dichloromethane gradient over 60 min. Fractions 48-57 were combined and the solvent was evaporated in-vacuo to yield the title compound as a brown solid (3.08 g, 94%). LCMS (System B) RT=1.38 min, ES+ve m/z 152 (M+H)$^+$.

Intermediate 37

3-[(3-Amino-4-fluoro-1H-indazol-1-yl)methyl]benzonitrile

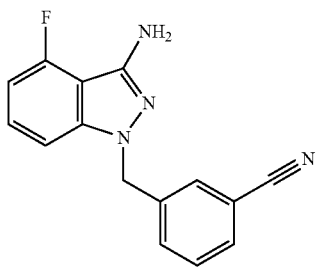 [SMILES: N#Cc1cccc(Cn2nc(N)c3c(F)cccc32)c1]

To a suspension of ground potassium hydroxide (0.483 g, 8.60 mmol) in anhydrous dimethyl sulfoxide (15 mL) at room temperature under nitrogen was added a solution of 4-fluoro-1H-indazol-3-amine (for a preparation see Intermediate 36) (0.52 g, 3.44 mmol) in anhydrous dimethyl sulfoxide (10 mL). The resulting deep red solution was treated after 10 minutes with 3-cyanobenzyl bromide (0.843 g, 4.30 mmol) in one portion. The reaction mixture was stirred for 30 min and then poured into water (100 mL), forming a yellow emulsion. This was extracted using chloroform (2×100 mL). The combined organic solutions were washed with water-brine (1:1) (100 mL), passed through a hydrophobic frit and evaporated in-vacuo to yield a red oil (2.263 g). The residue was applied to a 100 g silica SPE cartridge and purified by chromatography on Flashmaster II eluting with a 0-100% ethyl acetate in cyclohexane gradient over 80 min. Fractions 159-173 were combined and the solvent was evaporated in-vacuo to yield a yellow solid the title compound (0.77 g, 84%) LCMS (System B) RT=2.32 min, ES+ve m/z 267 (M+H)$^+$.

Intermediate 38

5-Chloro-N-{1-[(3-cyanophenyl)methyl]-4-fluoro-1H-indazol-3-yl}-2-thiophenesulfonamide

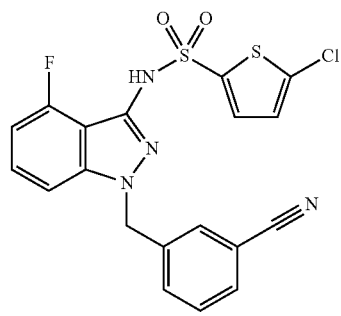 [SMILES: N#Cc1cccc(Cn2nc(NS(=O)(=O)c3ccc(Cl)s3)c3c(F)cccc32)c1]

To a solution of 3-[(3-amino-4-fluoro-1H-indazol-1-yl)methyl]benzonitrile (for a preparation see Intermediate 37) (695 mg, 2.61 mmol) in anhydrous pyridine (3 mL) cooled in an ice/water bath was added 5-chloro-2-thiophenesulfonyl chloride (567 mg, 2.61 mmol) dropwise over 1 minute and the reaction mixture was stirred in the ice/water bath for 1 hour. The reaction mixture was partitioned between ethyl acetate (150 mL) and 2N hydrochloric acid (100 mL). The organic layer was separated, passed through a hydrophobic frit and evaporated in-vacuo to yield a dark red oil (1.264 g). The oil was dissolved in the minimum volume of dichloromethane, applied to a 100 g silica SPE cartridge and purified by chromatography on Flashmaster II using a 0-50% ethyl acetate in cyclohexane gradient over 60 min. Fractions 66-69 were combined and evaporated in-vacuo to yield a white foam (540 mg), which was further purified by chromatography on 100 g silica SPE cartridge on Flashmaster II using a 0-10% methanol in dichloromethane gradient over 60 min. Fractions 23-26 were evaporated in-vacuo to yield the title compound as a white foam (493 mg, 42%). LCMS (SystemB) RT=3.01 min, ES+ve m/z 447/449 (M+H)$^+$.

Intermediate 39

N-(1-{[3-(Aminomethyl)phenyl]methyl}-4-fluoro-1H-indazol-3-yl)-5-chloro-2-thiophenesulfonamide

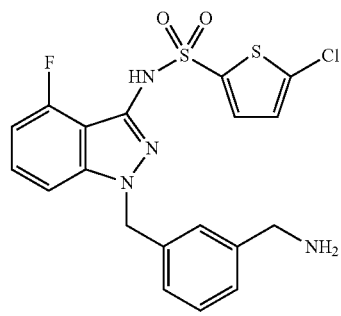 [SMILES: NCc1cccc(Cn2nc(NS(=O)(=O)c3ccc(Cl)s3)c3c(F)cccc32)c1]

To an ice/water bath cooled solution of 5-chloro-N-{1-[(3-cyanophenyl)methyl]-4-fluoro-1H-indazol-3-yl}-2-thiophenesulfonamide (for a preparation see Intermediate 38) (493 mg, 1.10 mmol) in anhydrous tetrahydrofuran (7 mL) under nitrogen atmosphere was added dropwise over 5 min lithium aluminium hydride (1M solution in diethyl ether) (2.76 mL, 2.76 mmol). The reaction was stirred in the ice/water bath for 30 min and then at room temperature for 1 hour. Further quantity of lithium aluminium hydride (1M solution in diethyl ether, 1 mL) was added dropwise over 1 min. Reaction stirred at room temperature for 1 hour. The reaction mixture was cooled in an ice/water bath and quenched with water (10 mL) (dropwise with care). The reaction was then partitioned between saturated aqueous sodium hydrogen carbonate solution and 20% methanol in dichloromethane—large amount of white solid suspended in the aqueous layer. The organic layer was passed through a hydrophobic frit and evaporated in-vacuo to yield a white solid (<20 mg). Product not soluble in organic layer—majority of material either soluble in aqueous or suspended in aqueous. Methanol was added to the retained aqueous layer until an opaque milky solution formed—applied to two methanol pre-conditioned 50 g SCX-2 ion-exchange cartridges. The cartridges were washed with methanol and then eluted using 2M ammonia in methanol. The 2M ammonia in methanol fractions from each cartridge were combined and evaporated in-vacuo to yield a pale yellow solid (480 mg), which was absorbed onto Florisil (60-100 mesh), applied to a 100 g silica SPE cartridge and purified by chromatography on Flashmaster II using a 0-25% methanol in dichloromethane gradient over 60 min. Appropriate fractions were combined and evaporated under reduced pressure to give the title compound (284 mg, 57%) as a white solid. LCMS (System B) RT=1.67 min, ES+ve m/z 451/453 (M+H)+.

Intermediate 40

4-Chloro-1H-indazol-3-amine

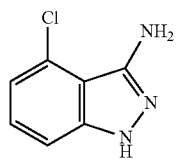

To a solution of 2-chloro-6-fluorobenzonitrile (ABCR) (3 g, 19 mmol) in anhydrous ethanol (50 mL) was added hydrazine hydrate (3.74 mL, 77 mmol). The reaction was heated at 90° C. under a nitrogen for 3.5 hours. The reaction mixture was cooled to room temperature, treated with acetone (20 mL) and left to stand for 19 hours. The mixture was evaporated in-vacuo to yield an orange/brown solid, which was partitioned between saturated aqueous sodium hydrogen carbonate solution and dichloromethane. The organic layer was passed through a hydrophobic frit and evaporated in-vacuo to yield a brown solid, which was absorbed onto Florisil (60-100 mesh), applied to a 100 g silica SPE cartridge and purified by chromatography on Flashmaster II using a 0-10% methanol in dichloromethane gradient over 60 min. Fractions 24-29 were combined and the solvent was evaporated in-vacuo to yield the title compound as a yellow solid (2.14 g, 66%) LCMS (System B) RT=1.58 min, ES+ve m/z 168 (M+H)+.

Intermediate 41

3-[(3-Amino-4-chloro-1H-indazol-1-yl)methyl]benzonitrile

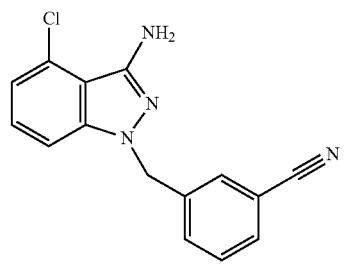 [SMILES: N#Cc1cccc(Cn2nc(N)c3c(Cl)cccc32)c1]

To a suspension of ground potassium hydroxide (421 mg, 7.50 mmol) in anhydrous dimethyl sulfoxide (5 mL) at room temperature under nitrogen was added a solution of 4-chloro-1H-indazol-3-amine (for a preparation see Intermediate 40) (503 mg, 3.0 mmol) in anhydrous dimethyl sulfoxide (15 mL). After 30 minutes 3-cyanobenzyl bromide (Aldrich) (735 mg, 3.75 mmol) was added in one portion. The reaction mixture was stirred for 2 hours. The reaction mixture was poured into water (200 mL), forming a yellow/brown emulsion. This was extracted using chloroform (2×200 mL). The combined organic solutions were washed with water:brine (1:1) (200 mL), passed through a hydrophobic frit, and evaporated in-vacuo to yield a brown oil. The oil was applied to a 100 g silica SPE cartridge and purified by chromatography on Flashmaster II using a 0-100% ethyl acetate in cyclohexane gradient over 80 min. Fractions 32-34 were combined and the solvent was evaporated in-vacuo to yield the title compound as an off white solid (216 mg, 25%). LCMS (System B) RT=2.51 min, ES+ve m/z 283 (M+H)+.

Intermediate 42

5-Chloro-N-{4-chloro-1-[(3-cyanophenyl)methyl]-1H-indazol-3-yl}-2-thiophenesulfonamide

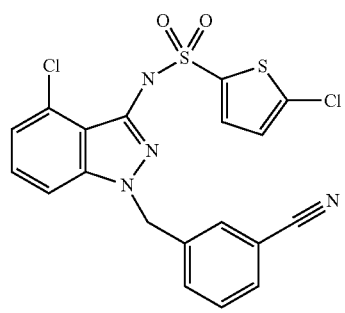 [SMILES: N#Cc1cccc(Cn2nc(NS(=O)(=O)c3ccc(Cl)s3)c3c(Cl)cccc32)c1]

To a solution of 3-[(3-amino-4-chloro-1H-indazol-1-yl) methyl]benzonitrile (for a preparation see Intermediate 41) (201 mg, 0.711 mmol) in anhydrous pyridine (2 mL) under nitrogen was added 5-chloro-2-thiophenesulfonyl chloride (154 mg, 0.711 mmol) dropwise, and the reaction mixture was stirred at room temperature for 30 min. The reaction mixture was partitioned between ethyl acetate (150 mL) and 2N hydrochloric acid (100 mL). The organic layer was separated, passed through a hydrophobic frit, and evaporated in-vacuo to yield a dark red oil. This was dissolved in the minimum volume of dichloromethane, applied to a 100 g silica SPE cartridge and purified by chromatography on Flashmaster II using a 0-50% ethyl acetate in cyclohexane gradient over 60 min. Fractions 149-154 were combined and evaporated in-vacuo to yield a white solid (90 mg). Fractions 155 and 156 were combined and evaporated in-vacuo to yield a yellow solid (78 mg) which was dissolved in MeOH:DMSO (1:1) (1 mL) and further purified by Mass Directed Auto-Preparative HPLC (Sunfire C18 column 150 mm×30 mm i.d. 5 µm packing diameter at ambient temperature) eluting with solvents A/B (A: 0.1% v/v solution of formic acid in water, B: 0.1% v/v solution of formic acid in acetonitrile) over 25 min. Appropriate fractions were evaporated in-vacuo to yield a white solid (5 mg) which was combined with the earlier white solid to give the title compound (95 mg, 29%) LCMS (System B) RT=3.01 min, ES+ve m/z 463/465 (M+H)$^+$.

Intermediate 43

7-Fluoro-4-(methyloxy)-1H-indazol-3-amine

To a suspension of 2-[7-fluoro-4-(methyloxy)-1H-indazol-3-yl]-1H-isoindole-1,3(2H)-dione (for a preparation see Intermediate 13) (1.36 g, 4.37 mmol) in ethanol (15 mL) at 0° C. (ice/water bath) was added hydrazine hydrate (0.638 mL, 13.11 mmol) dropwise. The ice/water bath was removed and the reaction mixture was allowed to warm to room temperature. Stirring was continued for a further 40 min. During this time the reaction mixture became very viscous. Acetone (10 mL) was added to the reaction and the resultant reaction mixture was allowed to stand at room temperature overnight. The solid was removed by filtration and washed with acetone (×2). The combined filtrates were concentrated in vacuo. The solid was triturated in cyclohexane-ethyl acetate (2:1; ~25 mL) and then collected by filtration to give the title compound (479 mg, 60%) as a light brown powder. LCMS (System A) RT=0.69 min, ES+ve m/z 182 (M+H)$^+$. The filtrate was concentrated and the resultant oil was loaded in dichloromethane (and minimum amount of methanol) to a silica cartridge 70 g and purified by chromatography on Flashmaster eluting with a 0-50% ethyl acetate-cyclohexane over 30 min. The appropriate fractions were combined and evaporated in vacuo to give another batch of the required product (316 mg, 40%) as a brown oil. LCMS (System A) RT=0.62 min, ES+ve m/z 182 (M+H)$^+$.

Intermediate 44

3-{[3-Amino-7-fluoro-4-(methyloxy)-1H-indazol-1-yl]methyl}benzonitrile

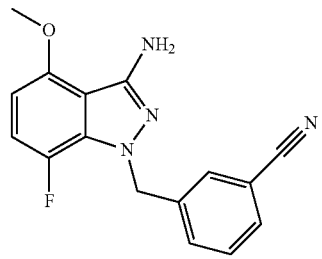 [SMILES: COc1ccc(F)c2c1c(N)nn2Cc1cccc(C#N)c1]

To a fine suspension of ground potassium hydroxide (566 mg, 10.09 mmol) in dimethyl sulfoxide (5 mL) at room temperature under nitrogen was added a solution of 7-fluoro-4-(methyloxy)-1H-indazol-3-amine (for a preparation see Intermediate 43) (727 mg, 4.01 mmol) in dimethyl sulfoxide (2 mL). After 5 min the resulting dark brown solution was treated with 3-(chloromethyl)benzonitrile (730 mg, 4.82 mmol). The reaction mixture was stirred for 30 min and then the mixture was poured into water, forming an emulsion. This was extracted with DCM and the combined extracts were washed with water and passed through a hydrophobic frit. The aqueous was extracted with ethyl acetate and the combined organic solutions were washed with water and brine, dried (Na$_2$SO$_4$) and then combined with the initial DCM extracts and concentrated in vacuo to leave a brown oil. The residue was loaded in dichloromethane to a silica 100 g cartridge and purified by chromatography on Flashmaster eluting with 0-100% ethyl acetate-cyclohexane over 40 min. The appropriate fractions were combined and evaporated in vacuo to give the required product (665 mg, 56%) as a yellow powder. LCMS (System A) RT=1.02 min, ES+ve m/z 297 (M+H)$^+$.

Intermediate 45

5-Chloro-N-[1-[(3-cyanophenyl)methyl]-7-fluoro-4-(methyloxy)-1H-indazol-3-yl]-2-thiophenesulfonamide

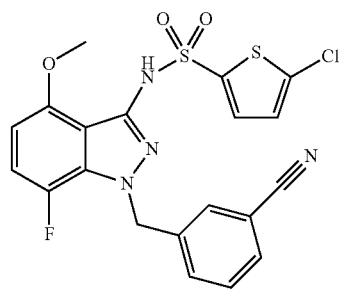 [SMILES: COc1ccc(F)c2c1c(NS(=O)(=O)c1ccc(Cl)s1)nn2Cc1cccc(C#N)c1]

To a solution of 3-{[3-amino-7-fluoro-4-(methyloxy)-1H-indazol-1-yl]methyl}benzonitrile (for a preparation see Intermediate 44) (665 mg, 2.24 mmol) in dry DCM (10 mL) was added 5-chloro-2-thiophenesulfonyl chloride (0.300 mL, 2.24 mmol), followed with pyridine (2 mL). The resultant dark yellow solution was stirred at room temperature overnight. More 5-chloro-2-thiophenesulfonyl chloride was added (0.100 mL) and the reaction stirred for a further 1 h.

The reaction mixture was partitioned between ethyl acetate and 2N hydrochloric acid. The aqueous phase was extracted with ethyl acetate (×2). The combined organic solutions were washed with water and brine, dried ($Na_2SO_4$) and concentrated in vacuo to leave a deep red oil. This residue was loaded in dichloromethane to a silica 100 g cartridge and purified by chromatography on Flashmaster eluting with a 0-100% ethyl acetate-dichloromethane over 40 min. The appropriate fractions were combined and evaporated in vacuo to give the title compound (323 mg, 30%) as a pale yellow powder. LCMS (System A) RT=1.2 min, ES+ve m/z 476/478 (M+H)$^+$.

Intermediate 46

N-[1-{[3-(Aminomethyl)phenyl]methyl}-7-fluoro-4-(methyloxy)-1H-indazol-3-yl]-5-chloro-2-thiophene-sulfonamide

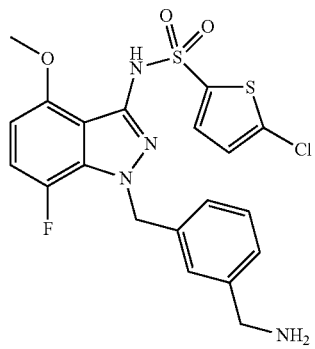 [SMILES: COc1ccc(F)c2c1c(NS(=O)(=O)c1ccc(Cl)s1)nn2Cc1cccc(CN)c1]

5-Chloro-N-[1-[(3-cyanophenyl)methyl]-7-fluoro-4-(methyloxy)-1H-indazol-3-yl]-2-thiophenesulfonamide (for a preparation see Intermediate 45)(600 mg, 1.26 mmol) was dissolved in THF (13 mL) and stirred in an ice bath. The solution was then treated dropwise with lithium aluminium hydride (1M in diethyl ether) (0.881 mL, 0.881 mmol) and stirred under nitrogen overnight. Further six portions of lithium aluminium hydride (1M in diethyl ether, 0.126 mL at a time) were added dropwise to the reaction and stirred for another day. The reaction was quenched with 2M NaOH solution (4 mL) and extracted with ethyl acetate (100 mL). The organic layer was washed with brine (100 mL) before being dried over anhydrous magnesium sulphate and evaporated in vacuo. The residue was dissolved in methanol and loaded onto a methanol conditioned sulfonic acid cartridge (SCX-2) 50 g. The cartridge was washed with methanol and eluted with 2M ammonia in methanol. Ammoniacal fractions were evaporated to give a brown gum (100 mg). The aqueous layer was back extracted with ethyl acetate (100 mL). The organic layer was washed with brine (100 mL) and dried over anhydrous magnesium sulphate before being evaporated in vacuo to give a brown gum (60 mg). The aqueous layer was back extracted with chloroform-isopropanol 3:1 (100 mL). The organic layer was dried over anhydrous magnesium sulphate before being evaporated in vacuo to a further 40 mg. The solids in the aqueous layer were collected by filtration. The solid was dissolved in methanol and filtered to remove any insoluble material. The filtrate was evaporated in vacuo to a further batch of 300 mg. The combined batches were dissolved in methanol and loaded onto a methanol pre-conditioned 50 g sulfonic acid (SCX-2) cartridge. The cartridge was washed with methanol and then eluted with 2M ammonia in methanol. Ammoniacal fractions were evaporated in vacuo to give the title compound as a brown gum (220 mg) LCMS (System A) RT=0.81 min, ES+ve m/z 481/483 (M+H)$^+$.

Intermediate 47

2,4-Difluoro-6-methoxybenzaldehyde

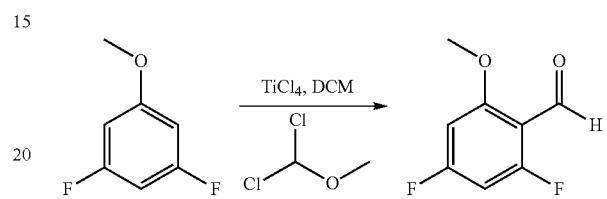

3,5-Difluoroanisole (50 g, 0.35 mol) was charged to a 3-neck flask fitted with thermometer, dropping funnel and argon bubbler. Dichloromethane (200 mL) was added and the solution was cooled in ice-water. Titanium (IV) chloride (61.5 mL, 0.56 mol) was added dropwise (15 min), followed by dropwise addition of α,α-dichloromethyl methyl ether (31.5 mL, 0.35 mol) so that the temperature was maintained <10° C. (approx 20 min). The reaction was stirred in ice-water for a further 140 min, poured into ice-water (1 L), then extracted thrice with DCM. The organic solutions were washed with water, brine then dried ($MgSO_4$) and evaporated. The crude product was purified using the Versaflash (80×300 mm $SiO_2$ cartridge, gradient from DCM to 5% EtOAc) in 7 separate batches to give the title compound (34.5 g, 57%) as an orange solid.

Intermediate 48

2,4-Difluoro-6-methoxybenzonitrile

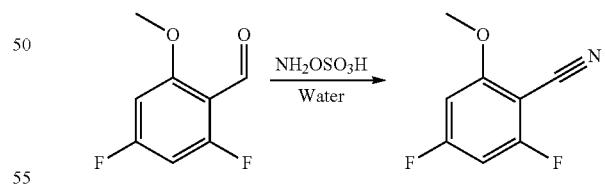

2,4-Difluoro-6-methoxybenzaldehyde (for a preparation see Intermediate 47) (34.5 g, 0.20 mol) and hydroxylamine-o-sulfonic acid (24.95 g, 0.22 mol) were charged to a round-bottom flask. Water (500 mL) was added and the suspension was heated at 110° C. for 3 h. After TLC shows reaction to be complete, it was cooled in ice-water and extracted thrice with ethyl acetate. The organic solutions were dried ($MgSO_4$) and evaporated, and the residue was purified by dry flash chromatography (DCM eluent) to give the title compound (32.05 g, 95%) as a pale pink solid.

Intermediate 49

6-Fluoro-4-methoxy-1H-indazol-3-amine

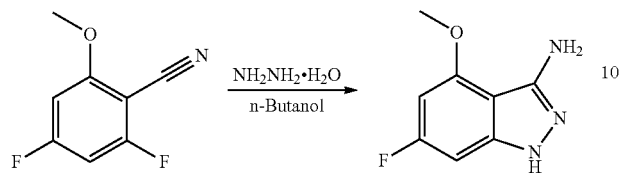

2,4-Difluoro-6-methoxybenzonitrile (for a preparation see Intermediate 48) (29.2 g, 0.17 mol) was suspended in n-butanol (250 mL) and hydrazine hydrate (16.6 mL, 0.34 mol) was added. The suspension was heated at 110° C. for 19 h, then 115° C. for 4 h. The reaction was allowed to cool and a solid formed overnight. The solid was collected by filtration, and washed with n-butanol. Solid is mainly an aryl hydrazine by-product (uncyclised or regioisomer). The filtrate was concentrated and azeotroped with toluene to give 15.6 g of crude product (84% by LCMS). The crude product was taken up in ~400 mL water, ~5 mL AcOH and ~350 mL ethyl acetate and any insoluble material was discarded. The organic layer was washed with water, dried (MgSO$_4$) and evaporated. The residue was taken up in hot ethyl acetate (75 mL, 55° C.) and heptane was added (20 mL). The solid was collected by filtration, washed with heptane. This was repeated twice to give the title compound (6.7 g, 21%) as a purple solid.

Intermediate 49

Alternative Preparation

To a solution of a 1:1 mixture of 2,4-difluoro-6-(methyloxy)benzonitrile (for a preparation see Intermediate 50) (5.15 g, 30.4 mmol) in anhydrous ethanol (50 mL) was added hydrazine hydrate (5.91 mL, 122 mmol) dropwise. The reaction was stirred at 80° C. under a nitrogen overnight. The reaction was cooled to room temperature, treated with acetone (20 mL) and left to stand for 18 hours. The mixture was evaporated in-vacuo and the residue was partitioned between saturated aqueous sodium hydrogen carbonate solution (50 mL) and dichloromethane (50 mL). Aqueous phase was further extracted with DCM (50 mL). The organic layers were combined and passed through a hydrophobic frit and evaporated in-vacuo to yield a brown solid, which was absorbed onto Florisil, and purified on a silica 100 g cartridge eluting with 0-100% B in A, A being neat CHCl$_3$ and B being a 10% MeOH in CHCl$_3$ over 60 min. The purest fractions were combined and evaporated in vacuo, and residue was loaded in a 1:1 mixture DMSO-MeOH and further purified by reverse phase (C18) chromatography on 330 g cartridge eluting with a gradient of acetonitrile (containing 0.1% NH$_3$)-water (containing 0.1% NH$_3$) starting from 5 to 35% over 3 CV, then from 35 to 55% in 8 CV, and from 55 to 85 over 4 CV. The appropriate fractions were combined and evaporated in vacuo to give the title compound (1.1 g, 20%) as a pale brown solid LCMS (System A) RT=0.58 min and 0.59 min, ES+ve m/z 182 (M+H)$^+$.

Intermediate 50

2,4-Difluoro-6-(methyloxy)benzonitrile and 2,6-difluoro-4-(methyloxy)benzonitrile

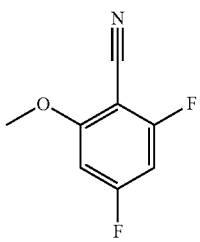

A solution of 2,4,6-trifluorobenzonitrile (10 g, 63.7 mmol) in methanol (30 mL) was treated dropwise at 0° C. with 30% sodium methoxide solution in methanol (12.13 mL, 63.7 mmol). The resulting mixture was stirred at room temperature for 2 h. The reaction mixture was evaporated in vacuo and the crude solid obtained was partitioned between water (100 mL) and EtOAc (100 mL). The organic layer was separated and the aqueous one was further extracted with EtOAc (100 mL). The combined organic solutions were washed with water (100 mL) and brine (100 mL), dried through an hydrophobic frit, and concentrated under reduced pressure. The sample was loaded in cyclohexane and dichloromethane (1:1) to a 750 g silica cartridge, and purified by chromatography on Flashmaster II eluting with 0-100% methyl tert-butyl ether—cyclohexane over 40 min. The appropriate fractions were combined and evaporated in vacuo to give a mixture of the expected product (2,4-difluoro-6-(methyloxy)benzonitrile) and its regioisomer (2,6-difluoro-4-(methyloxy)benzonitrile) (1:1) LCMS (System A) RT=0.92 min, 0.95 min, ES+ve m/z 170 (M+H)$^+$.

Intermediate 51

3-{[3-Amino-6-fluoro-4-(methyloxy)-1H-indazol-1-yl]methyl}benzonitrile

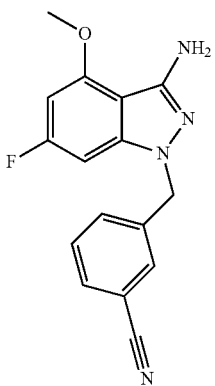 [SMILES: COc1cc(F)cc2c1c(N)nn2Cc1cccc(C#N)c1]

Potassium hydroxide (85% pure, 0.84 g, 12.7 mmol) was powdered and added to DMSO (25 mL) and the mixture was stirred for 5 min. A solution of 1:1 mixture of 6-fluoro-4-(methyloxy)-1H-indazol-3-amine and 4-fluoro-6-(methyloxy) regioisomer) (1.085 g, 6 mmol) in DMSO (5 mL) was added and the mixture was stirred for 5 min. The colour of the reaction mixture turned to dark red. Solid 3-(chloromethyl) benzonitrile (1.0 g, 7.1 mmol) was added and the mixture stirred for 1 h. The mixture was diluted with water, treated with 2M HCl (3 mL) and extracted with ethyl acetate. The organic solution was washed with water (4 times) and once with brine, dried (MgSO$_4$) and evaporated. The residue was dissolved in DCM and MeOH and pre-absorbed on florisil (5 g). The pre-absorbed compound was placed on two 100 g Silica cartridges and purified by chromatography on Flashmaster using a 0-100% ethyl acetate-cyclohexane over 60 min. The appropriate fractions (RT=48 min) were evaporated under reduced pressure to give impure title compound as an orange solid. This required further purification and was pre-absorbed on florisil and purified by chromatography on Flashmaster silica 100 g using a 0-100% ethyl acetate-cyclohexane over 100 min. The appropriate fractions (RT=46-70 min) were combined and evaporated in vacuo to give the title compound (362 mg, 20%) as a yellow solid: LCMS (System A) RT=0.96 min, ES+ve m/z 297 (M+H)$^+$, NMR δ (CDCl$_3$) 7.57-7.53 (1H, m), 7.43-7.38 (3H, m), 6.37 (1H, dd, J 10, 2 Hz), 6.15 (1H, dd, J 12, 2 Hz), 5.23 (2H, s), 4.45 (2H, br), 3.94 (3H, s).

Intermediates 52 and 53

5-Chloro-N-[1-[(3-cyanophenyl)methyl]-6-fluoro-4-(methyloxy)-1H-indazol-3-yl]-2-thiophenesulfonamide (Intermediate 52) and 5-chloro-N-[(5-chloro-2-thienyl)sulfonyl]-N-[1-[(3-cyanophenyl)methyl]-6-fluoro-4-(methyloxy)-1H-indazol-3-yl]-2-thiophenesulfonamide (Intermediate 53)

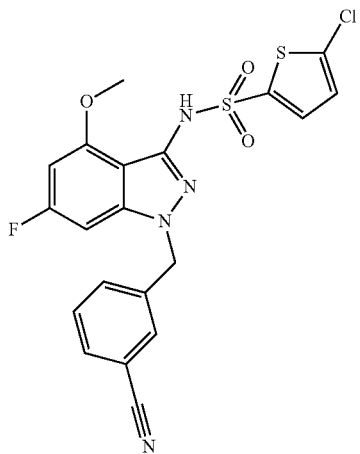 [SMILES: COc1cc(F)cc2c1c(NS(=O)(=O)c1ccc(Cl)s1)nn2Cc1cccc(C#N)c1]

A suspension of 3-{[3-amino-6-fluoro-4-(methyloxy)-1H-indazol-1-yl]methyl}benzonitrile (for a preparation see Intermediate 51) (362 mg, 1.22 mmol) in chloroform (6 mL) and pyridine (2 mL) was added to 5-chloro-2-thiophenesulfonyl chloride (398 mg, 1.83 mmol) at room temperature and the mixture was stirred for 5 h. The reaction mixture was partitioned between chloroform and 2M HCl solution. The organic phase was washed three times with HCl, dried (MgSO$_4$), and evaporated under reduced pressure. The residual gum (1 g) was dissolved in chloroform and applied to one silica 100 g cartridge and purified by chromatography on Flashmaster using a 0-100% ethyl acetate-cyclohexane over 60 min. The appropriate fractions were combined and evaporated in vacuo to give Intermediate 52 (260 mg, 45%) as an off-white solid. LCMS (System A) RT=1.17 min, ES+ve m/z 477/479 (M+H)$^+$. Less polar fractions were combined and evaporated to give 5-chloro-N-[(5-chloro-2-thienyl)sulfonyl]-N-[(3-cyanophenyl)methyl]-6-fluoro-4-(methyloxy)-1H-indazol-3-yl]-2-thiophenesulfonamide (Intermediate 53) (53 mg, 7%) LCMS (System A) RT=1.42 min, ES+ve m/z 657/659 (M+H)$^+$.

Intermediate 54

N-[1-{[3-(Aminomethyl)phenyl]methyl}-6-fluoro-4-(methyloxy)-1H-indazol-3-yl]-5-chloro-2-thiophenesulfonamide Formic Acid Salt

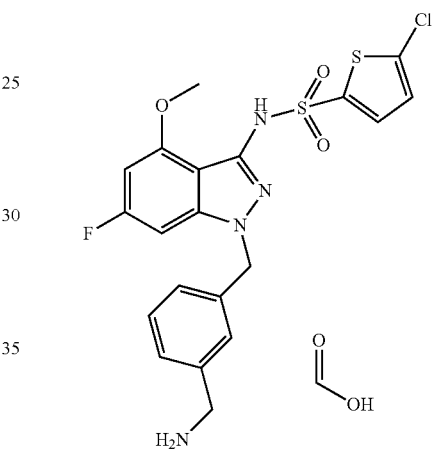

A solution of 5-chloro-N-[1-[(3-cyanophenyl)methyl]-6-fluoro-4-(methyloxy)-1H-indazol-3-yl]-2-thiophenesulfonamide (for a preparation see Intermediate 52) (260 mg, 0.54 mmol) in THF (10 mL) was cooled in an ice-bath and treated under nitrogen with a lithium aluminium hydride solution in ether (1M, 0.38 mL). After 3 h the reaction mixture was quenched by addition of 2M NaOH solution (1 mL) and the mixture was stirred under nitrogen for 0.5 h. The mixture was then partitioned between ethyl acetate and water, and the organic solution was evaporated under reduced pressure. The residue was dissolved in MeOH and applied to an ion-exchange SCX-2 cartridge eluting with MeOH, followed by 10% aqueous ammonia in MeOH. The ammoniacal solution was evaporated under reduced pressure to give impure product as a yellow solid (100.2 mg). The solid was treated with 2M HCl and chloroform was added. An emulsion formed which was concentrated under reduced pressure, and the residue was dissolved in MeOH-DMSO (1:1) (2 mL) and purified by Mass Directed AutoPrep on Sunfire C18 column using Acetonitrile Water with a Formic acid modifier (Method A) collecting fraction with RT=6 min. The solvent was evaporated in vacuo to give the title compound (53 mg, 18%) as the formate salt. LCMS (System A) RT=0.82 min, ES+ve m/z 481/483 (M+H)$^+$.

Intermediate 55

3,6-Difluoro-2-methoxy-benzonitrile

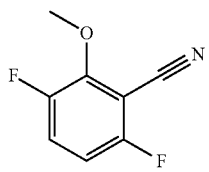

Methanol (600 mL) was treated portionwise with sodium (Alfa, 16.1 g, 0.702 gatoms, 1.05 equiv.). The sodium methoxide solution was cooled to room temperature and added dropwise to a solution of 2,3,6-trifluorobenzonitrile (Matrix, 105 g, 0.699 mol) in methanol (600 ml) at room temperature. After addition was complete the mixture was stirred for 1 hour at room temperature before removing the methanol under reduced pressure. The residue was partitioned between diethyl ether (500 ml) and water (500 mL). The organic layer was removed, dried over MgSO$_4$, filtered and evaporated to give the crude product. This was purified by distillation using a 6" vigreux column @ 20 mmHg, oil bath 160° C., head temp 120° C. to give the title compound as a white solid (108 g, 91%)

Intermediate 56

5-Fluoro-4-(methyloxy)-1H-indazol-3-amine

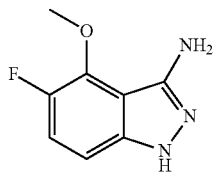

A mixture of 3,6-difluoro-2-methyloxybenzonitrile (for a preparation see Intermediate 55) (30 g, 184 mmol) in ethanol (300 mL) was reacted with Hydrazine Monohydrate (Alfa, 89 mL, 1.84 mol, 10 equiv.). The resulting mixture was heated at reflux overnight then allowed to cool to room temperature. Silica was added to the mixture which was then evaporated to dryness. The pre-absorbed crude reaction mixture was then purified by chromatography eluting with petrol up to EtOAc (10% steps, 500 mL per step) to give the title compound (8.4 g, 25%) as a yellow solid.

Intermediate 57

3-{[3-Amino-5-fluoro-4-(methyloxy)-1H-indazol-1-yl]methyl}benzonitrile

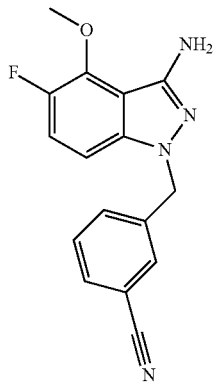 [SMILES: COc1c(F)ccc2c1c(N)nn2Cc1cccc(C#N)c1]

Finely ground potassium hydroxide (6.59 g, 118 mmol, 2.5 equiv.) was treated with DMSO (100 mL). To this was added 5-fluoro-4-(methyloxy)-1H-indazol-3-amine (for a preparations see Intermediate 56) (8.5 g, 47 mmol) and the mixture stirred at room temperature for 50 minutes. To the red coloured mixture was added 3-chloromethyl benzonitrile (8.9 g, 59 mmol, 1.25 equiv.) in one portion. A small exotherm of −5° C. was observed. The mixture was allowed to stir at room temperature for 25 minutes before pouring into water (600 mL) and extracting with chloroform (400 mL). The aqueous was re-extracted with chloroform (2×400 mL). The organic extracts were combined, washed with water (3×500 mL), dried over MgSO$_4$, filtered and evaporated to give the crude product. This was dry loaded onto silica and chromatographed eluting with 20% petrol up to 70% EtOAc-petrol. The material came off impure so was re-chromatographed on a suction column. The impure material was loaded in DCM and eluted with DCM up to 30% EtOAc-DCM to give the title compound (8.25 g, 48%) as an off-white solid. LCMS (System A) RT=0.96 min, ES+ve m/z 297 (M+H)$^+$.

Intermediate 58

3-{[3-Amino-5-fluoro-4-(methyloxy)-1H-indazol-1-yl]methyl}benzonitrile

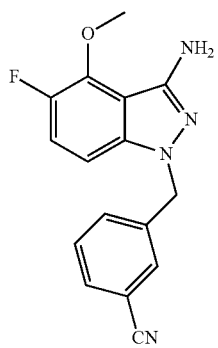 [SMILES: COc1c(F)ccc2c1c(N)nn2Cc1cccc(C#N)c1]

To a solution of 3-{[3-amino-5-fluoro-4-(methyloxy)-1H-indazol-1-yl]methyl}benzonitrile (for a preparation see Intermediate 57) (470 mg, 1.59 mmol) in dry DCM (3 mL) and pyridine (1 mL, 12 mmol) was added 5-chloro-2-thiophenesulfonyl chloride (517 mg, 2.38 mmol). The reaction mixture was stirred at room temperature overnight. The reaction mixture was partitioned between ethyl acetate (15 mL) and 2 M hydrochloric acid (15 mL). The aqueous was extracted with ethyl acetate and the combined organic solutions washed with water and brine, passed through a hydrophic frit and then concentrated in vacuo to leave a dark red oil. This was loaded in dichloromethane on to a silica 100 g cartridge and purified by chromatography on Flashmaster eluting with 0-100% ethyl acetate-cyclohexane over 40 min. The appropriate fractions were combined and evaporated in vacuo to give the title compound (206 mg, 27%) as a pale brown powder. LCMS (System A) RT=1.17 min ES+ve m/z 477/479 (M+H)$^+$.

Intermediate 59

1,1-Dimethylethyl[(3-{[3-amino-5-fluoro-4-(methyloxy)-1H-indazol-1-yl]methyl}phenyl)methyl]carbamate

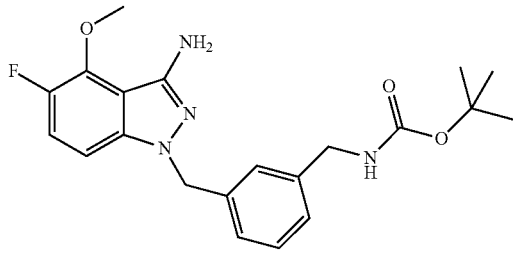 [SMILES: COc1c(F)ccc2c1c(N)nn2Cc1cccc(CNC(=O)OC(C)(C)C)c1]

3-{[3-Amino-5-fluoro-4-(methyloxy)-1H-indazol-1-yl]methyl}benzonitrile (for a preparation see Intermediate 58) (5 g, 16.9 mmol), Nickel (II) chloride (4.37 g, 33.7 mmol) and di-tert-butyl dicarbonate (5.52 g, 25.3 mmol) were dissolved in a mixture of THF (75 mL) and Methanol (113 mL). The reaction was cooled to −10° C. and sodium borohydride (4.47 g, 118 mmol) was added portion wise to the reaction. The reaction was left to stir at room temperature overnight. LCMS showed no starting material remaining so the reaction mixture was concentrated in vacuo to give a black residue. The residue was dissolved in ethyl acetate (500 mL) and washed 3 times with water (500 mL). The organic layer was washed with brine (500 mL) and dried over anhydrous magnesium sulfate before being evaporated in vacuo to give a residue (5.5 g). A 500 mg portion of the residue was dissolved in dichloromethane, loaded onto a 20 g silica cartridge and purified by chromatography on Flashmaster II using a 0-100% ethyl acetate-cyclohexane gradient over 30 min. Appropriate fractions were combined and the solvent was evaporated. The remaining residue was dissolved in dichloromethane and loaded onto two 100 g silica cartridges and purified on Flashmaster II using a 0-100% ethyl acetate-cyclohexane gradient over 60 min. Appropriate fractions were combined and the solvent was evaporated. The products from all three columns were combined to give the title compound (4.4 g, 65%) as a yellow solid. LCMS (System A) RT=1.08 min, ES+ve m/z 401 (M+H)$^+$.

Intermediate 60

1,1-Dimethylethyl[(3-{[3-{[(5-chloro-2-thienyl)sulfonyl]amino}-5-fluoro-4-(methyloxy)-1H-indazol-1-yl]methyl}phenyl)methyl]carbamate

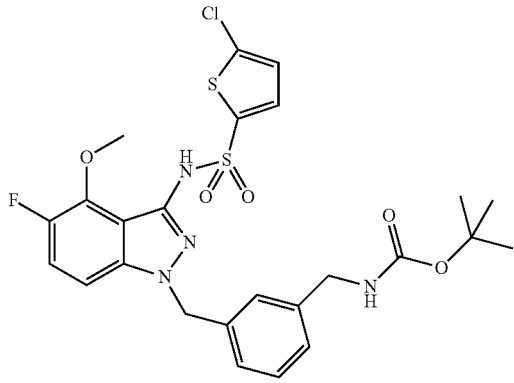 [SMILES: COc1c(F)ccc2c1c(NS(=O)(=O)c1ccc(Cl)s1)nn2Cc1cccc(CNC(=O)OC(C)(C)C)c1]

1,1-Dimethylethyl[(3-{[3-amino-5-fluoro-4-(methyloxy)-1H-indazol-1-yl]methyl}phenyl)methyl]carbamate (for a preparation see Intermediate 59) (3.4 g, 8.49 mmol) was dissolved in a mixture of dichloromethane (14 mL) and pyridine (21 mL) and the reaction was left to stir under nitrogen for 2 h. LCMS showed starting material remaining, so an extra portion of 5-chloro-2-thiophenesulfonyl chloride (0.461 g, 2.12 mmol) was added to the reaction mixture and stirred for 45 min. The reaction mixture was evaporated in vacuo and the residue was dissolved in ethyl acetate (250 mL) and washed with water (3×250 mL). The organic layer was washed once with brine (200 mL) and dried over anhydrous magnesium sulfate before being evaporated in vacuo. The residue was dissolved in dichloromethane, loaded onto a 100 g silica cartridge and purified by chromatography on Flashmaster II using a 0-100% ethyl acetate-cyclohexane gradient over 80 min. Appropriate fractions were combined and the solvent was evaporated to give the title compound (2.7 g, 55%) as an orange solid. LCMS (System A) RT=1.27 min, ES+ve m/z 581/583 (M+H)$^+$.

Intermediate 61

N-[1-{[3-(Aminomethyl)phenyl]methyl}-5-fluoro-4-(methyloxy)-1H-indazol-3-yl]-5-chloro-2-thiophenesulfonamide

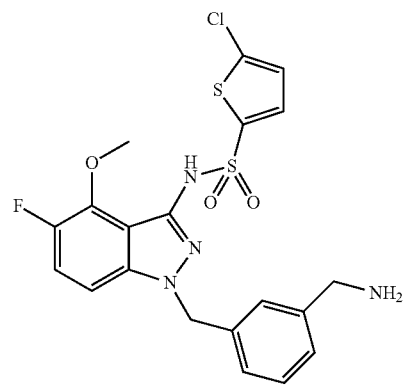 [SMILES: COc1c(F)ccc2c1c(NS(=O)(=O)c1ccc(Cl)s1)nn2Cc1cccc(CN)c1]

1,1-Dimethylethyl[(3-{[3-{[(5-chloro-2-thienyl)sulfonyl]amino}-5-fluoro-4-(methyloxy)-1H-indazol-1-yl]methyl}phenyl)methyl]carbamate (for a preparation see Intermediate 60) (2.7 g, 4.65 mmol) was dissolved in dichloromethane (20 mL). Trifluoroacetic acid (5.00 mL) was added to the reaction and stirred for 1 h. The reaction mixture was concentrated in vacuo to leave a purple residue. The residue was dissolved in methanol and loaded onto a methanol pre-conditioned SCX-2 ion-exchange cartridge (70 g). The cartridge was washed well with methanol, followed by HCl in methanol, then methanol and finally ammonia in methanol. Fractions were combined and evaporated in vacuo to give an off white solid, which was dissolved in DMSO, filtered and loaded onto a methanol pre-conditioned SCX-2 ion-exchange cartridge (70 g). The cartridge was washed well with Methanol followed by 2M ammonia in methanol. Evaporation of the solvent from the ammoniacal fractions gave the title compound (1 g, 45%) as a white solid: LCMS (System A) RT=0.84 min, ES+ve m/z 481/483 (M+H)$^+$.

Intermediate 62

3-Amino-1H-indazole-4-carbonitrile

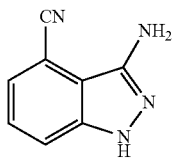 [SMILES: N#Cc1cccc2[nH]nc(N)c12]

3-Fluoro-1,2-benzenedicarbonitrile (APIN) (5 g, 34.2 mmol) was dissolved in ethanol (80 mL) and hydrazine monohydrate (4.98 mL, 103 mmol) was added to the solution. The reaction was heated at 70° C. overnight. The reaction mixture was concentrated in vacuo and the residue was partitioned between ethyl acetate (200 mL) and water (200 mL). The organic layer was washed with water (100 mL). The aqueous layers were extracted with ethyl acetate (200 mL). Organic layers were combined, dried over anhydrous magnesium sulfate and evaporated in vacuo to give the title compound (4.7 g, 87%) as a yellow solid. LCMS (System A) RT=0.53 min, ES+ve m/z 159 (M+H)+.

Intermediate 63

1,1-Dimethylethyl 3-amino-4-cyano-1H-indazole-1-carboxylate

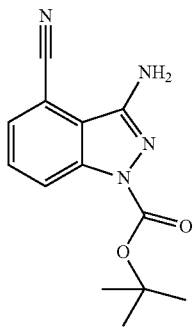 [SMILES: CC(C)(C)OC(=O)n1nc(N)c2c(C#N)cccc21]

Di-tert-butyl dicarbonate (7.13 g, 32.7 mmol) in dichloromethane (150 mL) was added to a solution of 3-amino-1H-indazole-4-carbonitrile (for a preparation see Intermediate 62) (4.7 g, 29.7 mmol), 4-dimethylaminopyridine (0.726 g, 5.94 mmol) and triethylamine (8.28 mL, 59.4 mmol) in acetonitrile (150 mL) and stirred for 0.5 h under nitrogen. LCMS showed no starting material remaining so the reaction mixture was concentrated in vacuo to give a residue which was partitioned between DCM (250 mL) and water (250 mL). The organic layer was washed a further two times with water (250 mL) and once with brine (200 mL) before being dried over anhydrous magnesium sulfate and evaporated in vacuo to give the title compound (4.3 g, 56%) as a yellow solid. LCMS (System A): RT=0.94 min, ES+ve m/z 259 (M+H)+.

Intermediate 64

1,1-Dimethylethyl 3-{bis[(5-chloro-2-thienyl)sulfonyl]amino}-4-cyano-1H-indazole-1-carboxylate

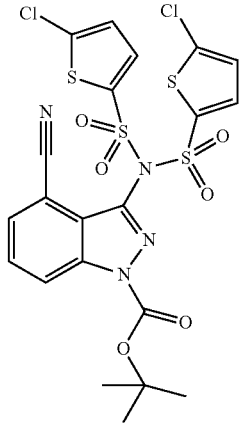 [SMILES: CC(C)(C)OC(=O)n1nc(N(S(=O)(=O)c2ccc(Cl)s2)S(=O)(=O)c2ccc(Cl)s2)c2c(C#N)cccc21]

1,1-Dimethylethyl 3-amino-4-cyano-1H-indazole-1-carboxylate (for a preparation see Intermediate 63) (4.3 g, 16.65 mmol) was dissolved in a mixture of dichloromethane (40 mL) and pyridine (40 mL). 5-Chloro-2-thiophenesulfonyl chloride (7.23 g, 33.3 mmol) was added to the solution and it was stirred at 45° C. under nitrogen for 60 h. LCMS showed approx 30% starting material remaining, so further quantity of 5-chloro-2-thiophenesulfonyl chloride (3.5 g, 16.12 mmol) was added to the reaction, and the mixture was stirred for 2 h. LCMS showed no change in product so the reaction was concentrated under vacuo. The residue was dissolved in DCM (200 mL) and washed 3 times with water (200 mL). The organic layer was dried over anhydrous magnesium sulfate and evaporated in vacuo. The residue (10 g) was dissolved in DCM and loaded onto a 750 g silica column and purified by chromatography on the Companion system using a 0-25% ethyl acetate-DCM gradient. Appropriate fractions were evaporated in vacuo to give the title compound (5.8 g, 56%) as an orange solid. LCMS (System A) RT=1.45 min, ES+ve m/z 636/638 (M+NH4)+.

Intermediate 65

5-Chloro-N-[(5-chloro-2-thienyl)sulfonyl]-N-(4-cyano-1H-indazol-3-yl)-2-thiophenesulfonamide

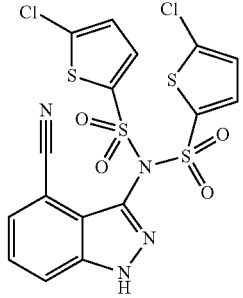 [SMILES: N#Cc1cccc2[nH]nc(N(S(=O)(=O)c3ccc(Cl)s3)S(=O)(=O)c3ccc(Cl)s3)c12]

1,1-Dimethylethyl 3-{bis[(5-chloro-2-thienyl)sulfonyl]amino}-4-cyano-1H-indazole-1-carboxylate (for a preparation see Intermediate 64) (5.6 g, 9.04 mmol) was dissolved in a mixture of dichloromethane (44 mL) and trifluoroacetic acid (11 mL) and stirred for 40 min. LCMS showed starting material remaining so the reaction was left to stir for a further 30 min. LCMS showed no starting material remaining so the mixture was evaporated in vacuo to give a cream solid (5.7 g).

A portion of this solid (1 g) of was adsorbed onto florisil and loaded onto a 50 g silica cartridge and purified by chromatography on Flashmaster II using a 0-100% ethyl acetate cyclohexane gradient over 80 min. Appropriate fractions were combined and evaporated to give the title compound (400 mg, 9%). The rest of the residue was dissolved in THF and loaded onto a 360 g pre-conditioned C18 cartridge and purified on a 50-99% acetonitrile-water gradient with an ammonium carbonate modifier. Appropriate fractions were combined and evaporated in vacuo to give the title compound (1.6 g, 34%) as a yellow solid. LCMS (System A) RT=1.20 min, ES+ve m/z 536/538 (M+NH$_4$)$^+$.

Intermediate 66

1,1-Dimethylethyl {[3-(hydroxymethyl)phenyl]methyl}carbamate

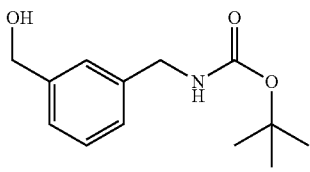 [SMILES: CC(C)(C)OC(=O)NCc1cccc(CO)c1]

3-(Hydroxymethyl)benzonitrile (1 g, 7.51 mmol), Nickel (II) Chloride (0.973 g, 7.51 mmol) and di-tert-butyl dicarbonate (3.28 g, 15.02 mmol) were dissolved in a solution of methanol (48 mL) and THF (32 mL) and cooled to 0° C. in an ice-bath. Sodium borohydride (1.989 g, 52.6 mmol) was added portionwise and the mixture was stirred for 3 h. LCMS showed the reaction had gone to completion so the reaction mixture was evaporated in vacuo to leave a black residue. The residue was partitioned between ethyl acetate (100 mL) and water (100 mL). The aqueous layer was washed a further two times with ethyl acetate (100 mL). The combined organic solutions were washed with brine (100 mL) and dried over anhydrous magnesium sulfate before being evaporated in vacuo. The residue was dissolved in dichloromethane, loaded onto a 100 g silica cartridge and purified by chromatography on Flashmaster II using a 0-100% ethyl acetate-cyclohexane gradient over 80 min. Appropriate fractions were combined and the solvent was evaporated to give the title compound (1.248 g, 70%) as a colourless oil. LCMS (System A) RT=0.82 min.

Intermediate 67

1,1-Dimethylethyl({3-[(3-{bis[(5-chloro-2-thienyl)sulfonyl]amino}-4-cyano-1H-indazol-1-yl)methyl]phenyl}methyl)carbamate

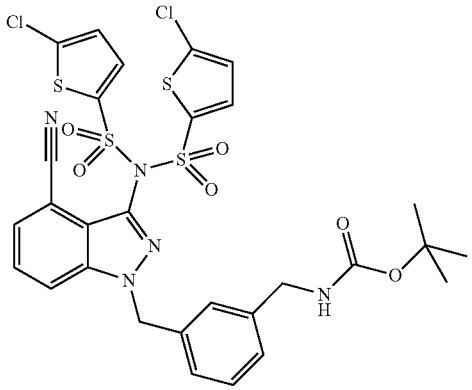 [SMILES: CC(C)(C)OC(=O)NCc1cccc(Cn2nc(N(S(=O)(=O)c3ccc(Cl)s3)S(=O)(=O)c3ccc(Cl)s3)c3c(C#N)cccc32)c1]

5-Chloro-N-[(5-chloro-2-thienyl)sulfonyl]-N-(4-cyano-1H-indazol-3-yl)-2-thiophenesulfonamide (for a preparation see Intermediate 65) (1.1 g, 2.118 mmol), triphenylphosphine (1.111 g, 4.24 mmol) and 1,1-dimethylethyl {[3-(hydroxymethyl)phenyl]methyl}carbamate (for a preparation see Intermediate 66) (1.005 g, 4.24 mmol) were suspended in tetrahydrofuran (10 mL) and treated with DIAD (0.824 mL, 4.24 mmol). The reaction mixture became homogeneous and was stirred at 60° C. for 1 h. LCMS showed no starting material remaining so the solution was concentrated in vacuo, and the residue was partitioned between ethyl acetate (100 mL) and water (100 mL). The organic layer was washed two further times with water (100 mL) and once with brine (100 mL) before being dried over anhydrous magnesium sulfate and evaporated in vacuo to give a yellow oil (4 g). The residue was dissolved in DCM and loaded onto two 100 g silica cartridges and purified by chromatography on Flashmaster II using a 0-100% ethyl acetate-cyclohexane gradient over 80 min. Appropriate fractions were combined and the solvent was evaporated to give the title compound (1.5 g, 96%) as a yellow oil. LCMS (System A) RT=1.48 min, ES+ve m/z 755/757 (M+NH$_4$)$^+$.

Intermediate 68

1,1-Dimethylethyl({3-[(3-{bis[(5-chloro-2-thienyl)sulfonyl]amino}-4-formyl-1H-indazol-1-yl)methyl]phenyl}methyl)carbamate

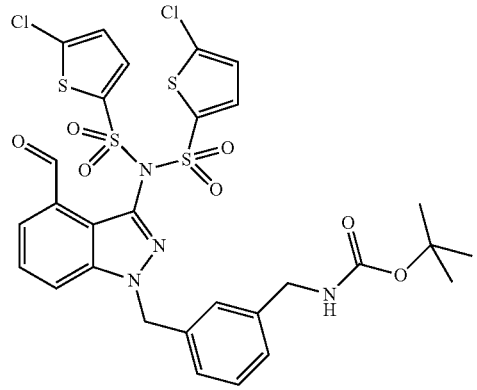 [SMILES: CC(C)(C)OC(=O)NCc1cccc(Cn2nc(N(S(=O)(=O)c3ccc(Cl)s3)S(=O)(=O)c3ccc(Cl)s3)c3c(C=O)cccc32)c1]

1,1-Dimethylethyl({3-[(3-{bis[(5-chloro-2-thienyl)sulfonyl]amino}-4-cyano-1H-indazol-1-yl)methyl]phenyl}methyl)carbamate (for a preparation see Intermediate 67) (1.5 g, 2.031 mmol) was dissolved in toluene (5 mL) and cooled to −10° C. DIBAL-H (4.06 mL, 6.09 mmol) was added over 1 h, monitoring the temperature and keeping it under 0° C. The reaction was stirred for 75 min, and then more DIBAL-H (1.354 mL, 2.031 mmol) was added dropwise, and the reaction mixture was stirred overnight. LCMS showed some starting material remaining so the reaction was cooled to −10° C. and DIBAL-H (0.677 mL, 1.015 mmol) was added dropwise and the reaction was stirred for 90 min. LCMS showed only 5% starting material remaining so the reaction was quenched with methanol, acidified to pH3 with 5M HCl and neutralised with 2M NaOH. The mixture was extracted with ethyl acetate (100 mL). The organic layer was washed 3 times with water (100 mL) and once with brine (100 mL), before being dried over anhydrous magnesium sulfate and evaporated in vacuo to give a yellow foam (1.4 g). A portion of this (200 mg) was dissolved in DCM and loaded onto a 50 g silica cartridge and purified by chromatography on Flashmaster II using a 0-100% ethyl acetate-cyclohexane gradient over 60 min. The sample degraded on the silica and the rest of the product was used in the next step without any further purification.

Intermediate 69

1,1-Dimethylethyl[(3-{[3-{bis[(5-chloro-2-thienyl)sulfonyl]amino}-4-(difluoromethyl)-1H-indazol-1-yl]methyl}phenyl)methyl]carbamate

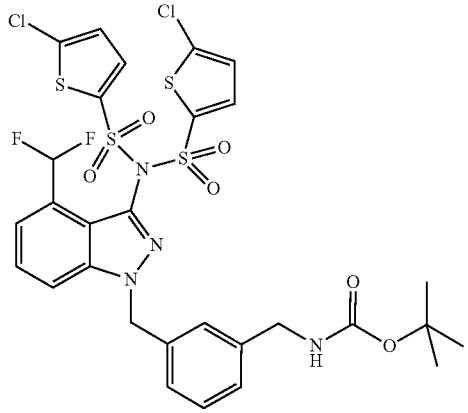 [SMILES: CC(C)(C)OC(=O)NCc1cccc(Cn2nc(N(S(=O)(=O)c3ccc(Cl)s3)S(=O)(=O)c3ccc(Cl)s3)c3c(C(F)F)cccc32)c1]

1,1-Dimethylethyl({3-[(3-{bis[(5-chloro-2-thienyl)sulfonyl]amino}-4-formyl-1H-indazol-1-yl)methyl]phenyl}methyl)carbamate (for a preparation see Intermediate 68) (400 mg, 0.539 mmol) was dissolved in dichloromethane (6 mL). (Diethylamino)sulfur trifluoride (DAST) (Aldrich) (0.107 mL, 0.809 mmol) was added to the solution and it was stirred for 5 h. Further portion of DAST (0.071 mL, 0.539 mmol) was added to the reaction mixture and stirred overnight. The reaction mixture was treated with water (2 mL) and stirred 15 min. The reaction mixture was diluted with DCM (50 mL), washed three times with water (50 mL) and once with brine (50 mL) before being dried over anhydrous magnesium sulfate and evaporated in vacuo. The residue (200 mg) was dissolved in dichloromethane, loaded onto a 50 g silica cartridge and purified by chromatography on Flashmaster II using a 0-100% ethyl acetate-cyclohexane gradient over 80 min. Appropriate fractions were combined and the solvent was evaporated to give the title compound (60 mg, 15%) as a yellow solid. LCMS (System A) RT=1.48 min, ES+ve m/z 780/782/784 $(M+NH_4)^+$.

Intermediate 70

N-[1-{[3-(Aminomethyl)phenyl]methyl}-4-(difluoromethyl)-1H-indazol-3-yl]-5-chloro-N-[(5-chloro-2-thienyl)sulfonyl]-2-thiophenesulfonamide

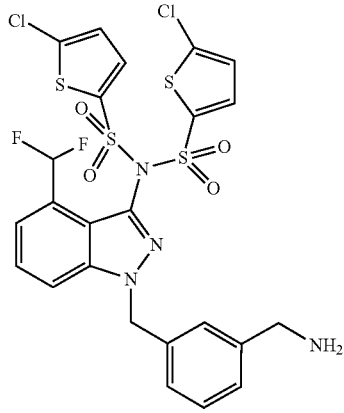 [SMILES: NCc1cccc(Cn2nc(N(S(=O)(=O)c3ccc(Cl)s3)S(=O)(=O)c3ccc(Cl)s3)c3c(C(F)F)cccc32)c1]

1,1-Dimethylethyl[(3-{[3-{bis[(5-chloro-2-thienyl)sulfonyl]amino}-4-(difluoromethyl)-1H-indazol-1-yl]methyl}phenyl)methyl]carbamate (for a preparation see Intermediate 69) (60 mg, 0.079 mmol) was dissolved in dichloromethane (0.5 mL) and trifluoroacetic acid (0.125 mL) was added to the solution. and stirred for 1 h under nitrogen. The solution was concentrated under a stream of nitrogen and the off-white residue was dissolved in methanol and loaded onto a methanol conditioned sulphonic acid (SCX-2) cartridge (10 g). The cartridge was washed well with methanol, followed by 2M ammonia in methanol. Evaporation of the solvent from the ammoniacal fractions gave the title compound (26 mg, 54%) as a white solid. LCMS (System A) RT=1.11 min, ES+ve m/z 663/665 $(M+H)^+$.

Intermediate 71

1,1-Dimethylethyl[(3-{[3-{bis[(5-chloro-2-thienyl)sulfonyl]amino}-4-(hydroxymethyl)-1H-indazol-1-yl]methyl}phenyl)methyl]carbamate

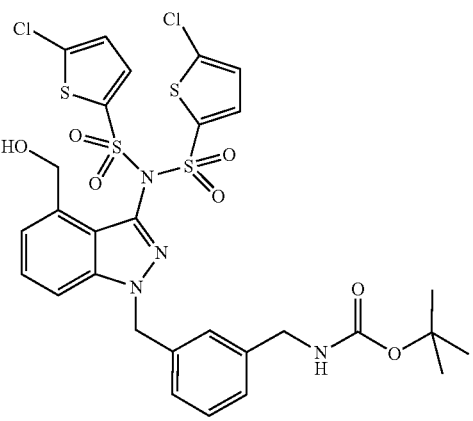 [SMILES: CC(C)(C)OC(=O)NCc1cccc(Cn2nc(N(S(=O)(=O)c3ccc(Cl)s3)S(=O)(=O)c3ccc(Cl)s3)c3c(CO)cccc32)c1]

1,1-Dimethylethyl({3-[(3-{bis[(5-chloro-2-thienyl)sulfonyl]amino}-4-formyl-1H-indazol-1-yl)methyl]phenyl}methyl)carbamate (for a preparation see Intermediate 68) (400 mg, 0.539 mmol) was dissolved in methanol (3 mL) and sodium borohydride (30.6 mg, 0.809 mmol) was added portionwise to the solution and the reaction mixture was stirred under nitrogen at room temperature for 3 h. The reaction mixture was concentrated under vacuo and partitioned between ethyl acetate (50 mL) and water (50 mL). The organic layer was washed 2 times with water (50 mL) and once with brine (50 mL) before being dried over anhydrous magnesium sulfate and evaporated in vacuo. The residue was dissolved in dichloromethane, loaded onto a 50 g silica cartridge and purified by chromatography on Flashmaster II using a 0-100% ethyl acetate-cyclohexane gradient over 80 min. Appropriate fractions were combined and the solvent was evaporated to give the title compound (67 mg, 17%) as an off-white gum. LCMS (System A) RT=1.35 min, ES+ve m/z 743/745 $(M+H)^+$.

Intermediate 72

N-[1-{[3-(Aminomethyl)phenyl]methyl}-4-(hydroxymethyl)-1H-indazol-3-yl]-5-chloro-N-[(5-chloro-2-thienyl)sulfonyl]-2-thiophenesulfonamide

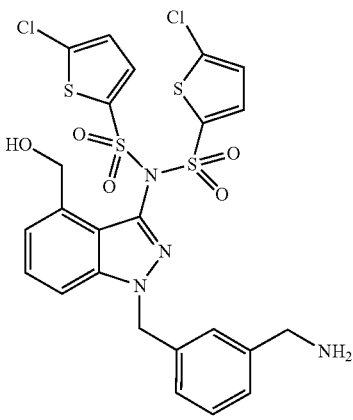 [SMILES: NCc1cccc(Cn2nc(N(S(=O)(=O)c3ccc(Cl)s3)S(=O)(=O)c3ccc(Cl)s3)c3c(CO)cccc32)c1]

1,1-Dimethylethyl[(3-{[3-{bis[(5-chloro-2-thienyl)sulfonyl]amino}-4-(hydroxymethyl)-1H-indazol-1-yl]methyl}phenyl)methyl]carbamate (for a preparation see Intermediate 71) (93 mg, 0.125 mmol) was dissolved in dichloromethane (0.5 mL), trifluoroacetic acid (0.125 mL) was added to the solution and stirred for 1 h under nitrogen. The reaction mixture was concentrated under a stream of nitrogen and the residue was dissolved in methanol and loaded onto a methanol pre-conditioned sulphonic acid (SCX-2) cartridge (10 g). The cartridge was washed well with methanol, followed by 2M ammonia in methanol. Evaporation of the solvent from the ammoniacal fractions gave the title compound (53 mg, 66%) as a white solid. LCMS (System A) RT=0.89 min, ES+ve m/z 643/645 (M+H)$^+$.

Intermediate 73

1,1-Dimethylethyl({3-[(3-{[(5-chloro-2-thienyl)sulfonyl]amino}-4-cyano-1H-indazol-1-yl)methyl]phenyl}methyl)carbamate (

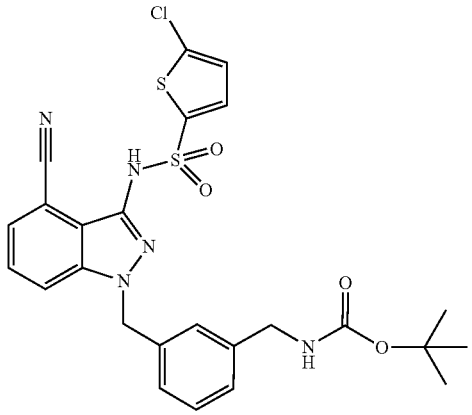 [SMILES: CC(C)(C)OC(=O)NCc1cccc(Cn2nc(NS(=O)(=O)c3ccc(Cl)s3)c3c(C#N)cccc32)c1]

2M Sodium hydroxide (54.8 mL, 40.6 mmol) was added to 1,1-dimethylethyl({3-[(3-{bis[(5-chloro-2-thienyl)sulfonyl]amino}-4-cyano-1H-indazol-1-yl)methyl]phenyl}methyl)carbamate (for a preparation see Intermediate 68) (5.4 g, 7.3 mmol) dissolved in methanol (100 mL) and THF (20 mL) and the reaction was stirred at 45° C. for 1 h. The solvents were evaporated in vacuo and the product was extracted with EtOAc (300 mL×2). The combined organic layers were washed with 1M HCl (150 mL), brine (100 mL), dried by passing through a hydrophobic frit, and concentrated to afford the crude title compound as a white solid. LCMS (System A) RT=1.17 min, ES+ve m/z 558/560 (M+H)$^+$.

Intermediate 74

N-({3-[(3-{[(5-Chloro-2-thienyl)sulfonyl]amino}-4-cyano-1H-indazol-1-yl)methyl]phenyl}methyl)acetamide

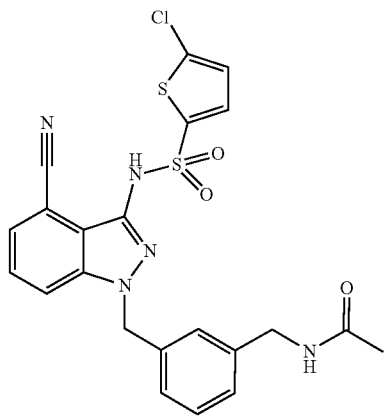 [SMILES: CC(=O)NCc1cccc(Cn2nc(NS(=O)(=O)c3ccc(Cl)s3)c3c(C#N)cccc32)c1]

TFA (1 mL) was added to 1,1-dimethylethyl({3-[(3-{[(5-chloro-2-thienyl)sulfonyl]amino}-4-cyano-1H-indazol-1-yl)methyl]phenyl}methyl)carbamate (for a preparation see Intermediate 73) (630 mg, 1.13 mmol) in DCM (4 mL) and the reaction was stirred at room temperature for 30 min. LCMS showed the boc group was removed and the reaction mixture was concentrated. The residue was dissolved in DCM (7 mL), triethylamine (1.573 mL, 11.29 mmol) and acetic anhydride (0.128 mL, 1.355 mmol) were added, and the reaction mixture was stirred for 30 min. The reaction was treated with water (10 mL) and the product was extracted with DCM (2×30 mL). The combined organic layers were dried by passing through a hydrophobic frit and concentrated to afford the crude product as a yellow oil (0.57 g). The residue was purified by chromatography on Flashmaster (silica 20 g cartridge), eluting with a gradient 25-100% EtOAc in DCM, followed by 0-30% MeOH in DCM) and the appropriate fractions were combined and concentrated to afford the title compound as a white solid (44 mg, 7%). Other fractions from the column were combined and concentrated to afford a yellow oil, (0.25 g), which was dissolved in MeOH (5 mL), potassium carbonate (300 mg) was added and the mixture was stirred at room temp for 30 min. LCMS showed one of the two acetyl groups was cleaved to afford more of the desired product. The mixture was concentrated and acidified with 2N HCl. The product was extracted with EtOAc (3×15 mL) and the combined organic layers were washed with saturated brine (5 mL), dried using a hydrophobic frit and evaporated in vacuo to give the crude product as a brown oil. The residue was dissolved in DMSO (1 mL) and purified by Mass Directed AutoPrep on Sunfire C18 column using Acetonitrile Water with a Formic acid modifier (Method A). The solvent was evaporated in vacuo to give the title compound (70 mg, 12%). LCMS (System A) RT=0.92 min, ES+ve m/z 500/502 (M+H)$^+$.

Intermediate 75

N-({3-[(4-Acetyl-3-{[(5-chloro-2-thienyl)sulfonyl]amino}-1H-indazol-1-yl)methyl]phenyl}methyl)acetamide

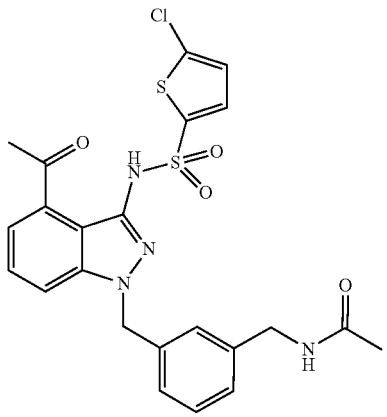 [SMILES: CC(=O)NCc1cccc(Cn2nc(NS(=O)(=O)c3ccc(Cl)s3)c3c(C(C)=O)cccc32)c1]

Methylmagnesium bromide (3M solution in diethyl ether) (0.176 mL, 0.528 mmol) was added slowly to a stirring solution of N-({3-[(3-{[(5-chloro-2-thienyl)sulfonyl]amino}-4-cyano-1H-indazol-1-yl)methyl]phenyl}methyl)acetamide (for a preparation see Intermediate 74) (44 mg, 0.088 mmol) in tetrahydrofuran (1 mL) at room temp. The reaction was stirred for 2 hours. LCMS showed starting material still remaining, so more methylmagnesium bromide (3M solution in diethyl ether) (0.176 mL, 0.528 mmol) was added and stirred at room temp. overnight. LCMS showed no more starting material remaining. The reaction mixture was cooled to 0° C., 0.5M HCl (4 mL) was added and the product was extracted with EtOAc (10 mL×3). The combined organic layers were washed with brine, dried by passing through a hydrophobic frit, and concentrated in vacuo to give the title compound as a yellow oil. LCMS (System A) RT=1.03 min, ES+ve m/z 517/519 (M+H)+.

Intermediate 76

1,1-Dimethylethyl({3-[(4-acetyl-3-{[(5-chloro-2-thienyl)sulfonyl]amino}-1H-indazol-1-yl)methyl]phenyl}methyl)carbamate

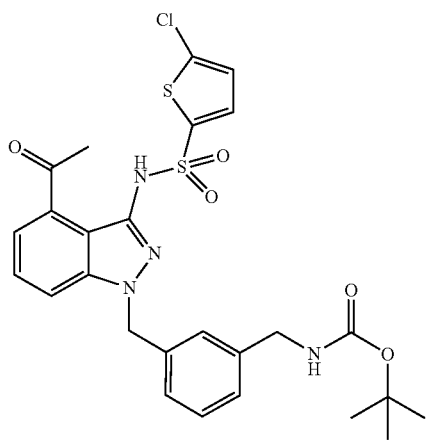 [SMILES: CC(=O)c1cccc2c1c(NS(=O)(=O)c1ccc(Cl)s1)nn2Cc1cccc(CNC(=O)OC(C)(C)C)c1]

Methylmagnesium bromide (3M solution in diethyl ether) (1.792 mL, 5.38 mmol) was added dropwise to a stirring solution of 1,1-dimethylethyl({3-[(3-{[(5-chloro-2-thienyl)sulfonyl]amino}-4-cyano-1H-indazol-1-yl)methyl]phenyl}methyl)carbamate (for a preparation see Intermediate 73) (1 g, 1.792 mmol) in tetrahydrofuran (8 mL) at 0° C. The reaction was slowly warmed to room temp. and stirred for 1 h. More methylmagnesium bromide (3M solution in diethyl ether) (0.896 mL, 2.69 mmol) was added and stirred for a further 1 hours. LCMS showed starting material still remaining. The reaction mixture was cooled again and more methylmagnesium bromide (3M solution in diethyl ether) (1.792 mL, 5.38 mmol) was added and stirred for a further 1 h. The reaction mixture was cooled to 0° C. and 0.5 N HCl (20 mL) was slowly added. The product was extracted with EtOAc (100 mL×3) and the combined organic layers were washed with brine, dried by passing through a hydrophobic frit and concentrated in vacuo. The residue (1.07 g) was loaded in dichloromethane to a silica 100 g cartridge and purified by chromatography using a 0-25% ethyl acetate-dichloromethane over 40 min. The appropriate fractions were combined and evaporated in vacuo to give the title compound (550 mg, 53%) as a yellow solid. LCMS (System A) RT=1.27 min, ES+ve m/z 575/577 (M+H)+.

Intermediate 77

N-[1-{[3-(Aminomethyl)phenyl]methyl}-4-(1-hydroxyethyl)-1H-indazol-3-yl]-5-chloro-2-thiophenesulfonamide

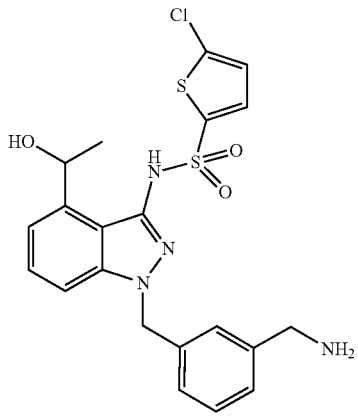 [SMILES: CC(O)c1cccc2c1c(NS(=O)(=O)c1ccc(Cl)s1)nn2Cc1cccc(CN)c1]

Sodium borohydride (20.52 mg, 0.543 mmol) was added to a stirring solution of 1,1-dimethylethyl({3-[(4-acetyl-3-{[(5-chloro-2-thienyl)sulfonyl]amino}-1H-indazol-1-yl)methyl]phenyl}methyl)carbamate (for a preparation see Intermediate 75) (260 mg, 0.452 mmol) in MeOH (5 mL) at 25° C. under $N_2$. The reaction mixture was stirred at room temp for 2 h. About ~⅔ of the methanol was evaporated in vacuo and the residue was treated slowly with 1M HCl (5 mL). The product was extracted with EtOAc (2×40 mL) and the combined organic layers were dried by passing through a hydrophobic frit and concentrated to afford a yellow oil. 4N HCl in Dioxane (2 mL, 8.00 mmol) was added to the residue at 25° C. and the reaction mixture was stirred for 30 min. The crude sample was loaded straight on to a pre-washed (MeOH)SPE sulphonic acid (SCX-2) cartridge (20 g). The SCX cartridge was washed with 2 column volumes of MeOH and the product was collected by washing with 3 column volumes of 2N Ammonia in MeOH. The appropriate fractions were combined and evaporated in vacuo to give the title compound (235 mg, 91) %. LCMS (System A) RT=0.77 min, ES+ve m/z 477/479 (M+H)+.

Intermediate 78

N-[1-{[3-(Aminomethyl)phenyl]methyl}-4-(1-hydroxy-1-methylethyl)-1H-indazol-3-yl]-5-chloro-2-thiophenesulfonamide

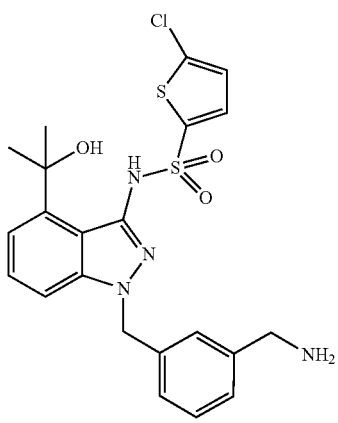 [SMILES: CC(C)(O)c1cccc2c1c(NS(=O)(=O)c1ccc(Cl)s1)nn2Cc1cccc(CN)c1]

Methylmagnesium bromide (3M solution in diethyl ether) (0.730 mL, 2.191 mmol) was added slowly dropwise to a stirring solution of 1,1-dimethylethyl({3-[(4-acetyl-3-{[(5-chloro-2-thienyl)sulfonyl]amino}-1H-indazol-1-yl)methyl]phenyl}methyl)carbamate (for a preparation see Intermediate 76) (210 mg, 0.365 mmol) in THF (3 mL) at room temp. The reaction was stirred for 2 h and then more methylmagnesium bromide (3M solution in diethyl ether) (0.730 mL, 2.191 mmol) was added and stirred overnight. LCMS indicated molecular ion 592 [M+1] corresponding to the desired alcohol and that the starting material co-eluted with the product. 1N HCl (5 mL) was added and the product was extracted with EtOAc (15 mL×3). The combined organic layers were dried by passing through a hydrophobic frit and concentrated in vacuo. The residue was dissolved in 4N HCl in Dioxane (2 mL, 8.00 mmol) and the reaction was stirred at room temp over 1 h. The reaction mixture was loaded on an SCX-2 ion-exchange 20 g cartridge eluting with methanol and 2M ammonia in methanol. The appropriate ammoniacal fractions were combined and evaporated in vacuo to give the title compound (168 mg, 76%) as a brown oil. LCMS (System A) RT=0.79 min, ES+ve m/z 491/493 (M+H)$^+$.

Intermediate 79

4-{[3-[[(5-Chloro-2-thienyl)sulfonyl]({[2-(trimethylsilyl)ethyl]oxy}methyl)amino]-4-(methyloxy)-1H-indazol-1-yl]methyl}-N,N-dimethylbenzamide

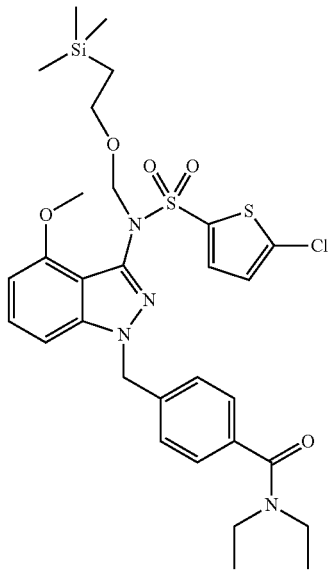 [SMILES: CCN(CC)C(=O)c1ccc(Cn2nc(N(COCC[Si](C)(C)C)S(=O)(=O)c3ccc(Cl)s3)c3c(OC)cccc32)cc1]

A solution of 5-chloro-N-[4-(methyloxy)-1H-indazol-3-yl]-N-({[2-(trimethylsilyl)ethyl]oxy}methyl)-2-thiophenesulfonamide (Intermediate 8) (150 mg, 0.32 mmol) was treated with 4-(chloromethyl)-N,N-diethylbenzamide (86 mg, 0.38 mmol) and potassium hydroxide (21.3 mg, 0.38 mmol), and the mixture was heated to 50° C. overnight. Reaction mixture was partitioned between DCM (3 mL) and water (3 mL). The organic phase was separated and the aqueous layer was further extracted with 2 mL of DCM. The combined organic solutions were dried (hydrophobic frit) and concentrated under a nitrogen stream in a blowdown unit. The residue was purified by chromatography using a Flash Master system (Solo machine), on a 50 g silica cartridge, eluting with 0 to 100% A in B, A being a 20% EtOAC in DCM solution and B being neat DCM over 60 min. Evaporation of the appropriate fractions gave the title compound (125 mg, 60%) LCMS (System A) RT=1.52 min, ES+ve m/z 680/682 (M+NH$_4$)$^+$.

Intermediate 80

1-{[3-Fluoro-4-(methyloxy)phenyl]methyl}-4-(methyloxy)-1H-indazol-3-amine

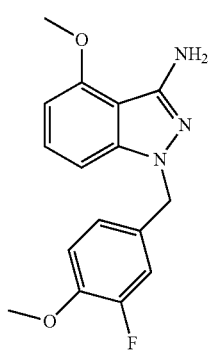 [SMILES: COc1ccc(Cn2nc(N)c3c(OC)cccc32)cc1F]

4-(Methyloxy)-1H-indazol-3-amine (for a preparation see Intermediate 1) (490 mg, 3 mmol) and potassium hydroxide (185 mg, 3.30 mmol) were dissolved in DMSO (30 mL). The reaction was left to stir for 30 min, before 4-(bromomethyl)-2-fluoro-1-(methyloxy)benzene (657 mg, 3.00 mmol) was added to the reaction mixture and stirred for 1 h at room temperature under nitrogen. The reaction mixture was diluted with ethyl acetate (250 mL) and washed with water (2×250 mL) and brine (250 mL). The organic layer was dried over anhydrous magnesium sulphate and filtered before being evaporated in vacuo to afford a brown oil. The residue was loaded in dichloromethane on a silica 100 g cartridge and purified by chromatography on Flashmaster using a 0-100% ethyl acetate-dichloromethane over 40 min. The appropriate fractions were combined and evaporated in vacuo and the residue re-purified by chromatography on silica 70 g using a 0-50% ethyl acetate-dichloromethane over 40 min. The appropriate fractions were combined and evaporated in vacuo to give the title compound (432 mg, 48%) as an off-white solid. LCMS (System A) RT=0.96 min, ES+ve m/z 302 (M+H)$^+$.

Example 1

N-[(3-{[3-{[(5-Chloro-2-thienyl)sulfonyl]amino}-4-(methyloxy)-1H-indazol-1-yl]methyl}phenyl)methyl]acetamide

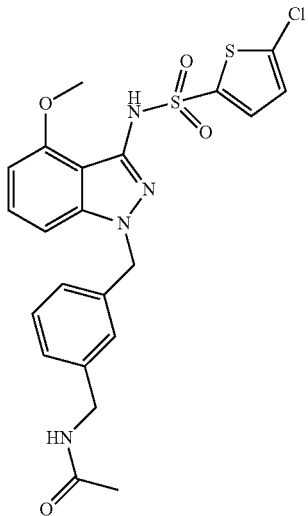 [SMILES: COc1cccc2c1c(NS(=O)(=O)c1ccc(Cl)s1)nn2Cc1cccc(CNC(C)=O)c1]

To N-[1-{[3-(aminomethyl)phenyl]methyl}-4-(methyloxy)-1H-indazol-3-yl]-5-chloro-2-thiophenesulfonamide hydrochloride (for a preparation see Intermediate 4) (700 mg, 1.40 mmol) was added triethylamine (0.583 mL, 4.20 mmol) and DCM (3 mL) to give a suspension. Acetic anhydride (0.146 mL, 1.54 mmol) was added dropwise at room temperature and the resulting mixture was stirred at ambient temperature for 2 h. LCMS showed completion of the reaction. The reaction mixture was diluted with DCM (20 mL) and a saturated solution of NaHCO$_3$ in water (20 mL). The organic solution was separated and the aqueous layer was further extracted with DCM (20 mL). Organic solutions were combined, washed with brine (20 mL), dried through an hydrophobic frit and concentrated under reduced pressure. The residue was loaded in 1:1 MeOH-DMSO and purified on reverse phase (C18) silica (330 g) using a gradient of 5% to 80% MeCN (+0.1% of NEt$_3$) in water (pH=10 with ammonium bicarbonate) over 14 column lengths. The appropriate fractions were combined and evaporated in vacuo to give the title compound (570 mg, 81%) as a white solid. LCMS (System A) RT=1.01 min, ES+ve m/z 505/507 (M+H)$^+$.

Examples 2-4 were prepared in a similar way from N-[1-{[3-(aminomethyl)phenyl]methyl}-4-(methyloxy)-1H-indazol-3-yl]-5-chloro-2-thiophenesulfonamide hydrochloride and the appropriate carboxylic anhydride:

Example 2

N-[(3-{[3-{[(5-chloro-2-thienyl)sulfonyl]amino}-4-(methyloxy)-1H-indazol-1-yl]methyl}phenyl)methyl]propanamide

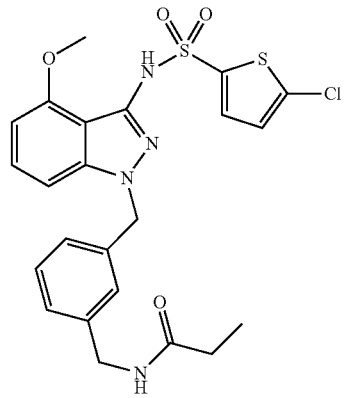 [SMILES: CCC(=O)NCc1cccc(Cn2nc(NS(=O)(=O)c3ccc(Cl)s3)c3c(OC)cccc32)c1]

LCMS (System A) RT=1.07 min, ES+ve m/z 519/521 (M+H)$^+$.

Example 3

N-[(3-{[3-{[(5-chloro-2-thienyl)sulfonyl]amino}-4-(methyloxy)-1H-indazol-1-yl]methyl}phenyl)methyl]-2-methylpropanamide

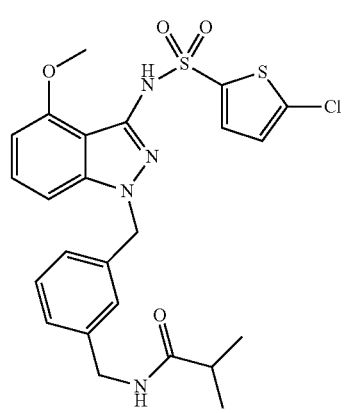 [SMILES: COc1cccc2c1c(NS(=O)(=O)c1ccc(Cl)s1)nn2Cc1cccc(CNC(=O)C(C)C)c1]

LCMS (System A) RT=1.13 min, ES+ve m/z 533/535 (M+H)$^+$.

Example 4

N-[(3-{[3-{[(5-chloro-2-thienyl)sulfonyl]amino}-4-(methyloxy)-1H-indazol-1-yl]methyl}phenyl)methyl]-2,2-dimethylpropanamide

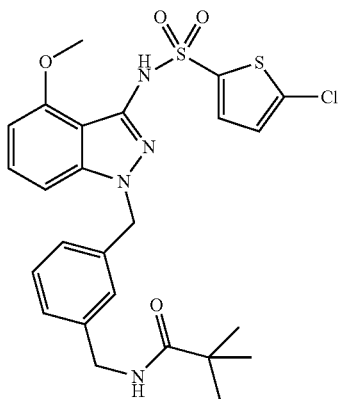 [SMILES: COc1cccc2c1c(NS(=O)(=O)c1ccc(Cl)s1)nn2Cc1cccc(CNC(=O)C(C)(C)C)c1]

LCMS (System A) RT=1.19 min, ES+ve m/z 547/549 (M+H)⁺.

Example 5

5-Chloro-N-[1-({3-[(formylamino)methyl]phenyl}methyl)-4-(methyloxy)-1H-indazol-3-yl]-2-thiophenesulfonamide

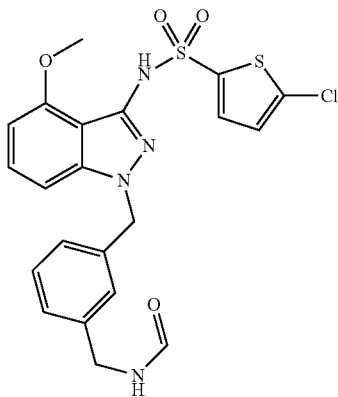 [SMILES: COc1cccc2c1c(NS(=O)(=O)c1ccc(Cl)s1)nn2Cc1cccc(CNC=O)c1]

To a solution of formic acid (5 μL, 0.13 mmol) in dry DMF (0.3 mL) was added TBTU (34.7 mg, 0.108 mmol) followed with triethylamine (50.2 μl, 0.360 mmol). This mixture was stirred at room temperature for about 10 min before adding N-[1-{[3-(aminomethyl)phenyl]methyl}-4-(methyloxy)-1H-indazol-3-yl]-5-chloro-2-thiophenesulfonamide hydrochloride (for a preparation see Intermediate 4) (45 mg, 0.09 mmol). The resultant pale yellow mixture was stirred at room temperature overnight. LCMS showed very little reaction, so more acid (~0.25 mL), followed with TBTU (~30 mg) were added. This addition was repeated 3 more times over 20 h until by LCMS analysis, there was more product than SM. The reaction mixture was partitioned between ethylacetate (2 mL) and saturated sodium bicarbonate solution (2 mL). The aqueous was extracted with ethyl acetate (×2). The combined organic solutions were washed with water, brine, dried (Na₂SO₄) and concentrated in vacuo to leave a pale oil which crystalised on standing. This was dissolved in 1:1 MeOH:DMSO (1 mL) and purified by Mass Directed AutoPrep on supelcosil ABZ+Plus column eluting with a gradient of MeCN-Water (95:5+0.05% Formic acid)–Water (+0.1% Formic acid). The solvent was evaporated in vacuo to give the title compound (15.9 mg, 36%) as a pale yellow powder: LCMS (System A) RT=1.02 min, ES+ve m/z 491/493 (M+H)⁺.

Example 6

N-[(3-{[3-{[(5-chloro-2-thienyl)sulfonyl]amino}-4-(methyloxy)-1H-indazol-1-yl]methyl}phenyl)methyl]-3-morpholinecarboxamide trifluoroacetate

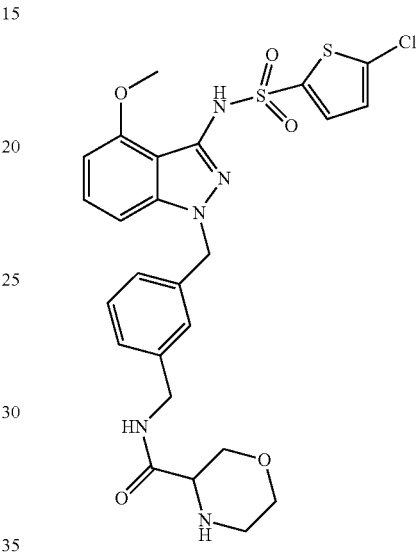

A solution of 3-morpholinecarboxylic acid (121 mg, 0.523 mmol) in acetonitrile (10 mL) was treated with HATU (199 mg, 0.523 mmol) and then DIPEA (0.248 mL, 1.426 mmol). The resulting mixture was stirred for 15 min at ambient temperature and then was treated with N-[1-{[3-(aminomethyl)phenyl]methyl}-4-(methyloxy)-1H-indazol-3-yl]-5-chloro-2-thiophenesulfonamide hydrochloride (for a preparation see Intermediate 4) (220 mg, 0.475 mmol). The resulting mixture was stirred at ambient temperature over night. The reaction mixture was diluted with DCM (20 mL) and water (30 mL). The organic phase was separated and the aqueous layer was further extracted with DCM (20 mL). The combined organic solutions were washed with water (20 mL), brine (20 mL), dried through an hydrophobic frit, and concentrated under reduced pressure. The residue was dissolved in DCM (10 mL) and to this was added Hydrogen Chloride (0.6 mL, 2.4 mmol) and the resulting solution was stirred at rt 3 h. LCMS indicated a mixture of product and Starting Material (1:1). More Hydrogen Chloride (0.6 ml, 2.4 mmol) was added to the mixture and after 3 h of stirring at ambient temperature, LCMS showed complete reaction. The reaction mixture was concentrated under reduced pressure, the residue was treated and co-evaporate twice with DCM (20 mL). The samples were dissolved in 1:1 MeOH:DMSO (1 mL) (×4) and purified by Mass Directed AutoPrep on standard C18 column using Acetonitrile-Water with a TFA modifier. The solvent was evaporated in vacuo to give the title product as TFA salt (244.5 mg, 75%). LCMS (System E) RT=2.18 min, ES+ve m/z 576/578 (M+H)⁺.

Examples 7-16 were similarly prepared from N-[1-{[3-(aminomethyl)phenyl]methyl}-4-(methyloxy)-1H-indazol- 3-yl]-5-chloro-2-thiophenesulfonamide hydrochloride and the appropriate carboxylic acid, followed by HCl deprotection.

Example 7

(3R)—N-[(3-{[3-{[(5-Chloro-2-thienyl)sulfonyl]amino}-4-(methyloxy)-1H-indazol-1-yl]methyl}phenyl)methyl]-3-morpholinecarboxamide Hydrochloride

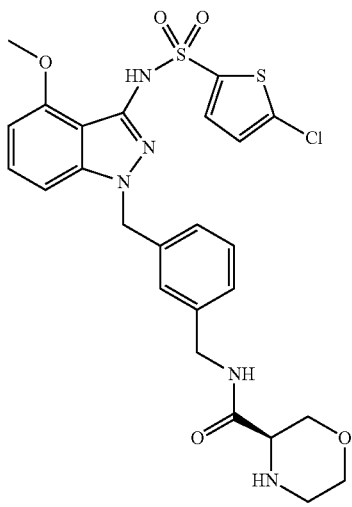

LCMS (System D) RT=0.92 min, ES+ve m/z 576/578 (M+H)+.

Example 8

(3S)—N-[(3-{[3-{[(5-Chloro-2-thienyl)sulfonyl]amino}-4-(methyloxy)-1H-indazol-1-yl]methyl}phenyl)methyl]-3-morpholinecarboxamide Hydrochloride

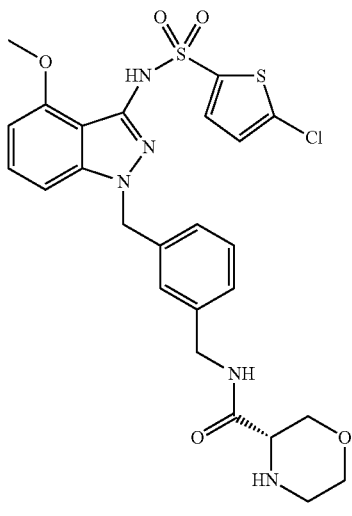

LCMS (System D) RT=0.92 min, ES+ve m/z 576/578 (M+H)+.

Example 9

(2R)—N-[(3-{[3-{[(5-chloro-2-thienyl)sulfonyl]amino}-4-(methyloxy)-1H-indazol-1-yl]methyl}phenyl)methyl]-2-piperidinecarboxamide Trifluoroacetate Salt

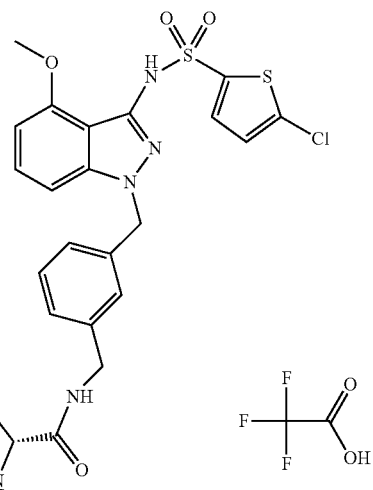

LCMS (System E) RT=2.13 min, ES+ve m/z 574/576 (M+H)+.

Example 10

$N^1$-[(3-{[3-{[(5-chloro-2-thienyl)sulfonyl]amino}-4-(methyloxy)-1H-indazol-1-yl]methyl}phenyl)methyl]-$N^2$-methyl-D-alaninamide Hydrochloride

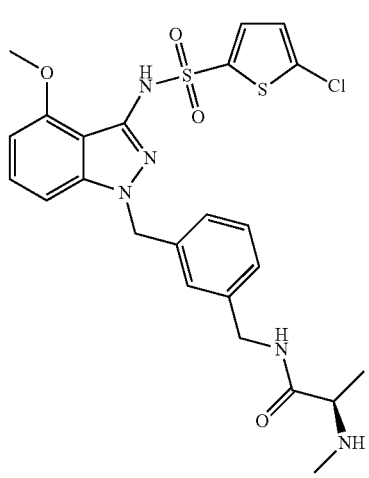

LCMS (System F) RT=0.80 min, ES+ve m/z 548/550 (M+H)+.

Example 11

3-Amino-N-[(3-{[3-{[(5-chloro-2-thienyl)sulfonyl]amino}-4-(methyloxy)-1H-indazol-1-yl]methyl}phenyl)methyl]-2,2-dimethylpropanamide Hydrochloride

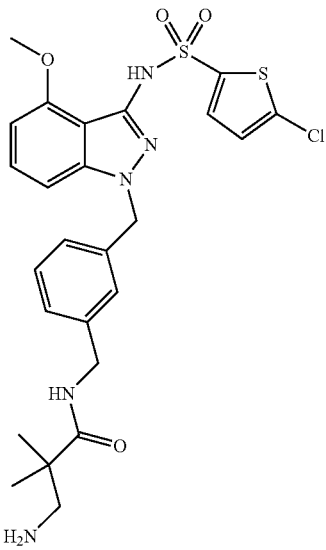

LCMS (System C) RT=0.81 min, ES+ve m/z 562/564 (M+H)+.

Example 12

N¹-[(3-{[3-{[(5-chloro-2-thienyl)sulfonyl]amino}-4-(methyloxy)-1H-indazol-1-yl]methyl}phenyl)methyl]-N²-methylglycinamide Hydrochloride

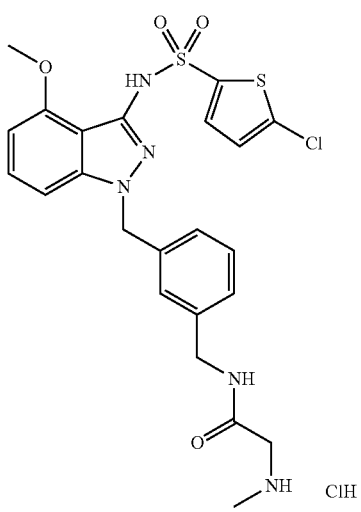 [SMILES: CNCC(=O)NCc1cccc(Cn2nc(NS(=O)(=O)c3ccc(Cl)s3)c3c(OC)cccc32)c1 ; Cl]

LCMS (System C) RT=0.78 min, ES+ve m/z 534/536 (M+H)+.

Example 13

N-[(3-{[3-{[(5-Chloro-2-thienyl)sulfonyl]amino}-4-(methyloxy)-1H-indazol-1-yl]methyl}phenyl)methyl]-2-methyl-D-prolinamide

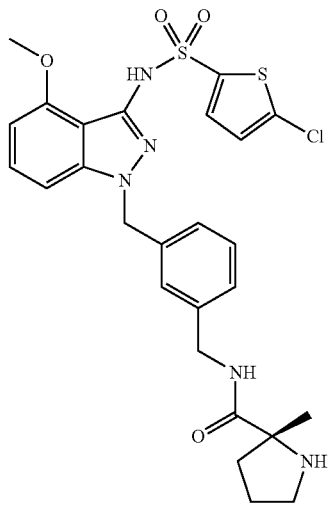 [SMILES: COc1cccc2c1c(NS(=O)(=O)c1ccc(Cl)s1)nn2Cc1cccc(CNC(=O)[C@@]2(C)CCCN2)c1]

LCMS (System C) RT=2.21 min, ES+ve m/z 574/576 (M+H)+.

Example 14

N-[(3-{[3-{[(5-chloro-2-thienyl)sulfonyl]amino}-4-(methyloxy)-1H-indazol-1-yl]methyl}phenyl)methyl]-2-methyl-2-piperidinecarboxamide

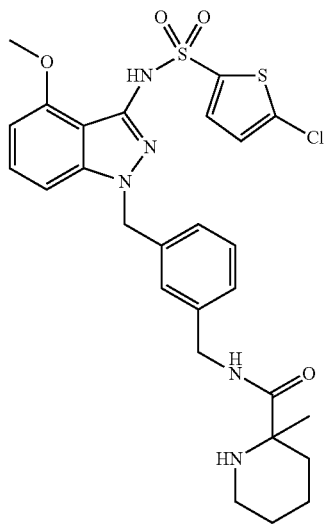 [SMILES: COc1cccc2c1c(NS(=O)(=O)c1ccc(Cl)s1)nn2Cc1cccc(CNC(=O)C2(C)CCCCN2)c1]

LCMS (System F) RT=0.87 min, ES+ve m/z 588/590 (M+H)+.

Example 15

N-[(3-{[3-{[(5-Chloro-2-thienyl)sulfonyl]amino}-4-(methyloxy)-1H-indazol-1-yl]methyl}phenyl)methyl]-1-(methylamino)cyclopropanecarboxamide Hydrochloride

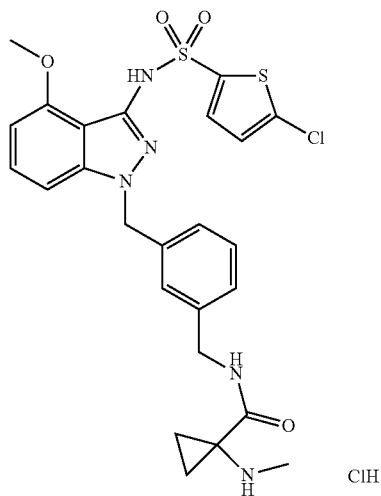 [SMILES: CNC1(C(=O)NCc2cccc(Cn3nc(NS(=O)(=O)c4ccc(Cl)s4)c4c(OC)cccc43)c2)CC1 ; Cl]

LCMS (System D) RT=0.94 min, ES+ve m/z 560/562 (M+H)+.

Example 16

N-[(3-{[3-{[(5-chloro-2-thienyl)sulfonyl]amino}-4-(methyloxy)-1H-indazol-1-yl]methyl}phenyl)methyl]-2-piperazinecarboxamide Hydrochloride

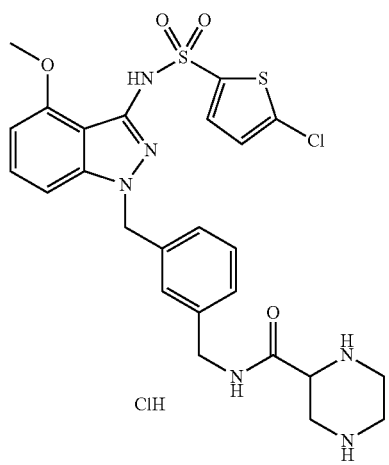 [SMILES: COc1cccc2c1c(NS(=O)(=O)c1ccc(Cl)s1)nn2Cc1cccc(CNC(=O)C2CNCCN2)c1 ; Cl]

LCMS (System C) RT=0.76 min, ES+ve m/z 575/577 (M+H)+.

Examples 17-28

Generic method for the acylation of N-[1-{[3-(aminomethyl)phenyl]methyl}-4-(methyloxy)-1H-indazol-3-yl]-5-chloro-2-thiophenesulfonamide in array format using HATU and HCl removal of Boc protecting group:

HATU (190 mg, 0.500 mmol) dissolved in DMF (2 mL) and aliquot dispensed (0.2 ml, 0.05 mmole) to each acid monomer (pre-weighed 0.049 mmol). DIPEA (20 μL, 3 eq) was added to each acid, capped and shaken to aid dispersion. N-[1-{[3-(aminomethyl)phenyl]methyl}-4-(methyloxy)-1H-indazol-3-yl]-5-chloro-2-thiophenesulfonamide (255 mg, 0.551 mmol) was dissolved in DMF (2 mL) and aliquot dispensed (0.2 mL, 0.044 mmol) and added to each acid well. The reaction mixtures were shaken and stood at room temperature for 72 h (over weekend for convenience). 4N HCl in dioxane (100 μL) was added to each well, shaken and stood at room temperature for 24 h. LCMS indicated incomplete reaction, therefore DMF was removed by a nitrogen stream (Radley's blowdown unit) to almost dryness, and added more 4N HCl in dioxane solution (500 μL) and stood at room temperature for a further 18 h. To the residues was added DMSO (0.5 mL) and the solutions were purified by Mass Directed AutoPrep on Sunfire C18 column using Acetonitrile Water with a TFA modifier. The solvent was removed under a stream of nitrogen in the Radleys blowdown apparatus to give the required products.

Example 17

N$^1$-[(3-{[3-{[(5-chloro-2-thienyl)sulfonyl]amino}-4-(methyloxy)-1H-indazol-1-yl]methyl}phenyl)methyl]-N$^2$-methyl-L-alaninamide Trifluoroacetate

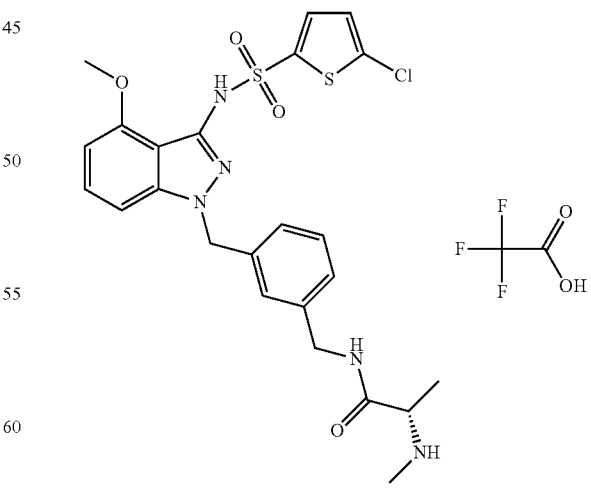

LCMS (System A) RT=0.83 min, ES+ve m/z 548/550 (M+H)+.

Example 18

N¹-[(3-{[3-{[(5-chloro-2-thienyl)sulfonyl]amino}-4-(methyloxy)-1H-indazol-1-yl]methyl}phenyl)methyl]-L-alaninamide Trifluoroacetate

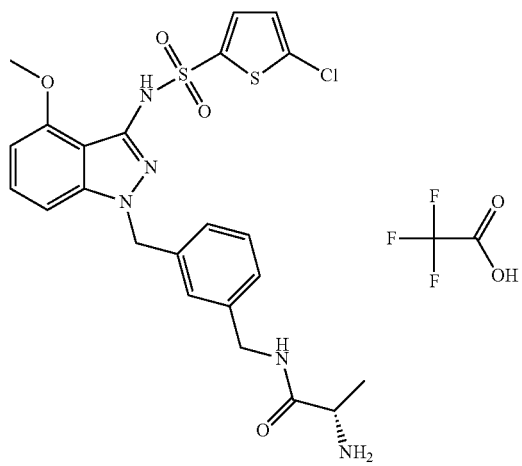 [SMILES: COc1cccc2c1c(NS(=O)(=O)c1ccc(Cl)s1)nn2Cc1cccc(CNC(=O)[C@H](C)N)c1 ; O=C(O)C(F)(F)F]

LCMS (System A) RT=0.82 min, ES+ve m/z 534/536 (M+H)⁺.

Example 19

N¹-[(3-{[3-{[(5-chloro-2-thienyl)sulfonyl]amino}-4-(methyloxy)-1H-indazol-1-yl]methyl}phenyl)methyl]-D-alaninamide Trifluoroacetate

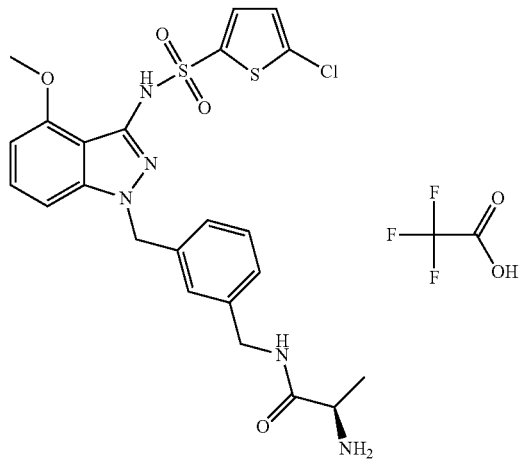 [SMILES: COc1cccc2c1c(NS(=O)(=O)c1ccc(Cl)s1)nn2Cc1cccc(CNC(=O)[C@@H](C)N)c1 ; O=C(O)C(F)(F)F]

LCMS (System A) RT=0.82 min, ES+ve m/z 534/536 (M+H)⁺.

Example 20

N¹-[(3-{[3-{[(5-chloro-2-thienyl)sulfonyl]amino}-4-(methyloxy)-1H-indazol-1-yl]methyl}phenyl)methyl]glycinamide Trifluoroacetate

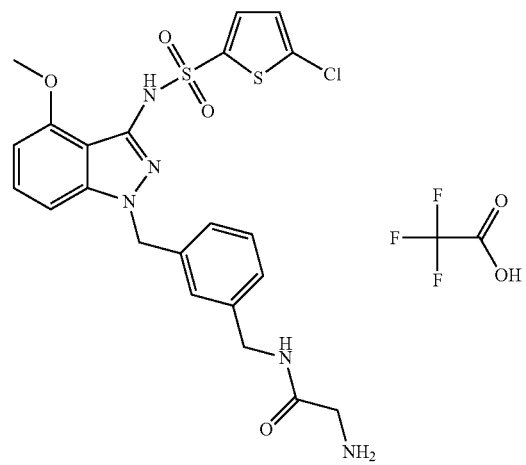 [SMILES: COc1cccc2c1c(NS(=O)(=O)c1ccc(Cl)s1)nn2Cc1cccc(CNC(=O)CN)c1 ; O=C(O)C(F)(F)F]

LCMS (System A) RT=0.81 min, ES+ve m/z 520/522 (M+H)⁺.

Example 21

N-[(3-{[3-{[(5-chloro-2-thienyl)sulfonyl]amino}-4-(methyloxy)-1H-indazol-1-yl]methyl}phenyl)methyl]propanediamide

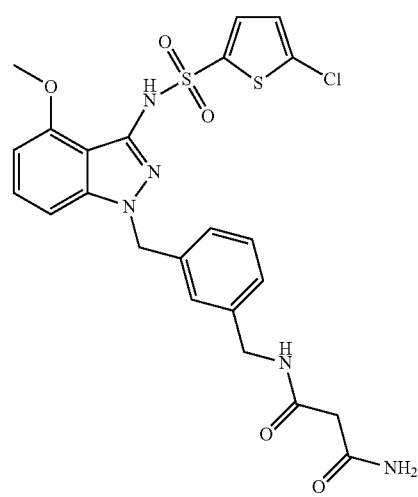 [SMILES: COc1cccc2c1c(NS(=O)(=O)c1ccc(Cl)s1)nn2Cc1cccc(CNC(=O)CC(N)=O)c1]

LCMS (System A) RT=0.93 min, ES+ve m/z 548/550 (M+H)⁺.

Example 22

N⁴-[(3-{[3-{[(5-chloro-2-thienyl)sulfonyl]amino}-4-(methyloxy)-1H-indazol-1-yl]methyl}phenyl)methyl]-N¹-methyl-L-aspartamide Trifluoroacetate

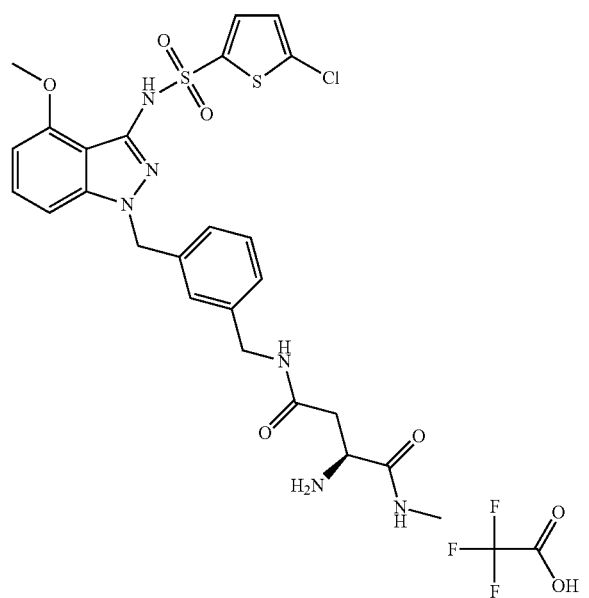

LCMS (System A) RT=0.79 min, ES+ve m/z 591/593 (M+H)⁺.

Example 23

Methyl N⁴-[(3-{[3-{[(5-chloro-2-thienyl)sulfonyl]amino}-4-(methyloxy)-1H-indazol-1-yl]methyl}phenyl)methyl]asparaginate Trifluoroacetate

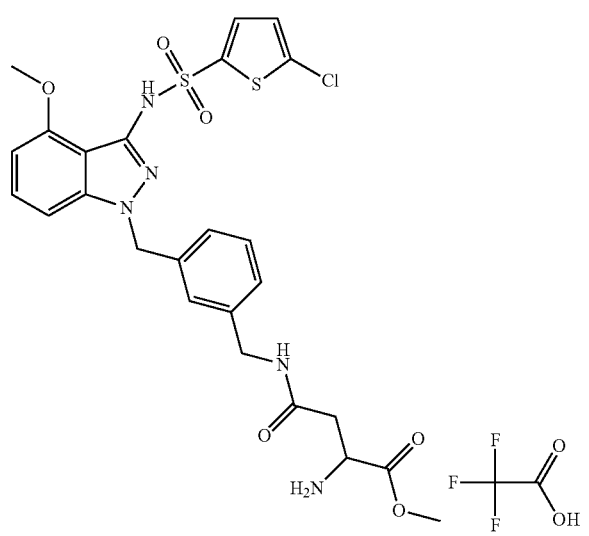

LCMS (System A) RT=0.82 min, ES+ve m/z 592/594 (M+H)⁺.

Example 24

N-[(3-{[3-{[(5-chloro-2-thienyl)sulfonyl]amino}-4-(methyloxy)-1H-indazol-1-yl]methyl}phenyl)methyl]-2-(2-pyrrolidinyl)acetamide Trifluoroacetate

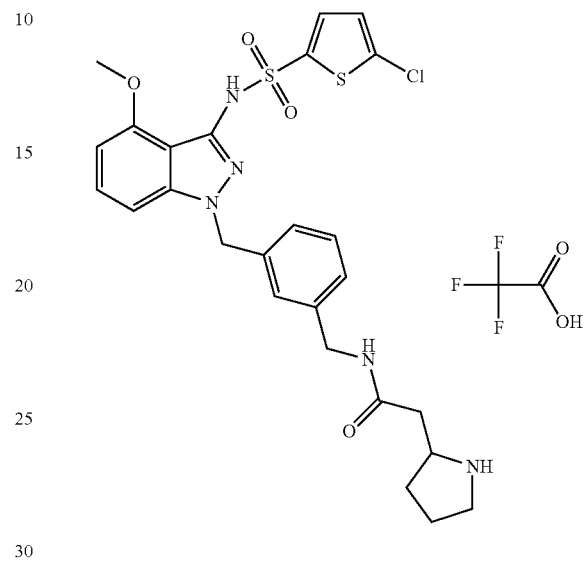

LCMS (System A) RT=0.82 min, ES+ve m/z 574/576 (M+H)⁺.

Example 25

3-Amino-N-[(3-{[3-{[(5-chloro-2-thienyl)sulfonyl]amino}-4-(methyloxy)-1H-indazol-1-yl]methyl}phenyl)methyl]butanamide Trifluoroacetate

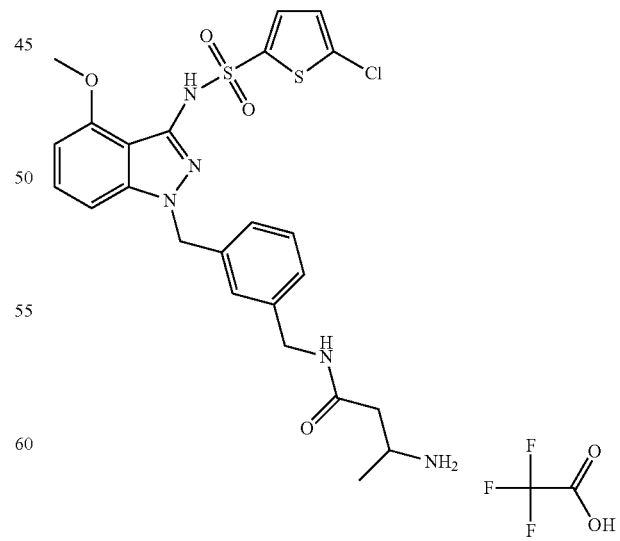

LCMS (System A) RT=0.81 min, ES+ve m/z 548/550 (M+H)⁺.

Example 26

3-Amino-N-[(3-{[3-{[(5-chloro-2-thienyl)sulfonyl]amino}-4-(methyloxy)-1H-indazol-1-yl]methyl}phenyl)methyl]-2-methylpropanamide Trifluoroacetate

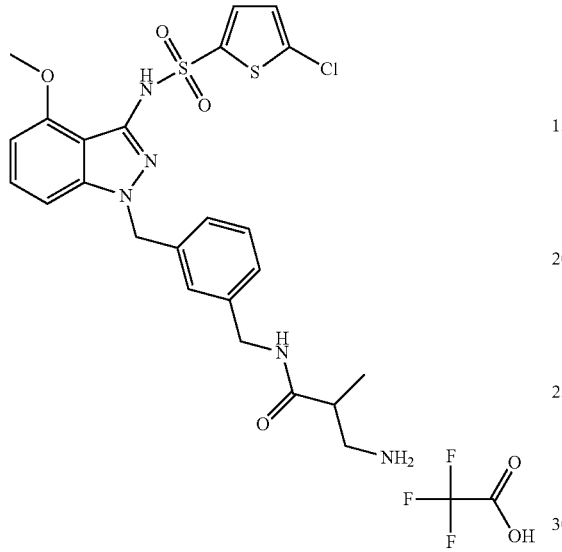

LCMS (System A) RT=0.81 min, ES+ve m/z 548/550 (M+H)+.

Example 27

N-[(3-{[3-{[(5-chloro-2-thienyl)sulfonyl]amino}-4-(methyloxy)-1H-indazol-1-yl]methyl}phenyl)methyl]-2-methyl-L-prolinamide Trifluoroacetate

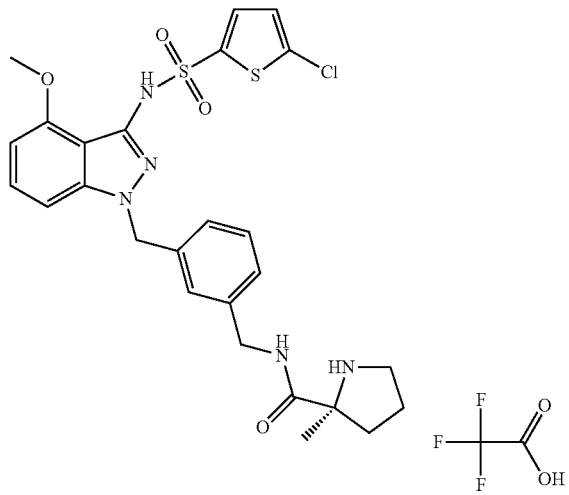

LCMS (System A) RT=0.84 min, ES+ve m/z 574/576 (M+H)+.

Example 28

(4S)—N-[(3-{[3-{[(5-chloro-2-thienyl)sulfonyl]amino}-4-(methyloxy)-1H-indazol-1-yl]methyl}phenyl)methyl]-4-fluoro-L-prolinamide Trifluoroacetate

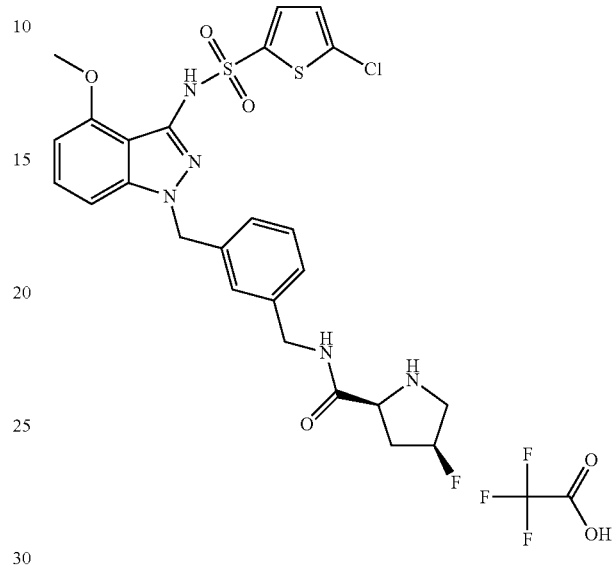

LCMS (System A) RT=0.82 min, ES+ve m/z 578/580 (M+H)+.

Example 29

$N^1$-[(3-{[3-{[(5-Chloro-2-thienyl)sulfonyl]amino}-4-(methyloxy)-1H-indazol-1-yl]methyl}phenyl)methyl]-$N^3$-methyl-β-alaninamide Trifluoroacetate

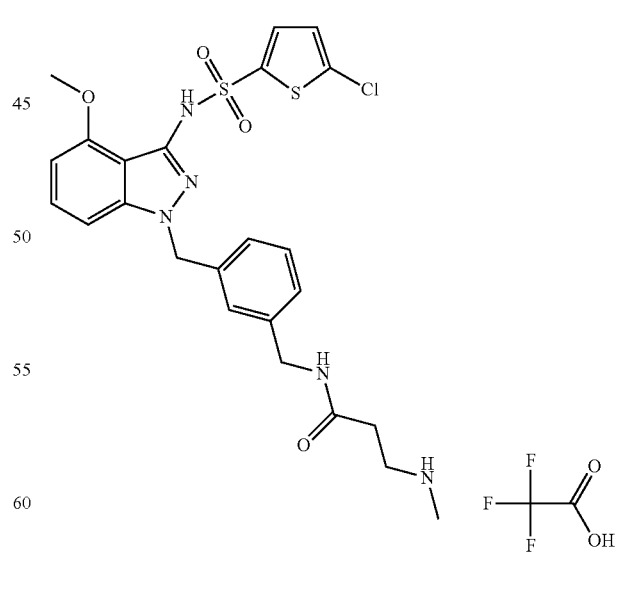

LCMS (System A) RT=0.81 min, ES+ve m/z 548/550 (M+H)+.

Examples 30-43 were prepared in array format from N-[1-{[3-(aminomethyl)phenyl]methyl}-4-(methyloxy)-1H-inda-

Example 30

N-[(3-{[3-{[(5-Chloro-2-thienyl)sulfonyl]amino}-4-(methyloxy)-1H-indazol-1-yl]methyl}phenyl)methyl]-2-(methyloxy)acetamide

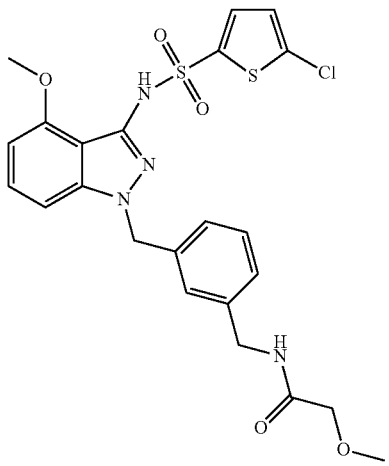 [SMILES: COCC(=O)NCc1cccc(Cn2nc(NS(=O)(=O)c3ccc(Cl)s3)c3c(OC)cccc32)c1]

LCMS (System A) RT=1.05 min, ES+ve m/z 535/537 (M+H)⁺.

Example 31

N¹-[(3-{[3-{[(5-Chloro-2-thienyl)sulfonyl]amino}-4-(methyloxy)-1H-indazol-1-yl]methyl}phenyl)methyl]-N², N²-dimethylalaninamide Trifluoroacetate

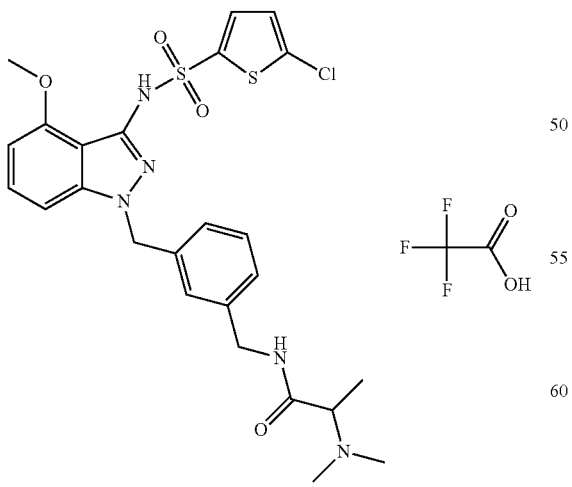

LCMS (System A) RT=0.83 min, ES+ve m/z 562/564 (M+H)⁺.

Example 32

N-[(3-{[3-{[(5-Chloro-2-thienyl)sulfonyl]amino}-4-(methyloxy)-1H-indazol-1-yl]methyl}phenyl)methyl]-2-hydroxyacetamide

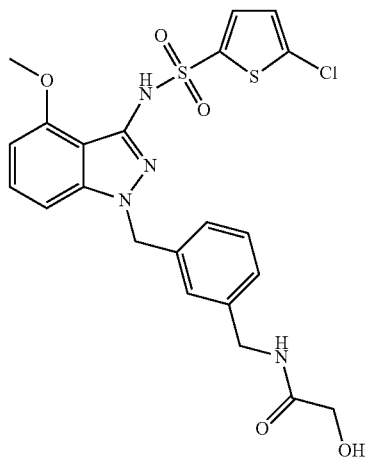 [SMILES: COc1cccc2c1c(NS(=O)(=O)c1ccc(Cl)s1)nn2Cc1cccc(CNC(=O)CO)c1]

LCMS (System E) RT=2.50 min, ES+ve m/z 521/523 (M+H)⁺.

Example 33

N-[(3-{[3-{[(5-Chloro-2-thienyl)sulfonyl]amino}-4-(methyloxy)-1H-indazol-1-yl]methyl}phenyl)methyl]-1H-pyrazole-4-carboxamide

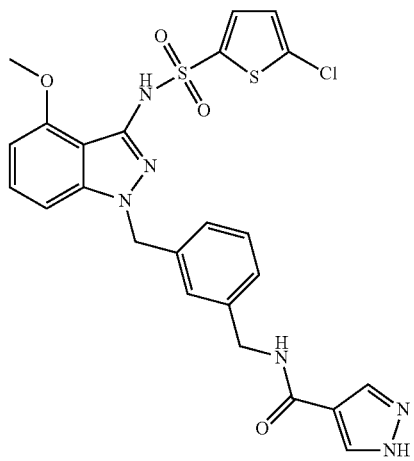 [SMILES: COc1cccc2c1c(NS(=O)(=O)c1ccc(Cl)s1)nn2Cc1cccc(CNC(=O)c2cn[nH]c2)c1]

LCMS (System E) RT=2.53 min, ES+ve m/z 557/559 (M+H)⁺.

Example 34

N¹-[(3-{[3-{[(5-Chloro-2-thienyl)sulfonyl]amino}-4-(methyloxy)-1H-indazol-1-yl]methyl}phenyl)methyl]-N²,N²,2-trimethylalaninamide Trifluoroacetate

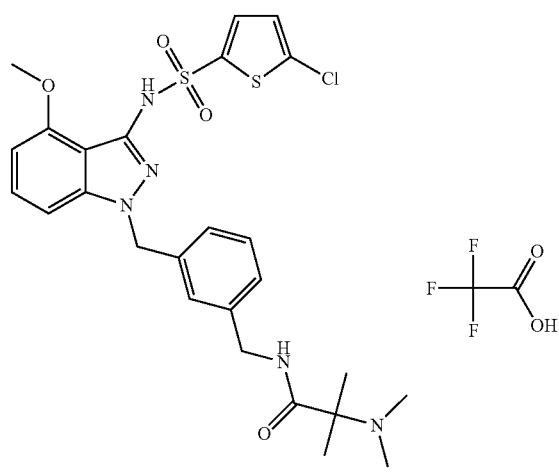 [SMILES: COc1cccc2c1c(NS(=O)(=O)c1ccc(Cl)s1)nn2Cc1cccc(CNC(=O)C(C)(C)N(C)C)c1 ; O=C(O)C(F)(F)F]

LCMS (System E) RT=1.83 min, ES+ve m/z 576/578 (M+H)+.

Example 35

N-[(3-{[3-{[(5-Chloro-2-thienyl)sulfonyl]amino}-4-(methyloxy)-1H-indazol-1-yl]methyl}phenyl)methyl]tetrahydro-3-furancarboxamide

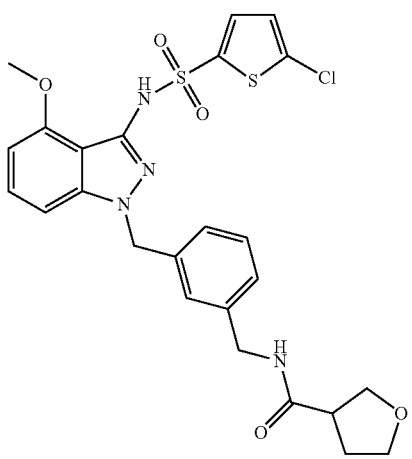 [SMILES: COc1cccc2c1c(NS(=O)(=O)c1ccc(Cl)s1)nn2Cc1cccc(CNC(=O)C2CCOC2)c1]

LCMS (System E) RT=2.69 min, ES+ve m/z 561/563 (M+H)+.

Example 36

N¹-[(3-{[3-{[(5-Chloro-2-thienyl)sulfonyl]amino}-4-(methyloxy)-1H-indazol-1-yl]methyl}phenyl)methyl]-N²-methyl-N²-[2-(methyloxy)ethyl]glycinamide Trifluoroacetate

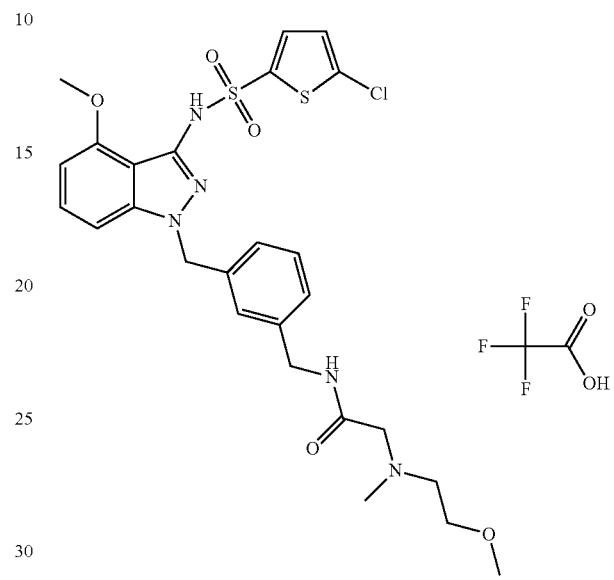

LCMS (System E) RT=1.87 min, ES+ve m/z 592/594 (M+H)+.

Example 37

N-[(3-{[3-{[(5-Chloro-2-thienyl)sulfonyl]amino}-4-(methyloxy)-1H-indazol-1-yl]methyl}phenyl)methyl]-2-hydroxypropanamide

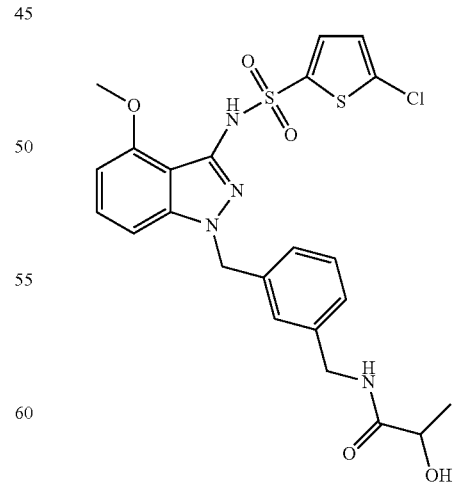

LCMS (System E) RT=2.57 min, ES+ve m/z 535/537 (M+H)+.

Example 38

N-[(3-{[3-{[(5-Chloro-2-thienyl)sulfonyl]amino}-4-(methyloxy)-1H-indazol-1-yl]methyl}phenyl)methyl]-1,3-oxazole-5-carboxamide

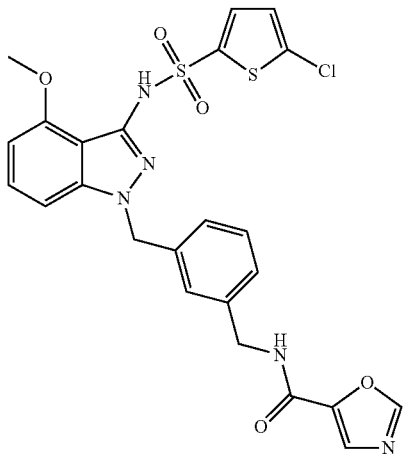 [SMILES: COc1cccc2c1c(NS(=O)(=O)c1ccc(Cl)s1)nn2Cc1cccc(CNC(=O)c2cnco2)c1]

LCMS (System E) RT=2.59 min, ES+ve m/z 558/560 (M+H)+.

Example 39

N-[(3-{[3-{[(5-Chloro-2-thienyl)sulfonyl]amino}-4-(methyloxy)-1H-indazol-1-yl]methyl}phenyl)methyl]-1-methyl-L-prolinamide Trifluoroacetate

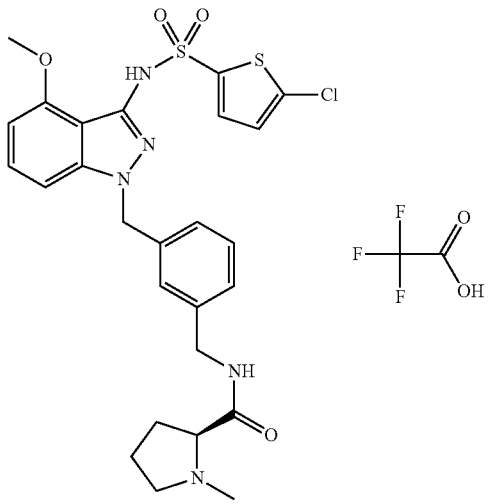 [SMILES: COc1cccc2c1c(NS(=O)(=O)c1ccc(Cl)s1)nn2Cc1cccc(CNC(=O)[C@@H]2CCCN2C)c1 ; O=C(O)C(F)(F)F]

LCMS (System D) RT=0.94 min, ES+ve m/z 574/576 (M+H)+.

Example 40

N-[(3-{[3-{[(5-Chloro-2-thienyl)sulfonyl]amino}-4-(methyloxy)-1H-indazol-1-yl]methyl}phenyl)methyl]-1-methyl-D-prolinamide Trifluoroacetate

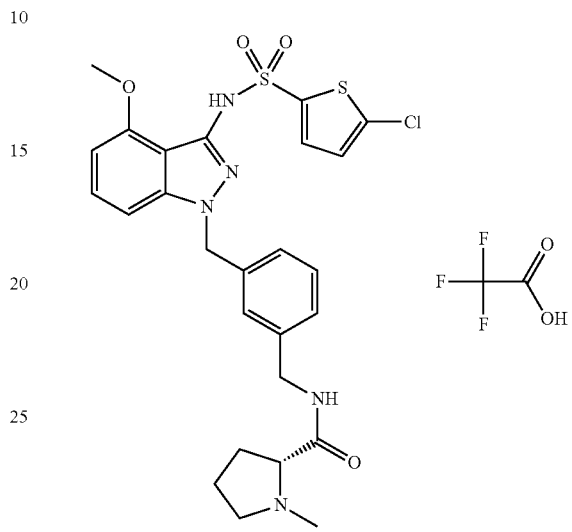

LCMS (System D) RT=0.95 min, ES+ve m/z 574/576 (M+H)+.

Example 41

N-[(3-{[3-{[(5-Chloro-2-thienyl)sulfonyl]amino}-4-(methyloxy)-1H-indazol-1-yl]methyl}phenyl)methyl]-3-furancarboxamide

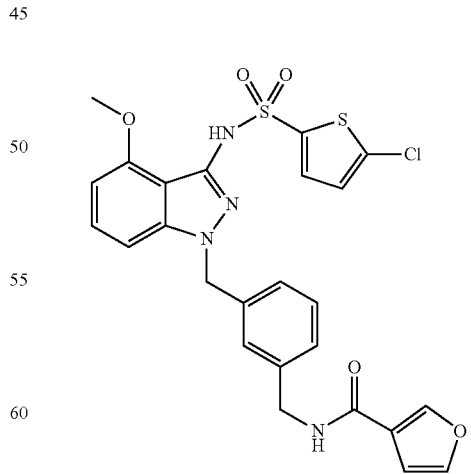

LCMS (System A) RT=1.13 min, ES+ve m/z 556/558 (M+H)+.

Example 42

N-[(3-{[3-{[(5-chloro-2-thienyl)sulfonyl]amino}-4-(methyloxy)-1H-indazol-1-yl]methyl}phenyl)methyl]-1-methyl-2-piperidinecarboxamide Trifluoroacetate

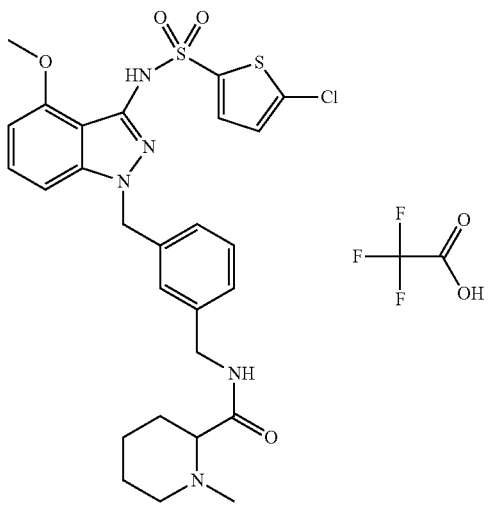 [SMILES: COc1cccc2c1c(NS(=O)(=O)c1ccc(Cl)s1)nn2Cc1cccc(CNC(=O)C2CCCCN2C)c1 ; O=C(O)C(F)(F)F]

LCMS (System D) RT=0.96 min, ES+ve m/z 588/590 (M+H)+.

Example 43

N-[(3-{[3-{[(5-chloro-2-thienyl)sulfonyl]amino}-4-(methyloxy)-1H-indazol-1-yl]methyl}phenyl)methyl]tetrahydro-2H-pyran-4-carboxamide

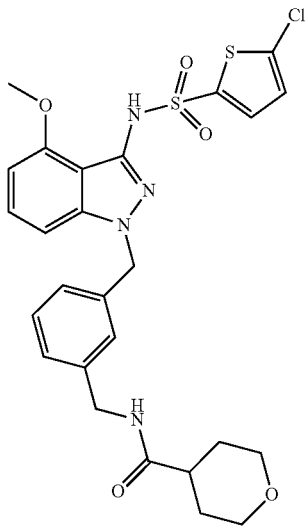 [SMILES: COc1cccc2c1c(NS(=O)(=O)c1ccc(Cl)s1)nn2Cc1cccc(CNC(=O)C2CCOCC2)c1]

LCMS (System B) RT=2.71 min, ES+ve m/z 576/578 (M+H)+.

Examples 44-52

Generic method for the acylation of N-[1-{[3-(aminomethyl)phenyl]methyl}-4-(methyloxy)-1H-indazol-3-yl]-5-chloro-2-thiophenesulfonamide in array format using HATU and TFA removal of the Boc protecting group:

HATU (456 mg, 1.2 mmol) dissolved in DMF (1.2 mL) and aliquot dispensed (0.1 ml, 0.1 mmol) to each acid monomer (pre-weighed 0.1 mmol). DIPEA (40 µL, 2.2 eq) was added to each acid, capped and shaken for 2 min to aid dispersion. N-[1-{[3-(aminomethyl)phenyl]methyl}-4-(methyloxy)-1H-indazol-3-yl]-5-chloro-2-thiophenesulfonamide chloride (599 mg, 1.2 mmol) was dissolved in DMF (2.4 mL) and aliquot dispensed (0.2 mL, 0.1 mmol) and added to each acid well. The reaction mixtures were shaken and stood at room temperature for 48 h. DMF was removed by a nitrogen stream (Radley's blowdown unit) to half-volume. TFA (100 µL) was added to each well, shaken and stood at room temperature for 1 h. LCMS indicated incomplete reaction, DMF was removed by a nitrogen stream (Radley's blowdown unit) to almost dryness. To the residues was added DMSO (0.5 mL) and the solutions were purified by Mass Directed AutoPrep on Sunfire C18 column using Acetonitrile Water with a TFA modifier. The solutions were de-salted by passing through PL-HCO3 SPE (0.2 mg, 6 mL, pre-conditioned MeOH). The solvent was evaporated in vacuo using the Genevac to give the required products:

Example 44

N$^1$-[(3-{[3-{[(5-Chloro-2-thienyl)sulfonyl]amino}-4-(methyloxy)-1H-indazol-1-yl]methyl}phenyl)methyl]-L-histidinamide

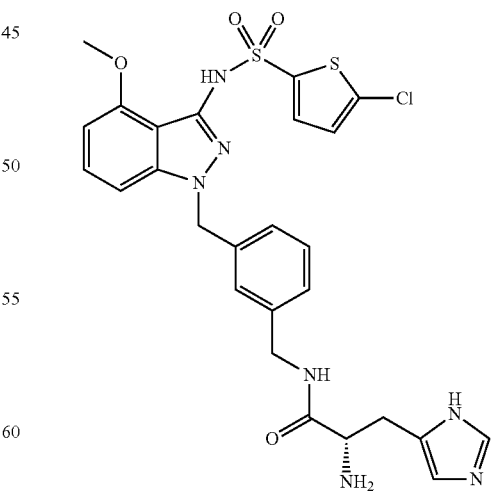

LCMS (System B) RT=1.42 min, ES+ve m/z 600/602 (M+H)+.

Example 45

N[1]-[(3-{[3-{[(5-Chloro-2-thienyl)sulfonyl]amino}-4-(methyloxy)-1H-indazol-1-yl]methyl}phenyl)methyl]-L-leucinamide

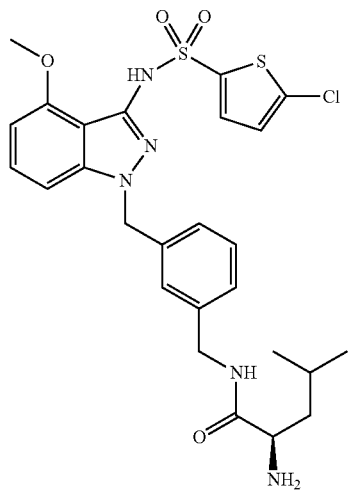 [SMILES: COc1cccc2c1c(NS(=O)(=O)c1ccc(Cl)s1)nn2Cc1cccc(CNC(=O)[C@H](N)CC(C)C)c1]

LCMS (System B) RT=1.97 min, ES+ve m/z 576/578 (M+H)+.

Example 46

N[1]-[(3-{[3-{[(5-Chloro-2-thienyl)sulfonyl]amino}-4-(methyloxy)-1H-indazol-1-yl]methyl}phenyl)methyl]-D-alloisoleucinamide

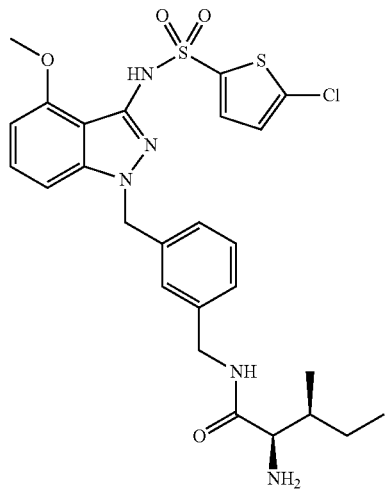 [SMILES: CC[C@H](C)[C@@H](N)C(=O)NCc1cccc(Cn2nc(NS(=O)(=O)c3ccc(Cl)s3)c3c(OC)cccc32)c1]

LCMS (System B) RT=1.95 min, ES+ve m/z 576/578 (M+H)+.

Example 47

N-[(3-{[3-{[(5-Chloro-2-thienyl)sulfonyl]amino}-4-(methyloxy)-1H-indazol-1-yl]methyl}phenyl)methyl]-L-phenylalaninamide

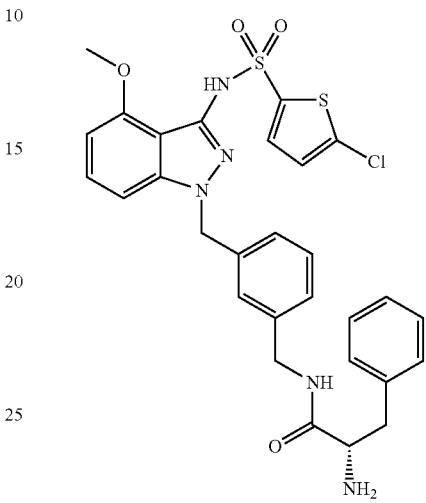

LCMS (System B) RT=2.01 min, ES+ve m/z 610/612 (M+H)+.

Example 48

N[1]-[(3-{[3-{[(5-Chloro-2-thienyl)sulfonyl]amino}-4-(methyloxy)-1H-indazol-1-yl]methyl}phenyl)methyl]-D-valinamide

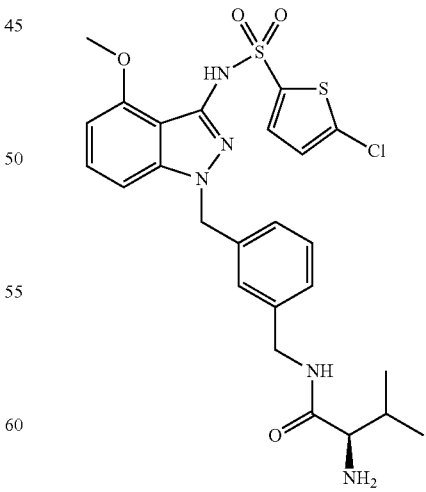

LCMS (System B) RT=1.90 min, ES+ve m/z 562/564 (M+H)+.

Example 49

N¹-[(3-{[3-{[(5-Chloro-2-thienyl)sulfonyl]amino}-4-(methyloxy)-1H-indazol-1-yl]methyl}phenyl)methyl]-L-lysinamide

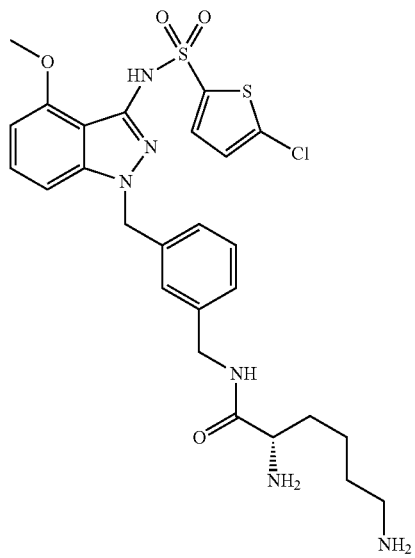 [SMILES: COc1cccc2c1c(NS(=O)(=O)c1ccc(Cl)s1)nn2Cc1cccc(CNC(=O)[C@@H](N)CCCCN)c1]

LCMS (System B) RT=1.46 min, ES+ve m/z 591/593 (M+H)⁺.

Example 50

(2R)—N-[(3-{[3-{[(5-Chloro-2-thienyl)sulfonyl]amino}-4-(methyloxy)-1H-indazol-1-yl]methyl}phenyl)methyl]-2-azetidinecarboxamide Trifluoroacetate

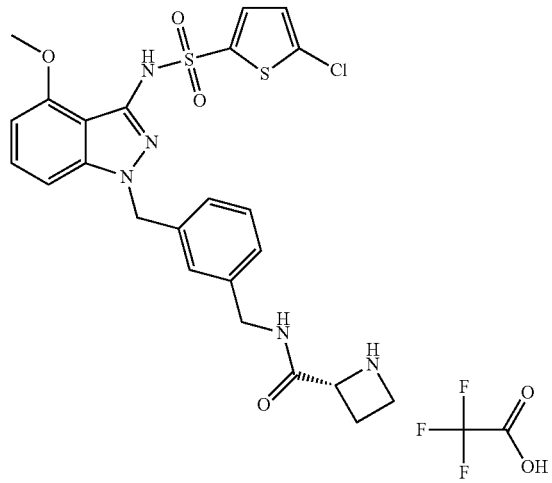

LCMS (System E) RT=1.80 min, ES+ve m/z 546/548 (M+H)⁺.

Example 51

(2S)—N-[(3-{[3-{[(5-Chloro-2-thienyl)sulfonyl]amino}-4-(methyloxy)-1H-indazol-1-yl]methyl}phenyl)methyl]-2-piperidinecarboxamide Trifluoroacetate

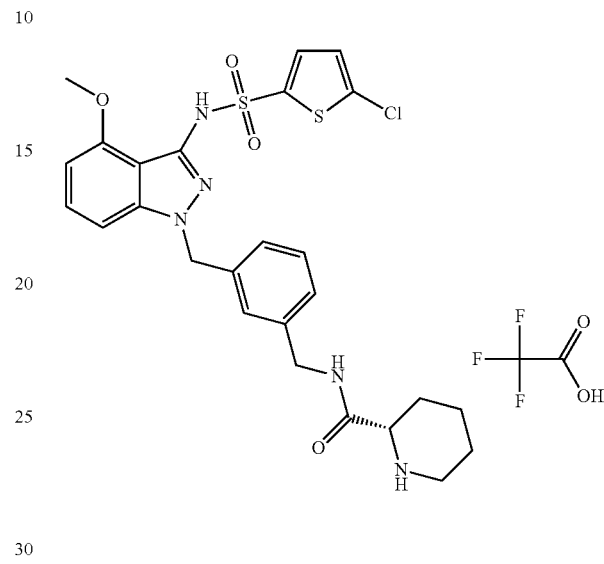

LCMS (System E) RT=1.85 min, ES+ve m/z 574/576 (M+H)⁺.

Example 52

(4R)—N-[(3-{[3-{[(5-Chloro-2-thienyl)sulfonyl]amino}-4-(methyloxy)-1H-indazol-1-yl]methyl}phenyl)methyl]-4-fluoro-L-prolinamide Trifluoroacetate

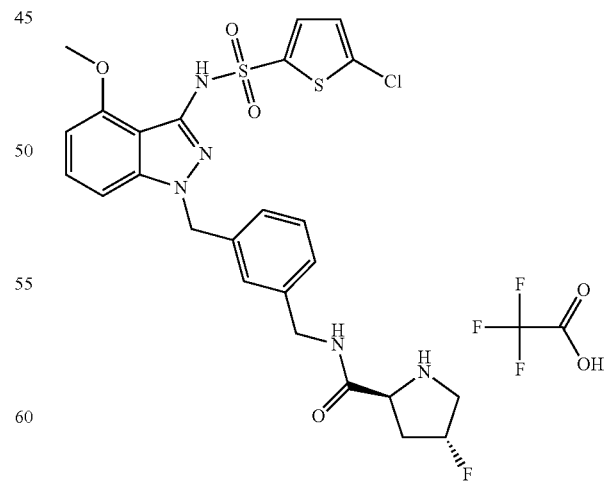

LCMS (System E) RT=1.82 min, ES+ve m/z 578/580 (M+H)⁺.

Example 53

N-[1-{[3,4-Bis(methyloxy)phenyl]methyl}-4-(methyloxy)-1H-indazol-3-yl]-5-chloro-2-thiophenesulfonamide

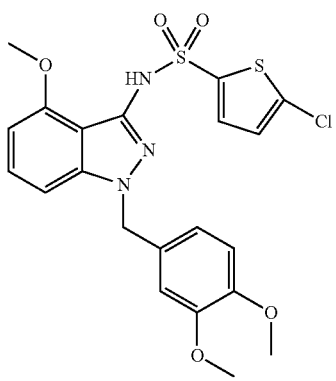 [SMILES: COc1ccc(Cn2nc(NS(=O)(=O)c3ccc(Cl)s3)c3c(OC)cccc32)cc1OC]

To a solution of 5-chloro-N-[(5-chloro-2-thienyl)sulfonyl]-N-[4-(methyloxy)-1H-indazol-3-yl]-2-thiophenesulfonamide (for a preparation see Intermediate 10) (150 mg, 0.286 mmol), triphenylphosphine (150 mg, 0.572 mmol) and [3,4-bis(methyloxy)phenyl]methanol (Aldrich) (96 mg, 0.57 mmol) in THF (3 mL) was added at room temperature di-isopropyl azodicarboxylate (0.113 mL, 0.572 mmol). The resulting mixture was stirred at 60° C. for 3 hours. DCM (3 mL) and water (3 mL) were added and the organic phase was separated. The aqueous layer was further extracted with 3 mL of DCM. The combine organic solutions were dried over an hydrophobic frit and concentrated under a nitrogen stream in a blowdown unit. The residue was purified by chromatography on silica 50 g cartridge on Flashmaster II using a gradient of 0-100% EtOAc in DCM over 60 min. The appropriate fractions were combined and evaporated in vacuo and the residue was dissolved in methanol (5 mL) and treated with a solution of sodium hydroxide (2M, 1.43 mL, 2.86 mmol). The resulting mixture was stirred at 60° C. for 2 hours. The solvents were evaporated off under reduced pressure, and the residue was partitioned between 2 mL of DCM, 3 mL of water. A solution of dilute HCl solution was added until the pH of the aqueous layer was around 1. The organic phase was separated and the aqueous layer was further extracted with 2 mL of DCM. The combined organic solutions were dried over an hydrophobic frit and concentrated under a stream of nitrogen in a blowdown unit. The residue was dissolved in 1:1 MeOH-DMSO (1 mL) and purified by MDAP (supelcosil ABZ+Plus column) eluting with solvents NB (A: Water+ 0.1% Formic acid, B: MeCN:Water 95:5+0.05% Formic acid). The solvent was removed from appropriate fractions under a stream of nitrogen in the Radleys blowdown apparatus to give the title compound (52.6 mg, 37%). LCMS (System A) RT=1.17 min, ES+ve m/z 494/496 (M+H)$^+$.

Example 54

N$^1$-[(3-{[3-{[(5-Chloro-2-thienyl)sulfonyl]amino}-4-(methyloxy)-1H-indazol-1-yl]methyl}phenyl)methyl]-O-methylserinamide Trifluoroacetate The title compound was prepared according to the generic procedure described above by acylation of N-[1-{[3-(aminomethyl)phenyl]methyl}-4-(methyloxy)-1H-indazol-3-yl]-5-chloro-2-thiophenesulfonamide in array format using HATU and TFA removal of the Boc protecting group:

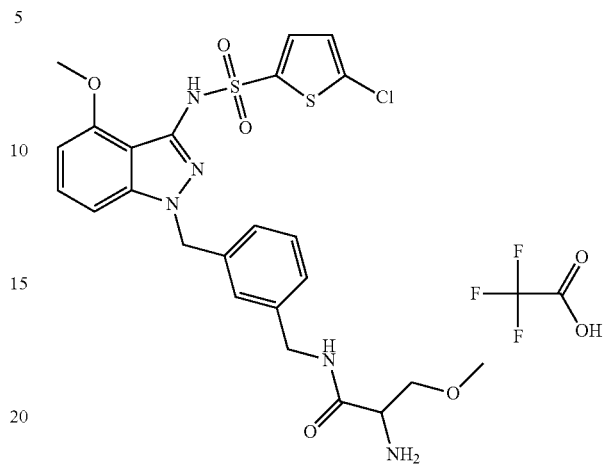

LCMS (System E) RT=1.83 min, ES+ve m/z 564/566 (M+H)$^+$.

Example 55

N-[(3-{[3-{[(5-Chloro-2-thienyl)sulfonyl]amino}-4-(methyloxy)-1H-indazol-1-yl]methyl}phenyl)methyl]-4,4-difluoro-D-prolinamide Trifluoroacetate

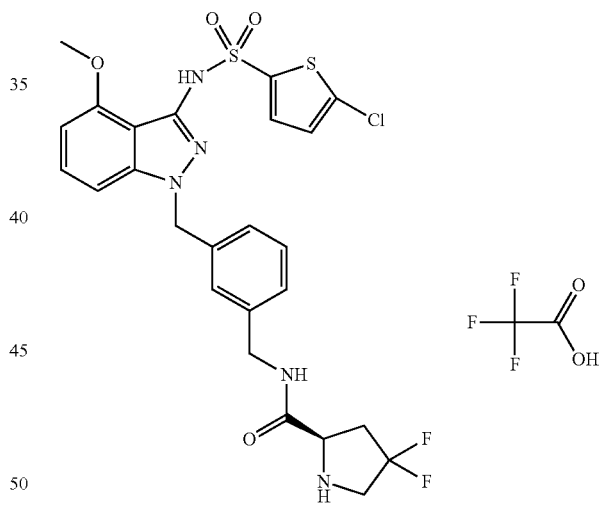

A solution of 1-{[(1,1-dimethylethyl)oxy]carbonyl}-4,4-difluoro-L-proline (Alfa Aesar) (215 mg, 0.857 mmol) in DIPEA (0.150 mL, 0.857 mmol) and dry tetrahydrofuran (1 mL) was stirred at room temperature for 2 min before adding dropwise 1-chloro-N,N,2-trimethyl-1-propen-1-amine (113 µL, 0.857 mmol). The resultant cloudy mixture was stirred at room temperature for 45 min before adding N-[1-{[3-(aminomethyl)phenyl]methyl}-4-(methyloxy)-1H-indazol-3-yl]-5-chloro-2-thiophenesulfonamide hydrochloride (for a preparation see Intermediate 4) (214 mg, 0.428 mmol) followed with DIPEA (0.224 mL, 1.28 mmol) and more THF (5 mL). The reaction mixture was not in solution, and was allowed to stand at room temperature for 3 days. It was then concentrated in vacuo and the residue partitioned between ethyl acetate and saturated sodium bicarbonate solution. The aqueous was extracted with ethyl acetate (×2) and the combined organic solutions were washed with water and brine, dried (Na₂SO₄) and concentrated in vacuo to leave a pale yellow oil. This was divided into 3 equal portions and purified by Mass Directed AutoPrep on Sunfire C18 column using Acetonitrile Water with a Formic acid modifier. The required fractions were combined and concentrated in vacuo to give the product (35 mg, 12%) as a white powder. LCMS showed that there was more product in the HPLC waste, so the waste was concentrated in vacuo and the resultant residue was loaded in dichloromethane onto a silica 50 g cartridge and purified by chromatography on Flashmaster using a 0-50% ethyl acetate-dichloromethane over 40 min. The appropriate fractions were combined and evaporated in vacuo to give more product 1,1-dimethylethyl (2R)-2-({[(3-{[3-{[(5-chloro-2-thienyl)sulfonyl]amino}-4-(methyloxy)-1H-indazol-1-yl]methyl}phenyl)methyl]amino}carbonyl)-4,4-difluoro-1-pyrrolidinecarboxylate (176 mg, as a pale yellow oil. This material was taken through to the next step without further purification. LCMS (System A) RT=1.22 min, ES+ve m/z 696/698 (M+H)⁺. The second batch of the product (176 mg) was dissolved in dry DCM (2 mL) and treated with a 4:1 mixture of dichloromethane and trifluoroacetic acid solution (3 mL). The resultant reaction mixture was stirred at room temperature for 1 h. LCMS showed a small amount of starting material still present, so more DCM-TFA (4:1, 1 mL) was added to the reaction mixture and allowed to stand at room temperature overnight. The reaction mixture was concentrated in vacuo, and the residue was dissolved in the minimum amount of MeOH, and then loaded onto a pre-conditioned (MeOH)SCX-2 cartridge (50 g). The cartridge was washed with MeOH (4 volumes) and then eluted with 10% aqueous NH₃ in MeOH solution. The required fractions were concentrated in vacuo to give the free base of the title compound. This material was dissolved in minimum amount of methanol and treated with trifluoroacetic acid (0.007 mL). This was then concentrated in vacuo to leave the title compound (78 mg, 36%) as a light brown oil. LCMS (System A) RT=0.89 min, ES+ve m/z 596/598 (M+H)⁺.

Example 56

N1-[(3-{[3-{[(5-Chloro-2-thienyl)sulfonyl]amino}-4-(methyloxy)-1H-indazol-1-yl]methyl}phenyl)methyl]-N2,2-dimethylalaninamide Formate

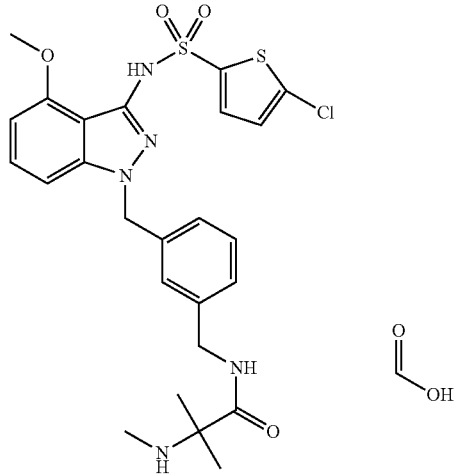 [SMILES: CNC(C)(C)C(=O)NCc1cccc(Cn2nc(NS(=O)(=O)c3ccc(Cl)s3)c3c(OC)cccc32)c1 ; O=CO]

To a solution of N-Boc-N,2-dimethylalanine (174 mg, 0.801 mmol) in anhydrous THF (8 mL) was added dropwise at room temperature 1-chloro-N,N,2-trimethylpropenylamine (0.106 mL, 0.801 mmol) and the resulting mixture was stirred for 30 min. N-[1-{[3-(aminomethyl)phenyl]methyl}-4-(methyloxy)-1H-indazol-3-yl]-5-chloro-2-thiophenesulfonamide hydrochloride (for a preparation see Intermediate 4) (200 mg, 0.4 mmol), followed by N,N-diisopropylethylamine (0.209 mL, 1.20 mmol) were then added and the reaction mixture was stirred at room temperature for 90 min (heterogeneous reaction). A further 8 mL of anhydrous tetrahydrofuran and 70 µL of N,N-diisopropylethylamine was added in order to try to improve solubility. The reaction mixture was stirred at room temperature for 30 min and then evaporated in-vacuo and partitioned between saturated aqueous sodium hydrogen carbonate solution and ethyl acetate. The organic layer was separated, passed through a hydrophobic frit and evaporated in-vacuo to yield a cream oil. The residue (286 mg) was dissolved in MeOH: DMSO (1:1) (3×1 mL) and purified by MDAP on (Sunfire C18 column 150 mm×30 mm i.d. 5 µm packing diameter at ambient temperature) eluting with solvents NB (A: 0.1% v/v solution of formic acid in water, B: 0.1% v/v solution of formic acid in acetonitrile) over 25 min. Appropriate fractions were combined and evaporated in-vacuo to yield the title compound as a clear oil (211 mg, 87%). LCMS (System B) RT=1.75 min, ES+ve m/z 562/564 (M+H)⁺.

Example 57

N-[(3-{[3-{[(5-Chloro-2-thienyl)sulfonyl]amino}-4-(methyloxy)-1H-indazol-1-yl]methyl}phenyl)methyl]-2-hydroxy-2-methylpropanamide

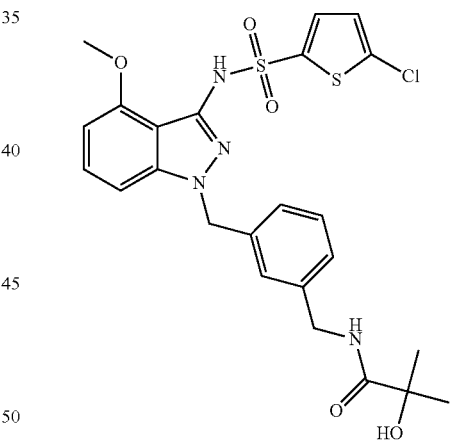

To a solution of 2-hydroxy-2-methylpropanoic acid (Aldrich) (20.84 mg, 0.200 mmol) in THF (2 mL) was added dropwise at room temperature 1-chloro-N,N,2-trimethyl-1-propen-1-amine (0.026 mL, 0.200 mmol). The resulting mixture was stirred at room temperature for 30 min. To this were successively added N-[1-{[3-(aminomethyl)phenyl]methyl}-4-(methyloxy)-1H-indazol-3-yl]-5-chloro-2-thiophenesulfonamide hydrochloride (for a preparation see Intermediate 4) (50 mg, 0.100 mmol) and DIPEA (0.052 mL, 0.300 mmol). After 1 hour of stirring at room temperature LCMS showed product as the major peak. The reaction mixture was concentrated under a stream of nitrogen in the Radleys blowdown apparatus, the residue was dissolved in 1:1 MeOH: DMSO (1 mL) and purified by MDAP on Sunfire C18 column using Acetonitrile Water with a Formic acid modifier. The solvent was removed under a stream of nitrogen in the Radleys blowdown apparatus to give the title compound (48.5 mg, 88%). LCMS (System A) RT=1.05 min, ES+ve m/z 549/551 (M+H)+.

Example 57

Alternative Preparation

N-[(3-{[3-{[(5-Chloro-2-thienyl)sulfonyl]amino}-4-(methyloxy)-1H-indazol-1-yl]methyl}phenyl)methyl]-2-hydroxy-2-methylpropanamide

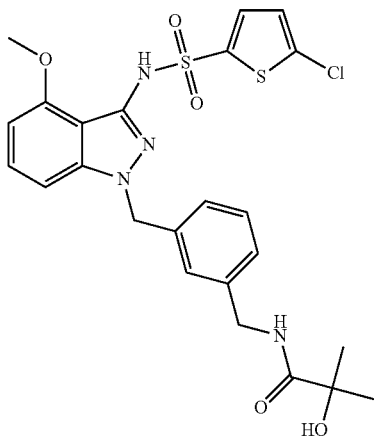 [SMILES: COc1cccc2c1c(NS(=O)(=O)c1ccc(Cl)s1)nn2Cc1cccc(CNC(=O)C(C)(C)O)c1]

To a solution of 2-{[(3-{[3-{[(5-chloro-2-thienyl)sulfonyl]amino}-4-(methyloxy)-1H-indazol-1-yl]methyl}phenyl)methyl]amino}-1,1-dimethyl-2-oxoethyl acetate (for a preparation see Intermediate 27) (37 g, 62.6 mmol) in methanol (2000 ml) was added potassium carbonate (26.0 g, 188 mmol) and the reaction mixture was stirred at room temperature. After stirring for 10 mins the reaction mixture started to crystallise. It was stirred for 3 hours. The solid was filtered and the filtrate was evaporated in vacuo. The residue was acidified with 2M HCl and it was extracted with ethyl acetate (500 ml).

The filtered solid was treated with water (1000 ml) and the resulting suspension was acidified with 2M HCl. It was then extracted with ethyl acetate (2×500 ml). The combined organic layers were washed with brine, dried over magnesium sulphate and evaporated in vacuo. The residue was dissolved in DCM and loaded onto a 1500 g silica column. It was eluted with 50-100% ethyl acetate in cyclohexane over 8CV. The required fractions were combined and evaporated in vacuo to give the title compound (30.42 g, 89%) as a white solid. LCMS (System A) RT=1.00 min, ES+ve m/z 549/551 (M+H)+; 1H NMR 6 (DMSO-d6, 600 MHz): 10.40 (s, 1H), 8.13 (t, J=6.0 Hz, 1H), 7.37 (d, J=4.0 Hz, 1H), 7.26 (t, J=8.0 Hz, 1H), 7.23 (t, J=7.5 Hz, 1H), 7.17 (d, J=4.0 Hz, 1H), 7.17 (d, J=8.0 Hz, 1H), 7.14 (br. s., 1H), 7.13 (d, J=8.0 Hz, 1H), 6.98 (d, J=7.5 Hz, 1H), 6.50 (d, J=7.5 Hz, 1H), 5.48 (s, 2H), 5.34 (s, 1H), 4.22 (d, J=6.0 Hz, 2H), 3.76 (s, 3H), 1.24 (s, 6H).

Example 58

5-Chloro-N-{4-(methyloxy)-1-[(3-{[(methylsulfonyl)amino]methyl}phenyl)methyl]-1H-indazol-3-yl}-2-thiophenesulfonamide

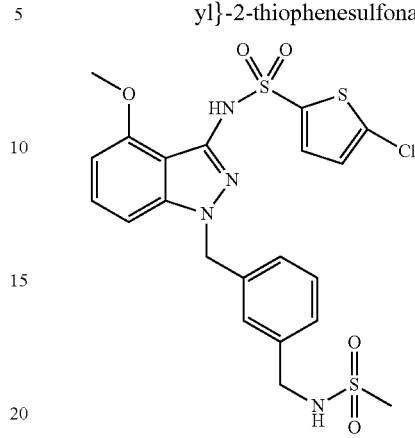

To a suspension of N-[1-{[3-(aminomethyl)phenyl]methyl}-4-(methyloxy)-1H-indazol-3-yl]-5-chloro-2-thiophenesulfonamide hydrochloride ((for a preparation see Intermediate 4) 51 mg, 0.10 mmol) in dry DCM (3 mL) was added methanesulfonyl chloride (8 μL, 0.1 mmol), followed by pyridine (1 mL). The resultant pale yellow solution was stirred at room temperature overnight. LCMS showed only 19% of required product. Triethylamine (14 μL, 0.10 mmol), followed by more methanesulfonyl chloride (8 μL, 0.1 mmol) were added and stirring was continued for a further 30 min. The reaction mixture was then concentrated in vacuo and the residue dissolved in 1:1 MeOH:DMSO (1 mL) and purified by MDAP (supelcosil ABZ+Plus column) eluting with solvents A/B (A: Water+0.1% Formic acid, B: MeCN:Water 95:5+0.05% Formic acid). The solvent was evaporated in vacuo to give the title product (10.7 mg, 19%) as a white solid. LCMS (System A) RT=1.13 min, ES+ve m/z 541/543 (M+H)+.

Example 59

N-[1-[(3-{[(Aminocarbonyl)amino]methyl}phenyl)methyl]-4-(methyloxy)-1H-indazol-3-yl]-5-chloro-2-thiophenesulfonamide

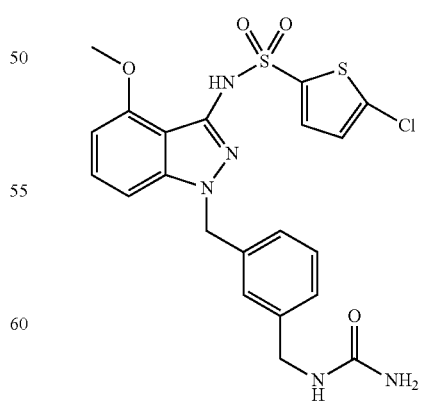

To a suspension of N-[1-{[3-(aminomethyl)phenyl]methyl}-4-(methyloxy)-1H-indazol-3-yl]-5-chloro-2-thiophenesulfonamide hydrochloride ((for a preparation see Intermediate 4) 47 mg, 0.094 mmol) in ethyl acetate (0.4 mL) and triethylamine (0.013 mL, 0.094 mmol) was added acetic acid (1.5 mL). A solution of potassium cyanate (11 mg, 0.14 mmol) in water (0.2 mL) was added portionwise. The resultant clear solution was stirred at room temperature overnight. LCMS showed incomplete reaction and a higher percentage of product to SM. The reaction mixture was concentrated in vacuo and the resultant oil was divided into 2 equal portions. Each was dissolved in 1:1 MeOH:DMSO (1 mL) and purified by MDAP on Xbridge column using Acetonitrile Water with an ammonium carbonate modifier. The appropriate fractions were combined and concentrated in vacuo to give two respective batches, which were not clean, so these were combined and re-purified by MDAP to give the title compound (2.4 mg, 5%). LCMS (System A) RT=0.95 min, ES+ve m/z 506/508 (M+H)$^+$.

Example 60

5-Chloro-N-[1-({3-[({[(1,1-dimethylethyl)amino] carbonyl}amino)methyl]phenyl}methyl)-4-(methyloxy)-1H-indazol-3-yl]-2-thiophenesulfonamide

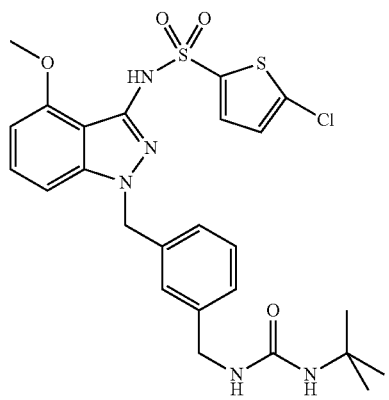 [SMILES: COc1cccc2c1c(NS(=O)(=O)c1ccc(Cl)s1)nn2Cc1cccc(CNC(=O)NC(C)(C)C)c1]

To a suspension of N-[1-{[3-(aminomethyl)phenyl]methyl}-4-(methyloxy)-1H-indazol-3-yl]-5-chloro-2-thiophenesulfonamide hydrochloride (for a preparation see Intermediate 4) (55 mg, 0.11 mmol) in dry DCM (0.5 mL) was added triethylamine (0.015 mL, 0.11 mmol), followed by tert-butyl isocyanate (0.013 mL, 0.11 mmol). The reaction mixture was stirred at room temperature for 1.5 h. LCMS showed mainly required product with 6% SM. The reaction mixture was diluted with DCM and methanol and then concentrated in vacuo. The resultant residue was dissolved in 1:1 MeOH:DMSO (1 mL) and purified by MDAP (supelcosil ABZ+Plus column) eluting with solvents A/B (A: Water+0.1% Formic acid, B: MeCN:Water 95:5+0.05% Formic acid). The solvent was evaporated in vacuo to give the title compound (52 mg, 84%). LCMS (System A) RT=1.15 min, ES+ve m/z 562/564 (M+H)$^+$.

Example 61

5-Chloro-N-[1-({3-[(({[(1-methylethyl)amino] carbonyl}amino)methyl]phenyl}methyl)-4-(methyloxy)-1H-indazol-3-yl]-2-thiophenesulfonamide

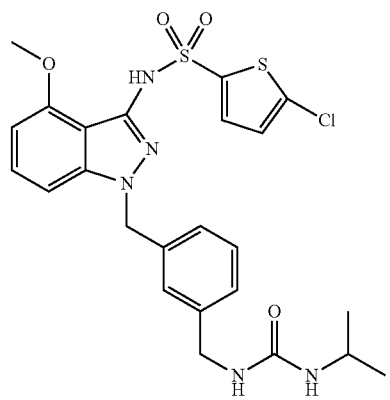 [SMILES: COc1cccc2c1c(NS(=O)(=O)c1ccc(Cl)s1)nn2Cc1cccc(CNC(=O)NC(C)C)c1]

To a suspension of N-[1-{[3-(aminomethyl)phenyl]methyl}-4-(methyloxy)-1H-indazol-3-yl]-5-chloro-2-thiophenesulfonamide hydrochloride (for a preparation see Intermediate 4) (52 mg, 0.10 mmol) in dry DCM (0.5 mL) was added triethylamine (15 µL, 0.11 mmol), followed with isopropyl isocyanate (11 µL, 0.11 mmol). The reaction mixture was stirred at room temperature for 45 min. LCMS showed mainly product. The reaction mixture was diluted with DCM and methanol and then concentrated in vacuo. The resultant residue was dissolved in 1:1 MeOH:DMSO (1 mL) and purified MDAP (supelcosil ABZ+Plus column) eluting with solvents A/B (A: Water+0.1% Formic acid, B: MeCN:Water 95:5+0.05% Formic acid). The solvent was evaporated in vacuo to give the title compound (43 mg, 75%) as a white powder. LCMS (System A) RT=1.11 min, ES+ve m/z 548/550 (M+H)$^+$.

Example 62

N-[1-{[4-(Aminosulfonyl)phenyl]methyl}-4-(methyloxy)-1H-indazol-3-yl]-5-chloro-2-thiophenesulfonamide

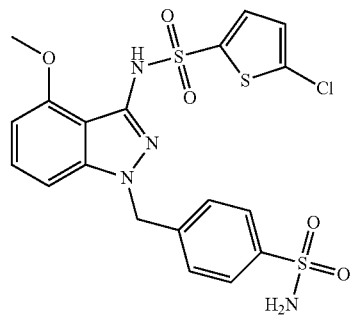 [SMILES: COc1cccc2c1c(NS(=O)(=O)c1ccc(Cl)s1)nn2Cc1ccc(S(N)(=O)=O)cc1]

5-Chloro-N-[4-(methyloxy)-1H-indazol-3-yl]-N-({[2-(trimethylsilyl)ethyl]oxy}methyl)-2-thiophenesulfonamide (for a preparation see Intermediate 8) (1.734 g, 3.66 mmol) was dissolved in DMF (2.4 mL) and an aliquot (0.1 mL, 0.15 mmol) added to 4-(bromomethyl)benzenesulfonamide (APAC Pharm) (0.15 mmol) and potassium carbonate (0.15 mmol) added last. The tubes were capped and shaken. Stood at room temperature for 18 h, more potassium carbonate (excess) added and reshaken the tubes. Filtered through alltech tube to remove inorganic solids, and washed tubes with MeOH (1 mL) and blown to dryness under a stream of nitrogen in a Radley's blow down unit. Redissolved in DCM (0.5 mL) and applied to a 10 g silica cartridge, and purified by chromatography on Flashmaster using a gradient of 0-100% DCM-(DCM with 20% EtOAc) over 20 min. The appropriate fractions were combined and evaporated in vacuo using the Genevac. The residue was dissolved in TBAF (1M, 0.5 mL) and heated in a microwave oven (50 Watts, 10 min, at approx 110° C. The sample was purified by MDAP on Atlantis column using Acetonitrile Water with a Formic acid modifier. The solvent was evaporated in vacuo using the Genevac to give the title compound (7.9 mg, 10%) LCMS (System A) RT=0.92 min, ES+ve m/z 513/515 (M+H)$^+$ Example 63

2-(3-{[3-{[(5-Chloro-2-thienyl)sulfonyl]amino}-4-(methyloxy)-1H-indazol-1-yl]methyl}phenyl)-N-methylacetamide

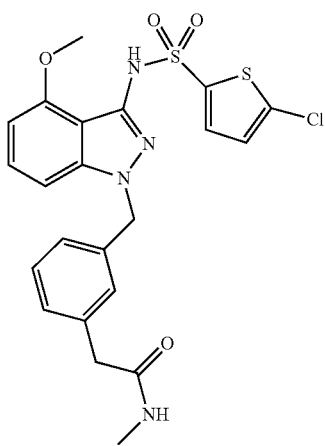 [SMILES: CNC(=O)Cc1cccc(Cn2nc(NS(=O)(=O)c3ccc(Cl)s3)c3c(OC)cccc32)c1]

A mixture of 5-chloro-N-[4-(methyloxy)-1H-indazol-3-yl]-2-thiophenesulfonamide (for a preparation see Intermediate 26) (900 mg, 1.9 mmol), phenylmethyl[3-(bromomethyl)phenyl]acetate (*J. Med. Chem.* 1992, 35, 2551-2562, compound 13) (1.23 g, 3.84 mmol) and potassium carbonate (525 mg, 3.80 mmol) in dry N,N-Dimethylformamide (50 mL) was stirred and heated at reflux for 2 h. The reaction mixture was partitioned between water (50 mL) and ethyl acetate (50 mL). The aqueous was extracted with ethylacetate (×2). The combined organic solutions were washed with water and brine, dried (Na$_2$SO$_4$) and concentrated in vacuo to leave a dark yellow oil. The sample was loaded in dichloromethane and purified by chromatography on a silica 100 g cartridge on Flashmaster using a gradient of 0-50% ethyl acetate-cyclohexane over 40 min. The appropriate fractions were combined and evaporated in vacuo to give phenylmethyl (3-{[3-[[(5-chloro-2-thienyl)sulfonyl]({[2-(trimethylsilyl)ethyl]oxy}methyl)amino]-4-(methyloxy)-1H-indazol-1-yl]methyl}phenyl)acetate (1.038 g, 77%) as a yellow oil. LCMS RT=1.63 min, ES+ve m/z 729/731 (M+NH$_4$)$^+$. To a portion of this (103 mg, 0.145 mmol) was added a solution of methylamine THF (2M, 2.1 mL, 4.20 mmol) (excess was added to aid transfer of ester to microwave vessel) and 1,3,4,6,7,8-hexahydro-2H-pyrimido[1,2-a]pyrimidine (TBD) (6 mg, 0.04 mmol). The microwave vessel was sealed and heated at 80° C. in Biotage Initiator for 60 min. LCMS showed that the reaction was complete. The reaction mixture was concentrated in vacuo to leave a pale yellow oil. This was divided into 2 equal portions and each portion dissolved in 1:1 MeOH:DMSO (1 mL) and purified by MDAP (supelcosil ABZ+ Plus column) eluting with solvents NB (A: Water+0.1% Formic acid, B: MeCN:Water 95:5+0.05% Formic acid). The solvent was evaporated in vacuo to give 2-(3-{[3-[[(5-chloro-2-thienyl)sulfonyl]({[2-(trimethylsilyl)ethyl]oxy}methyl)amino]-4-(methyloxy)-1H-indazol-1-yl]methyl}phenyl)-N-methylacetamide (39 mg, 42%) as a colourless oil. LCMS RT=1.43 min, ES+ve m/z 635/637 (M+H)$^+$. A mixture of this product and TBAF in THF (1M, 0.62 mL, 0.62 mmol) was sealed in a 0.2-2 mL miccrowave vessel. Tetrahydrofuran (0.8 mL) was added to the mixture, and heated in Biotage Initiator microwave oven using normal to 100° C. for 10 min. This was repeated 2 more times. The reaction mixture was then partitioned between water and dichloromethane. The phases were separated using a hydrophobic frit. The aqueous was extracted with DCM (×2) and the combined organic solutions were concentrated in vacuo to leave a white oil (46 mg). This was dissolved in 1:1 MeOH:DMSO (1 mL) and purified by MDAP (supelcosil ABZ+Plus column) eluting with solvents A/B (A: Water+0.1% Formic acid, B: MeCN:Water 95:5+ 0.05% Formic acid). The solvent was evaporated in vacuo to give the title compound (9 mg, 29%) as a white powder. LCMS (System A) RT=1.06 min, ES+ve m/z 505/507 (M+H)$^+$.

Example 64

3-{[3-{[(5-Chloro-2-thienyl)sulfonyl]amino}-4-(methyloxy)-1H-indazol-1-yl]methyl}benzamide

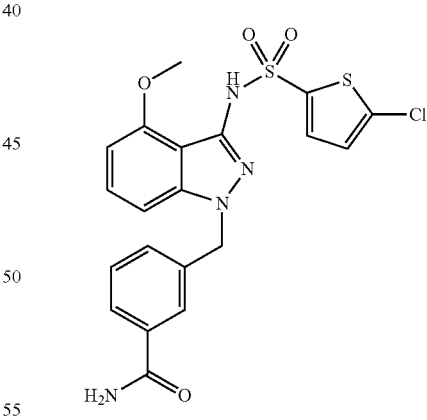

To a solution of 5-chloro-N-[4-(methyloxy)-1H-indazol-3-yl]-N-({[2-(trimethylsilyl)ethyl]oxy}methyl)-2-thiophenesulfonamide (for a preparation see Intermediate 8) (150 mg, 0.316 mmol) into DMF (2 mL) was added at ambient temperature potassium carbonate (87 mg, 0.63 mmol) and 3-(chloromethyl)benzamide (Maybridge) (64.4 mg, 0.380 mmol). The resulting mixture was stirred at 50° C. overnight, and then diluted with DCM (2 mL) and water (2 mL). The organic mixture was partitioned and the aqueous layer was further extracted with 2 mL of DCM. The organic solutions were combined together, dried over an hydrophobic frit and evaporated under a nitrogen stream in a blowdown unit. The crude product was judged by LCMS to be pure enough to be engaged in the next step without any further purification. LCMS (System A) RT=1.37 min, ES+ve m/z 607/609 (M+H)+. In a 2 to 5 mL Biotage microwave vial were added the crude indazole product and TBAF solution in THF (1M, 3.16 mL, 3.16 mmol). The reaction vessel was sealed and heated in a Biotage Initiator at 110° C. for 10 min (very high absorption level). The crude mixture was then diluted with 2 mL of DCM and 2 mL of water. The organic layer was separated and the aqueous layer was further extracted with 2 mL of DCM. The combined organic solutions were dried over an hydrophobic frit, and evaporated under a nitrogen stream in a blowdown unit. The residue was dissolved in 1:1 MeOH: DMSO (1 mL) and purified by MDAP (supelcosil ABZ+Plus column) eluting with solvents NB (A: Water+0.1% Formic acid, B: MeCN:Water 95:5+0.05% Formic acid). The solvent was removed under a stream of nitrogen in a Radleys blowdown apparatus to give the title compound (76 mg, 50%). LCMS (System A) RT=0.97 min, ES+ve m/z 477/479 (M+H)+.

Example 65

3-{[3-{[(5-Chloro-2-thienyl)sulfonyl]amino}-4-(methyloxy)-1H-indazol-1-yl]methyl}-N-[2-(dimethylamino)ethyl]benzamide

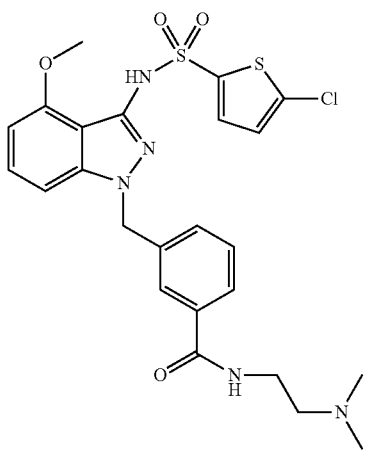 [SMILES: COc1cccc2c1c(NS(=O)(=O)c1ccc(Cl)s1)nn2Cc1cccc(C(=O)NCCN(C)C)c1]

To a solution of 5-chloro-N-[4-(methyloxy)-1H-indazol-3-yl]-N-({[2-(trimethylsilyl)ethyl]oxy}methyl)-2-thiophenesulfonamide (for a preparation see Intermediate 8) (1 g, 2.1 mmol) in DMF (10 mL) was added at ambient temperature K$_2$CO$_3$ (0.583 g, 4.22 mmol) and methyl 3-(bromomethyl) benzoate (Alfa Aesar) (0.580 g, 2.53 mmol). The resulting mixture was stirred at 50° C. for 2 h by which time LCMS showed product as the major peak. The reaction mixture was diluted with 20 mL of DCM and 20 mL of water. The organic phase was separated and the aqueous layer was further extracted with 20 mL of DCM. The combined organic solutions were washed with brine, dried over an hydrophobic frit, and concentrated under reduced pressure. The residue was loaded on to a silica 100 g cartridge in dichloromethane and purified by chromatography on Flashmaster using a 0-100% gradient EtOAc in DCM, over 40 min to give methyl 3-{[3-[[(5-chloro-2-thienyl)sulfonyl]({[2-(trimethylsilyl)ethyl] oxy}methyl)amino]-4-(methyloxy)-1H-indazol-1-yl] methyl}benzoate (571 mg, 43%). LCMS (System A) RT=1.60 min, ES+ve m/z 622/624. A portion of the product (70 mg, 0.11 mmol) was placed in a 0.2 to 0.5 mL Biotage microwave vial, followed by N,N-dimethyl-1,2-ethanediamine (Aldrich) (246 μL, 2.25 mmol), 1,3,4,6,7,8-hexahydro-2H-pyrimido[1,2-a]pyrimidine (TBD) (7.83 mg, 0.056 mmol). The reaction vessel was sealed and heated in a Biotage Initiator using initial very high absorption level to 80° C. for 75 min. After cooling the reaction, an LCMS showed the product as a single peak. The reaction mixture was diluted with DCM (2 mL) and water (3 mL). The organic phase was separated and the aqueous layer was further extracted with 2 mL of DCM. The combined organic solutions were dried through an hydrophobic frit and concentrated in a nitrogen blowdown unit. LCMS (System A) RT=1.46 min, ES+ve m/z 678/680 (M+H)+. The crude product was placed in a 0.5 to 2 mL Biotage microwave vial and a solution of TBAF in THF (1.125 mL, 1.125 mmol) was added. The reaction vessel was sealed and heated in a Biotage Initiator at 110° C. for 15 min (very high absorption level). The solvent was removed under a nitrogen stream in a blowdown unit at 35° C. overnight. The residue was dissolved in 1:1 MeOH:DMSO (1 mL) and purified by MDAP on standard C18 column using Acetonitrile Water with a TFA modifier. The solvent was removed under a stream of nitrogen in the Radleys blowdown apparatus, and the residue was further purified on SCX-2 ion-exchange cartridge (pre-conditioned with MeOH, compound loaded in Methanol, eluted with Methanol (2× column volumes), followed by 2M NH$_3$ in Methanol. The ammoniacal fractions were concentrated under reduced pressure to provide the title compound (55.3 mg, 90%). LCMS (System E) RT=2.15 min, ES+ve m/z 548/550 (M+H)+.

Example 66

3-[(4-(Methyloxy)-3-{[(5-methyl-2-thienyl)sulfonyl] amino}-1H-indazol-1-yl)methyl]benzamide

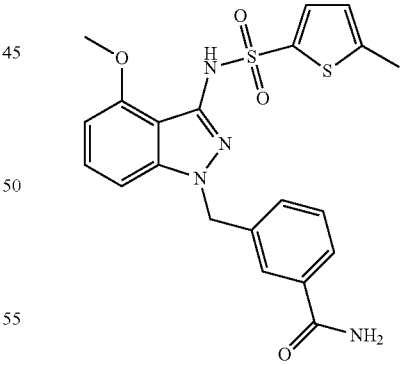

3-{[3-Amino-4-(methyloxy)-1H-indazol-1-yl] methyl}benzamide (for a preparation see Intermediate 12) 22 mg, 0.07 mmol) was dissolved in pyridine (1.6 mL) and added to 5-methyl-2-thiophenesulfonyl chloride (20 mg, 0.1 mmol). The reaction mixture was shaken at room temperature for 5 min and then stood overnight at room temperature. DMSO (0.2 mL) was added to the reaction mixture and purified by MDAP on Atlantis column using Acetonitrile Water with a Formic acid modifier. The solvent was evaporated in vacuo using the Genevac to give the title compound (14.2 mg, 44%) LCMS (System A) RT=0.92 min, ES+ve m/z 457 (M+H)+.

Example 67

3-{[3-{[(5-Bromo-2-thienyl)sulfonyl]amino}-4-(methyloxy)-1H-indazol-1-yl]methyl}benzamide

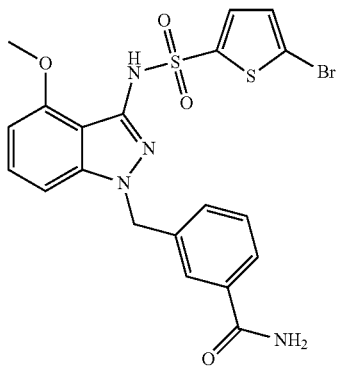 [SMILES: COc1cccc2c1c(NS(=O)(=O)c1ccc(Br)s1)nn2Cc1cccc(C(N)=O)c1]

3-{[3-Amino-4-(methyloxy)-1H-indazol-1-yl]methyl}benzamide (for a preparation see Intermediate 12) (22 mg, 0.07 mmol) was dissolved in pyridine (1.6 mL) and added to 5-bromo-2-thiophenesulfonyl chloride (27 mg, 0.1 mmol). The reaction mixture was shaken at room temperature for 5 min and then stood overnight at room temperature. DMSO (0.2 mL) was added to the reaction mixture and purified by MDAP on Atlantis column using Acetonitrile Water with a Formic acid modifier. The solvent was evaporated in vacuo using the Genevac to give the title compound (4.6 mg, 12%) LCMS (System A) RT=1.04 min, ES+ve m/z 521/523 (M+H)+.

Example 68

3-{[3-{[(5-Chloro-2-thienyl)sulfonyl]amino}-7-fluoro-4-(methyloxy)-1H-indazol-1-yl]methyl}benzamide

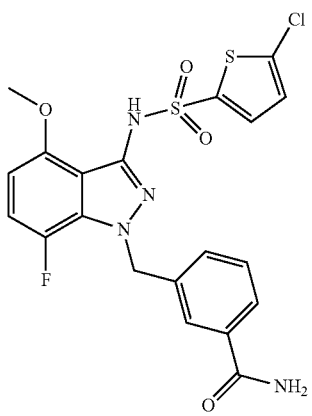 [SMILES: COc1ccc(F)c2c1c(NS(=O)(=O)c1ccc(Cl)s1)nn2Cc1cccc(C(N)=O)c1]

To a solution of 3-{[3-amino-7-fluoro-4-(methyloxy)-1H-indazol-1-yl]methyl}benzamide (for a preparation see Intermediate 14) (22 mg, 0.07 mmol) in anhydrous pyridine (1 mL) and anhydrous dichloromethane (3 mL) (gentle heating of the mixture for a few minutes with a heatgun was required in order for the starting material to go in solution) was added a solution of 5-chloro-2-thiophenesulfonyl chloride (16.71 mg, 0.077 mmol) in anhydrous dichloromethane (0.5 mL). The reaction was stirred at room temperature for 45 min, then at 45° C. for 30 min. A solution of 5-chloro-2-thiophenesulfonyl chloride (16.7 mg) in anhydrous dichloromethane (0.2 mL) was added to the reaction mixture and stirred at 45° C. for 25 h. The reaction mixture was cooled and then partitioned between water and dichloromethane. The organic layer was passed through an hydrophobic frit and evaporated in-vacuo to yield a pale yellow solid. The solid was dissolved in MeOH-DMSO (1 mL) and purified by MDAP on Sunfire C18 column, eluting with solvents NB (A: 0.1% v/v solution of formic acid in water, B: 0.1% v/v solution of formic acid in acetonitrile). Appropriate fraction was evaporated in-vacuo to yield the title compound as a white solid (15.7 mg, 45%). LCMS (5 min run) RT=2.62 min, ES+ve m/z 495/497 (M+H)+.

Example 69

3-[(3-{[(5-Chloro-2-thienyl)sulfonyl]amino}-7-fluoro-4-hydroxy-1H-indazol-1-yl)methyl]benzamide

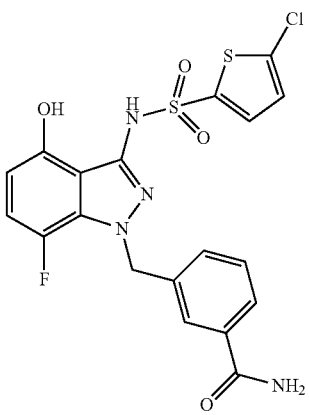 [SMILES: NC(=O)c1cccc(Cn2nc(NS(=O)(=O)c3ccc(Cl)s3)c3c(O)ccc(F)c32)c1]

A suspension of 3-{[3-{[(5-chloro-2-thienyl)sulfonyl]amino}-7-fluoro-4-(methyloxy)-1H-indazol-1-yl]methyl}benzamide (for a preparation see Example 68) (15.7 mg, 0.032 mmol) in anhydrous DCM (2 mL) under nitrogen atmosphere was treated with boron tribromide solution in DCM (1M, 0.032 mL) at room temperature. The reaction mixture was stirred at room temperature for 45 min and then saturated aqueous sodium bicarbonate solution was added dropwise to quench the reaction. The mixture was then partitioned between further saturated aqueous sodium bicarbonate solution and 10% methanol in ethyl acetate (white precipitate was present which was insoluble in both the organic and aqueous layer). The organic layer was separated, passed through an hydrophobic frit and evaporated in-vacuo to yield a yellow solid (13 mg). This was dissolved in MeOH:DMSO (1:1) (0.5 mL) and purified by MDAP on Sunfire C18 column, eluting with solvents NB (A: 0.1% v/v solution of formic acid in water, B: 0.1% v/v solution of formic acid in acetonitrile). Appropriate fraction was evaporated in-vacuo to yield the title compound as a yellow solid (8.5 mg, 56%). LCMS (System B) RT=2.41 min, ES+ve m/z 481/483 (M+H)⁺.

Example 70

3-[(3-{[(5-Chloro-2-thienyl)sulfonyl]amino}-4-hydroxy-1H-indazol-1-yl)methyl]benzamide

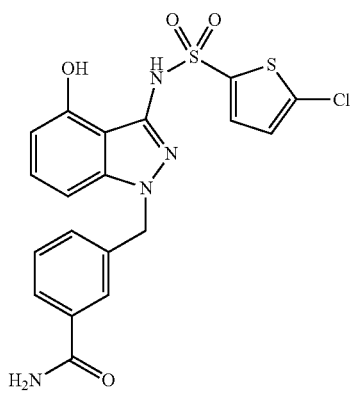 [SMILES: NC(=O)c1cccc(Cn2nc(NS(=O)(=O)c3ccc(Cl)s3)c3c(O)cccc32)c1]

A suspension of 3-{[3-{[(5-chloro-2-thienyl)sulfonyl]amino}-4-(methyloxy)-1H-indazol-1-yl]methyl}benzamide (for a preparation see Example 64) (50.0 mg, 0.105 mmol) in anhydrous DCM (1.5 mL) under nitrogen atmosphere was treated with boron tribromide solution in DCM (1M, 0.105 mL, 0.105 mmol) at room temperature, and the mixture was stirred at room temperature for 45 min. A further 0.2 ml portion of boron tribromide solution was added and the reaction mixture was stirred at room temperature for 90 min. Saturated aqueous sodium bicarbonate solution was added dropwise to quench the reaction. The reaction was then partitioned between further saturated aqueous sodium bicarbonate solution and 10% methanol in ethyl acetate (off white precipitate was present, which was insoluble in both the organic and aqueous layer). The organic layer was separated, passed through a hydrophobic frit and evaporated in-vacuo to yield an off white solid (58 mg), which was dissolved in MeOH-DMSO (1:1) (1 mL) and purified by MDAP on Sunfire C18 column eluting with solvents NB (A: 0.1% v/v solution of formic acid in water, B: 0.1% v/v solution of formic acid in acetonitrile 25 min run). The appropriate fraction was evaporated in-vacuo to yield a white solid (17 mg, 35%). LCMS (System B) RT=2.18 min, ES+ve m/z 463/465 (M+H)⁺.

Example 71

$N^1$-({3-[(3-{[(5-Chloro-2-thienyl)sulfonyl]amino}-4-hydroxy-1H-indazol-1-yl)methyl]phenyl}methyl)-$N^2$-methyl-D-alaninamide Formic Acid Salt

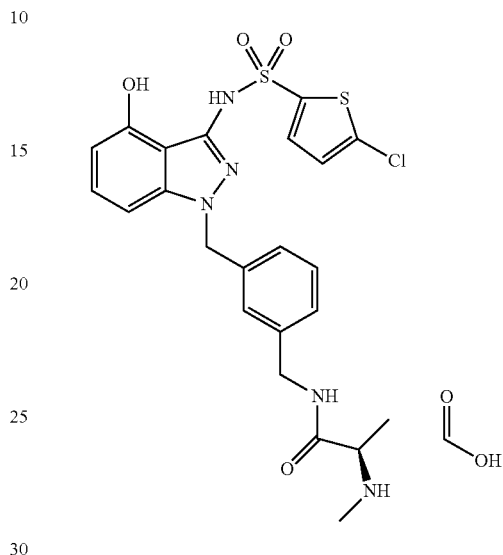

To a solution of O-(7-azabenzotriazol-1-yl)-N,N,N',N'-tetramethyluronium-hexafluorophosphate (39.7 mg, 0.064 mmol) in anhydrous DMF (1 mL) was added at room temperature N-Boc-N-methyl-D-alanine (11.91 mg, 0.059 mmol), followed by N,N-diisopropylethylamine (0.0306 mL, 0.176 mmol) and finally a solution of N-(1-{[3-(aminomethyl)phenyl]methyl}-4-hydroxy-1H-indazol-3-yl)-5-chloro-2-thiophenesulfonamide formate salt (for a preparation see Intermediate 15) (29 mg, 0.059 mmol) in anhydrous DMF (1 mL). The reaction mixture was stirred at room temperature for 1 hour and then was partitioned between saturated aqueous sodium hydrogen carbonate solution and ethyl acetate. The organic layer was separated, washed with brine-water (1:1), passed through a hydrophobic frit, and evaporated in-vacuo to yield a colourless oil. LCMS (System B) RT=3.01 min, ES+ve m/z 634/636 (M+H)+ for desired BOC protected product. This product was suspended in a solution of hydrogen chloride in 1,4-dioxane (4M, 0.5 mL) and methanol was added until the reaction was in solution. The mixture was stirred at room temperature for 18 hours and then evaporated in-vacuo to yield a colourless oil. The residual oil was dissolved in MeOH-DMSO (0.5 mL) and purified by MDAP) on OA MDAP on Sunfire C18 column, eluting with solvents A/B (A: 0.1% v/v solution of formic acid in water, B: 0.1% v/v solution of formic acid in acetonitrile) (25 min run). The appropriate fractions were combined and evaporated in-vacuo to yield the title compound as a colourless oil (15 mg, 44%). LCMS (System B) RT=1.63 min, ES+ve m/z 534/536 (M+H)⁺

Example 72

N-({3-[(3-{[(5-Chloro-2-thienyl)sulfonyl]amino}-4-hydroxy-1H-indazol-1-yl)methyl]phenyl}methyl)acetamide

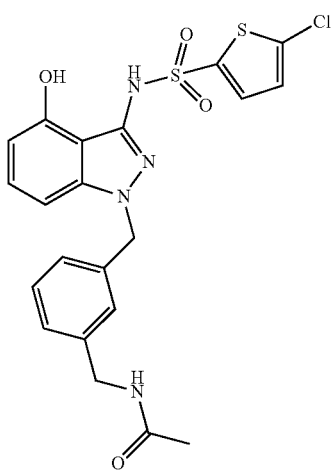 [SMILES: CC(=O)NCc1cccc(Cn2nc(NS(=O)(=O)c3ccc(Cl)s3)c3c(O)cccc32)c1]

To a solution of O-(7-azabenzotriazol-1-yl)-N,N,N',N'-tetramethyluronium-hexafluorophosphate (39.7 mg, 0.064 mmol) in anhydrous DMF (1 mL) was added at room temperature acetic acid (3.36 µL, 0.059 mmol), followed by N,N-diisopropylethylamine (0.031 mL, 0.18 mmol) and finally a solution of N-(1-{[3-(aminomethyl)phenyl]methyl}-4-hydroxy-1H-indazol-3-yl)-5-chloro-2-thiophenesulfonamide formate salt (for a preparation see Intermediate 15) (29 mg, 0.059 mmol) in anhydrous DMF (1 mL) and the reaction mixture was stirred at room temperature for 30 min. The mixture was partitioned between saturated aqueous sodium hydrogen carbonate solution and ethyl acetate. The organic layer was separated, washed with brine:water (1:1), passed through a hydrophobic frit and evaporated in-vacuo to yield a colourless oil (23 mg). This was dissolved in MeOH:DMSO (1 mL) and purified by MDAP Sunfire C18 column eluting with solvents A/B (A: 0.1% v/v solution of formic acid in water, B: 0.1% v/v solution of formic acid in acetonitrile) (25 min run). The appropriate fraction was evaporated in-vacuo to yield the title compound as a colourless oil (20 mg, 69%). LCMS (System B) RT=2.41 min, ES+ve m/z 491/493 (M+H)$^+$.

Example 73

N-({3-[(3-{[(5-Chloro-2-thienyl)sulfonyl]amino}-4-hydroxy-1H-indazol-1-yl)methyl]phenyl}methyl)-3-morpholinecarboxamide Formate Salt

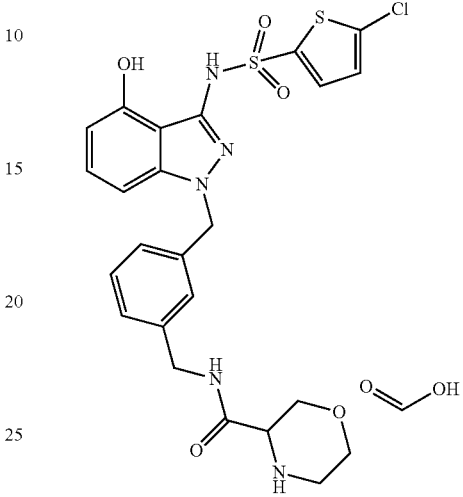

To a solution of O-(7-azabenzotriazol-1-yl)-N,N,N',N'-tetramethyluronium-hexafluorophosphate (43.8 mg, 0.071 mmol) in anhydrous DMF (1 mL) was added at room temperature morpholine-3,4-dicarboxylic acid 4-tert-butyl ester (Fluorochem) (14.95 mg, 0.065 mmol) followed by N,N-diisopropylethylamine (0.034 ml, 0.19 mmol) and finally a solution of N-(1-{[3-(aminomethyl)phenyl]methyl}-4-hydroxy-1H-indazol-3-yl)-5-chloro-2-thiophenesulfonamide formate salt (for a preparation see Intermediate 15) (32 mg, 0.065 mmol) in anhydrous DMF (1 mL) and the reaction mixture was stirred at room temperature for 30 min. The reaction mixture was partitioned between saturated aqueous sodium hydrogen carbonate solution and ethyl acetate. The organic layer was separated, washed with brine-water (1:1), passed through a hydrophobic frit, and evaporated in-vacuo to yield a colourless oil. LCMS (System B) RT=2.91 min, ES+ve m/z 662/664 (M+H)$^+$ for 1,1-dimethylethyl 3-{[({3-[(3-{[(5-chloro-2-thienyl)sulfonyl]amino}-4-hydroxy-1H-indazol-1-yl)methyl]phenyl}methyl)amino]carbonyl}-4-morpholinecarboxylate. This was suspended in anhydrous dichloromethane (2 mL) and treated with a solution of hydrogen chloride in 1,4-dioxane (4M, 0.162 mL, 0.646 mmol). The reaction mixture was still a suspension, therefore methanol was added dropwise until the reaction was in solution. The mixture was stirred at room temperature for 1 hour, and a further portion of hydrogen chloride solution (4M, 0.162 mL) was added to the reaction mixture and stirred for 90 min. Yet another portion of hydrogen chloride solution (4M, 0.162 mL) was added to the reaction mixture and stirred for 90 min. The reaction mixture was evaporated in-vacuo to yield a colourless oil. The residual oil was dissolved in MeOH:DMSO (1 mL) and purified by MDAP Sunfire C18 column, eluting with solvents A/B (A: 0.1% v/v solution of formic acid in water, B: 0.1% v/v solution of formic acid in acetonitrile) (25 min run). Appropriate fractions were combined and evaporated in-vacuo to yield the title compound as a colourless oil (17 mg, 43%). LCMS (System B) RT=1.62 min, ES+ve m/z 562/564 (M+H)$^+$.

Example 74

5-Chloro-N-[1-[(3-{[2-(dimethylamino)ethyl]oxy}phenyl)methyl]-4-(methyloxy)-1H-indazol-3-yl]-2-thiophenesulfonamide

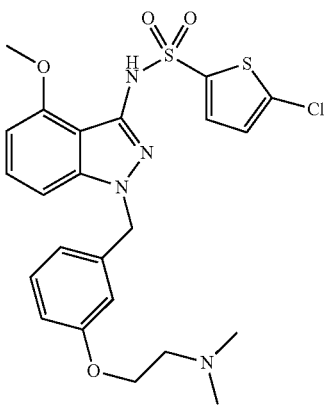 [SMILES: COc1cccc2c1c(NS(=O)(=O)c1ccc(Cl)s1)nn2Cc1cccc(OCCN(C)C)c1]

5-Chloro-N-[(5-chloro-2-thienyl)sulfonyl]-N-[1-[(3-{[2-(dimethylamino)ethyl]oxy}phenyl)methyl]-4-(methyloxy)-1H-indazol-3-yl]-2-thiophenesulfonamide (for a preparation see Intermediate 18) (140 mg, 0.2 mmol) was suspended in methanol (25 mL) and treated with 2M NaOH aqueous solution (2 mL). The mixture was heated to 60° C. for 4 h and then concentrated under reduced pressure. The residue was partitioned between 2M HCl (2 mL) and ethyl acetate. The aq. layer was back-extracted and the organic solution was washed with brine, dried (MgSO$_4$) and evaporated. The residue was dissolved in 1:1 MeOH:DMSO (1.5 mL) and purified by MDAP on Xbridge column using Acetonitrile Water with an ammonium carbonate modifier. Appropriate fractions were evaporated in vacuo to give the title product (40 mg, 39%). LCMS (System C) RT=2.29 min, ES+ve m/z 521/523 (M+H)$^+$.

Example 75

5-Chloro-N-[1-[(4-{[2-(dimethylamino)ethyl]oxy}phenyl)methyl]-4-(methyloxy)-1H-indazol-3-yl]-2-thiophenesulfonamide

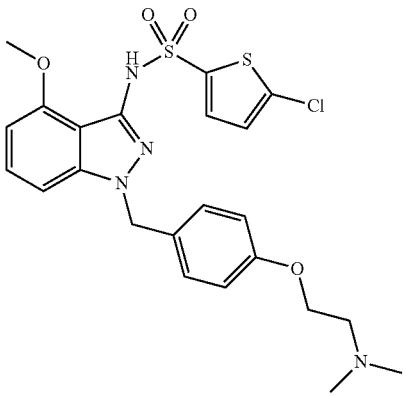 [SMILES: COc1cccc2c1c(NS(=O)(=O)c1ccc(Cl)s1)nn2Cc1ccc(OCCN(C)C)cc1]

A solution of 5-chloro-N-[(5-chloro-2-thienyl)sulfonyl]-N-[1-[(4-{[2-(dimethylamino)ethyl]oxy}phenyl)methyl]-4-(methyloxy)-1H-indazol-3-yl]-2-thiophenesulfonamide (for a preparation see Intermediate 18) (91 mg, 0.13 mmol) in MeOH (5 mL) was treated with a 2M aq. NaOH solution (1 mL) and the mixture was heated to 70° C. for 2 h, and then allowed to stand at RT over the weekend. The solvents evaporated by this time and the white solid residue was diluted with water and 2M HCl solution (1 mL) and extracted with ethyl acetate. The organic solution was washed with brine, dried (MgSO$_4$) and evaporated to dryness (72 mg). The residue was dissolved in 1:1 MeOH:DMSO (1 mL) and purified by MDAP on Xbridge column using acetonitrile-water with an ammonium carbonate modifier. The solvent was evaporated in vacuo to give the title compound (43 mg, 64%) as a colourless gum. LCMS (System C) RT=2.20 min, ES+ve m/z 521/523 (M+H)$^+$.

Example 76

5-Chloro-N-[1-{[4-{[2-(dimethylamino)ethyl]oxy}-3-(methyloxy)phenyl]methyl}-4-(methyloxy)-1H-indazol-3-yl]-2-thiophenesulfonamide

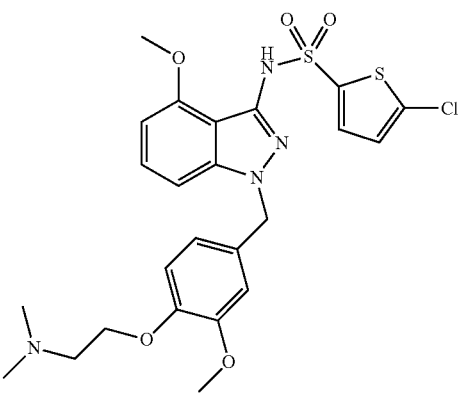 [SMILES: COc1cc(Cn2nc(NS(=O)(=O)c3ccc(Cl)s3)c3c(OC)cccc32)ccc1OCCN(C)C]

4-{[2-(Dimethylamino)ethyl]oxy}-3-(methyloxy)phenyl]methanol (for a preparation see Intermediate 20) (1.2 g, 5.3 mmol), triphenylphosphine (2.1 g, 8 mmol), di-tert-butyl azodicarboxylate (1.53 g, 6.7 mmol) and 5-chloro-N-[(5-chloro-2-thienyl)sulfonyl]-N-[4-(methyloxy)-1H-indazol-3-yl]-2-thiophenesulfonamide (for a preparation see Intermediate 10) (2.79 g, 5.3 mmol) in THF (60 mL) was heated under nitrogen to 80° C. for 20 h. The mixture was concentrated under reduced pressure and then applied to two 50 g SCX-2 ion-exchange cartridges eluting with MeOH, followed by 10% aqueous ammonia in MeOH. The ammoniacal solution was then concentrated to give a gum. The residue was dissolved in MeOH (100 mL) and THF (25 mL), and then treated with 2M NaOH aq solution (10 mL) and heated to 80° C. for 2 h. LCMS indicated completion and formation of two products RT=0.95 min, 42% and 0.98 min, 25% ES+ve m/z 551/553 (M+H)$^+$. The mixture was treated with 2M HCl (10 mL) and concentrated under reduced pressure. The residue was partitioned between ethyl acetate and NaHCO$_3$ solution (pH of solution after addition of HCl was 5-6 so NaHCO$_3$ was added to pH 8 before extractions). The organic solution was diluted with THF (20 mL) as a gum separated out of solution. The organic solution was washed with brine, dried (MgSO$_4$) and evaporated under reduced pressure to give a gum (1.92 g). This was dissolved in chloroform and purified by chromatography on two 100 g silica cartridges on Flashmaster using a 0-15% methanol (containing 1% Et₃N)-dichloromethane over 40 min for one cartridge and 0-30% methanol (containing 1% Et₃N)-dichloromethane over 40 min for the second cartridge. The earlier fractions of the first cartridge RT=0.97 min, 95%, ES+ve m/z 551/553 (M+H)⁺ were combined with the earlier fractions from the second cartridge and evaporated in vacuo to give a expected product but still impure (788 mg) as a yellow gum LCMS RT=2.15 min, 85%, ES+ve m/z 551/553. The compound was further purified by chromatography on Flashmaster on silica (100 g cartridge) using a 0-15% methanol (containing 1% Et₃N)-dichloromethane over 60 min. The appropriate fractions (RT=35-48 min) were combined and evaporated in vacuo to give the crude product, (674 mg) as a white foam. LCMS RT=2.15 min, 89%, ES+ve m/z 551/553). This was dissolved in 1:1 MeOH-DMSO (7×1 mL) and purified by MDAP on Xbridge column using acetonitrile-water with an ammonium carbonate modifier. The solvent was evaporated in vacuo to give the title compound, (374 mg, 13%), as a white solid:

LCMS (System C) RT=2.14 min, 99%, ES+ve m/z 551/553 (M+H)⁺; NMR δ (CDCl₃) 7.42 (1H, d, J=4 Hz), 7.20 (1H, dd, J=8 Hz), 6.83 (1H, d, J=8 Hz), 6.81 (1H, d, J=2 Hz), 6.79 (1H, d, J 8 Hz), 6.74 (1H, d, J=4 Hz), 6.70 (1H, dd, J 8.2 Hz), 6.35 (1H, d, J=8 Hz), 5.37 (2H, s), 4.08 (2H, t, J=6 Hz), 3.90 (3H, s), 3.78 (3H, s), 2.76 (2H, t, J=6 Hz), 2.33 (6H, s). NOE effect observed on irradiation of the benzylic protons at 5.39 ppm (spectrum run in DMSO-d₆) to the 7-H indazole proton, compatible with the expected product.

Example 77

N-[1-{[3-(aminosulfonyl)phenyl]methyl}-4-(methyloxy)-1H-indazol-3-yl]-5-chloro-2-thiophenesulfonamide

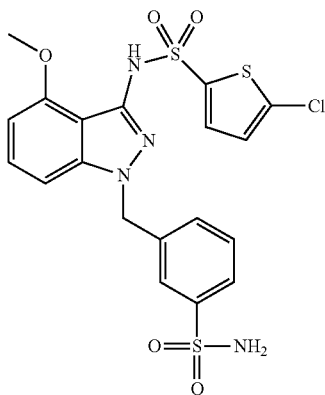 [SMILES: COc1cccc2c1c(NS(=O)(=O)c1ccc(Cl)s1)nn2Cc1cccc(S(N)(=O)=O)c1]

To a solution of 5-chloro-N-[(5-chloro-2-thienyl)sulfonyl]-N-[4-(methyloxy)-1H-indazol-3-yl]-2-thiophenesulfonamide (for a preparation see Intermediate 10) (120 mg, 0.229 mmol), triphenylphosphine (120 mg, 0.458 mmol) and 3-(hydroxymethyl)benzenesulfonamide (85.8 mg, 0.458 mmol) in THF (3 mL) was added at rt diisopropyl azodicarboxylate (DIAD) (0.090 mL, 0.458 mmol). The resulting mixture was stirred at 65° C. for 7 hours. The mixture was partitioned between DCM (3 mL) and water (3 mL). The organic phase was separated and the aqueous layer was further extracted with 3 mL of DCM. The combined organic solutions were dried over an hydrophobic frit and evaporated under a nitrogen stream in a blowdown unit. The residue was loaded in dichloromethane on a silica cartridge (50 g) and purified by chromatography on Flashmaster using a 0-100% EtOAc in DCM over 40 min. The appropriate fractions were combined and evaporated in vacuo, and the residue was dissolved in methanol (3 mL) and treated with sodium hydroxyde (2M, 1.146 mL, 2.291 mmol). The resulting mixture was stirred at 60° C. for 2 hours. The solvents were evaporated under reduced pressure. The residue was dissolved in DCM (2 mL) and 3 mL of water was added, followed by dilute HCl solution until the pH of the aqueous layer was around 1. The organic phase was separated and the aqueous layer was further extracted with 2 mL of DCM. The combined organic solutions were dried over an hydrophobic frit and concentrated under a stream of nitrogen in a blowdown unit. The residue was dissolved in 1:1 MeOH:DMSO (1 mL) and purified by MDAP (supelcosil ABZ+Plus column) eluting with solvents NB (A: Water+0.1% Formic acid, B: MeCN:Water 95:5+0.05% Formic acid). The solvent was removed under a stream of nitrogen in the Radleys blowdown apparatus to give the title compound, (51.6 mg, 22%). LCMS (System A) RT=1.02 min, ES+ve m/z 513/515 (M+H)⁺.

Examples 78-85 were prepared in array format according to the procedure described for Example 44.

Example 78

N¹-[(3-{[3-{[(5-Chloro-2-thienyl)sulfonyl]amino}-4-(methyloxy)-1H-indazol-1-yl]methyl}phenyl)methyl]-β-alaninamide Trifluoroacetate

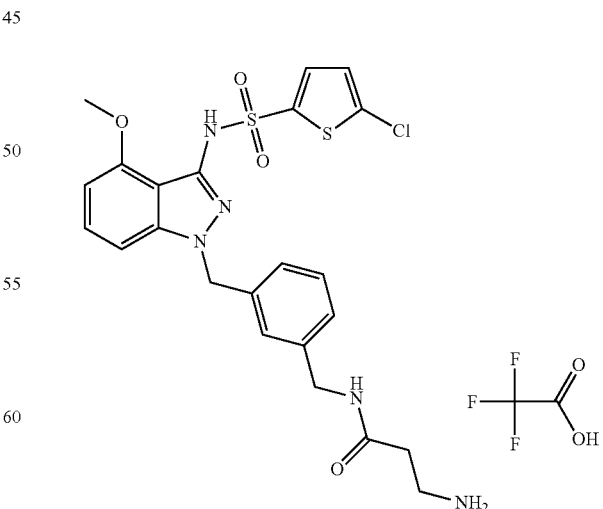

LCMS (System A) RT=0.89 min, ES+ve m/z 534/536 (M+H)⁺.

Example 79

N$^1$-[(3-{3-{[(5-Chloro-2-thienyl)sulfonyl]amino}-4-(methyloxy)-1H-indazol-1-yl]methyl}phenyl)methyl]-L-glutamamide Formate Salt

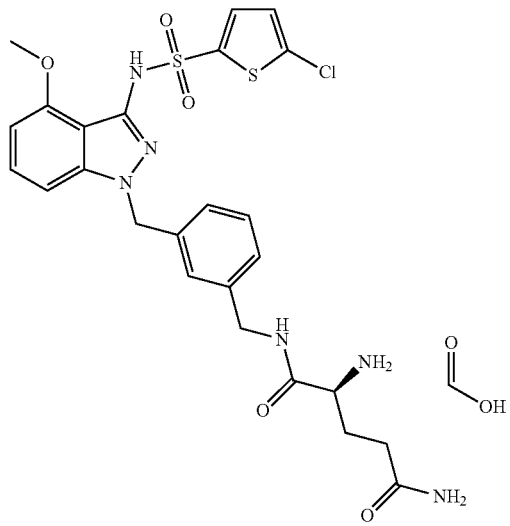 [SMILES: COc1cccc2c1c(NS(=O)(=O)c1ccc(Cl)s1)nn2Cc1cccc(CNC(=O)[C@@H](N)CCC(N)=O)c1 ; O=CO]

LCMS (System B) RT=1.76 min, ES+ve m/z 591/593 (M+H)$^+$.

Example 80

N$^4$-[(3-{3-{[(5-Chloro-2-thienyl)sulfonyl]amino}-4-(methyloxy)-1H-indazol-1-yl]methyl}phenyl)methyl]-L-asparagine Trifluoroacetate

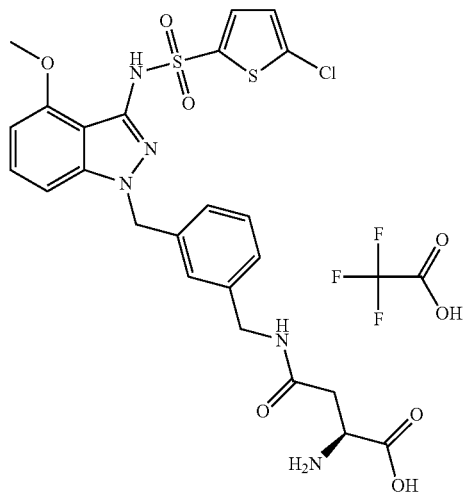 [SMILES: COc1cccc2c1c(NS(=O)(=O)c1ccc(Cl)s1)nn2Cc1cccc(CNC(=O)C[C@H](N)C(=O)O)c1 ; O=C(O)C(F)(F)F]

LCMS (System D) RT=1.76 min, ES+ve m/z 578/580 (M+H)$^+$.

Example 81

1,1-Dimethylethyl N$^4$-[(3-{3-{[(5-chloro-2-thienyl)sulfonyl]amino}-4-(methyloxy)-1H-indazol-1-yl]methyl}phenyl)methyl]-L-asparaginate Trifluoroacetate

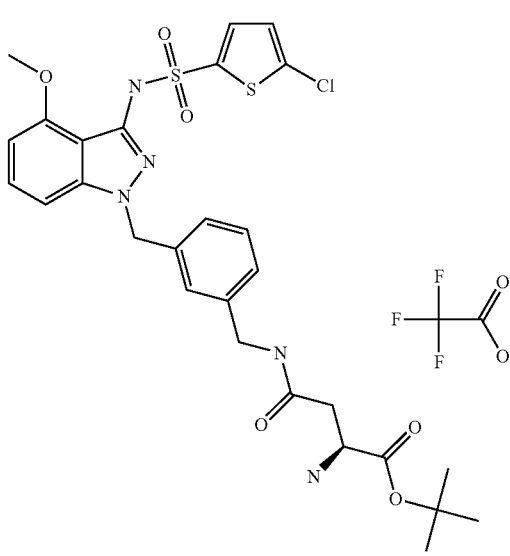 [SMILES: COc1cccc2c1c(NS(=O)(=O)c1ccc(Cl)s1)nn2Cc1cccc(CNC(=O)C[C@H](N)C(=O)OC(C)(C)C)c1 ; O=C(O)C(F)(F)F]

LCMS (System D) RT=0.99 min, ES+ve m/z 578/580 (M+H)$^+$.

Example 82

N-[(3-{3-{[(5-Chloro-2-thienyl)sulfonyl]amino}-4-(methyloxy)-1H-indazol-1-yl]methyl}phenyl)methyl]-D-prolinamide Trifluoroacetate

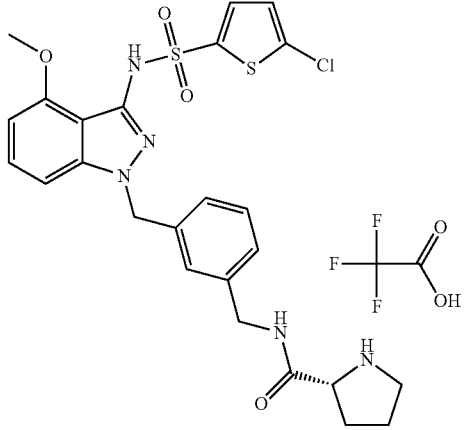

LCMS (System D) RT=0.91 min, ES+ve m/z 560/562 (M+H)$^+$.

Example 83

1-Amino-N-[3-{[3-{[(5-chloro-2-thienyl)sulfonyl]amino}-4-(methyloxy)-1H-indazol-1-yl]methyl}phenyl)methyl]cyclobutanecarboxamide Trifluoroacetate

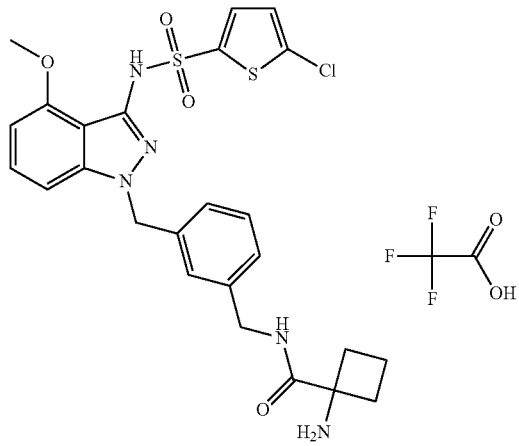 [SMILES: COc1cccc2c1c(NS(=O)(=O)c1ccc(Cl)s1)nn2Cc1cccc(CNC(=O)C2(N)CCC2)c1 ; O=C(O)C(F)(F)F]

LCMS (System B) RT=1.83 min, ES+ve m/z 560/562 (M+H)+.

Example 84

1-Amino-N-[(3-{[3-{[(5-chloro-2-thienyl)sulfonyl]amino}-4-(methyloxy)-1H-indazol-1-yl]methyl}phenyl)methyl]cyclopropanecarboxamide Trifluoroacetate

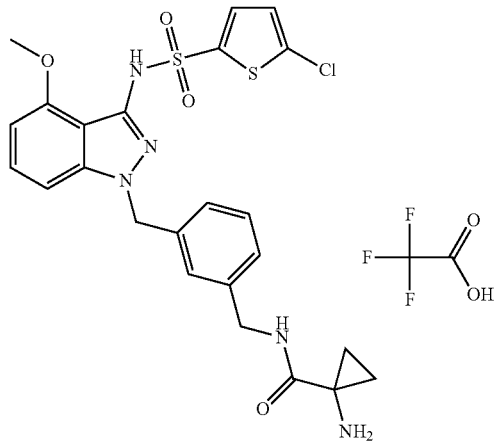 [SMILES: COc1cccc2c1c(NS(=O)(=O)c1ccc(Cl)s1)nn2Cc1cccc(CNC(=O)C2(N)CC2)c1 ; O=C(O)C(F)(F)F]

LCMS (System B) RT=1.81 min, ES+ve m/z 546/548 (M+H)+.

Example 85

$N^1$-[(3-{[3-{[(5-Chloro-2-thienyl)sulfonyl]amino}-4-(methyloxy)-1H-indazol-1-yl]methyl}phenyl)methyl]-$N^2$-methylglycinamide Trifluoroacetate

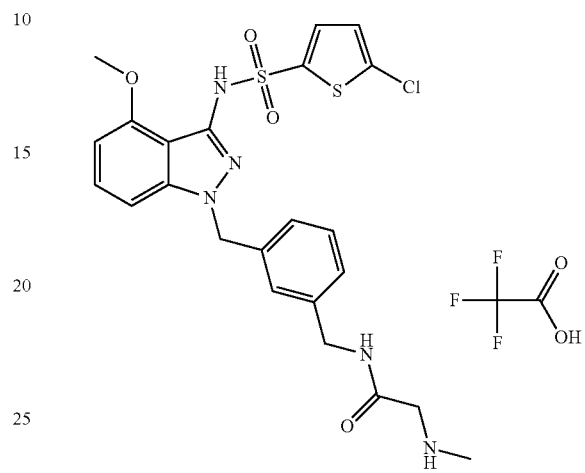

LCMS (System A) RT=0.89 min, ES+ve m/z 534/536 (M+H)+.

Examples 86-96 were prepared in array format according to the procedure described in Example 30.

Example 86

$N^1$-[(3-{[3-{[(5-Chloro-2-thienyl)sulfonyl]amino}-4-(methyloxy)-1H-indazol-1-yl]methyl}phenyl)methyl]$N^2$,$N^2$-dimethylglycinamide Trifluoroacetate

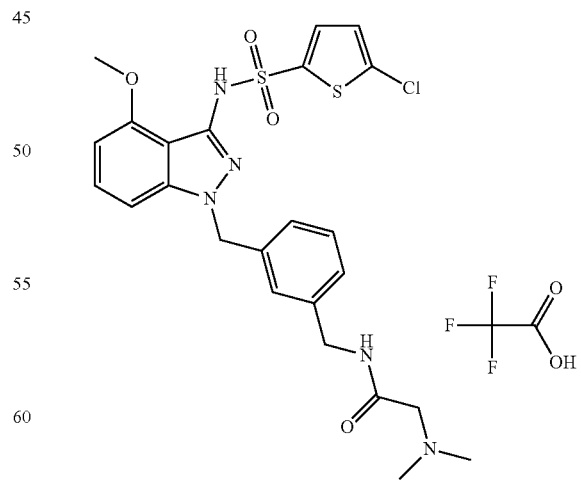

LCMS (System D) RT=0.90 min, ES+ve m/z 548/550 (M+H)+.

Example 87

N-[(3-{[3-{[(5-Chloro-2-thienyl)sulfonyl]amino}-4-(methyloxy)-1H-indazol-1-yl]methyl}phenyl)methyl]-3-(methyloxy)propanamide

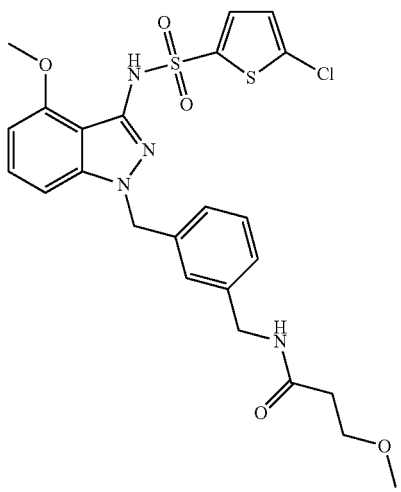 [SMILES: COCCC(=O)NCc1cccc(Cn2nc(NS(=O)(=O)c3ccc(Cl)s3)c3c(OC)cccc32)c1]

LCMS (System D) RT=1.03 min, ES+ve m/z 549/551 (M+H)+.

Example 88

N-[(3-{[3-{[(5-Chloro-2-thienyl)sulfonyl]amino}-4-(methyloxy)-1H-indazol-1-yl]methyl}phenyl)methyl]-1H-pyrrole-3-carboxamide

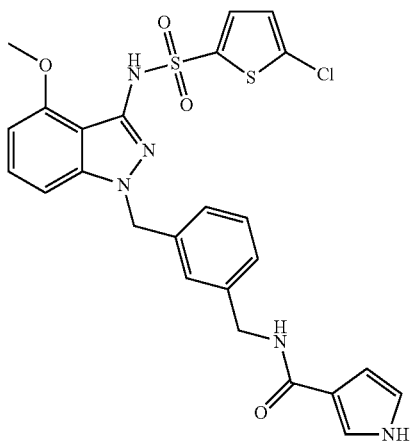 [SMILES: COc1cccc2c1c(NS(=O)(=O)c1ccc(Cl)s1)nn2Cc1cccc(CNC(=O)c2cc[nH]c2)c1]

LCMS (System B) RT=2.71 min, ES+ve m/z 556/558 (M+H)+.

Example 89

N-[(3-{[3-{[(5-Chloro-2-thienyl)sulfonyl]amino}-4-(methyloxy)-1H-indazol-1-yl]methyl}phenyl)methyl]tetrahydro-2-furancarboxamide

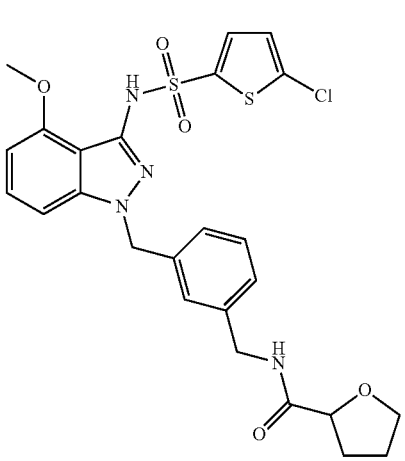 [SMILES: COc1cccc2c1c(NS(=O)(=O)c1ccc(Cl)s1)nn2Cc1cccc(CNC(=O)C2CCCO2)c1]

LCMS (System B) RT=2.81 min, ES+ve m/z 561/563 (M+H)+.

Example 90

N-[(3-{[3-{[(5-Chloro-2-thienyl)sulfonyl]amino}-4-(methyloxy)-1H-indazol-1-yl]methyl}phenyl)methyl]-1,3-oxazole-4-carboxamide

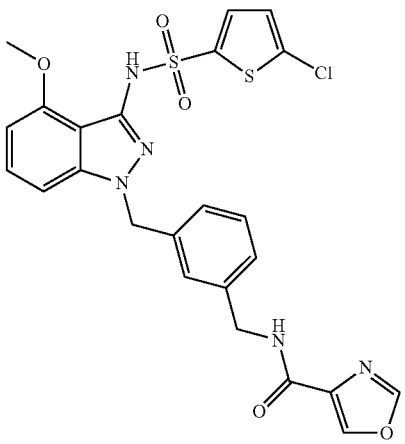 [SMILES: COc1cccc2c1c(NS(=O)(=O)c1ccc(Cl)s1)nn2Cc1cccc(CNC(=O)c2cocn2)c1]

LCMS (System B) RT=2.80 min, ES+ve m/z 558/560 (M+H)+.

Example 91

N-[(3-{[3-{[(5-Chloro-2-thienyl)sulfonyl]amino}-4-(methyloxy)-1H-indazol-1-yl]methyl}phenyl)methyl]-1H-pyrazole-3-carboxamide

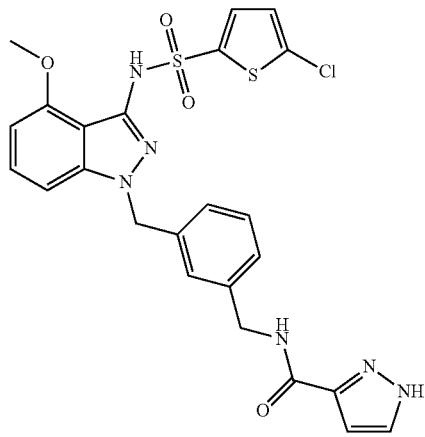 [SMILES: COc1cccc2c1c(NS(=O)(=O)c1ccc(Cl)s1)nn2Cc1cccc(CNC(=O)c2cc[nH]n2)c1]

LCMS (System B) RT=2.66 min, ES+ve m/z 557/559 (M+H)+.

Example 92

N-[(3-{[3-{[(5-Chloro-2-thienyl)sulfonyl]amino}-4-(methyloxy)-1H-indazol-1-yl]methyl}phenyl)methyl]-1H-pyrrole-2-carboxamide (

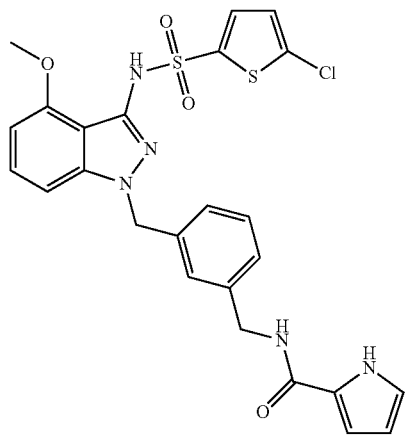 [SMILES: COc1cccc2c1c(NS(=O)(=O)c1ccc(Cl)s1)nn2Cc1cccc(CNC(=O)c2ccc[nH]2)c1]

LCMS (System B) RT=2.92 min, ES+ve m/z 556/558 (M+H)+.

Example 93

N-[(3-{[3-{[(5-Chloro-2-thienyl)sulfonyl]amino}-4-(methyloxy)-1H-indazol-1-yl]methyl}phenyl)methyl]-1H-imidazole-2-carboxamide

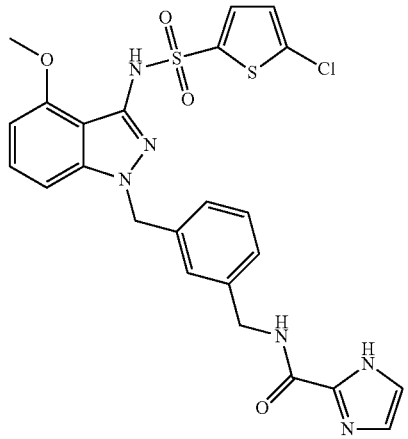 [SMILES: COc1cccc2c1c(NS(=O)(=O)c1ccc(Cl)s1)nn2Cc1cccc(CNC(=O)c2ncc[nH]2)c1]

LCMS (System B) RT=2.51 min, ES+ve m/z 557/559 (M+H)+.

Example 94

N-[(3-{[3-{[(5-Chloro-2-thienyl)sulfonyl]amino}-4-(methyloxy)-1H-indazol-1-yl]methyl}phenyl)methyl]-1H-imidazole-4-carboxamide

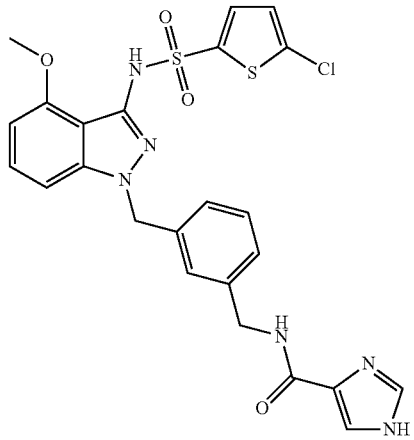 [SMILES: COc1cccc2c1c(NS(=O)(=O)c1ccc(Cl)s1)nn2Cc1cccc(CNC(=O)c2c[nH]cn2)c1]

LCMS (System B) RT=2.12 min, ES+ve m/z 557/559 (M+H)+.

Example 95

N-[(3-{[3-{[(5-Chloro-2-thienyl)sulfonyl]amino}-4-(methyloxy)-1H-indazol-1-yl]methyl}phenyl)methyl]-2-furancarboxamide

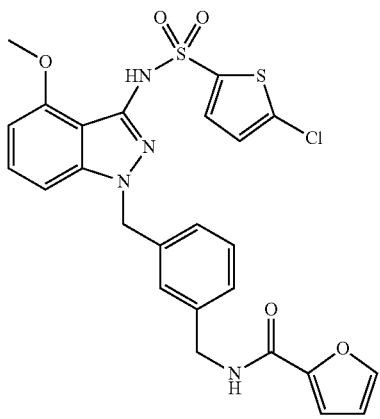 [SMILES: COc1cccc2c1c(NS(=O)(=O)c1ccc(Cl)s1)nn2Cc1cccc(CNC(=O)c2ccco2)c1]

LCMS (System D) RT=1.11 min, ES+ve m/z 557/559 (M+H)+.

Example 96

N-[(3-{[3-{[(5-Chloro-2-thienyl)sulfonyl]amino}-4-(methyloxy)-1H-indazol-1-yl]methyl}phenyl)methyl]-4-methyl-3-morpholinecarboxamide

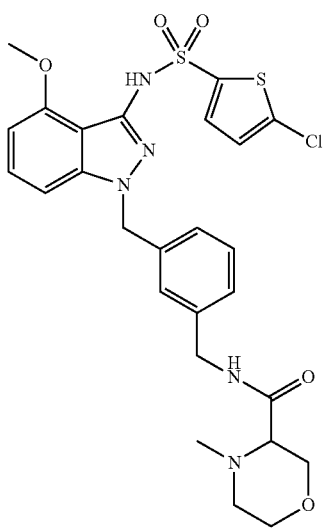 [SMILES: COc1cccc2c1c(NS(=O)(=O)c1ccc(Cl)s1)nn2Cc1cccc(CNC(=O)C2COCCN2C)c1]

LCMS (System C) RT=0.84 min, ES+ve m/z 590/592 (M+H)+.

Example 97

N-[(4-{[3-{[(5-Chloro-2-thienyl)sulfonyl]amino}-4-(methyloxy)-1H-indazol-1-yl]methyl}phenyl)methyl]acetamide

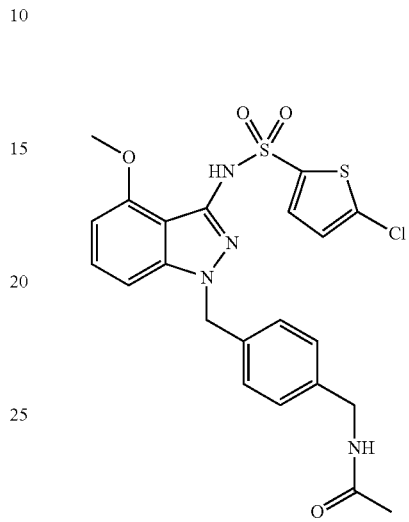

A solution of N-[1-{[4-(aminomethyl)phenyl]methyl}-4-(methyloxy)-1H-indazol-3-yl]-5-chloro-2-thiophenesulfonamide formate salt for a preparation see Intermediate 30) (15 mg, 0.03 mmol) and acetic acid (0.001 mL, 0.03 mmol) in acetonitrile (2 mL) and DIPEA (0.046 mL, 0.26 mmol) was treated with HATU (37.0 mg, 0.097 mmol) and the resulting mixture was stirred for 2 h and 15 min at ambient temperature. The reaction mixture was diluted with DCM (2 mL) and water (3 mL). The organic was separated and the aqueous layer was further extracted with DCM (2 mL). The combined organic solutions were dried through an hydrophobic frit and concentrated under reduced pressure. The residue was dissolved in 1:1 MeOH-DMSO (1 mL) and purified by Mass Directed AutoPrep on (supelcosil ABZ+Plus column) eluting with solvents NB (A: Water+0.1% Formic acid, B: MeCN:Water 95:5+0.05% Formic acid). The solvent was removed under a stream of nitrogen in a Radleys blowdown apparatus to give the title compound (13 mg, 87%) as a gum. LCMS (System A) RT=1.11 min, ES+ve m/z 505/507 (M+H)+.

Examples 98 and 99 were prepared in an array format as above from N-[1-{[4-(aminomethyl)phenyl]methyl}-4-(methyloxy)-1H-indazol-3-yl]-5-chloro-2-thiophenesulfonamide formate salt (15 mg, 0.03 mmol), HATU (37 mg, 0.09 mmol), DIPEA (0.046 mL, 0.26 mmol) in acetonitrile (2 mL), followed by cleavage of the BOC protecting group using hydrogen chloride in dioxane (4M, 0.074 ml):

Example 98

N-[(4-{[3-{[(5-Chloro-2-thienyl)sulfonyl]amino}-4-(methyloxy)-1H-indazol-1-yl]methyl}phenyl)methyl]-3-morpholinecarboxamide Trifluoroacetate

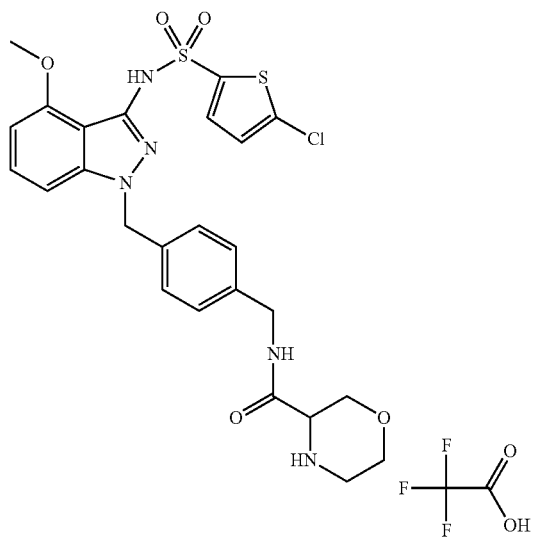

LCMS (System A) RT=0.91 min, ES+ve m/z 576/578 (M+H)+.

Example 99

N¹-[(4-{[3-{[(5-Chloro-2-thienyl)sulfonyl]amino}-4-(methyloxy)-1H-indazol-1-yl]methyl}phenyl)methyl]-N²-methyl-D-alaninamide Trifluoroacetate

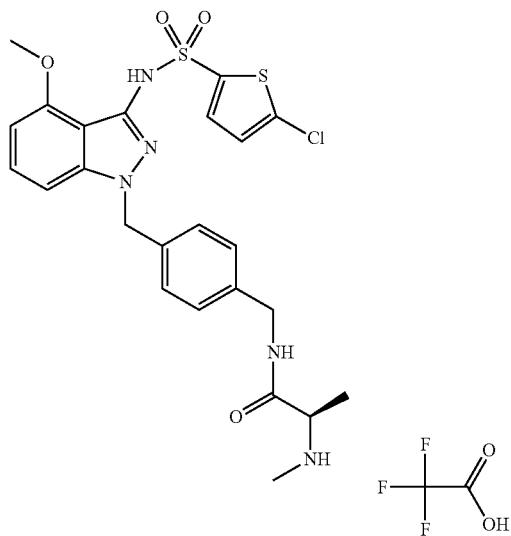 [SMILES: CN[C@H](C)C(=O)NCc1ccc(Cn2nc(NS(=O)(=O)c3ccc(Cl)s3)c3c(OC)cccc32)cc1 ; O=C(O)C(F)(F)F]

LCMS (System A) RT=0.92 min, ES+ve m/z 548/550 (M+H)+.

Example 100

3-{[3-{[(5-Chloro-2-thienyl)sulfonyl]amino}-4-(methyloxy)-1H-indazol-1-yl]methyl}-N-methylbenzamide

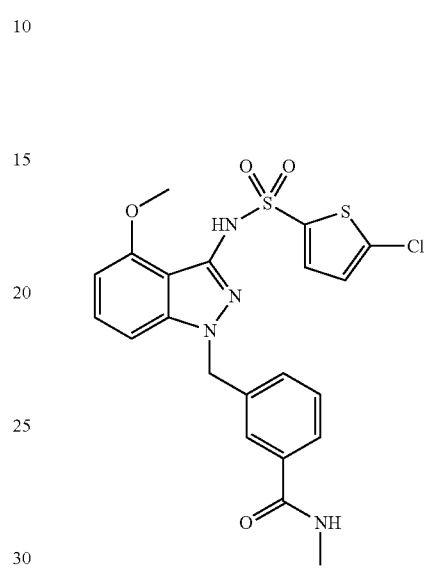

Methyl 3-{[3-[[(5-chloro-2-thienyl)sulfonyl]({[2-(trimethylsilyl)ethyl]oxy}methyl)amino]-4-(methyloxy)-1H-indazol-1-yl]methyl}benzoate (for a preparation see Intermediate 31) (70 mg, 0.112 mmol) in a Biotage microwave vial was added 1,3,4,6,7,8-hexahydro-2H-pyrimido[1,2-a]pyrimidine (Aldrich) (7.83 mg, 0.056 mmol) and methylamine solution in THF (2M, 1.125 mL). The reaction vessel was sealed and heated in a Biotage Initiator microwave oven using initial very high absorption level to 80° C. for 75 min. The reaction mixture was diluted with DCM (2 mL) and water (3 mL). The organic phase was separated, and the aqueous layer was further extracted with DCM (2 mL). The combined organic solutions were dried through an hydrophobic frit and concentrated under a nitrogen stream in a blowdown unit. The residue was treated TBAF in THF (1M, 1.125 mL, 1.125 mmol). The reaction vessel was sealed and heated in a Biotage Initiator at 110° C. for 15 min (very high absorption level). The solvent was removed under a nitrogen stream in a blowdown unit (T=35° C. overnight), dissolved in 1:1 MeOH-DMSO (2 mL) and purified by Mass Directed AutoPrep on standard C18 column using Acetonitrile Water with a TFA modifier (Method B). The solvent was removed under a stream of nitrogen in a Radleys blowdown apparatus to give the title compound (41.7 mg, 75%) LCMS (System A) RT=1.03 min, ES+ve m/z 491/493 (M+H)+.

Example 101

3-{[3-{[(5-Chloro-2-thienyl)sulfonyl]amino}-4-(methyloxy)-1H-indazol-1-yl]methyl}-N,N-dimethylbenzamide

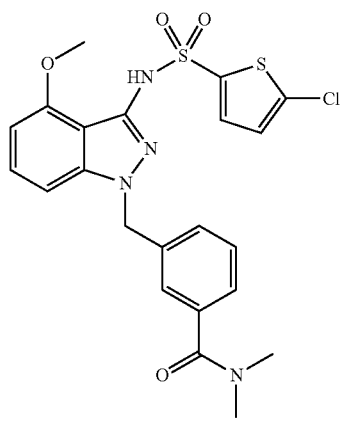 [SMILES: COc1cccc2c1c(NS(=O)(=O)c1ccc(Cl)s1)nn2Cc1cccc(C(=O)N(C)C)c1]

The title compound was prepared similarly to Example 100
LCMS (System A) RT=1.06 min, ES+ve m/z 505/507 (M+H)$^+$.

Example 102

$N^1$-[(3-{[3-{[(5-Chloro-2-thienyl)sulfonyl]amino}-4-(methyloxy)-1H-indazol-1-yl]methyl}phenyl)methyl]-L-serinamide

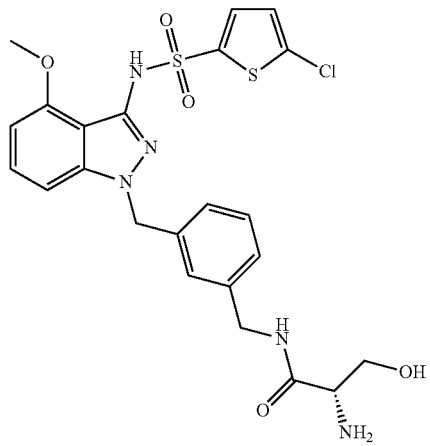 [SMILES: COc1cccc2c1c(NS(=O)(=O)c1ccc(Cl)s1)nn2Cc1cccc(CNC(=O)[C@@H](N)CO)c1]

The title compound was prepared in array format according to the procedure described in Example 17. LCMS (System A) RT=0.78 min, ES+ve m/z 550/552 (M+H)$^+$.

Examples 103-105 were prepared according to the procedure described for Example 62.

Example 103

4-{[3-{[(5-Chloro-2-thienyl)sulfonyl]amino}-4-(methyloxy)-1H-indazol-1-yl]methyl}benzamide

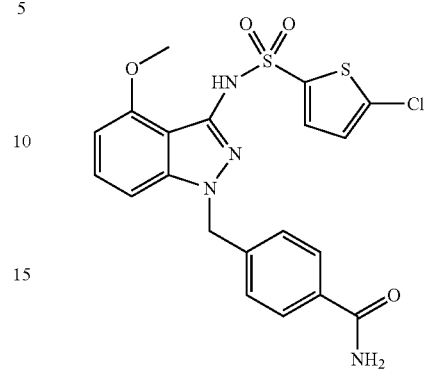

LCMS (System A) RT=0.95 min, ES+ve m/z 477/479 (M+H)$^+$.

Example 104

5-Chloro-N-(4-(methyloxy)-1-{[4-(methyloxy)phenyl]methyl}-1H-indazol-3-yl)-2-thiophenesulfonamide

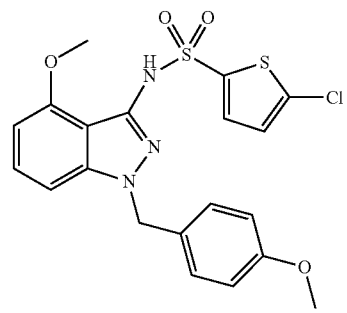 [SMILES: COc1ccc(Cn2nc(NS(=O)(=O)c3ccc(Cl)s3)c3c(OC)cccc32)cc1]

LCMS (System B) RT=3.11 min, ES+ve m/z 464/466 (M+H)$^+$.

Example 105

5-Chloro-N-(4-(methyloxy)-1-{[2-(methyloxy)phenyl]methyl}-1H-indazol-3-yl)-2-thiophenesulfonamide

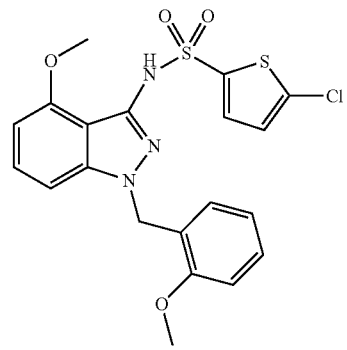 [SMILES: COc1ccccc1Cn1nc(NS(=O)(=O)c2ccc(Cl)s2)c2c(OC)cccc21]

LCMS (System B) RT=3.23 min, ES+ve m/z 464/466 (M+H)$^+$.

Examples 106 and 107 were prepared according to procedure described for Example 53.

Example 106

5-Chloro-N-[1-({3-[(methylamino)sulfonyl]phenyl}methyl)-4-(methyloxy)-1H-indazol-3-yl]-2-thiophenesulfonamide

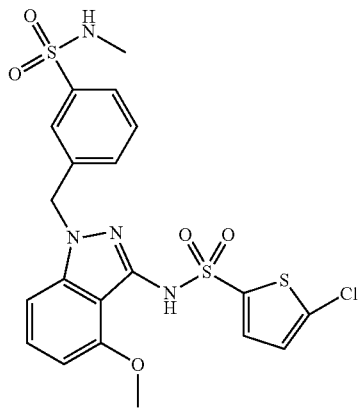 [SMILES: CNS(=O)(=O)c1cccc(Cn2nc(NS(=O)(=O)c3ccc(Cl)s3)c3c(OC)cccc32)c1]

LCMS (System B) RT=2.74 min, ES+ve m/z 527/529 (M+H)+.

Example 107

5-Chloro-N-[1-({3-[(dimethylamino)sulfonyl]phenyl}methyl)-4-(methyloxy)-1H-indazol-3-yl]-2-thiophenesulfonamide

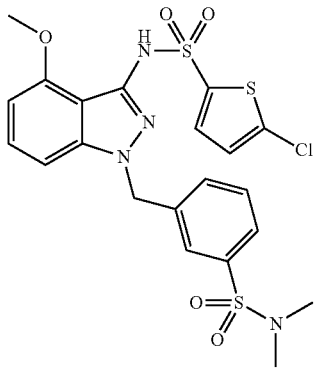 [SMILES: COc1cccc2c1c(NS(=O)(=O)c1ccc(Cl)s1)nn2Cc1cccc(S(=O)(=O)N(C)C)c1]

LCMS (System B) RT=2.94 min, ES+ve m/z 541/543 (M+H)+.

Examples 108 and 109 were prepared by sulfonylation of Intermediate 12 and the appropriate sulfonyl chloride in a similar procedure to that of Example 66

Example 108

3-({4-(Methyloxy)-3-[(2-thienylsulfonyl)amino]-1H-indazol-1-yl}methyl)benzamide

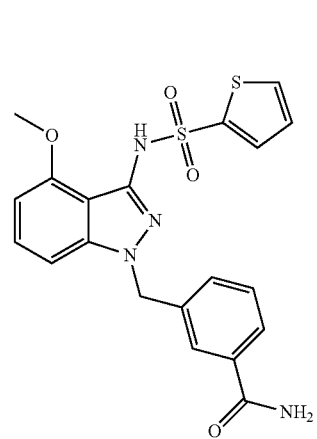 [SMILES: COc1cccc2c1c(NS(=O)(=O)c1cccs1)nn2Cc1cccc(C(N)=O)c1]

LCMS (System A) RT=0.93 min, ES+ve m/z 443 (M+H)+.

Example 109

3-{[3-{[(4,5-Dichloro-2-thienyl)sulfonyl]amino}-4-(methyloxy)-1H-indazol-1-yl]methyl}benzamide

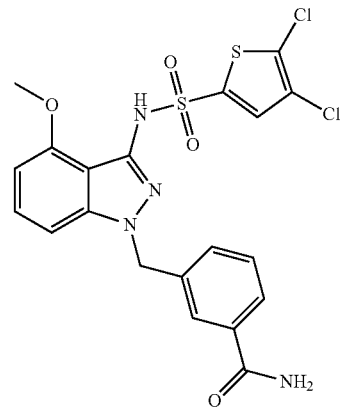 [SMILES: COc1cccc2c1c(NS(=O)(=O)c1cc(Cl)c(Cl)s1)nn2Cc1cccc(C(N)=O)c1]

LCMS (System A) RT=0.99 min, ES+ve m/z 511/513 (M+H)+.

Example 110

5-Chloro-N-[1-{[3-{[2-(dimethylamino)ethyl]oxy}-4-(methyloxy)phenyl]methyl}-4-(methyloxy)-1H-indazol-3-yl]-2-thiophenesulfonamide

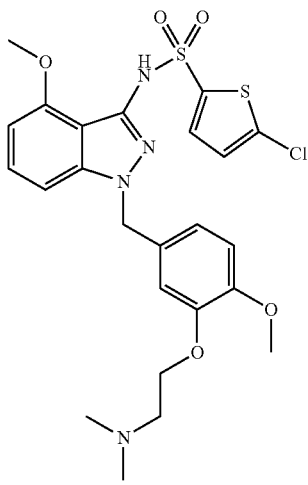 [SMILES: COc1ccc(Cn2nc(NS(=O)(=O)c3ccc(Cl)s3)c3c(OC)cccc32)cc1OCCN(C)C]

The title compound was prepared according to Example 76 using Intermediate 10 and [3-{[2-(dimethylamino)ethyl]oxy}-4-(methyloxy)phenyl]methanol, which was prepared in a similar way to Intermediate 23.

LCMS (System A) RT=0.86 min, ES+ve m/z 551/553 (M+H)+.

Example 111

(3R)—N-({3-[(3-{[(5-chloro-2-thienyl)sulfonyl]amino}-4-hydroxy-1H-indazol-1-yl)methyl]phenyl}methyl)-3-morpholinecarboxamide Formate Salt

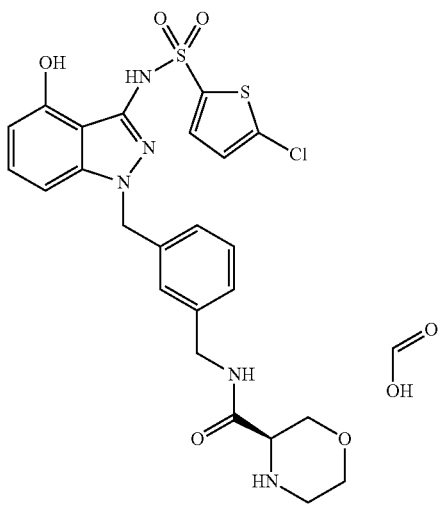 [SMILES: O=C(NCc1cccc(Cn2nc(NS(=O)(=O)c3ccc(Cl)s3)c3c(O)cccc32)c1)[C@H]1COCCN1 ; O=CO]

The title compound was prepared according to the procedure described in Example 73 LCMS (System B) RT=1.61 min, ES+ve m/z 562/564 (M+H)+.

Example 112

N1-({3-[(3-{[(5-chloro-2-thienyl)sulfonyl]amino}-4-hydroxy-1H-indazol-1-yl)methyl]phenyl}methyl)-N2-methylglycinamide Formate Salt

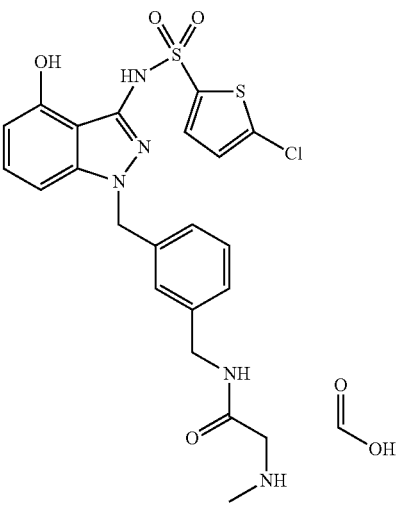 [SMILES: CNCC(=O)NCc1cccc(Cn2nc(NS(=O)(=O)c3ccc(Cl)s3)c3c(O)cccc32)c1 ; O=CO]

The title compound was prepared according to procedure described in Example 73. LCMS (System B) RT=1.74 min, ES+ve m/z 520/522 (M+H)+.

Example 113

5-Chloro-N-[1-{[3-({[(ethylamino)carbonyl]amino}methyl)phenyl]methyl}-4-(methyloxy)-1H-indazol-3-yl]-2-thiophenesulfonamide

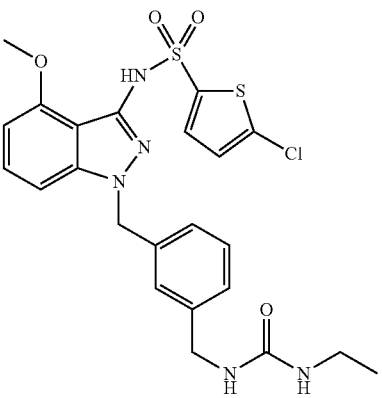 [SMILES: CCNC(=O)NCc1cccc(Cn2nc(NS(=O)(=O)c3ccc(Cl)s3)c3c(OC)cccc32)c1]

The title compound was prepared according to the procedure described in Example 61 using Intermediate 4 and ethyl isocyanate LCMS (System A) RT=1.43 min, ES+ve m/z 534/536 (M+H)+.

Example 114

N-[(3-{[3-{[(5-Chloro-2-thienyl)sulfonyl]amino}-4-(methyloxy)-1H-indazol-1-yl]methyl}phenyl)methyl]-L-tryptophanamide

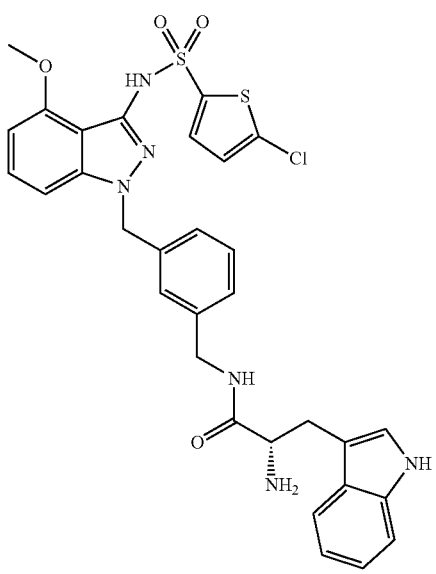 [SMILES: COc1cccc2c1c(NS(=O)(=O)c1ccc(Cl)s1)nn2Cc1cccc(CNC(=O)[C@@H](N)Cc2c[nH]c3ccccc23)c1]

The title compound was prepared by the generic array method described in Example 44 LCMS (System B) RT=2.06 min, ES+ve m/z 649/651 (M+H)+.

Example 115

N$^1$-[(3-{[3-{[(5-chloro-2-thienyl)sulfonyl]amino}-4-(methyloxy)-1H-indazol-1-yl]methyl}phenyl)methyl]-D-allothreoninamide Formate Salt

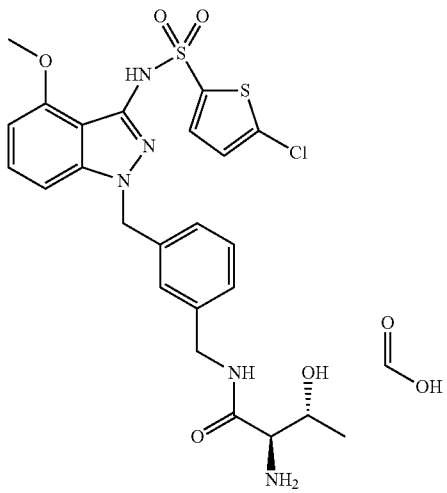 [SMILES: COc1cccc2c1c(NS(=O)(=O)c1ccc(Cl)s1)nn2Cc1cccc(CNC(=O)[C@H](N)[C@@H](C)O)c1 ; O=CO]

The title compound was prepared by the generic array method described in Example 44 LCMS (System B) RT=1.71 min, ES+ve m/z 564/566 (M+H)+.

Example 116

N-{[3-({4-(Methyloxy)-3-[(2-thienylsulfonyl)amino]-1H-indazol-1-yl}methyl)phenyl]methyl}acetamide

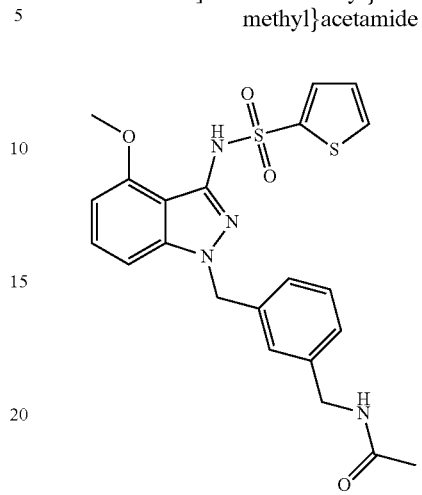

To a cooled (ice/water bath) solution of N-[(3-{[3-{[(5-chloro-2-thienyl)sulfonyl]amino}-4-(methyloxy)-1H-indazol-1-yl]methyl}phenyl)methyl]acetamide (for a preparation see Example 1) (30 mg, 0.06 mmol) in THF (1 mL) was added dropwise 2M lithium aluminium hydride in THF (0.074 mL, 0.149 mmol), and the suspension was stirred 10 min at 0° C. and then at room temperature for one hour. Reaction was quenched with 4 drops of water and then with aqueous solution of sodium hydroxide (2M, 0.5 mL). After stirring for 30 min, solid was removed and washed with THF (10 mL). The filtrate was concentrated under reduced pressure and the residue was dissolved in 1:1 MeOH-DMSO (1 mL) and purified by Mass Directed AutoPrep on Sunfire C18 column using Acetonitrile Water with a TFA modifier (Method B). The solvent from appropriate fractions was evaporated under a stream of nitrogen in a Radleys blowdown apparatus to give the title compound (18 mg, 64%). LCMS (System A) RT=0.89 min, ES+ve m/z 471 (M+H)+.

Example 117

4-[(4-(Methyloxy)-3-{[(5-methyl-2-thienyl)sulfonyl]amino}-1H-indazol-1-yl)methyl]benzamide

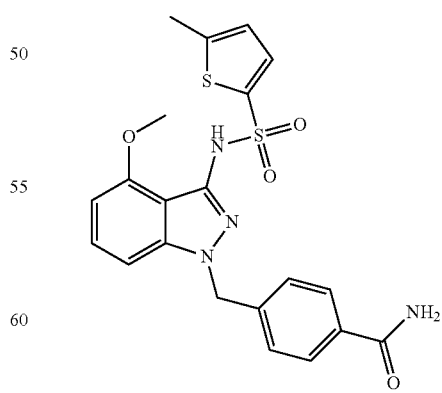

A solution of 4-{[3-amino-4-(methyloxy)-1H-indazol-1-yl]methyl}benzamide (32.4 mg, 0.2 mmol) in pyridine 3.6 mL) was added to 5-methyl-thiophenesulfonyl chloride (for a preparation see Intermediate 32) (0.30 mmol). The reaction

Example 118

N-[1-{[3,4-Bis(methyloxy)phenyl]methyl}-4-(methyloxy)-1H-indazol-3-yl]-5-methyl-2-thiophenesulfonamide

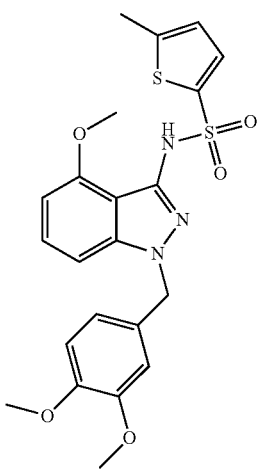 [SMILES: COc1ccc(Cn2nc(NS(=O)(=O)c3ccc(C)s3)c3c(OC)cccc32)cc1OC]

The title compound was prepared in array format according to the procedure described in Example 117 using Intermediate 33.

LCMS (System A) RT=1.08 min, ES+ve m/z 474 (M+H)$^+$.

Example 119

N-({3-[(4-(Methyloxy)-3-{[(5-methyl-2-thienyl)sulfonyl]amino}-1H-indazol-1-yl)methyl]phenyl}methyl)acetamide

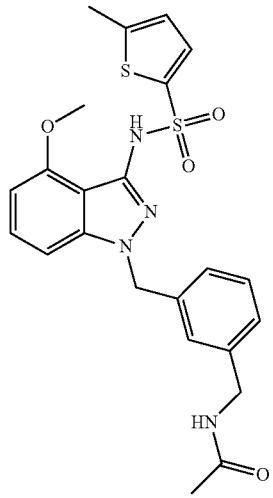 [SMILES: COc1cccc2c1c(NS(=O)(=O)c1ccc(C)s1)nn2Cc1cccc(CNC(C)=O)c1]

The title compound was prepared in array format according to the procedure described in Example 117 using Intermediate 34.

LCMS (System A) RT=0.96 min, ES+ve m/z 485 (M+H)$^+$.

Example 120

(3R)—N-({4-[(4-(methyloxy)-3-{[(5-methyl-2-thienyl)sulfonyl]amino}-1H-indazol-1-yl)methyl]phenyl}methyl)-3-morpholinecarboxamide Trifluoroacetate

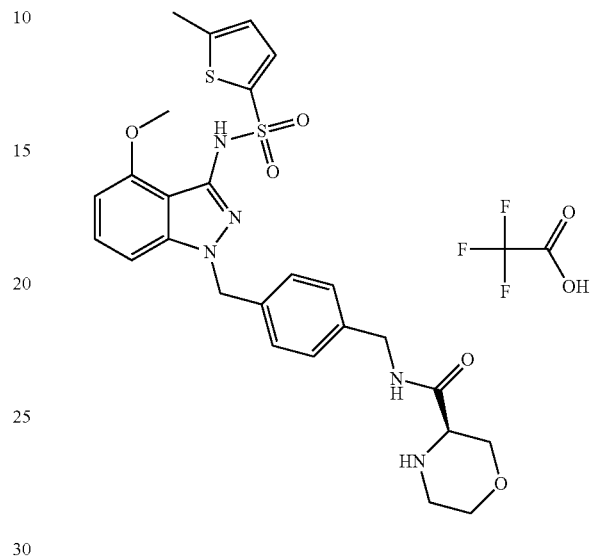

The title compound was prepared in array format according to the procedure described in Example 117 using Intermediate 35 followed by TFA cleavage of the BOC protecting group. LCMS (System A) RT=0.69 min, ES+ve m/z 556 (M+H)$^+$.

Example 121

N-({3-[(3-{[(5-Chloro-2-thienyl)sulfonyl]amino}-4-fluoro-1H-indazol-1-yl)methyl]phenyl}methyl)acetamide

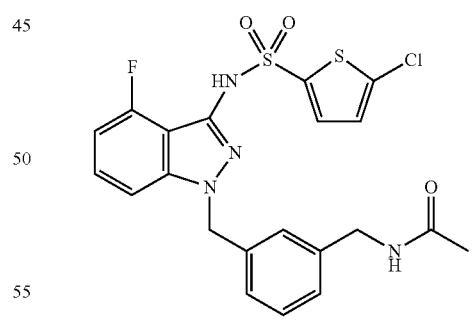

To a solution of HATU (122 mg, 0.198 mmol) in anhydrous N,N-dimethylformamide (3 mL) was added at room temperature acetic acid (10.29 mL, 0.180 mmol) followed by N,N-diisopropylethylamine (0.094 mL, 0.539 mmol) and finally a solution of N-(1-{[3-(aminomethyl)phenyl]methyl}-4-fluoro-1H-indazol-3-yl)-5-chloro-2-thiophenesulfonamide (for a preparation see Intermediate 39) (81 mg, 0.18 mmol) in anhydrous N,N-dimethylformamide (2 mL). The reaction mixture was stirred at room temperature for 30 min, and then partitioned between saturated aqueous sodium hydrogen carbonate solution and ethyl acetate. The organic layer was separated, washed with brine-water (1:1), passed through a hydrophobic frit and evaporated in-vacuo to yield a colourless oil. The residue was dissolved in MeOH-DMSO (1 mL) and purified by Mass Directed AutoPreparative HPLC MDAP (Sunfire C18 column 150 mm×30 mm i.d. 5 μm packing diameter at ambient temperature) eluting with solvents NB (A: 0.1% v/v solution of formic acid in water, B: 0.1% v/v solution of formic acid in acetonitrile) over 25 min. The appropriate fraction was evaporated in-vacuo to yield a colourless oil (5.9 mg, 6%). LCMS (System B): RT=2.53 min, ES+ve m/z 493/495 (M+H)+.

Example 122

N-({3-[(4-Chloro-3-{[(5-chloro-2-thienyl)sulfonyl]amino}-1H-indazol-1-yl)methyl]phenyl}methyl)acetamide

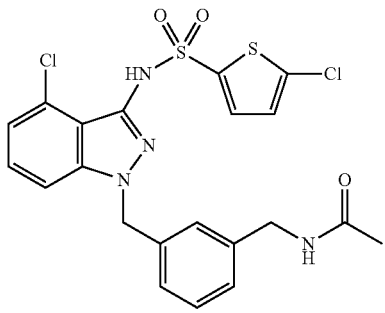 [SMILES: CC(=O)NCc1cccc(Cn2nc(NS(=O)(=O)c3ccc(Cl)s3)c3c(Cl)cccc32)c1]

To an ice/water bath cooled solution of 5-chloro-N-{4-chloro-1-[(3-cyanophenyl)methyl]-1H-indazol-3-yl}-2-thiophenesulfonamide (for a preparation see Intermediate 42) (95 mg, 0.20 mmol) in anhydrous tetrahydrofuran (4 mL) under nitrogen atmosphere was added dropwise over 1 min lithium aluminium hydride (1M solution in diethyl ether, 0.513 mL, 0.513 mmol). The reaction was stirred in the ice/water bath for 10 min, and then at room temperature for 30 min. Reaction re-cooled in the ice/water bath and a further portion of lithium aluminium hydride (1M solution in diethyl ether, 0.2 mL) was added dropwise over 1 min. Reaction stirred at room temperature for 1.5 h, then cooled (ice/water bath) and cautiously quenched with water (dropwise) until no more effervescence. The reaction mixture was then diluted with 1:1 methanol-dichloromethane in order to try to improve solubility and applied to a methanol pre-conditioned 20 g SCX-2 cartridge. The cartridge was washed with methanol and then eluted using 2M ammonia in methanol solution. The 2M ammonia in methanol fractions were combined and evaporated in-vacuo to yield N-(1-{[3-(aminomethyl)phenyl]methyl}-4-chloro-1H-indazol-3-yl)-5-chloro-2-thiophenesulfonamide (68 mg, 0.15 mmol) as an off-white solid. This amine was dissolved in DMF (2 mL) and added to a mixture of HATU (99 mg, 0.16 mmol), acetic acid (8.3 μL, 0.14 mmol), N,N-diisopropylethylamine (0.076 mL, 0.44 mmol) in anhydrous DMF (1 mL). The reaction mixture was stirred at room temperature for 4 h, partitioned between saturated aqueous sodium hydrogen carbonate solution and ethyl acetate. The organic layer was separated, washed with brine-water (1:1), passed through a hydrophobic frit and evaporated in-vacuo to yield a yellow oil, which was dissolved in MeOH-DMSO (1:1) (1 mL) and purified by Mass Directed Auto-Preparative HPLC (Sunfire C18 column 150 mm×30 mm i.d. 5 μm packing diameter at ambient temperature) eluting with solvents A/B (A: 0.1% v/v solution of formic acid in water, B: 0.1% v/v solution of formic acid in acetonitrile) over 25 min. Appropriate fraction was evaporated in-vacuo to yield the title compound as a yellow oil (6.7 mg, %). LCMS (System B) RT=2.66 min, ES+ve m/z 509/511 (M+H)+.

Example 123

N-[(3-{[3-{[(5-chloro-2-thienyl)sulfonyl]amino}-4-(methyloxy)-1H-indazol-1-yl]methyl}phenyl)methyl]-4-methyl-3-morpholinecarboxamide

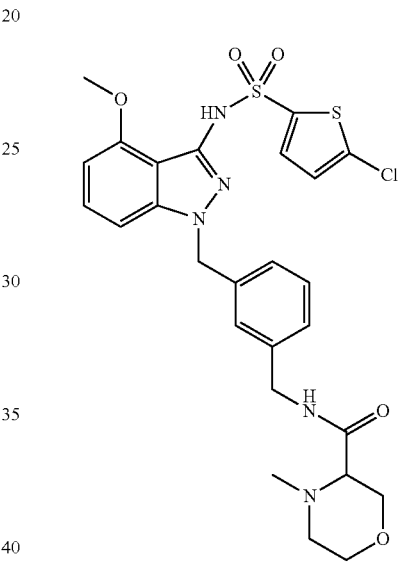

A solution of 4-methyl-3-morpholinecarboxylic acid hydrochloride (Chem-Impex International) (60.0 mg, 0.33 mmol) in acetonitrile (2 mL) was treated with HATU (126 mg, 0.33 mmol) and DIPEA (0.157 ml, 0.901 mmol). The resulting mixture was stirred for 15 min at ambient temperature and then N-[1-{[3-(aminomethyl)phenyl]methyl}-4-(methyloxy)-1H-indazol-3-yl]-5-chloro-2-thiophene-sulfonamide hydrochloride (for a preparation see Intermediate 4) (150 mg, 0.300 mmol) was added, and the resulting mixture was stirred at ambient temperature for 1 h. The reaction mixture was diluted with DCM (3 mL) and water (3 mL). Organic phase was separated and the aqueous layer was further extracted with 3 mL of DCM. The combined organic solutions were washed with water (3 mL), dried through an hydrophobic frit and concentrated in a nitrogen blow-down apparatus. The residue was dissolved in 1:1 MeOH-DMSO 2 mL and purified by Mass Directed AutoPrep (Method C) on Xbridge column using acetonitrile water with an ammonium carbonate modifier. The solvent was evaporated under reduced pressure to give the required product (53.1 mg, 30%). LCMS (System F) RT=0.85 min, ES+ve m/z 590/592 (M+H)+.

Examples 124 and 125

N-[(3-{[3-{[(5-Chloro-2-thienyl)sulfonyl]amino}-4-(methyloxy)-1H-indazol-1-yl]methyl}phenyl)methyl]-4-methyl-3-morpholinecarboxamide Enantiomer 1 (Example 124) and Enantiomer 2 (Example 125)

The racemic mixture above (22 mg) (for a preparation see Example 123) was resolved by chiral HPLC on Chiralpak AD (25 cm) eluting with 50% EtOH-heptane, 30 min isocratic run, flow rate 15 mL/min, detecting at 215 nm to give:

Enantiomer 1 (7.51 mg, 34%): Analytical chiral HPLC [on Chiralpak AD (25 cm) eluting with 50% EtOH-heptane flow rate 1 mL/min, detecting at 215 nm] RT=13.2 min, 100%, $[\alpha]_D^{20}$-34 (c=0.751 in chloroform) and Enantiomer 2 (8.3 mg, 38%): Analytical chiral HPLC RT=17.7 min, 98%, %, $[\alpha]_D^{20}$+22 (c=0.83 in chloroform).

Example 126

(2S)—N-[(3-{[3-{[(5-Chloro-2-thienyl)sulfonyl]amino}-4-(methyloxy)-1H-indazol-1-yl]methyl}phenyl)methyl]-2-hydroxypropanamide (S-enantiomer of Example 37)

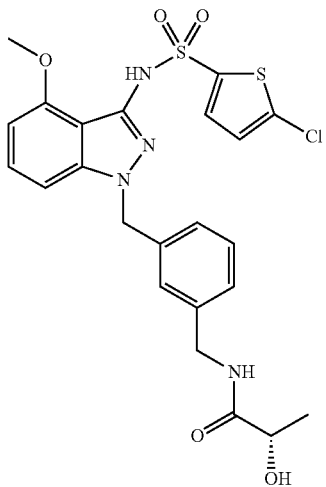 [SMILES: COc1cccc2c1c(NS(=O)(=O)c1ccc(Cl)s1)nn2Cc1cccc(CNC(=O)[C@H](C)O)c1]

A suspension of N-[1-{[3-(aminomethyl)phenyl]methyl}-4-(methyloxy)-1H-indazol-3-yl]-5-chloro-2-thiophenesulfonamide hydrochloride (for a preparation see Intermediate 4) (100 mg, 0.2 mmol) in DCM (5 mL) and triethylamine (0.28 mL, 2 mmol) was treated with the (S)-2-acetoxypropionyl chloride (0.065 mL). After 4 h, the solvent was removed by evaporation and the residue was dissolved in methanol (10 mL) and then treated with solid potassium carbonate (277 mg, 2 mmol) and the mixture was stood at RT for 3 days. The mixture was concentrated under reduced pressure, and the residue was partitioned between 2M HCl and ethyl acetate. The organic solution was washed with more HCl, brine and dried (MgSO$_4$). The filtrate was evaporated under reduced pressure to give a white solid (113 mg). The sample was dissolved in 1:1 MeOH-DMSO 2 mL and purified by Mass Directed AutoPrep on Sunfire C18 column using Acetonitrile Water with a Formic acid modifier (Method A). The solvent was evaporated in vacuo to give the title compound (86 mg, 80%): LCMS (System A) RT=0.97 min, 100%, ES+ve m/z 535/537 (M+H)$^+$; NMR δ (CD$_3$OD) 7.27-7.15 (5H, m), 7.05 (1H, br d, J=7 Hz), 6.97 (1H, d, J=8 Hz), 6.89 (1H, d, J 4 Hz), 6.42 (1H, d, J=8 Hz), 5.47 (2H, s), 4.33 (2H, s), 4.12 (1H, q, J=7 Hz), 3.76 (3H, s), 1.30 (3H, d, J=7 Hz).

Example 127

N$^1$-[(3-{(3-{[(5-Chloro-2-thienyl)sulfonyl]amino}-4-(methyloxy)-1H-indazol-1-yl]methyl}phenyl)methyl]-2-methylalaninamide

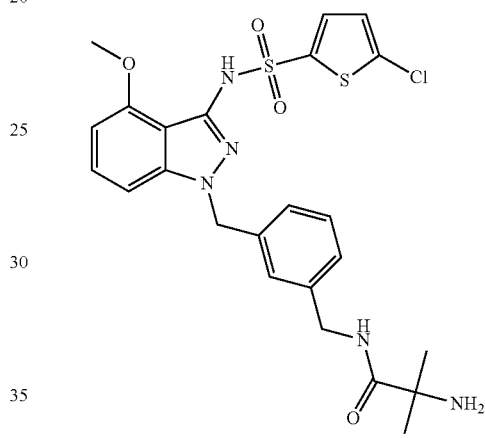

A mixture of N-[1-{[3-(aminomethyl)phenyl]methyl}-4-(methyloxy)-1H-indazol-3-yl]-5-chloro-2-thiophenesulfonamide hydrochloride (for a preparation see intermediate 4) (529 mg, 1.06 mmol), N-BOC-alpha-methylalanine (Sigma) (248 mg, 1.22 mmol), HATU (503 mg, 1.32 mmol) was stirred in DMF (2 mL) and DIPEA (0.75 mL, 4.4 mmol) until the mixture dissolved and then stood overnight at room temperature. The mixture was then treated with TFA (1.5 mL, 19.5 mmol) at room temperature and after 45 min more TFA (1.5 mL, 19.5 mmol) added. After 1.5 h more TFA (1 mL) was added and the mixture was stirred for 18 h. The mixture was concentrated under reduced pressure and the residue was loaded in methanol and purified by SPE on ion exchange cartridge (SCX-2) 50 g eluting with MeOH, followed by 10% aqueous ammonia in MeOH. The appropriate ammoniacal fractions were combined and evaporated in vacuo to give the crude product. The sample was dissolved in 1:1 MeOH-DMSO 8 mL and purified by Mass Directed AutoPrep on Xbridge column using Acetonitrile Water with an ammonium carbonate modifier (Method C) collecting the peak with RT-6.0 min. The solvent was evaporated in vacuo to give the title compound (242 mg, 42%): LCMS (System C) RT=2.01 min, ES+ve m/z 548/550 (M+H)$^+$; NMR δ (CD$_3$OD) 7.26-7.13 (4H, m), 7.10 (1H, br d, J=7 Hz), 7.05 (1H, br s), 6.92 (1H, d, J=8 Hz), 6.86 (1H, d, J=4 Hz), 6.40 (1H, d, J=8 Hz), 5.45 (2H, s), 4.31 (2H, s), 3.77 (3H, s), 1.31 (6H, s).

Example 128

N-[(3-{[3-{[(5-Chloro-2-thienyl)sulfonyl]amino}-7-fluoro-4-(methyloxy)-1H-indazol-1-yl]methyl}phenyl)methyl]acetamide

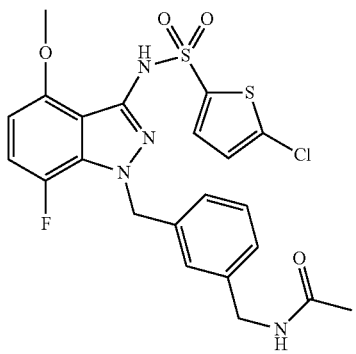 [SMILES: COc1ccc(F)c2c1c(NS(=O)(=O)c1ccc(Cl)s1)nn2Cc1cccc(CNC(C)=O)c1]

N-[1-{[3-(aminomethyl)phenyl]methyl}-7-fluoro-4-(methyloxy)-1H-indazol-3-yl]-5-chloro-2-thiophenesulfonamide (for a preparation see Intermediate 46) (70 mg, 0.15 mmol) was dissolved in DCM (0.75 mL) and triethylamine (0.203 mL, 1.45 mmol) was added to the solution. The solution was stirred for 5 min and acetic anhydride (0.013 mL, 0.13 mmol) was added. The reaction was stirred for 1 h, and then concentrated under a stream of nitrogen. The residue was dissolved in MeOH-DMSO (1:1) (1 mL) and purified by Mass Directed AutoPrep on Sunfire C18 column using Acetonitrile Water with a TFA modifier (Method B). The solvent was evaporated in vacuo to give the title compound (26 mg, 34%): LCMS (System A) RT=1.04 min, ES+ve m/z 523/524 $(M+H)^+$.

Example 129

N-[(3-{[3-{[(5-Chloro-2-thienyl)sulfonyl]amino}-6-fluoro-4-(methyloxy)-1H-indazol-1-yl]methyl}phenyl)methyl]acetamide

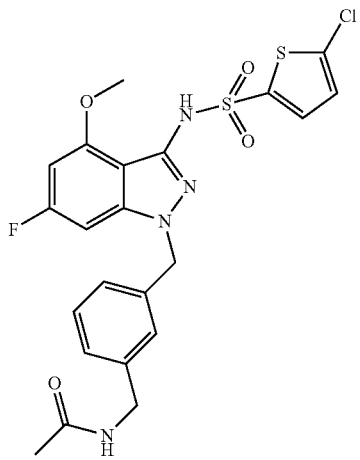 [SMILES: COc1cc(F)cc2c1c(NS(=O)(=O)c1ccc(Cl)s1)nn2Cc1cccc(CNC(C)=O)c1]

N-[1-{[3-(Aminomethyl)phenyl]methyl}-6-fluoro-4-(methyloxy)-1H-indazol-3-yl]-5-chloro-2-thiophenesulfonamide formate salt (for a preparation see Intermediate 54)(53 mg, 0.1 mmol) was dissolved in MeOH and applied to an SCX-2 cartridge (5 g) eluting with MeOH, followed by 10% aqueous ammonia in MeOH. The ammoniacal fraction was evaporated under reduced pressure to give the free base (44 mg, 0.09 mmol) as a white crystalline solid. This was suspended in chloroform (2 mL) and triethylamine (1 mL) and then treated with acetic anhydride (0.024 mL). The mixture was shaken briefly until homogeneous and then it was stood at room temperature for 2 h. The mixture was treated with MeOH and allowed to stand to consume excess acetic anhydride and then was concentrated under reduced pressure. The residue was dissolved in 1:1 MeOH-DMSO 1 mL and purified by Mass Directed AutoPrep on Xbridge column using Acetonitrile Water with an ammonium carbonate modifier (Method C). The solvent was evaporated in vacuo and the residue was dissolved in DCM and washed with 2M HCl solution, and evaporated under reduced pressure to give the title compound (25 mg, 52%) LCMS (System A) RT=1.02 min, ES+ve m/z 523/525 $(M+H)^+$.

Example 130

3-{[3-{[(5-Chloro-2-thienyl)sulfonyl]amino}-6-fluoro-4-(methyloxy)-1H-indazol-1-yl]methyl}benzamide

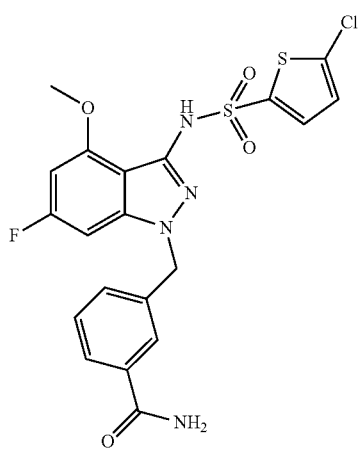 [SMILES: COc1cc(F)cc2c1c(NS(=O)(=O)c1ccc(Cl)s1)nn2Cc1cccc(C(N)=O)c1]

A solution of 5-chloro-N-[(5-chloro-2-thienyl)sulfonyl]-N-[1-[(3-cyanophenyl)methyl]-6-fluoro-4-(methyloxy)-1H-indazol-3-yl]-2-thiophenesulfonamide (for a preparation see Intermediate 53) (53 mg, 0.08 mmol) in methanol (10 mL) was treated with 2M NaOH solution (1 mL) was heated to 60° C. under nitrogen overnight. More 2M NaOH solution (0.5 mL) was added and the mixture was heated to 71° C. over the weekend. The mixture was allowed to cool to RT and then treated with 2M HCl solution to pH 0. The mixture was extracted with ethyl acetate and the organic solution was washed with 2M HCl, brine, dried (MgSO$_4$) and evaporated to a gum 54 mg. The residue was dissolved in 1:1 MeOH-DMSO 1 mL and purified by Mass Directed AutoPrep on Sunfire C18 column using Acetonitrile Water with a Formic acid modifier (Method A) collecting fractions with RT=7.77 min 19% and 8.73 min, 81%). The solvent was evaporated in vacuo from the major fraction (RT=8.73 min) to give 3-{[3-{[(5-chloro-2-thienyl)sulfonyl]amino}-6-fluoro-4-(methyloxy)-1H-indazol-1-yl]methyl}benzoic acid (26 mg, 65%), as a white solid: LCMS (System A) RT=1.04 min, ES+ve m/z 496/498 $(M+H)^+$ for carboxylic acid product. The minor component (RT=7.77 min) was evaporated under reduced pressure to give the title compound (6.2 mg, 15%) as a white solid: LCMS (System A) RT=0.97 min, ES+ve m/z 495/497 (M+H)+.

Example 131

(3R)—N-[(3-{[3-{[(5-Chloro-2-thienyl)sulfonyl] amino}-6-fluoro-4-(methyloxy)-1H-indazol-1-yl] methyl}phenyl)methyl]-3-morpholinecarboxamide

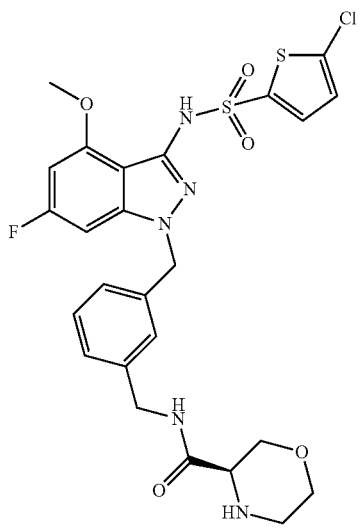 [SMILES: COc1cc(F)cc2c1c(NS(=O)(=O)c1ccc(Cl)s1)nn2Cc1cccc(CNC(=O)[C@H]2COCCN2)c1]

N-[1-{[3-(Aminomethyl)phenyl]methyl}-6-fluoro-4-(methyloxy)-1H-indazol-3-yl]-5-chloro-2-thiophene-sulfonamide (for a preparation see Intermediate 54) (100 mg, 0.208 mmol) was suspended in dichloromethane (1 mL), (3R)-4-{[(1,1-dimethylethyl)oxy]carbonyl}-3-morpholinecarboxylic acid (52.9 mg, 0.229 mmol) and HATU (87 mg, 0.229 mmol) were added to the reaction mixture and stirred for 5 min. DIPEA (0.109 mL, 0.624 mmol) was added to the reaction mixture and stirred over the weekend. Trifluoroacetic acid (0.25 mL, 3.24 mmol) was added to the reaction mixture and stirred for 3.5 h. The mixture was concentrated under a stream of nitrogen leaving a brown residue. The residue was dissolved in 1:1 MeOH-DMSO (1 mL) and purified by Mass Directed AutoPrep on Sunfire C18 column using Acetonitrile Water with a TFA modifier (Method B). The solvent was evaporated in vacuo to give the TFA salt of the required product as an off white residue. The residue was dissolved in methanol and loaded onto a methanol pre-conditioned polymeric carbonate (SAX) cartridge. The sample was eluted with 1.25M HCl in methanol. The fractions were concentrated in vacuo, dissolved in methanol and loaded onto a methanol pre-conditioned SCX-2 ion exchange cartridge (2 g). The cartridge was washed well with methanol, followed by 2M ammonia in methanol. Evaporation of the solvent from the ammoniacal fractions gave the title compound (30 mg, 24%): LCMS (System A) RT=0.88 min, ES+ve m/z 594/596 (M+H)+.

Example 132

N-[(3-{[3-{[(5-Chloro-2-thienyl)sulfonyl]amino}-6-fluoro-4-(methyloxy)-1H-indazol-1-yl] methyl}phenyl)methyl]-2-hydroxy-2-methylpropanamide

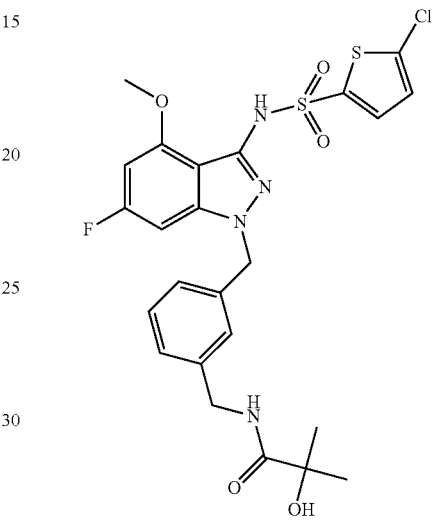

N-[1-{[3-(Aminomethyl)phenyl]methyl}-6-fluoro-4-(methyloxy)-1H-indazol-3-yl]-5-chloro-2-thiophene-sulfonamide (for a preparation see Intermediate 54) (100 mg, 0.208 mmol) (intermediate) was dissolved in dichloromethane (0.5 mL) and pyridine (0.5 mL), and then treated with 2-chloro-1,1-dimethyl-2-oxoethyl acetate (0.031 mL, 0.218 mmol). The mixture was stirred for 2 h. LCMS showed starting material remaining so more 2-chloro-1,1-dimethyl-2-oxoethyl acetate (0.021 mL, 0.146 mmol) was added to the reaction mixture and stirred for 1.5 hr. LCMS showed starting material remaining so a further portion of 2-chloro-1,1-dimethyl-2-oxoethyl acetate (0.015 mL, 0.104 mmol) was added to the reaction and stirred for 1.25 h. The reaction mixture was concentrated under a stream of nitrogen to leave a yellow residue, which was dissolved in methanol (1 mL) and potassium carbonate (86 mg, 0.624 mmol) was added to the solution. The reaction mixture was heated to 40° C. for 1 h and then neutralised with 2M HCl and concetrated in vacuo. The residue was dissolved in ethyl acetate (50 mL), washed three times with water (50 mL) and once with brine (50 mL). The organic layer was dried over anhydrous magnesium sulfate before being evaporated in vacuo to leave a yellow residue. The sample was dissolved in 1:1 MeOH-DMSO (1 mL) and purified by Mass Directed AutoPrep on Sunfire C18 column using Acetonitrile Water with a TFA modifier (Method B). The solvent was evaporated in vacuo to give the title compound (60 mg, 51%). LCMS (System A) RT=1.04 min, ES+ve m/z 481/483 (M+H)+.

Example 133

N-[(3-{[3-{[(5-Chloro-2-thienyl)sulfonyl]amino}-6-fluoro-4-(methyloxy)-1H-indazol-1-yl]methyl}phenyl)methyl]-4-methyl-3-morpholinecarboxamide

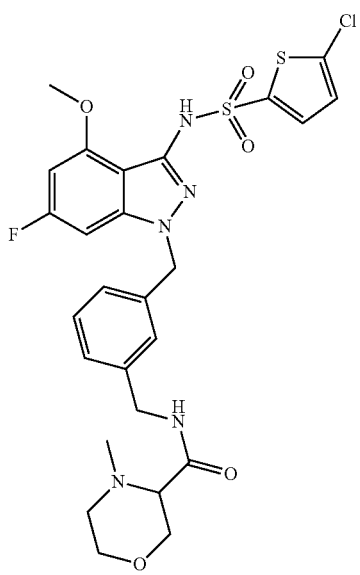 [SMILES: COc1cc(F)cc2c1c(NS(=O)(=O)c1ccc(Cl)s1)nn2Cc1cccc(CNC(=O)C2COCCN2C)c1]

N-[1-{[3-(Aminomethyl)phenyl]methyl}-6-fluoro-4-(methyloxy)-1H-indazol-3-yl]-5-chloro-2-thiophenesulfonamide (for a preparation see Intermediate 54) (250 mg, 0.520 mmol) was dissolved in dichloromethane (2.5 mL), 4-methyl-3-morpholinecarboxylic acid hydrochloride (104 mg, 0.572 mmol) and HATU (217 mg, 0.572 mmol) were added to the reaction mixture stirred for 5 min. DIPEA (0.272 mL, 1.559 mmol) was added to the mixture and stirred over the weekend. LCMS showed that the coupling was complete so the reaction was concentrated under a stream of nitrogen in a blow-down unit. The residue was dissolved in 1:1 MeOH: DMSO (1 mL) and purified by Mass Directed AutoPrep on Sunfire C18 column using Acetonitrile Water with a TFA modifier (Method B). The solvent was evaporated in vacuo to give the TFA salt of required product as an orange oil. The compound was dissolved in methanol and passed down a polymeric carbonate (SAX) cartridge, the cartridge was eluted with methanol and solvent was evaporated in vacuo to give the free base of the required product as an orange oil (80 mg). The carbonate cartridge was further eluted with 1.25M HCl in methanol, the solution was evaporated in vacuo, the residue (150 mg) dissolved in methanol and loaded onto a methanol pre-conditioned SCX-2 ion-exchange cartridge (1 g). The cartridge was washed well with methanol, followed by 2M ammonia in methanol. Evaporation of the solvent from the ammoniacal fractions gave a further portion of the free-base of the required product, which was combined with the earlier batch.

The racemic mixture (140 mg) was then resolved by chiral HPLC separation on Chiralpak IA (20 mm×250 mm, 10 mm packing), flow rate 15 mL/min, detecting at 300 nm, eluting with 25% ethanol-heptane (isocratically for 60 min) to give Enantiomer 1 of the title compound (67 mg, 20%): LCMS (System A) RT=0.86 min, ES+ve m/z 608/610 (M+H)$^+$, Analytical Chiral HPLC Chiralcel IA (4.6 mm×250 mm, 10 μm packing), flow rate 1 mL/min, detecting at 300 nm, eluting with 35% ethanol-heptane (isocratically for 22 min) RT=13.5 min, >99.5% and Enantiomer 2 (67 mg, 20%) RT=17.0 min, >99.5%

Example 134

N-[(3-{[3-{[(5-Chloro-2-thienyl)sulfonyl]amino}-5-fluoro-4-(methyloxy)-1H-indazol-1-yl]methyl}phenyl)methyl]acetamide(

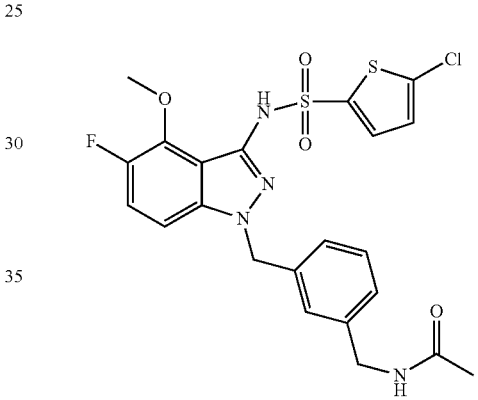

A solution of N-[1-{[3-(aminomethyl)phenyl]methyl}-5-fluoro-4-(methyloxy)-1H-indazol-3-yl]-5-chloro-2-thiophenesulfonamide (for a preparation see Intermediate 61) (49 mg, 0.10 mmol) in dry DMF (4 mL) was treated with HATU (38.7 mg, 0.10 mmol) and stirred under nitrogen for 3 min prior to the addition of DIPEA (0.018 mL, 0.10 mmol). The reaction mixture was stirred for a further 3 min prior to the addition of acetic acid (6.12 mg, 0.10 mmol) and stirring continued for a further 3 h. The reaction mixture was concentrated by nitrogen in a blowdown unit and the sample was loaded in dichloromethane onto aminopropyl ion-exchange cartridge (1 g) pre-equilibrated with DCM. The sample was eluted with methanol/dichloromethane and dried under a stream of nitrogen in the Radleys blowdown apparatus to give the crude product. The sample was dissolved in 1:1 MeOH-DMSO (1 mL) and purified by Mass Directed AutoPrep on Xbridge column using Acetonitrile Water with an ammonium carbonate modifier (Method C). The solvent was evaporated in vacuo using the Genevac to give the title compound (14.5 mg, 27%): LCMS (System A) RT=1.06 min, ES+ve m/z 523/525 (M+H)$^+$.

Example 135

(3S)—N-[(3-{[3-{[(5-Chloro-2-thienyl)sulfonyl]amino}-5-fluoro-4-(methyloxy)-1H-indazol-1-yl]methyl}phenyl)methyl]-3-morpholinecarboxamide

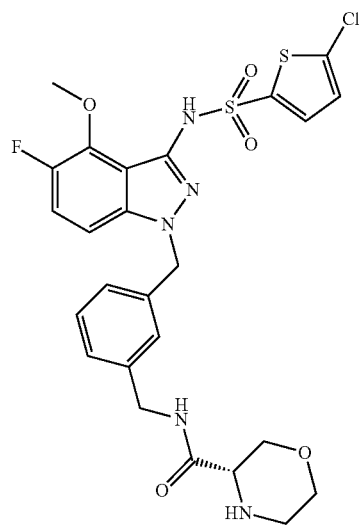 [SMILES: COc1c(F)ccc2c1c(NS(=O)(=O)c1ccc(Cl)s1)nn2Cc1cccc(CNC(=O)[C@@H]2COCCN2)c1]

N-[1-{[3-(Aminomethyl)phenyl]methyl}-5-fluoro-4-(methyloxy)-1H-indazol-3-yl]-5-chloro-2-thiophene-sulfonamide (for a preparation see Intermediate 61) (100 mg, 0.208 mmol) was suspended in DCM (1 mL), (3S)-4-{[(1,1-dimethylethyl)oxy]carbonyl}-3-morpholinecarboxylic acid (52.9 mg, 0.229 mmol) and HATU (87 mg, 0.229 mmol) were added to the reaction mixture and stirred for 5 min. DIPEA (0.109 mL, 0.624 mmol) was added to the reaction mixture and stirred over the weekend. LCMS showed the coupling had gone to completion. Trifluoroacetic acid (0.25 mL, 3.24 mmol) was added to the reaction and left to stir for 1 h and 50 min. LCMS showed the reaction had gone to completion so the mixture was concentrated under a stream of nitrogen. The sample was dissolved in 1:1 MeOH-DMSO (1 mL) and purified by Mass Directed AutoPrep on Sunfire C18 column using Acetonitrile Water with a TFA modifier (Method B). The solvent was evaporated in vacuo to give the required product (as TFA salts). The residue was dissolved in methanol and loaded onto a methanol pre-conditioned SCX-2 ion-exchange cartridge (10 g). The cartridge was washed well with methanol, followed by 2M ammonia in methanol. Evaporation of the solvent from the ammoniacal fractions gave the title compound as a colourless glassy solid (71 mg, 57%). LCMS (System A) RT=0.82 min, ES+ve m/z 594/596 (M+H)+.

Example 136

(3R)—N-[(3-{[3-{[(5-Chloro-2-thienyl)sulfonyl]amino}-5-fluoro-4-(methyloxy)-1H-indazol-1-yl]methyl}phenyl)methyl]-3-morpholinecarboxamide

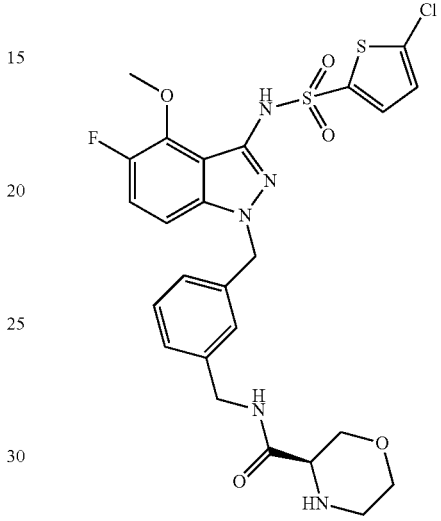

N-[1-{[3-(Aminomethyl)phenyl]methyl}-6-fluoro-4-(methyloxy)-1H-indazol-3-yl]-5-chloro-2-thiophene-sulfonamide (for a preparation see Intermediate 61) (100 mg, 0.208 mmol) was suspended in dichloromethane (1 mL), (3R)-4-{[(1,1-dimethylethyl)oxy]carbonyl}-3-morpholinecarboxylic acid (52.9 mg, 0.229 mmol) and HATU (87 mg, 0.229 mmol) were added to the reaction mixture and stirred for 5 min. DIPEA (0.109 mL, 0.624 mmol) was added to the reaction mixture and it was left to stir over the weekend. LCMS showed the coupling had gone to completion. Trifluoroacetic acid (0.25 mL, 3.24 mmol) was added to the reaction and left to stir for 1 h and 50 min. LCMS showed the reaction had gone to completion so the mixture was concentrated under a stream of nitrogen to afford a brown residue. The residue was dissolved in 1:1 MeOH-DMSO (1 mL) and purified by Mass Directed AutoPrep on Sunfire C18 column using Acetonitrile Water with a TFA modifier (Method B). The solvent was evaporated in vacuo to give the required product as an off white residue (as TFA salt). The residue was dissolved in methanol and loaded onto a methanol pre-conditioned SCX-2 ion-exchange cartridge (10 g). The cartridge was washed well with methanol, followed by 2M ammonia in methanol. Evaporation of the solvent from the ammoniacal fractions gave the title compound (76 mg, 61% yield). LCMS (System A) RT=0.83 min, ES+ve m/z 594/596 (M+H)+.

Example 137

N-[(3-{[3-{[(5-Chloro-2-thienyl)sulfonyl]amino}-5-fluoro-4-(methyloxy)-1H-indazol-1-yl]methyl}phenyl)methyl]-2-hydroxy-2-methylpropanamide

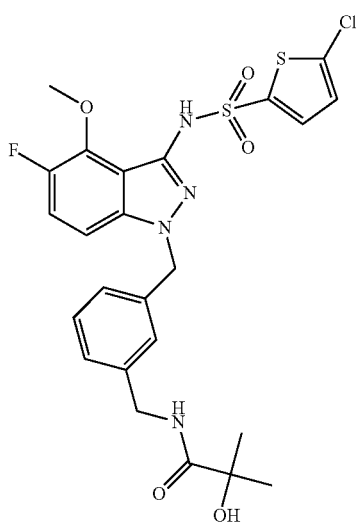 [SMILES: COc1c(F)ccc2c1c(NS(=O)(=O)c1ccc(Cl)s1)nn2Cc1cccc(CNC(=O)C(C)(C)O)c1]

A suspension of N-[1-{[3-(aminomethyl)phenyl]methyl}-5-fluoro-4-(methyloxy)-1H-indazol-3-yl]-5-chloro-2-thiophenesulfonamide (for a preparation see Intermediate 61) (100 mg, 0.208 mmol) in dichloromethane (0.5 mL), pyridine (0.5 mL) and potassium hydroxide (11.67 mg, 0.208 mmol) was treated with 2-chloro-1,1-dimethyl-2-oxoethyl acetate (0.054 mL, 0.37 mmol) and the mixture was stirred for 2.5 h. The reaction mixture was concentrated in vacuo and the orange residue was dissolved in 1:1 MeOH-DMSO (1 mL) and purified by Mass Directed AutoPrep on Sunfire C18 column using Acetonitrile Water with a TFA modifier (Method B). The solvent was evaporated in vacuo to give the title compound (58 mg, 49%). LCMS (System A) RT=1.04 min, ES+ve m/z 567/569 (M+H)+.

Example 138

4-{[(3-{[3-{[(5-Chloro-2-thienyl)sulfonyl]amino}-4-(methyloxy)-1H-indazol-1-yl]methyl}phenyl)methyl]amino}-4-oxobutanoic Acid

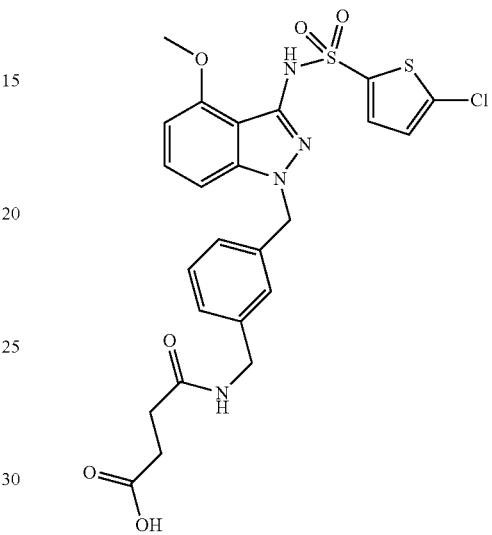

4-(Methyloxy)-4-oxobutanoic acid (0.013 g, 0.1 mmol) was treated with a solution of 2-(1H-7-azabenzotriazol-1-yl)-1,1,3,3-tetramethyluronium hexafluorophosphate (0.076 g, 0.2 mmol) in anhydrous DMF (0.2 ml) and N,N-diisopropylethylamine (0.052 ml, 0.3 mmol) and then the solution was stirred for 10 min.

N-[1-{[3-(Aminomethyl)phenyl]methyl}-4-(methyloxy)-1H-indazol-3-yl]-5-chloro-2-thiophenesulfonamide (for a preparation see Intermediate 4) (0.046 g, 0.1 mmol) was added to the solution and the resulting solution stirred for 18 h at room temperature. The solvent was removed by genevac, the residue was dissolved in DMSO (0.5 ml) and purified by mass directed auto-preparative HPLC to give methyl 4-{[(3-{[3-{[(5-chloro-2-thienyl)sulfonyl]amino}-4-(methyloxy)-1H-indazol-1-yl]methyl}phenyl)methyl]amino}-4-oxobutanoate. This was dissolved in methanol (0.2 ml), sodium hydroxide (2M, 0.15 ml) and water (0.09 ml) were added, and the reaction mixture was stirred at 30° C. for 1 h. The solution was neutralised and concentrated in a blow-down unit, and the residue was purified by mass directed auto-preparative HPLC (Method E) to give the title compound. LCMS (System A) RT=0.99 min, ES+ve m/z 563/565 (M+H)+

Examples 139-145 were similarly prepared to Example 138 using N-[1-{[3-(Aminomethyl)phenyl]methyl}-4-(methyloxy)-1H-indazol-3-yl]-5-chloro-2-thiophenesulfonamide and the appropriate carboxylic acid

Example 139

Example 5-{[(3-{[3-{[(5-Chloro-2-thienyl)sulfonyl] amino}-4-(methyloxy)-1H-indazol-1-yl] methyl}phenyl)methyl]amino}-5-oxopentanoic Acid

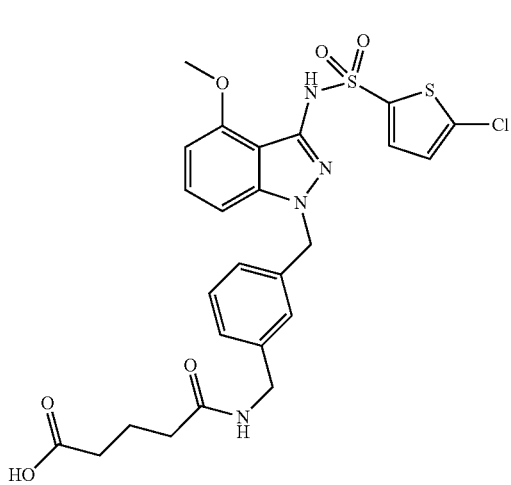 [SMILES: COc1cccc2c1c(NS(=O)(=O)c1ccc(Cl)s1)nn2Cc1cccc(CNC(=O)CCCC(=O)O)c1]

LCMS (System A) RT=0.97 min, ES+ve m/z 577/579 (M+H)+

Example 140

6-{[(3-{[3-{[(5-Chloro-2-thienyl)sulfonyl]amino}-4-(methyloxy)-1H-indazol-1-yl]methyl}phenyl)methyl]amino}-6-oxohexanoic Acid

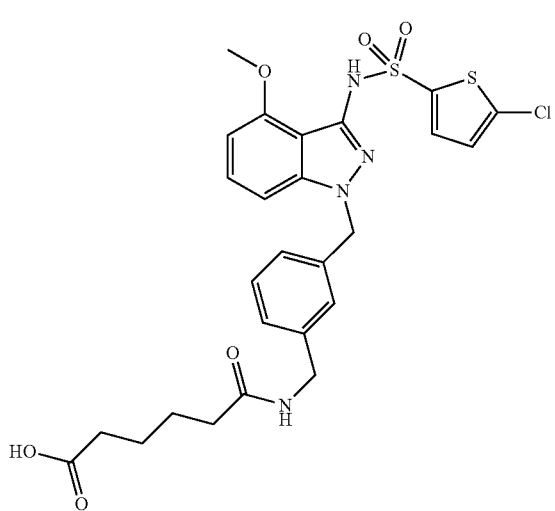 [SMILES: COc1cccc2c1c(NS(=O)(=O)c1ccc(Cl)s1)nn2Cc1cccc(CNC(=O)CCCCC(=O)O)c1]

LCMS (System A) RT=0.99 min, ES+ve m/z 591/593 (M+H)+

Example 141

3-({[(3-{[3-{[(5-Chloro-2-thienyl)sulfonyl]amino}-4-(methyloxy)-1H-indazol-1-yl]methyl}phenyl)methyl]amino}carbonyl)benzoic Acid

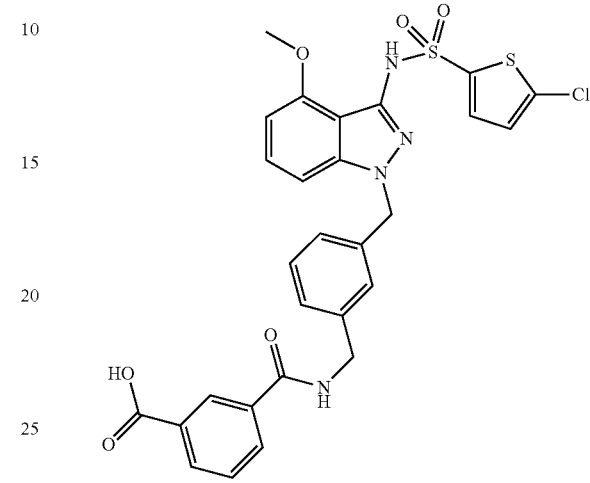

LCMS (System A) RT=1.05 min, ES+ve m/z 611/613 (M+H)+

Example 142

4-({[(3-{[3-{[(5-Chloro-2-thienyl)sulfonyl]amino}-4-(methyloxy)-1H-indazol-1-yl]methyl}phenyl)methyl]amino}carbonyl)benzoic Acid

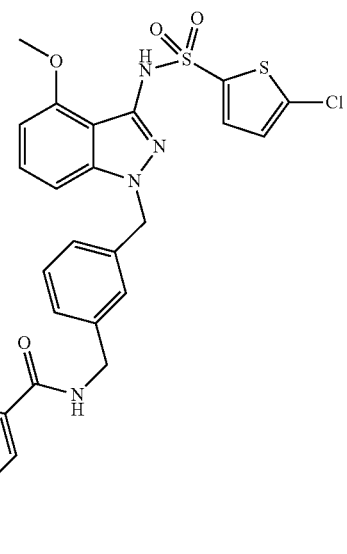

LCMS (System A) RT=1.04 min, ES+ve m/z 611/613 (M+H)+

Example 143 trans-4-({[(3-{[3-{[(5-Chloro-2-thienyl)sulfonyl]amino}-4-(methyloxy)-1H-indazol-1-yl]methyl}phenyl)methyl]amino}carbonyl)cyclohexanecarboxylic Acid

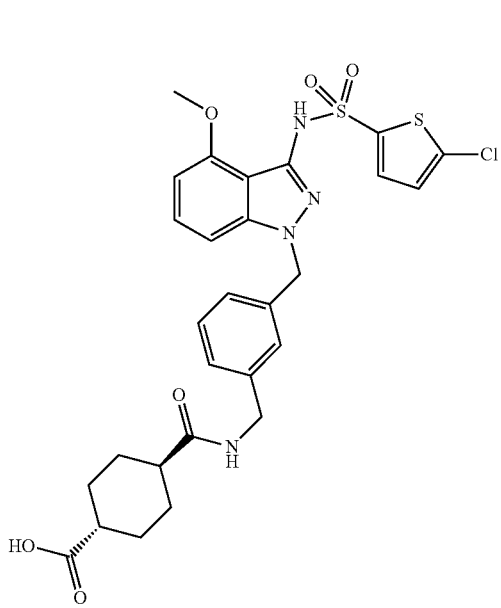 [SMILES: COc1cccc2c1c(NS(=O)(=O)c1ccc(Cl)s1)nn2Cc1cccc(CNC(=O)[C@H]2CC[C@H](C(=O)O)CC2)c1]

LCMS (System A) RT=1.01 min, ES+ve m/z 617/619 (M+H)+

Example 144

8-{[(3-{[3-{[(5-Chloro-2-thienyl)sulfonyl]amino}-4-(methyloxy)-1H-indazol-1-yl]methyl}phenyl)methyl]amino}-8-oxooctanoic Acid

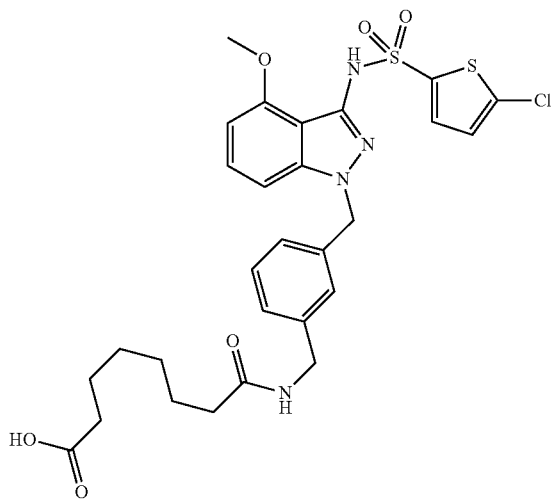 [SMILES: COc1cccc2c1c(NS(=O)(=O)c1ccc(Cl)s1)nn2Cc1cccc(CNC(=O)CCCCCCC(=O)O)c1]

LCMS (System A) RT=1.04 min, ES+ve m/z 619/621 (M+H)+

Example 145

9-{[(3-{[3-{[(5-Chloro-2-thienyl)sulfonyl]amino}-4-(methyloxy)-1H-indazol-1-yl]methyl}phenyl)methyl]amino}-9-oxononanoic Acid)

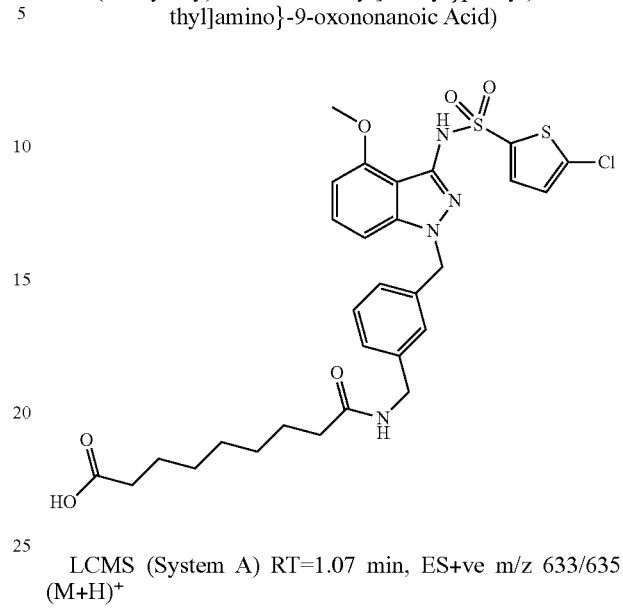

LCMS (System A) RT=1.07 min, ES+ve m/z 633/635 (M+H)+

Example 146

2-({[(3-{[3-{[(5-Chloro-2-thienyl)sulfonyl]amino}-4-(methyloxy)-1H-indazol-1-yl]methyl}phenyl)methyl]amino}carbonyl)benzoic Acid

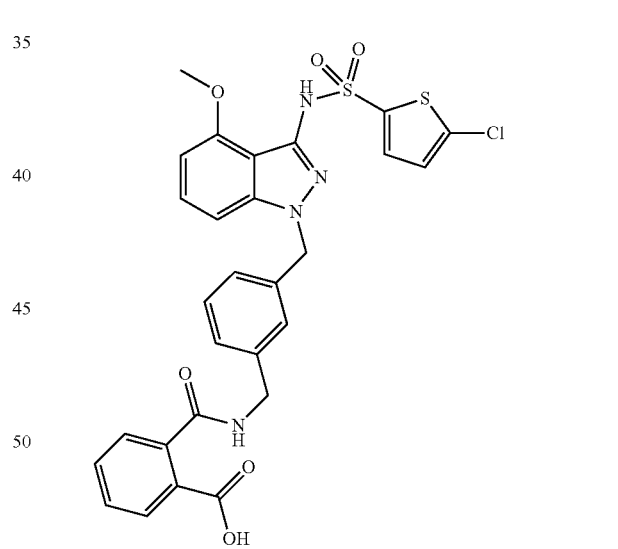

To a solution of N-[1-{[3-(aminomethyl)phenyl]methyl}-4-(methyloxy)-1H-indazol-3-yl]-5-chloro-2-thiophenesulfonamide (for a preparation see Intermediate 4) (0.046 g, 0.1 mmol) in THF (0.5 ml) was added N,N-diisopropylethylamine (0.035 ml, 0.2 mmol), followed by phthalic anhydride (0.014 g, 0.1 mmol). The solution was stirred for 18 hours at room temperature, concentrated in a blow-down unit and the residue was dissolved in DMSO (0.5 ml) and purified by mass directed auto-preparative HPLC (Method E) to give the title compound (35 mg, 51%).

LCMS (System A) RT=1.03 min, ES+ve m/z 611/613 (M+H)+

Example 147

N-[(3-{[3-{[(5-Chloro-2-thienyl)sulfonyl]amino}-4-(difluoromethyl)-1H-indazol-1-yl]methyl}phenyl)methyl]acetamide

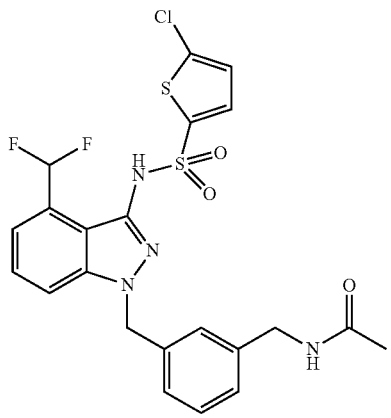 [SMILES: CC(=O)NCc1cccc(Cn2nc(NS(=O)(=O)c3ccc(Cl)s3)c3c(C(F)F)cccc32)c1]

N-[1-{[3-(Aminomethyl)phenyl]methyl}-4-(difluoromethyl)-1H-indazol-3-yl]-5-chloro-N-[(5-chloro-2-thienyl)sulfonyl]-2-thiophenesulfonamide (for a preparation see Intermediate 70) (26 mg, 0.039 mmol) was suspended in dichloromethane (0.5 mL) and triethylamine (0.055 mL, 0.39 mmol) and then acetic anhydride (0.004 mL, 0.043 mmol) was added to the suspension. The mixture was stirred for 1 h, and concentrated under a stream of nitrogen to give N-[(3-{[3-{Bis[(5-chloro-2-thienyl)sulfonyl]amino}-4-(difluoromethyl)-1H-indazol-1-yl]methyl}phenyl)methyl]acetamide, which was used without further purification. The residue was dissolved in methanol (2 mL) and treated with NaOH (0.553 mL, 1.105 mmol) and the reaction mixture was stirred at 60° C. for 3 h. LCMS showed the reaction had gone to completion so the mixture was concentrated in vacuo and acidified with 5% citric acid. The solution was extracted with ethyl acetate and the organic layer was washed twice with water (25 mL) and once with brine (25 mL). The organic layer was dried over anhydrous magnesium sulfate before being evaporated in vacuo to give a yellow residue which was dissolved in 1:1 MeOH-DMSO (1 mL) and purified by Mass Directed AutoPrep on Sunfire C18 column using Acetonitrile Water with a Formic acid modifier (Method A). The solvent was evaporated in vacuo to give the title compound (7 mg, 36%). LCMS (System A) RT=1.02 min, ES+ve m/z 525/527 (M+H)+.

Example 148

N-[(3-{[3-{[(5-Chloro-2-thienyl)sulfonyl]amino}-4-(hydroxymethyl)-1H-indazol-1-yl]methyl}phenyl)methyl]acetamide

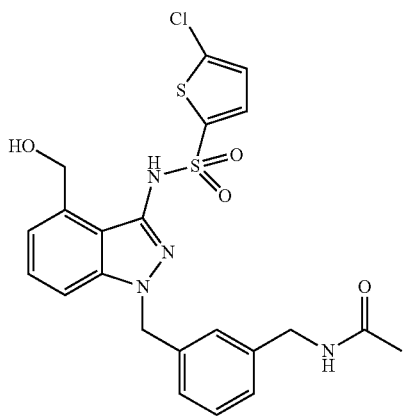 [SMILES: CC(=O)NCc1cccc(Cn2nc(NS(=O)(=O)c3ccc(Cl)s3)c3c(CO)cccc32)c1]

N-[1-{[3-(Aminomethyl)phenyl]methyl}-4-(hydroxymethyl)-1H-indazol-3-yl]-5-chloro-N-[(5-chloro-2-thienyl)sulfonyl]-2-thiophenesulfonamide (for a preparation see Intermediate 72) (53 mg, 0.082 mmol) was suspended in dichloromethane (0.5 mL) and triethylamine (0.115 mL, 0.823 mmol). Acetic anhydride (0.008 mL, 0.09 mmol) was added to the suspension and it stirred for 1 h. LCMS showed starting material remaining so dichloromethane (0.3 mL) and acetic anhydride (3.88 µL, 0.041 mmol) were added to the solution and stirred for 2 h. LCMS showed only a small amount of starting material remaining so the reaction mixture was concentrated in vacuo to leave an off-white residue, which was dissolved in methanol (3 mL) and treated with NaOH (1.546 mL, 3.09 mmol). The reaction was stirred at room temperature for 1 h and then was concentrated in vacuo, and acidified with 5% citric acid. The solution was extracted with ethyl acetate and the organic layer was washed twice with water (25 mL) and once with brine (25 mL). The organic layer was dried over anhydrous magnesium sulfate before being evaporated in vacuo. The yellow residue was dissolved in 1:1 MeOH-DMSO (1 mL) and purified by Mass Directed AutoPrep on Sunfire C18 column using Acetonitrile Water with a Formic acid modifier (Method A). The solvent was evaporated in vacuo to give the title compound (17 mg, 43%) as a colourless glassy solid. LCMS (System A) RT=0.91 min, ES+ve m/z 505/507 (M+H)+.

Example 149

N-[(3-{[3-{[(5-Chloro-2-thienyl)sulfonyl]amino}-4-(1-hydroxyethyl)-1H-indazol-1-yl]methyl}phenyl)methyl]acetamide

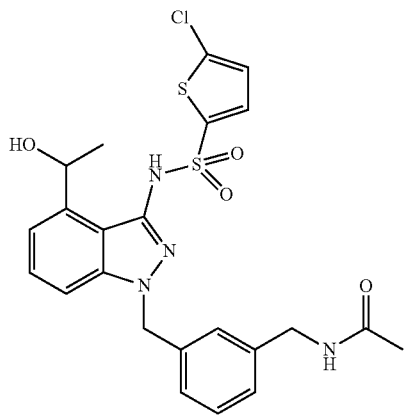 [SMILES: CC(=O)NCc1cccc(Cn2nc(NS(=O)(=O)c3ccc(Cl)s3)c3c(C(C)O)cccc32)c1]

Sodium borohydride (3.09 mg, 0.082 mmol) was added to a stirring solution of N-({3-[(4-acetyl-3-{[(5-chloro-2-thienyl)sulfonyl]amino}-1H-indazol-1-yl)methyl]phenyl}methyl)acetamide (for a preparation see Intermediate 75) (40 mg, 0.068 mmol) in MeOH (2 mL) at 25° C. under nitrogen. The reaction mixture was stirred at room temp. for 2 hours, and then 1N HCl (5 mL) was slowly added and the methanol was evaporated in vacuo. The product was extracted with EtOAc (2×20 mL) and the combined organic layers were dried by passing through a hydrophobic frit and concentrated. The residue was dissolved in DMSO (1 mL) and purified by Mass Directed AutoPrep on Sunfire C18 column using Acetonitrile Water with a Formic acid modifier (Method A). The solvent was evaporated in vacuo to give the title compound (18 mg, 48%). LCMS (System A) RT=0.97 min, ES+ve m/z 519/521 (M+H)+.

Example 150

N-[(3-{[3-{[(5-Chloro-2-thienyl)sulfonyl]amino}-4-(1-hydroxy-1-methylethyl)-1H-indazol-1-yl]methyl}phenyl)methyl]

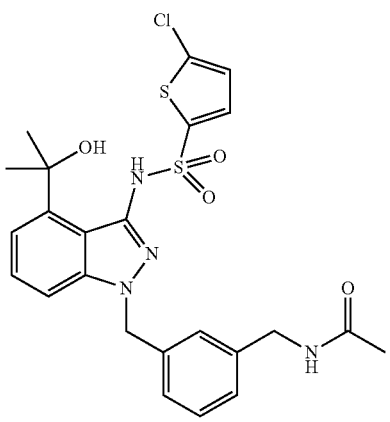 [SMILES: CC(=O)NCc1cccc(Cn2nc(NS(=O)(=O)c3ccc(Cl)s3)c3c(C(C)(C)O)cccc32)c1]

Methylmagnesium bromide (3M solution in diethyl ether) (0.256 mL, 0.768 mmol) was added slowly to a stirring solution of N-({3-[(3-{[(5-chloro-2-thienyl)sulfonyl]amino}-4-cyano-1H-indazol-1-yl)methyl]phenyl}methyl)acetamide (for a preparation see Intermediate 73) (64 mg, 0.128 mmol) in THF (1 mL) at room temp. The reaction was stirred for 2 h. LCMS showed starting material still remaining. Therefore, added more methylmagnesium bromide (3M solution in diethyl ether) (0.128 mL, 0.384 mmol) was added and stirred the reaction at room temp overnight. 0.5N HCl (4 mL) was added and the product was extracted with EtOAc (10 mL×3). The combined organic layers were dried by passing through a hydrophobic frit and concentrated in vacuo. The resulting yellow oil was dissolved in THF (1 mL) and methylmagnesium bromide (3M solution in diethyl ether) (0.256 mL, 0.768 mmol) was slowly added at 0° C. under nitrogen. The reaction was warmed to room temp over ~20 min and was stirred for 2 h. LCMS showed starting material co-elutes with the product—molecular ion at 533 [M+H] corresponding to the desired alcohol product. 1N HCl (4 mL) was slowly added and the product was extracted with EtOAc (15 mL×3). The combined organic layers were dried by passing through a hydrophobic frit and concentrated in vacuo to give a yellow oil, which was dissolved in DMSO (1 mL) and purified by Mass Directed AutoPrep on Sunfire C18 column using Acetonitrile Water with a Formic acid modifier (Method A). The solvent was evaporated in vacuo to give the title compound (23.2 mg, 30%) as a yellow solid. LCMS (System A) RT=1.03 min, ES+ve m/z 533/535 (M+H)$^+$.

Example 151

N-[(3-{[3-{[(5-Chloro-2-thienyl)sulfonyl]amino}-4-(1-hydroxyethyl)-1H-indazol-1-yl]methyl}phenyl)methyl]-2-hydroxy-2-methylpropanamide

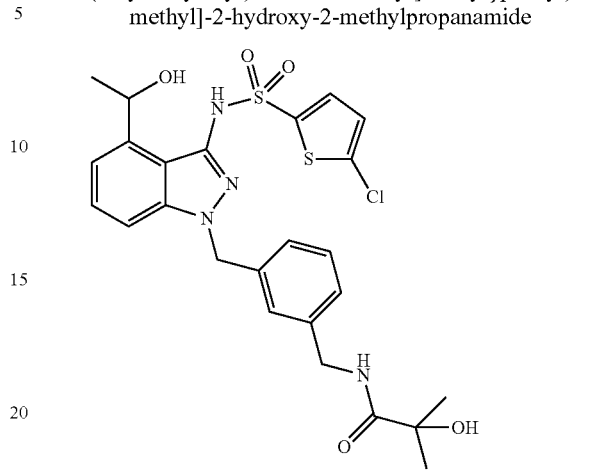

Triethylamine (0.021 mL, 0.151 mmol) was added to N-[1-{[3-(aminomethyl)phenyl]methyl}-4-(1-hydroxyethyl)-1H-indazol-3-yl]-5-chloro-2-thiophenesulfonamide (for a preparation see Intermediate 77) (24 mg, 0.050 mmol) in dichloromethane (1 mL). 2-Chloro-1,1-dimethyl-2-oxoethyl acetate (7.92 μL, 0.055 mmol) was added and the reaction mixture was stirred at room temp for 2 h. The reaction mixture was concentrated on the blowdown unit, potassium carbonate (69.5 mg, 0.503 mmol) and methanol (2 mL) was added and the mixture was stirred at room temp for 1 h. The mixture was concentrated, acidified with 2N HCl and extracted with EtOAc (2×15 mL). The combined organic layers were dried by passing through a hydrophobic frit and concentrated to afford the crude product. The residue was dissolved in DMSO (1 mL) and purified by Mass Directed AutoPrep on Sunfire C18 column using Acetonitrile Water with a Formic acid modifier (Method A). The solvent was removed under a stream of nitrogen in the Radleys blowdown apparatus to give the title compound (10.5 mg, 37%). LCMS (System A) RT=0.99 min, ES+ve m/z 563/565 (M+H)$^+$.

Example 152

(3R)—N-[(3-{[3-{[(5-Chloro-2-thienyl)sulfonyl]amino}-4-(1-hydroxyethyl)-1H-indazol-1-yl]methyl}phenyl)methyl]-3-morpholinecarboxamide Formate Salt

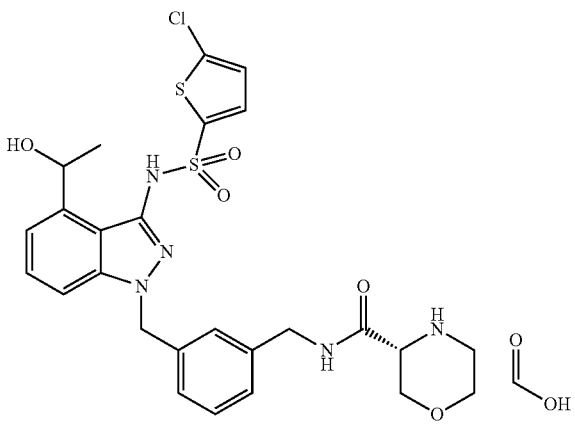

DIPEA (0.059 mL, 0.336 mmol) was added to a stirring solution of (3R)-4-{[(1,1-dimethylethyl)oxy]carbonyl}-3-morpholinecarboxylic acid (19.41 mg, 0.084 mmol) in DCM (1 mL). HATU (35.1 mg, 0.092 mmol) was then added followed by N-[1-{[3-(aminomethyl)phenyl]methyl}-4-(1-hydroxyethyl)-1H-indazol-3-yl]-5-chloro-2-thiophenesulfonamide (for a preparation see Intermediate 77) (44 mg, 0.084 mmol) and stirred for an hour at room temp. The mixture was treated with 4M hydrogen chloride in dioxane (0.5 mL, 2 mmol) and the reaction stirred at room temperature for 0.5 h. The reaction mixture was passed through an SCX-2 cartridge, washed with methanol and then eluted using 2M ammonia in methanol. The appropriate ammoniacal fractions were concentrated under reduced pressure and the residue was dissolved in DMSO-Methanol (1:1) (1 mL) and purified by MDAP (Method A) to give the title compound (31.2 mg, 58%). LCMS (System C) RT=2.04 min, ES+ve m/z 590/592 (M+H)+.

Example 153

(3S)—N-[(3-{[3-{[(5-Chloro-2-thienyl)sulfonyl]amino}-4-(1-hydroxyethyl)-1H-indazol-1-yl]methyl}phenyl)methyl]-3-morpholinecarboxamide Formate Salt

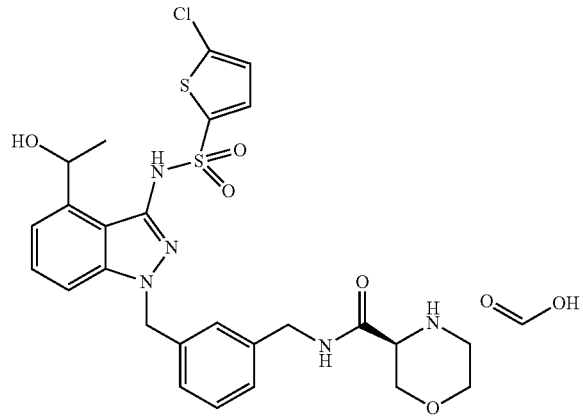

The title compound was similarly prepared to Example 152.

LCMS (System C) RT=2.04 min, ES+ve m/z 590/592 (M+H)+.

Example 154

N-[(3-{[3-{[(5-Chloro-2-thienyl)sulfonyl]amino}-4-(1-hydroxy-1-methylethyl)-1H-indazol-1-yl]methyl}phenyl)methyl]-2-hydroxy-2-methylpropanamide

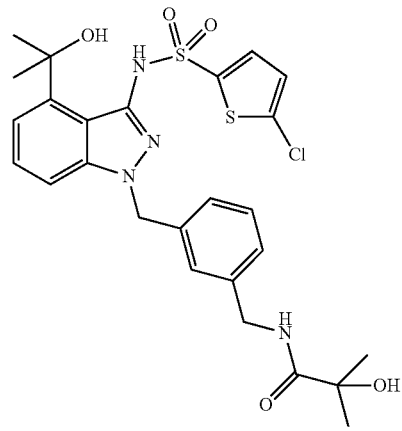 [SMILES: CC(C)(O)C(=O)NCc1cccc(Cn2nc(NS(=O)(=O)c3ccc(Cl)s3)c3c(C(C)(C)O)cccc32)c1]

Triethylamine (0.034 mL, 0.244 mmol) was added to N-[1-{[3-(aminomethyl)phenyl]methyl}-4-(1-hydroxy-1-methylethyl)-1H-indazol-3-yl]-5-chloro-2-thiophenesulfonamide (for a preparation see Intermediate 78) (40 mg, 0.081 mmol) in dichloromethane (1 mL). 2-Chloro-1,1-dimethyl-2-oxoethyl acetate (0.013 mL, 0.090 mmol) was added and the reaction mixture was stirred at room temp for 2 h. The reaction mixture was concentrated on the blowdown, potassium carbonate (113 mg, 0.815 mmol) and methanol (2 mL) was added and the reaction was stirred at room temp for 1 h. LCMS showed the acetate group was removed. The reaction mixture was concentrated, acidified with 2N HCl and extracted with EtOAc (2×15 mL). The combined organic layers were dried by passing through a hydrophobic frit and concentrated to afford the crude product as a yellow oil. The residue was dissolved in DMSO (1 mL) and purified by Mass Directed AutoPrep on Sunfire C18 column using Acetonitrile Water with a Formic acid modifier (Method A). The solvent was removed under a stream of nitrogen in the Radleys blowdown apparatus to give the title compound (11.5 mg, 24%). LCMS (System A) RT=1.05 min, ES+ve m/z 577/579 (M+H)+.

Example 155

(3R)—N-[(3-{[3-{[(5-Chloro-2-thienyl)sulfonyl]amino}-4-(1-hydroxy-1-methylethyl)-1H-indazol-1-yl]methyl}phenyl)methyl]-3-morpholinecarboxamide Formate Salt

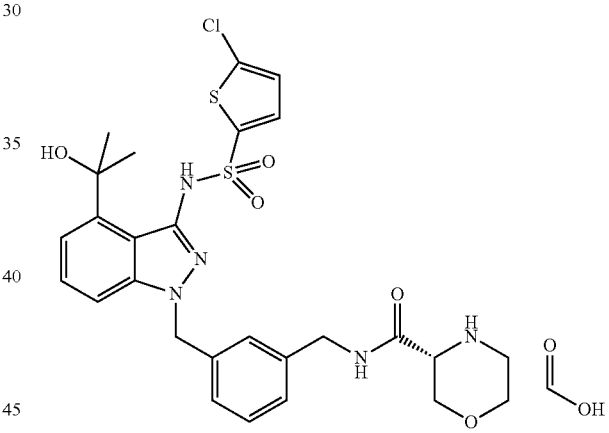

DIPEA (0.057 mL, 0.326 mmol) was added to a stirring solution of (3R)-4-{[(1,1-dimethylethyl)oxy]carbonyl}-3-morpholinecarboxylic acid (18.84 mg, 0.081 mmol) in DCM (1 mL). HATU (31.0 mg, 0.081 mmol) was then added, followed by N-[1-{[3-(aminomethyl)phenyl]methyl}-4-(1-hydroxy-1-methylethyl)-1H-indazol-3-yl]-5-chloro-2-thiophenesulfonamide (for a preparation see Intermediate 78) (40 mg, 0.081 mmol) and the reaction was stirred for an hour at room temp. The reaction mixture was concentrated and 4N Hydrogen chloride in dioxane (0.020 mL, 0.081 mmol) was then added and the reaction stirred at room temperature for 0.5 h. The reaction mixture was passed through a pre-conditioned (MeOH)SCX-2 cartridge, washed with methanol and then eluted using 2M ammonia in methanol. The appropriate ammoniacal fractions were concentrated, and the residue was dissolved in DMSO (0.5 mL) and purified by Mass Directed AutoPrep on Sunfire C18 column using Acetonitrile Water with a Formic acid modifier (Method A). The solvent was removed under a stream of nitrogen in the Radleys blowdown apparatus to give the title compound (2.7 mg, 5%). LCMS (System F) RT=0.84 min, ES+ve m/z 604/606 (M+H)+.

Example 156

(3S)—N-[(3-{(3-{[(5-Chloro-2-thienyl)sulfonyl]amino}-4-(1-hydroxy-1-methylethyl)-1H-indazol-1-yl]methyl}phenyl)methyl]-3-morpholinecarboxamide

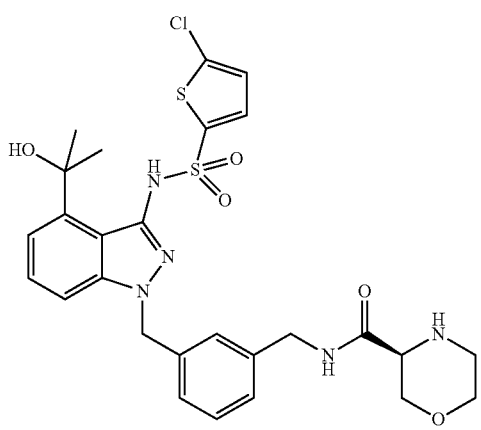 [SMILES: CC(C)(O)c1cccc2c1c(NS(=O)(=O)c1ccc(Cl)s1)nn2Cc1cccc(CNC(=O)[C@@H]2COCCN2)c1]

The title compound was similarly prepared to Example 155

LCMS (System F) RT=0.84 min, ES+ve m/z 604/606 (M+H)+.

Example 157-160 were prepared in array format from Intermediate 4 and the appropriate acid using HATU and cleavage of the BOC protecting group with TFA according to Example 44

Example 157

$N^1$-[(3-{[3-{[(5-Chloro-2-thienyl)sulfonyl]amino}-4-(methyloxy)-1H-indazol-1-yl]methyl}phenyl)methyl]-D-serinamide Trifluoroacetate

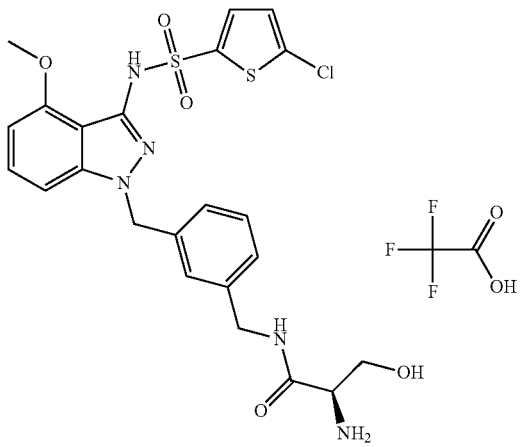 [SMILES: COc1cccc2c1c(NS(=O)(=O)c1ccc(Cl)s1)nn2Cc1cccc(CNC(=O)[C@H](N)CO)c1 ; O=C(O)C(F)(F)F]

LCMS (System D) RT=0.80 min, ES+ve m/z 550/552 (M+H)+.

Example 158

N-[(3-{[3-{[(5-Chloro-2-thienyl)sulfonyl]amino}-4-(methyloxy)-1H-indazol-1-yl]methyl}phenyl)methyl]-L-prolinamide Trifluoroacetate

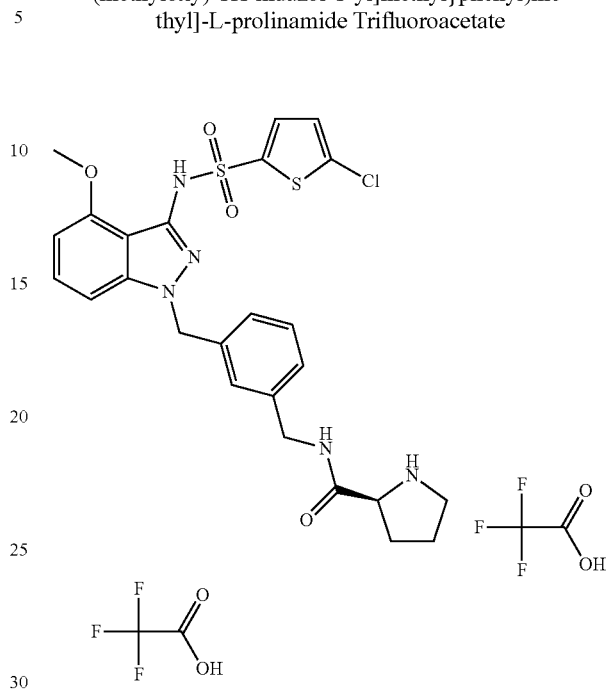

LCMS (System A) RT=0.82 min, ES+ve m/z 560/562 (M+H)+.

Example 159

(2S)—N-[(3-{[3-{[(5-Chloro-2-thienyl)sulfonyl]amino}-4-(methyloxy)-1H-indazol-1-yl]methyl}phenyl)methyl]-2-azetidinecarboxamide Trifluoroacetate

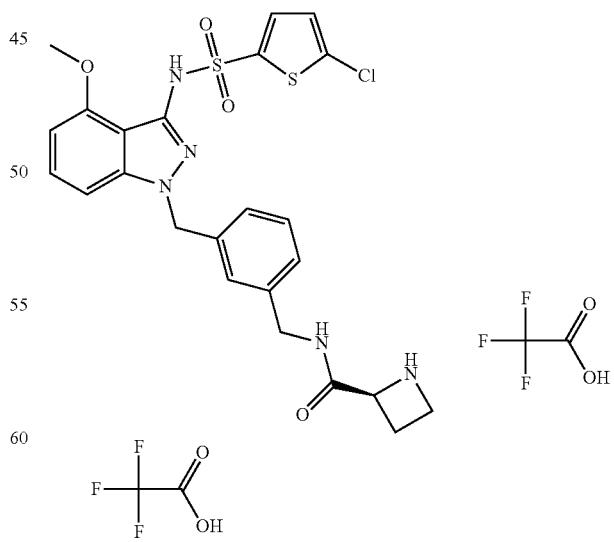

LCMS (System B) RT=1.82 min, ES+ve m/z 546/548 (M+H)+.

Example 160

(3R)—N-({3-[(4-(Methyloxy)-3-{[(5-methyl-2-thienyl)sulfonyl]amino}-1H-indazol-1-yl)methyl]phenyl}methyl)-3-

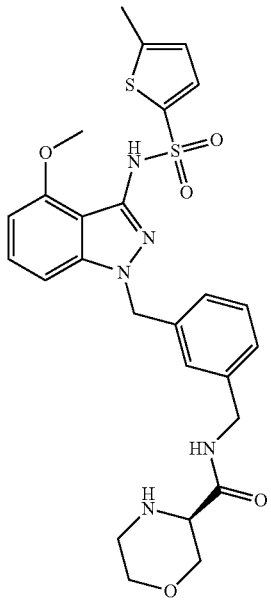 [SMILES: COc1cccc2c1c(NS(=O)(=O)c1ccc(C)s1)nn2Cc1cccc(CNC(=O)[C@H]2COCCN2)c1]

LCMS (System A) RT=0.68 min, ES+ve m/z 556 (M+H)+.

Examples 161 and 162 were prepared from N-[1-{[3-(aminomethyl)phenyl]methyl}-5-fluoro-4-(methyloxy)-1H-indazol-3-yl]-5-chloro-2-thiophenesulfonamide (for a preparation see Intermediate 61) following HATU coupling with 4-methyl-3-morpholinecarboxylic acid hydrochloride and then resolution of the resulting racemic mixture by chiral HPLC:

Example 161

N-[(3-{[3-{[(5-Chloro-2-thienyl)sulfonyl]amino}-5-fluoro-4-(methyloxy)-1H-indazol-1-yl]methyl}phenyl)methyl]-4-methyl-3-morpholinecarboxamide Enantiomer 1

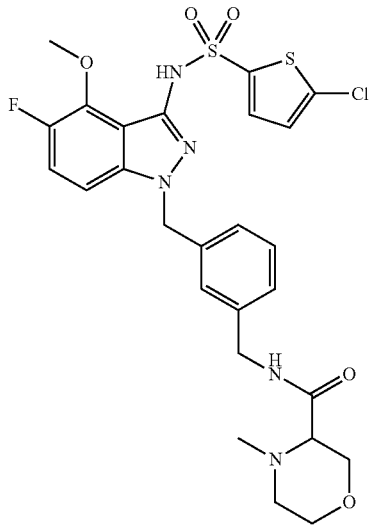 [SMILES: COc1c(F)ccc2c1c(NS(=O)(=O)c1ccc(Cl)s1)nn2Cc1cccc(CNC(=O)C2COCCN2C)c1]

LCMS (System A) RT=0.96 min, ES+ve m/z 608/610 (M+H)+.

Example 162

N-[(3-{[3-{[(5-Chloro-2-thienyl)sulfonyl]amino}-5-fluoro-4-(methyloxy)-1H-indazol-1-yl]methyl}phenyl)methyl]-4-methyl-3-morpholinecarboxamide Enantiomer 2

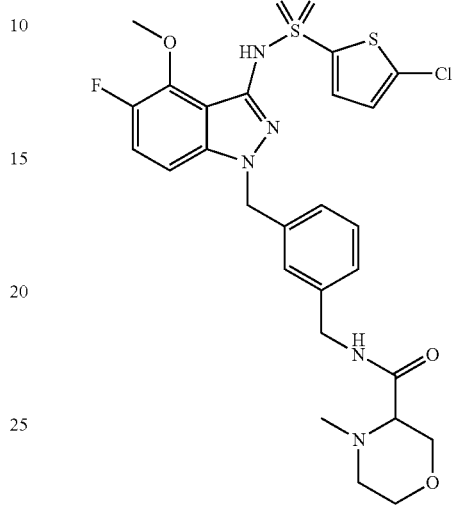

LCMS (System A) RT=0.96 min, ES+ve m/z 608/610 (M+H)+.

Example 163

4-{[3-{[(5-Chloro-2-thienyl)sulfonyl]amino}-4-(methyloxy)-1H-indazol-1-yl]methyl}-N,N-diethylbenzamide

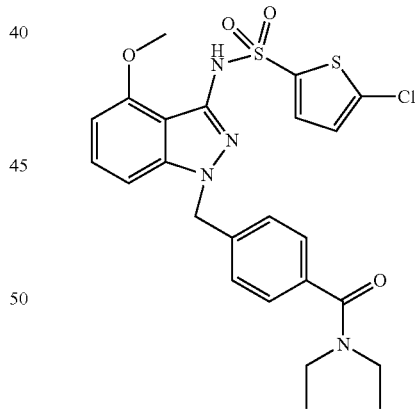

To a solution of 4-{[3-[[(5-chloro-2-thienyl)sulfonyl]({[2-(trimethylsilyl)ethyl]oxy}methyl)amino]-4-(methyloxy)-1H-indazol-1-yl]methyl}-N,N-diethylbenzamide (for a preparation see Intermediate 79) (125.5 mg, 0.189 mmol) in dichloromethane (DCM) (1 ml) was added dropwise TFA (0.292 ml, 3.78 mmol) at ambient temperature. The resulting mixture was stirred at ambient temperature for 30 h. Reaction mixture was concentrated under a stream of nitrogen in a blowdown unit. The residue was purified using the high pH-MDAP and further purified by MDAP to give the title compound (3 mg, 3%) LCMS (System A) RT=1.19 min, ES+ve m/z 533/535 (M+H)+.

Example 164

5-Chloro-N-(4-(methyloxy)-1-{[3-(methyloxy)phenyl]methyl}-1H-indazol-3-yl)-2-thiophenesulfonamide

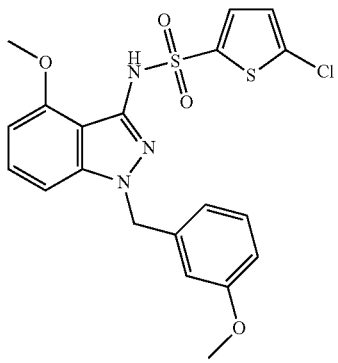 [SMILES: COc1cccc(Cn2nc(NS(=O)(=O)c3ccc(Cl)s3)c3c(OC)cccc32)c1]

Was prepared by alkylation of 5-chloro-N-[4-(methyloxy)-1H-indazol-3-yl]-N-({[2-(trimethylsilyl)ethyl]oxy}methyl)-2-thiophenesulfonamide (for a preparation see Intermediate 8) with 3-methoxybenzyl bromide and potassium carbonate in DMF as above. LCMS (System A) RT=1.25 min, ES+ve m/z 464/466 (M+H)+.

Example 165

N-[1-{[3-Fluoro-4-(methyloxy)phenyl]methyl}-4-(methyloxy)-1H-indazol-3-yl]-5-methyl-2-thiophenesulfonamide

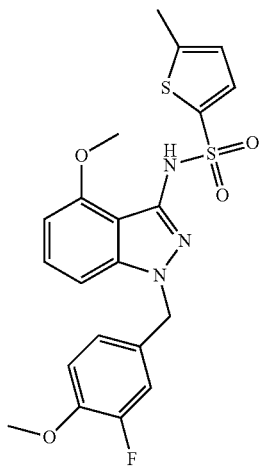 [SMILES: COc1ccc(Cn2nc(NS(=O)(=O)c3ccc(C)s3)c3c(OC)cccc32)cc1F]

A solution of 1-{[3-fluoro-4-(methyloxy)phenyl]methyl}-4-(methyloxy)-1H-indazol-3-amine (for a preparation see Intermediate 80) (130 mg, 0.8 mmol) in pyridine (2 mL) was added to 5-methyl-2-thiophenesulfonyl chloride (0.24 mmol). The reaction mixture was shaken briefly and allowed to stand for 3 h at 21° C. prior to concentration by blowdown. The residue was dissolved in 1:1 MeOH-DMSO (1 mL) and purified by Mass Directed AutoPrep on Xbridge column using Acetonitrile Water with an ammonium carbonate modifier (Method C). The solvent was evaporated in vacuo to give the title compound (76 mg) LCMS (System A) RT=1.11 min, ES+ve m/z 462 (M+H)+.

Example 166

(3S)—N-({3-[(3-{[(5-Chloro-2-thienyl)sulfonyl]amino}-4-hydroxy-1H-indazol-1-yl)methyl]phenyl}methyl)-3-morpholinecarboxamide formate salt

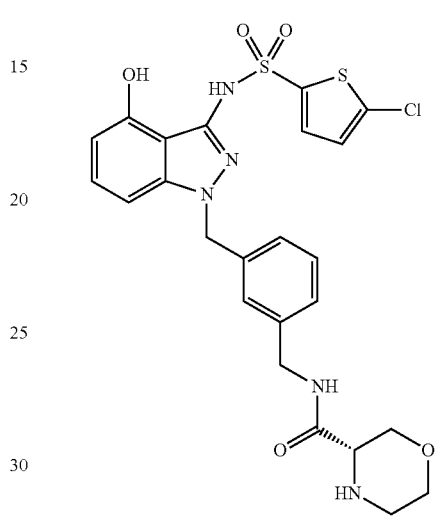

To a solution of O-(7-azabenzotriazol-1-yl)-N,N,N',N'-tetramethyluronium-hexafluorophosphate (77 mg, 0.124 mmol) in anhydrous N,N-dimethylformamide (1 mL) was added at room temperature (S)-4-Boc-morpholine-3-carboxylic acid (26.2 mg, 0.113 mmol), followed by N,N-diisopropylethylamine 0.059 mL, 0.339 mmol) and finally a solution of N-(1-{[3-(aminomethyl)phenyl]methyl}-4-hydroxy-1H-indazol-3-yl)-5-chloro-2-thiophenesulfonamide (formate salt) (for a preparation see intermediate 15) ((56 mg, 0.113 mmol) in anhydrous N,N-dimethylformamide (2 mL) and the reaction mixture was stirred at room temperature for 1 hour. The reaction mixture was partitioned between saturated aqueous sodium hydrogen carbonate solution and ethyl acetate. The organic layer was separated, washed with brine:water (1:1), passed through a hydrophobic frit and evaporated in-vacuo. The was treated with hydrogen chloride (4M solution in 1,4-dioxane) (1 mL) and then added methanol (~4 mL) until the reaction was in solution. Reaction stirred at room temperature for 2 hours. The reaction mixture was evaporated in-vacuo and the residue was dissolved in MeOH/DMSO (1 mL) and purified by Mass Directed AutoPreparative HPLC (MDAP) on (Sunfire C18 column Method A) eluting with solvents A/B (A: 0.1% v/v solution of formic acid in water, B: 0.1% v/v solution of formic acid in acetonitrile) using a method B over 25 min. Appropriate fractions were combined and evaporated in-vacuo to yield the title compound as a colourless oil (13 mg, 19%). LCMS (System B) RT=1.63 min, ES+ve m/z 562/564 (M+H)+.

Biological Test Methods

[35S]-GTPνS SPA Binding Assays for CCR4 Antagonist Activity

Antagonist potency was determined by a radioligand [$^{35}$S]-GTPγS competition assay. Briefly, CCR4 expressing CHO membranes were homogenised by passing through a 23G needle. These membranes were then adhered to WGA-coated Leadseeker SPA beads in assay buffer (20 mM HEPES, 10 mM MgCl$_2$, 100 mM NaCl, 0.05% BSA, 40 ug/ml Saponin and pH adjusted to 7.4 using KOH 5M) to generate a 3 μg/well final assay concentration (FAC) membrane and 250 μg/well FAC bead, solution.

After 60 minutes pre-coupling on ice, GDP was added to give a 4.4 uM FAC. [$^{35}$S]-GTPγS made in assay buffer was then added to the bead/membrane solution to give a 0.33 nM FAC. Human MDC was added to the bead/membrane/[$^{35}$S]-GTPγS suspension to give an FAC that exhibits 80% of the maximal agonist response (EC80). The bead/membrane/[$^{35}$S]-GTPγS/Agonist suspension was dispensed into white Greiner polypropylene 384-well plates (45 μl/well), containing 0.5 μl of compound. The final assay solution (45.5 μl) was then sealed, spun using a centrifuge and then incubated at room temp for 3-6 hours. Plates were then read on a Viewlux instrument and luminescence was then plotted as a percentage of the maximum inhibitional response elicited by an IC100 of a standard antagonist.

Examples 1-77, 80, 82, 85, 88-90, 95, 100-103, 114-157, 160, 164 and 165 were tested in the above assay.

All tested compounds were found to have pIC50≧7.0 and <8.4 with the exception of Examples 101, 116, 120 and 156 which had a pIC50≧6.4 and <7.0.

Examples 2-4, 6-8, 10, 12, 16-18, 21, 26-28, 33, 35, 37, 43, 44, 48, 51, 52, 55, 57, 70, 71-73, 80, 85, 102, 114, 124, 125, 127, 133, 134, 138-140, 142-144, 148, 149 and 151-153 were found to have pIC50≧7.8 and <8.4.

Chemokine Stimulated Increases in Cellular F-Actin Content

Blood was taken from normal volunteers who had taken no medication within the previous ten days and mixed with ⅑ of the volume of 3.8% tri-sodium citrate solution. Chemokine-induced increases in the F-actin content of CD4+ CCR4+ T cells were measured by a modification of the method of Pilette et al. (Eur. Respir. J; 23: 876-884, 2004). Peripheral blood mononuclear cells (PBMC) were isolated by dextran sedimentation followed by Percoll density gradient centrifugation. The PBMCs were incubated with FITC-conjugated anti-human CD4 and PE-conjugated anti-CCR4 antibodies or appropriate isotype controls for 15 min. The cell suspensions were then centrifuged at 400 g for 10 min and the pellets resuspended in assay buffer (phenol red-free RPMI 1640 medium containing 10 mM HEPES and 0.1% bovine serum albumin) at 10$^7$/mL. The resulting cell suspension was incubated with antagonist or vehicle (0.1% DMSO) for 30 min at 37° C. before stimulation with the agonist for 15 sec. The assay was terminated by addition of 3% formaldehyde. The fixed cells were washed twice with PBS (centrifuging at 1000 g for 5 min to recover the cells) and incubated at room temperature with Alexa fluor-647 phalloidin (0.075 U/mL) in the presence of lyso-phosphatidylcholine (93.75 μg/ml) for 20 min to stain F-actin. The cells were washed once more with PBS and the relative F-actin content of the cells was measured flow cytometrically. The mean fluorescence intensity of 1000 CD4$^+$ CCR4$^+$ cells per sample was determined and expressed as a fraction of the mean intensity of the CD4$^+$ CCR4$^-$ cells in that sample.

Examples 1-81, 83-86, 89, 90, 95, 96, 102, 103, 113, 110-113, 116-122, 124, 125, 128, 129, 157-160, 163, 164 and 166 were tested in the above assay.

All tested compounds were found to have a pA2≧6.0 with the exception of Example 163.

Examples 1-79, 83-86, 89, 96, 110-113, 118, 124, 125, 129, 158-160 and 166 were found to have a pA2≧6.9.

All publications, including but not limited to patents and patent applications, cited in this specification are herein incorporated by reference as if each individual publication were specifically and individually indicated to be incorporated by reference herein as though fully set forth.

What is claimed is:

1. A method for treating a disease or condition for which a CCR4 receptor antagonist is indicated in a subject in need thereof which comprises administering a therapeutically effective amount of a compound which is

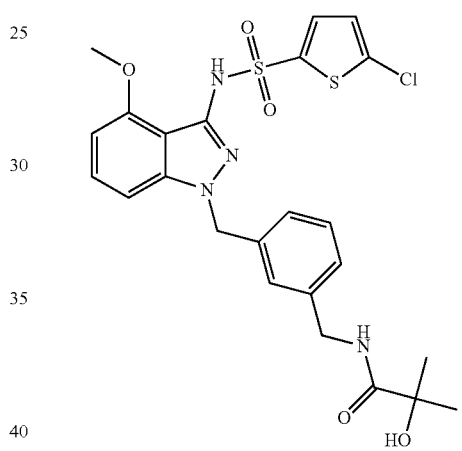

or a salt thereof.

2. A method according to claim 1 in which disease or condition for which a CCR4 antagonist is indicated is asthma.

3. A method according to claim 1, wherein the disease or condition for which a CCR4 antagonist is indicated is allergic bronchopulmonary aspergillosis.

4. A method according to claim 1, wherein the disease or condition for which a CCR4 antagonist is indicated is selected from the group consisting of immunoregulatory, inflammatory and allergic diseases.

* * * * *